US012453282B2

(12) United States Patent
Kang et al.

(10) Patent No.: US 12,453,282 B2
(45) Date of Patent: Oct. 21, 2025

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyun-Ju Kang, Gyeonggi-do (KR); So-Young Jung, Gyeonggi-do (KR); Eun-Joung Choi, Gyeonggi-do (KR); Hong-Yeop Na, Gyeonggi-do (KR); Sang-Hee Cho, Gyeonggi-do (KR); Su-Hyun Lee, Gyeonggi-do (KR); Jin-Ri Hong, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 880 days.

(21) Appl. No.: 17/374,908

(22) Filed: Jul. 13, 2021

(65) Prior Publication Data

US 2022/0020931 A1 Jan. 20, 2022

(30) Foreign Application Priority Data

Jul. 14, 2020 (KR) ........................ 10-2020-0086701

(51) Int. Cl.

| | |
|---|---|
| ***H10K 85/60*** | (2023.01) |
| ***C07D 413/12*** | (2006.01) |
| ***C07D 413/14*** | (2006.01) |
| ***C07D 487/04*** | (2006.01) |
| ***H10K 50/11*** | (2023.01) |
| ***H10K 101/00*** | (2023.01) |

(52) U.S. Cl.

CPC ......... *H10K 85/636* (2023.02); *C07D 413/12* (2013.01); *C07D 413/14* (2013.01); *C07D 487/04* (2013.01); *H10K 85/6572* (2023.02); *H10K 50/11* (2023.02); *H10K 85/657* (2023.02); *H10K 85/6574* (2023.02); *H10K 85/6576* (2023.02); *H10K 2101/90* (2023.02)

(58) Field of Classification Search

CPC .. C07D 487/04; C07D 498/22; C07D 513/22; H10K 85/6572

See application file for complete search history.

(56) References Cited

U.S. PATENT DOCUMENTS

| | | | |
|---|---|---|---|
| 2011/0303901 | A1 | 12/2011 | Cheng et al. |
| 2014/0225088 | A1 | 8/2014 | Hwang et al. |
| 2018/0208837 | A1 | 7/2018 | Ahn |
| 2021/0336153 | A1 | 10/2021 | Kim et al. |

FOREIGN PATENT DOCUMENTS

| | | | | | |
|---|---|---|---|---|---|
| CN | 106478672 | A | | 3/2017 | |
| CN | 107602568 | A | | 1/2018 | |
| CN | 110964019 | A | * | 4/2020 | C07D 487/04 |
| KR | 20130104451 | A | * | 9/2013 | C07D 487/04 |
| WO | WO-2010114264 | A2 | * | 10/2010 | C07D 209/56 |
| WO | WO-2019245164 | A1 | * | 12/2019 | C07D 209/56 |

OTHER PUBLICATIONS

Computer-generated English-language translation of CN-110964019-A.*

Search Report from China National Intellectual Property Administration for China patent application No. 202110658149.9; Application Date: Jun. 15, 2021.

* cited by examiner

*Primary Examiner* — Vu A Nguyen

(74) *Attorney, Agent, or Firm* — G. Creston Campbell

(57) ABSTRACT

The present disclosure relates to a plurality of host materials comprising at least one first host compound represented by formula 1 and at least one second host compound represented by formula 2, and an organic electroluminescent device comprising the same. By comprising the host materials according to the present disclosure, an organic electroluminescent device having low driving voltage and/or high luminous efficiency and/or long lifespan can be provided.

8 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

An organic electroluminescent device (OLED) was first developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an OLED is light-emitting materials, and the light-emitting material must have high quantum efficiency and high mobility of electrons and holes, and the formed light-emitting material layer must be uniform and stable. The light-emitting material is classified into a host material and a dopant material in a functional aspect. A light-emitting material can be used as a combination of a host and a dopant to improve color purity, luminous efficiency, and stability. When using such a dopant/host material system as a light-emitting material, their selection is important since host materials greatly influence the efficiency and lifespan of the light-emitting device.

Recently, an urgent task is the development of an OLED having high efficiency and long lifespan. In particular, the development of highly excellent light-emitting material over conventional light-emitting materials is urgently required, considering the electroluminescent (EL) properties necessary for medium and large-sized OLED panels.

KR 2010-0108924 A, US 2011/0303901 A1, KR 2014-0101699 A, and ON 107602568 A disclose a compound based on indoloquinoxaline derivatives. However, said references do not specifically disclose a specific combination of host materials as described in the present disclosure. In addition, there is continuous need to develop a light-emitting material having improved performances, such as improved driving voltage, luminous efficiency, and/or lifespan properties, compared to the conventional specific combination of compounds disclosed in said references.

DISCLOSURE OF THE INVENTION

Problems to be Solved

The object of the present disclosure is firstly, to provide a plurality of host materials which is able to produce an organic electroluminescent device having low driving voltage and/or high luminous efficiency and/or long lifespan, and secondly, to provide an organic electroluminescent device comprising the host materials.

Solution to Problems

As a result of intensive studies to solve the technical problem above, the present inventors found that the aforementioned objective can be achieved by a plurality of host materials comprising a first host material comprising a compound represented by the following formula 1 and a second host material comprising a compound represented by the following formula 2, so that the present invention was completed.

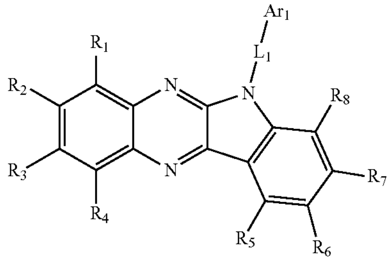

(1)

In formula 1, $L_1$ represents a single bond, a substituted or unsubstituted (C6-C30)arylene, or a substituted or unsubstituted (3- to 30-membered)heteroarylene;

$Ar_1$ represents a substituted or unsubstituted (C6-C30)aryl or a substituted or unsubstituted (3- to 30-membered)heteroaryl; and $R_1$ to Re, each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted (C1-C30)alkyl (C6-C30)arylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30) alkenyl(3- to 30-membered)heteroarylamino, or a substituted or unsubstituted (C6-C30)aryl(3- to 30-membered)heteroarylamino; or may be linked to the adjacent substituents to form a ring(s);

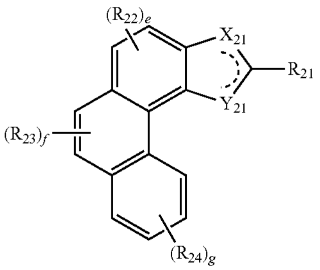

(2)

In formula 2, $X_{21}$ and $Y_{21}$ each independently represent —N═, —$R_{25}$—, —O—, or —S—, provided that one of $X_{21}$ and $Y_{21}$ is —N═, and the other of $X_{21}$ and $Y_{21}$ is —$NR_{25}$—, —O—, or —S—;

$R_{21}$ represents a substituted or unsubstituted (C6-C30)aryl or a substituted or unsubstituted (3- to 30-membered)heteroaryl;

$R_{22}$ to $R_{25}$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to the adjacent substituents to form a ring(s);

provided that at least one of $R_{22}$ to $R_{24}$ is $-L_{21}-Ar_{21}$;

$L_{21}$ represents a single bond or a substituted or unsubstituted (C6-C30)arylene;

$Ar_{21}$ represents a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, or $—NR_{31}R_{32}$;

$R_{31}$ and $R_{32}$ each independently represent a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl;

e and f each independently represent an integer of 1 or 2, and g represents an integer of 1 to 4; and when e to g are an integer of 2 or more, each of $R_{22}$, each of $R_{23}$, and each of $R_{24}$ may be the same or different.

Advantageous Effects of Invention

By using the plurality of host materials according to the present disclosure, an organic electroluminescent device having low driving voltage and/or high luminous efficiency and/or long lifespan can be prepared.

EMBODIMENTS OF THE INVENTION

Hereinafter, the present disclosure will be described in detail. However, the following description is intended to explain the invention, and is not meant in any way to restrict the scope of the invention.

The present disclosure relates to a plurality of host materials comprising at least one first host material represented by the formula 1 and at least one second host material represented by the formula 2, and an organic electroluminescent device comprising the host materials.

In addition, the present disclosure relates to an organic electroluminescent compound represented by formula 3, an organic electroluminescent material comprising the same, and an organic electroluminescent device comprising the organic electroluminescent material.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, or an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such at least two compounds may be comprised in the same layer or different layers, and may be mixture-evaporated or co-evaporated, or may be individually evaporated.

The term "a plurality of host materials" in the present disclosure means an organic electroluminescent material comprising a combination of at least two host materials. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The at least two compounds comprised in a plurality of host materials may be comprised together in one light-emitting layer, or may each be comprised in separate light-emitting layers. When at least two host materials are comprised in one layer, the at least two host materials may be mixture-evaporated to form a layer or may be individually and simultaneously co-evaporated to form a layer.

The term "(C1-C30)alkyl" in the present disclosure is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. Herein, the term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(C6-C30)aryl (ene)" in the present disclosure is a monocyclic or fused ring radical derived from an aromatic hydrocarbon having 6 to 30 ring backbone carbon atoms, in which the number of the ring backbone carbon atoms is preferably 6 to 20, more preferably 6 to 15, and may be partially saturated. The aryl may comprise a Spiro structure. Examples of the aryl specifically include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, tetramethyl-dihydrophenanthrenyl, etc. More specifically, the aryl may be o-tolyl, p-tolyl, 2,3-xylyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc. Herein, "(3- to 30-membered)heteroaryl(ene)" is an aryl having 3 to 30 ring backbone atoms including at least one, preferably 1 to 4 heteroatoms selected from the group consisting of B, N, O, S, Si, P, Se, and Ge, in which the number of ring backbone atoms is preferably 3 to 30, more preferably 5 to 20. The above heteroaryl may be a monocyclic ring, or a fused ring condensed with at least one benzene ring; and may be partially saturated. Also, the above heteroaryl or heteroarylene herein may be one formed by linking at least one heteroaryl or aryl group to a heteroaryl group via a single bond(s) and may comprise a Spiro structure. Examples of the heteroaryl specifically may include a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, dibenzoselenophenyl, benzofuroquinolinyl, benzofuroquinazolinyl, benzofuronaphthiridinyl, benzofuropyrimidinyl, naphthofuropyrimidinyl, benzothienoguinolinyl, benzothienoguinazolinyl, benzothienonaphthiridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, guinoxalinyl, carbazolyl, azacarbazolyl, benzocarbazolyl, dibenzocarbazolyl, phenoxazinyl, phenanthridinyl, benzodioxolyl, indolizidinyl, acridinyl, silafluorenyl, germafluorenyl, benzotriazolyl, phenazinyl, imidazopyridinyl, chromenoquinazolinyl, thiochromenoquinazolinyl, dimethylbenzopyrimidinyl, indolocarbazolyl, indenocarbazolyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 5-indolyl, 6 indolyl, 7-Indolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazol-1-yl, azacarbazol-2-yl, azacarbazol-3-yl, azacarbazol-A-yl, azacarbazol-5-yl, azacarbazol-6-yl, azacarbazol-7-yl, azacarbazol-8-yl, azacarbazol-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Herein, the term “a fused ring of (C3-C30) aliphatic ring and (C6-C30) aromatic ring” means a ring formed by fusing at least one aliphatic ring having 3 to 30 ring backbone carbon atoms in which the number of carbon atoms is preferably 3 to 25, more preferably 3 to 18, and at least one aromatic ring having 6 to 30 ring backbone carbon atoms in which the number of carbon atoms is preferably 6 to 25, more preferably 6 to 18. For example, the fused ring may be a fused ring of at least one benzene and at least one cyclohexane, or a fused ring of at least one naphthalene and at least one cyclopentane, etc. Herein, the carbon atoms in the fused ring of (C3-C30) aliphatic ring and (C6-C30) aromatic ring may be replaced with at least one heteroatoms selected from B, N, O, S, Si and P, preferably at least one heteroatoms selected from N, O and S. The term “Halogen” in the present disclosure includes F, Cl, Br, and I.

In addition, “ortho (o),” “meta (m),” and “para (p)” in the present disclosure are meant to signify the substitution position of all substituents. Ortho position is a compound with substituents, which are adjacent to each other, i.e., at the 1 and 2 positions on benzene. Meta position is the next substitution position of the immediately adjacent substitution position, i.e., a compound with substituents at the 1 and 3 positions on benzene. Para position is the next substitution position of the meta position, i.e., a compound with substituents at the 1 and 4 positions on benzene.

Herein, “a ring formed in linking to an adjacent substituent” means a substituted or unsubstituted (3- to 30-membered) mono- or polycyclic, alicyclic, aromatic ring, or a combination thereof, formed by linking or fusing two or more adjacent substituents, preferably may be a substituted or unsubstituted (5- to 25-membered) mono- or polycyclic, alicyclic, aromatic ring, or a combination thereof. Further, the formed ring may be included at least one heteroatom selected from the group consisting of B, N, O, S, Si and P, preferably, N, O and S. According to one embodiment of the present disclosure, the number of atoms in the ring skeleton is 5 to 20; according to another embodiment of the present disclosure, the number of atoms in the ring skeleton is 5 to 15. In one embodiment, the fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, a substituted or unsubstituted carbazole ring, etc.

In addition, “substituted” in the expression “substituted or unsubstituted” means that a hydrogen atom in a certain functional group is replaced with another atom or functional group, i.e., a substituent, and substituted with a group to which two or more substituents are connected among the substituents. For example, “a substituent to which two or more substituents are connected” may be pyridine-triazine. That is, pyridine-triazine may be heteroaryl or may be interpreted as a substituent in which two heteroaryls are connected. Preferably, the substituents of the substituted (C1-C30)alkyl, the substituted (C6-C30)aryl(ene), the substituted (3- to 30-membered)heteroaryl(ene), the substituted (C3-C30)cycloalkyl, the substituted (C1-C30)alkoxy, the substituted fused ring of (C3-C30) aliphatic ring and (C6-C30) aromatic ring, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C2-C30)alkenylamino, the substituted (C1-C30)alkyl(C2-C30)alkenylamino, the substituted mono- or di-(C6-C30)arylamino, the substituted (C1-C30)alkyl(C6-C30)arylamino, the substituted mono- or di-(3- to 30-membered)heteroarylamino, the substituted (C1-C30)alkyl(3- to 30-membered)heteroarylamino, the substituted (C2-C30)alkenyl(C6-C30)arylamino, the substituted (C2-C30)alkenyl(3- to 30-membered)heteroarylamino, and the substituted (C6-C30)aryl(3- to 30-membered)heteroarylamino in the formulas of the present disclosure, each independently are at least one selected from the group consisting of deuterium, halogen, cyano, carboxyl, nitro, hydroxy, phosphine oxide, (C1-C30) alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered) heterocycloalkyl, (C6-C30)aryloxy, (C6-C30)arylthio, (5- to 30-membered)heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, a fused ring of (C3-C30) aliphatic ring and (C6-C30) aromatic ring, amino, mono- or di-(C1-C30)alkylamino, mono- or di-(C2-C30)alkenylamino, (C1-C30)alkyl(C2-C30)alkenylamino, a substituted or unsubstituted mono- or di-(C6-C30)arylamino, (C1-C30)alkyl(C6-C30)arylamino, mono- or di-(3- to 30-membered)heteroarylamino, (C1-C30)alkyl(3- to 30-membered)heteroarylamino, (C2-C30)alkenyl(C6-C30) arylamino, (C2-C30)alkenyl(3- to 30-membered)heteroarylamino, (C6-C30)aryl(3- to 30-membered)heteroarylamino, (C1-C30)alkylcarbonyl, (C1-C30)alkoxycarbonyl, (C6-C30)arylcarbonyl, (C6-C30)arylphosphinyl, di(C6-C30) arylboronyl, di(C1-C30)alkylboronyl, (C1-C30)alkyl(C6-C30)arylboronyl, (C6-C30)ar(C1-C30)alkyl, and (C1-C30) alkyl(C6-C30)aryl. For example, the substituents may be deuterium, methyl, phenyl, biphenyl, naphthyl, or carbazolyl, etc.

Hereinafter, the host materials according to one embodiment will be described.

The plurality of host materials according to one embodiment comprise a first host material comprising a compound represented by the above formula 1 and a second host material comprising a compound represented by the above formula 2; and the plurality of host materials may be contained in a light-emitting layer of an organic electroluminescent device according to one embodiment.

The first host material as the host material according to one embodiment may comprise a compound represented by the following formula 1.

(1)

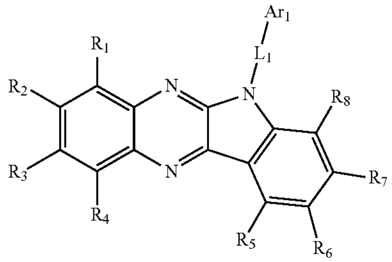

In formula 1, $L_1$ represents a single bond, a substituted or unsubstituted (C6-C30)arylene, or a substituted or unsubstituted (3- to 30-membered)heteroarylene;

$Ar_1$ represents a substituted or unsubstituted (C6-C30)aryl or a substituted or unsubstituted (3- to 30-membered)heteroaryl; and $R_1$ to $R_8$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted (C1-C30)alkyl (C6-C30)arylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30) alkenyl(3- to 30-membered)heteroarylamino, or a substituted or unsubstituted (C6-C30)aryl(3- to 30-membered)heteroarylamino; or may be linked to the adjacent substituents to form a ring(s).

In one embodiment, $L_1$ may be a single bond, a substituted or unsubstituted (C6-C25)arylene, or a substituted or unsubstituted (5- to 30-membered)heteroarylene, preferably a single bond, a substituted or unsubstituted (C6-C18)arylene, or a substituted or unsubstituted (5- to 25-membered)heteroarylene, more preferably a single bond, a substituted or unsubstituted (C6-C12)arylene, or a substituted or unsubstituted (5- to 18-membered)heteroarylene. For example, $L_1$ may be a single bond, phenylene unsubstituted or substituted with phenyl, unsubstituted naphthylene, or unsubstituted pyridinylene.

In one embodiment, $Ar_1$ may be a substituted or unsubstituted (C6-C30)aryl or a substituted or unsubstituted (5- to 30-membered)heteroaryl, preferably a substituted or unsubstituted (C6-C25)aryl or a substituted or unsubstituted (5- to 25-membered)heteroaryl, more preferably a substituted or unsubstituted (C6-C18)aryl or a substituted or unsubstituted (5- to 18-membered)heteroaryl. For example, $Ar_1$ may be phenyl substituted with at least two of phenyl unsubstituted or substituted with deuterium; phenyl; and naphthyl, phenyl substituted with dibenzofuran or dibenzothiophene, unsubstituted m-biphenyl, unsubstituted m-terphenyl, naphthyl unsubstituted or substituted with phenyl unsubstituted or substituted with one or more deuterium, pyridyl unsubstituted or substituted with phenyl unsubstituted or substituted with one or more deuterium, unsubstituted dibenzofuranyl, or unsubstituted dibenzothiophenyl.

In one embodiment, $R_1$ to $R_5$ each independently may be hydrogen, deuterium, halogen, cyano, a substituted or unsubstituted (C6-C30)aryl, or a substituted or unsubstituted (3- to 30-membered)heteroaryl, preferably hydrogen, (C6-C25)aryl unsubstituted or substituted with at least one of deuterium; (C6-C25)aryl unsubstituted or substituted with deuterium; (5- to 30-membered)heteroaryl; di(C6-C30)arylamino; and (C6-C30)aryl(5- to 30-membered)heteroarylamino, or a substituted or unsubstituted (5- to 30-membered)heteroaryl, more preferably hydrogen, (C6-C18)aryl unsubstituted or substituted with at least one of deuterium; (C6-C18)aryl unsubstituted or substituted with deuterium; (5- to 25-membered)heteroaryl; di(C6-C25)arylamino; and (C6-C25)aryl(5- to 25-membered)heteroarylamino, or a substituted or unsubstituted (5- to 25-membered)heteroaryl.

For example, at least one of $R_1$ to $R_4$, or at least one of $R_5$ to $R_8$ may be any one of the substituents listed in the following Group 1, and the substituents listed in the following Group 1 may be substituted with one or more deuterium, but are not limited thereto,

[Group 1]

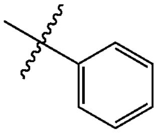
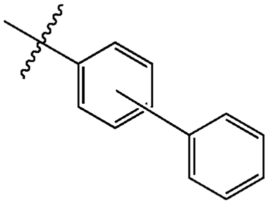
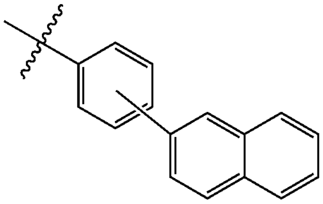
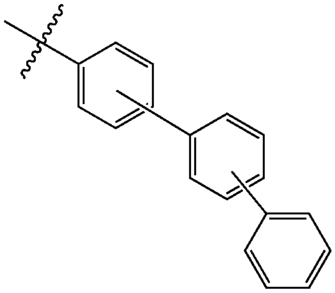
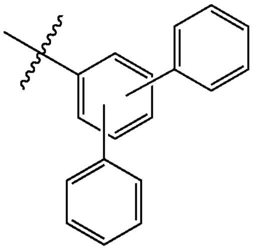
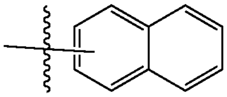
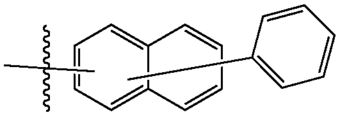
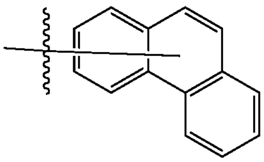
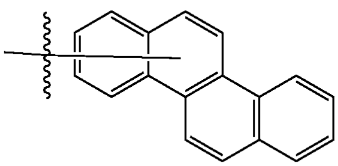

-continued

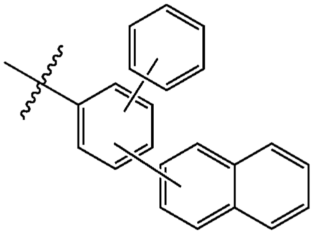
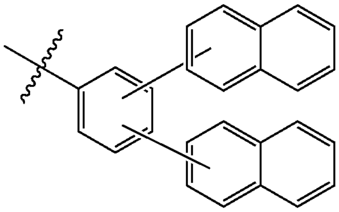
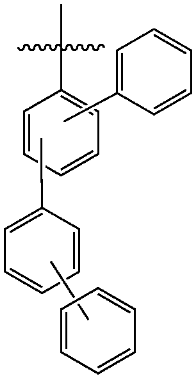
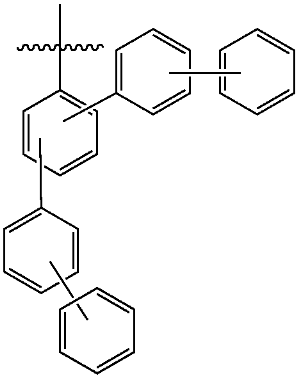
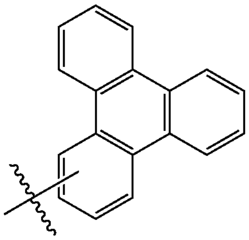
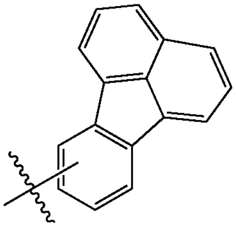
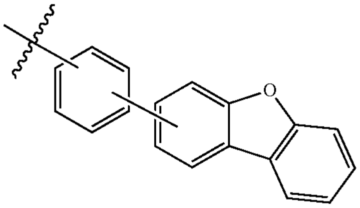
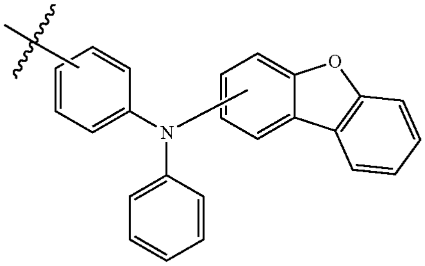

-continued

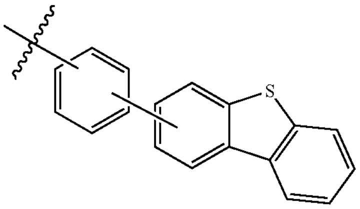

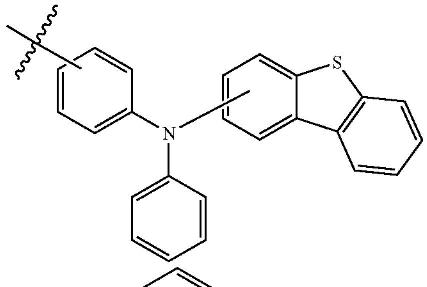

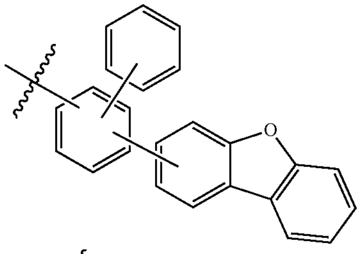

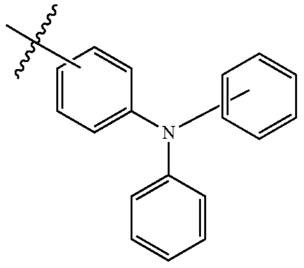

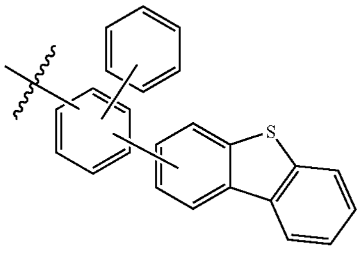

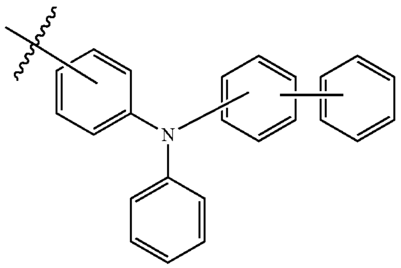

The compound represented by the formula 1 above according to one embodiment may be represented by the following formula 1-1 or 1-2.

(1-1)

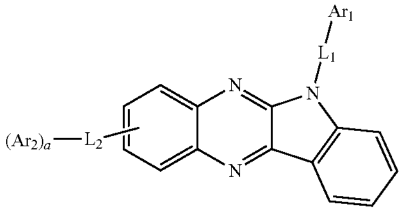

(1-2)

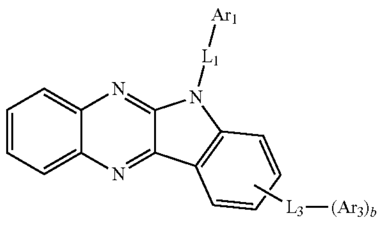

In formulas 1-1 and 1-2, $L_1$ and Art are as defined in the formula 1;

$L_2$ and $L_3$ each independently represent a single bond or a substituted or unsubstituted (C6-C30)arylene.

$Ar_2$ and $Ar_3$ each independently represent a substituted or unsubstituted (C6-C30)aryl, a substituted or unsubstituted (3- to 30-membered)heteroaryl, a substituted or unsubstituted di(C6-C30)arylamino, or a substituted or unsubstituted (C6-C30)aryl(3- to 30-membered)heteroarylamino:

a and b each independently represent an integer of 1 or 2; and when a and b are an integer of 2, each of $Ar_2$ and each of $Ar_3$ may be the same or different.

In one embodiment, $L_2$ and $L_3$ each independently may be a single bond, phenylene unsubstituted or substituted with phenyl unsubstituted or substituted with one or more deuterium, unsubstituted m-biphenylene, or unsubstituted p-biphenylene.

In one embodiment, when a and b are an integer of 2, $L_2$ and $L_3$ each independently may be a substituted or unsubstituted (C6-C30)arylene, for example, unsubstituted phenylene.

In one embodiment, $Ar_2$ and $Ar_3$ each independently may be (C6-C30)aryl unsubstituted or substituted with at least one of deuterium; (C6-C30)aryl unsubstituted or substituted with deuterium; (3- to 30-membered)heteroaryl, di(C6-C30)arylamino; and (C6-C30)aryl(3- to 30-membered)heteroarylamino, a substituted or unsubstituted (5- to 30-membered) heteroaryl, a substituted or unsubstituted di(C6-C30) arylamino, or a substituted or unsubstituted (C6-C30)aryl(5- to 30-membered)heteroarylamino, preferably (C6-C25)aryl unsubstituted or substituted with at least one of deuterium; (C6-C25)aryl unsubstituted or substituted with deuterium; (5- to 30-membered)heteroaryl; di(C6-C25)arylamino; and (C6-C25)aryl(5- to 30-membered)heteroarylamino, a substituted or unsubstituted (5- to 25-membered)heteroaryl, a substituted or unsubstituted di(C6-C25)arylamino, or a substituted or unsubstituted (C6-C25)aryl(5- to 25-membered) heteroarylamino, more preferably (C6-C18)aryl unsubstituted or substituted with at least one of deuterium; (C6-C18) aryl unsubstituted or substituted with deuterium; (5- to 25-membered)heteroaryl, di(C6-C18)arylamino; and (C6-C18)aryl(5- to 25-membered)heteroarylamino, a substituted or unsubstituted (5- to 18-membered)heteroaryl, a substituted or unsubstituted di(C6-C18)arylamino, or a substituted or unsubstituted (C6-C18)aryl(5- to 18-membered)heteroarylamino. For example, $Ar_2$ and $Ar_3$ each independently may be phenyl unsubstituted or substituted with at least one of one or more deuterium; phenyl unsubstituted or substituted with deuterium; naphthyl; dibenzofuranyl; dibenzothiophenyl; diphenylamino; phenylbiphenylamino; phenyldibenzofuranylamino; and phenyldibenzothiophenylamino, unsubstituted naphthyl, unsubstituted o-biphenyl, unsubstituted m-biphenyl, p-biphenyl unsubstituted or substituted with phenyl, p-terphenyl unsubstituted or substituted with phenyl unsubstituted or substituted with one or more deuterium, m-terphenyl unsubstituted or substituted with phenyl unsubstituted or substituted with one or more deuterium, unsubstituted o-terphenyl, unsubstituted phenanthrenyl, unsubstituted chrysenyl, unsubstituted dibenzofuranyl, unsubstituted dibenzothiophenyl, unsubstituted diphenylamino, unsubstituted phenylbiphenylamino, unsubstituted phenyldibenzofuranylamino, or unsubstituted phenyldibenzothiophenylamino.

The compound represented by the above formulas 1-1 and 1-2 according to one embodiment may be the first host material where $L_1$ represents a single bond; $Ar_1$ represents pyridyl substituted with deuterium or (C6-C30)aryl; $L_2$ and $L_3$ are a single bond or a substituted or unsubstituted phenylene; $Ar_2$ and $Ar_3$ each independently represent (C6-C30)aryl unsubstituted or substituted with deuterium or (C6-C30)aryl; and a and b each independently represent an integer of 1 or 2.

In one embodiment, the first host material represented by the above formula 1 may be more specifically illustrated by the following compounds, but is not limited thereto.

C-1

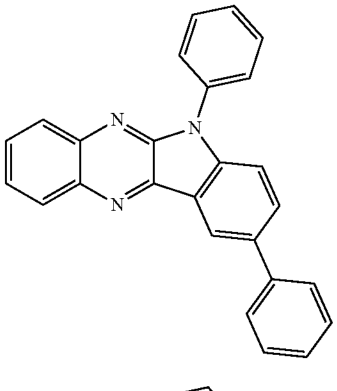

C-2

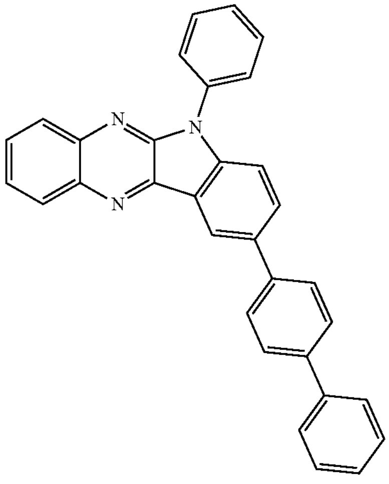

-continued

C-3

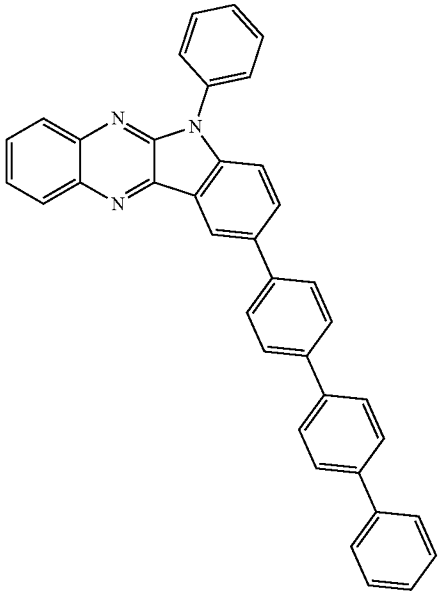

C-4

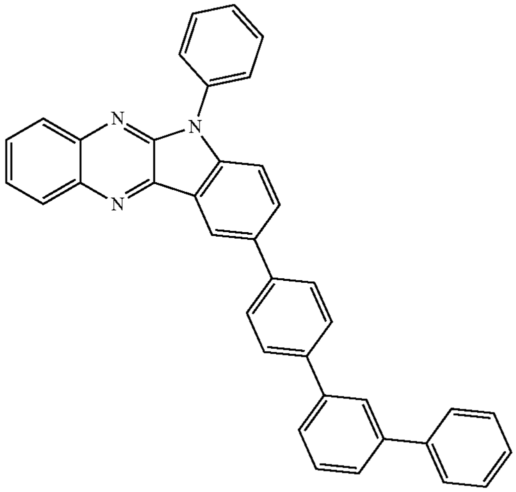

C-5

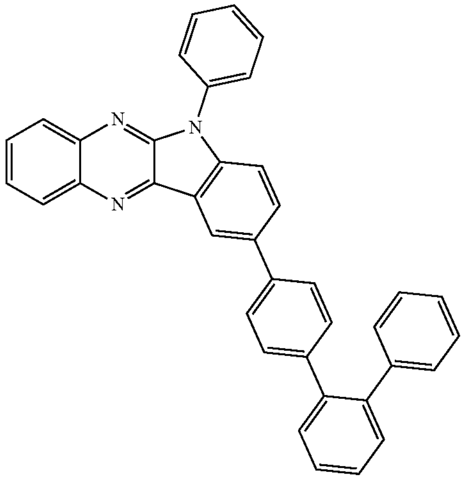

-continued
C-6
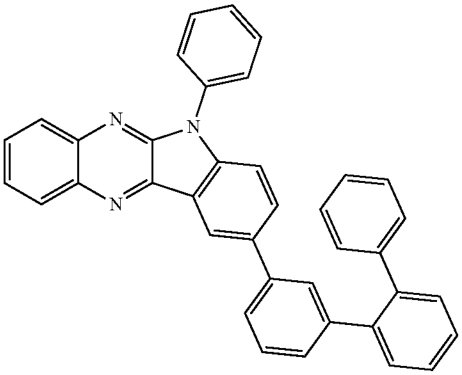
C-7
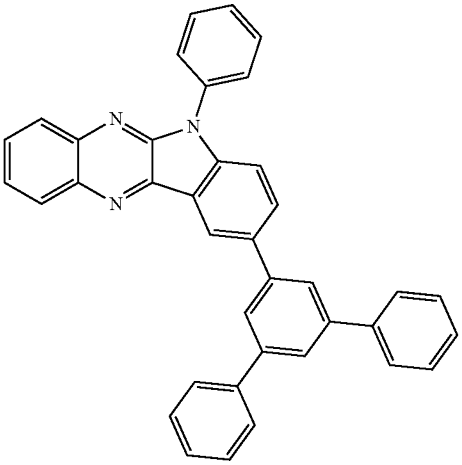
C-8
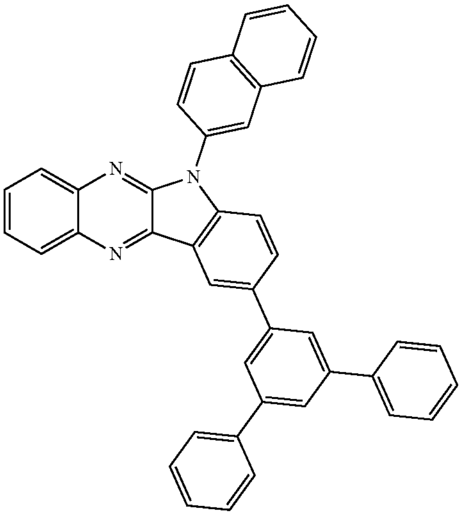
-continued
C-9
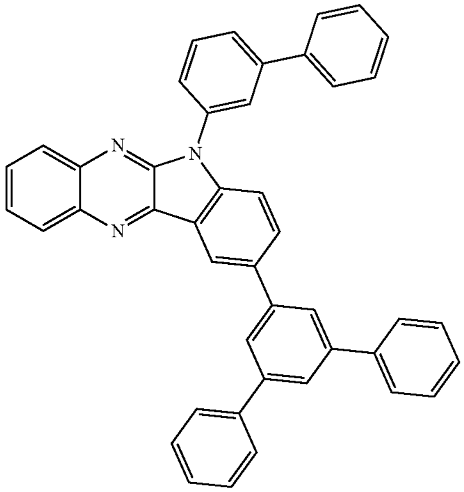
C-10
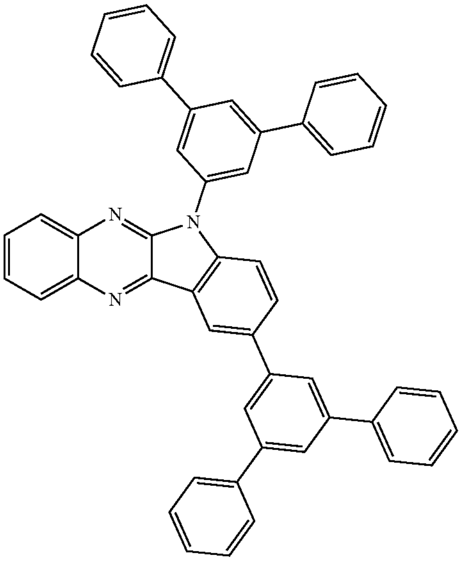
C-11
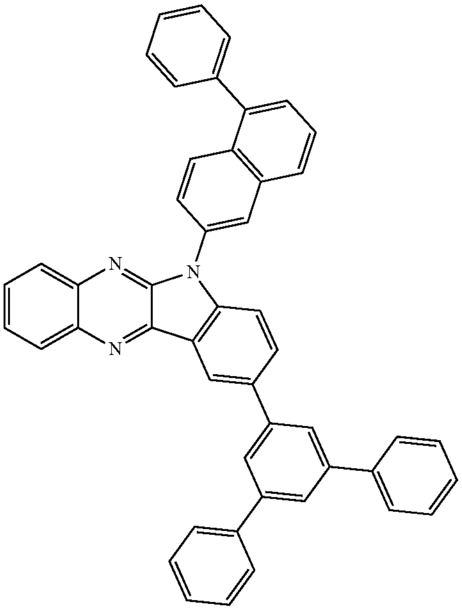

-continued
C-12
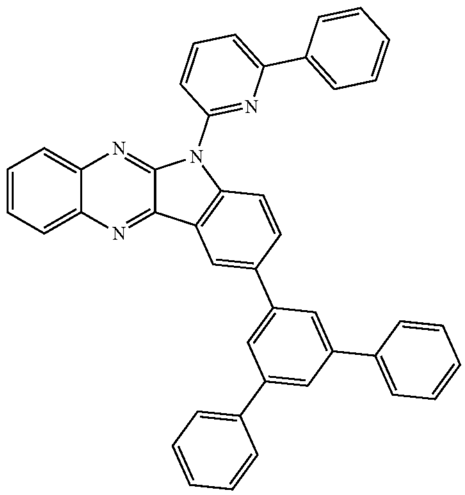
C-13
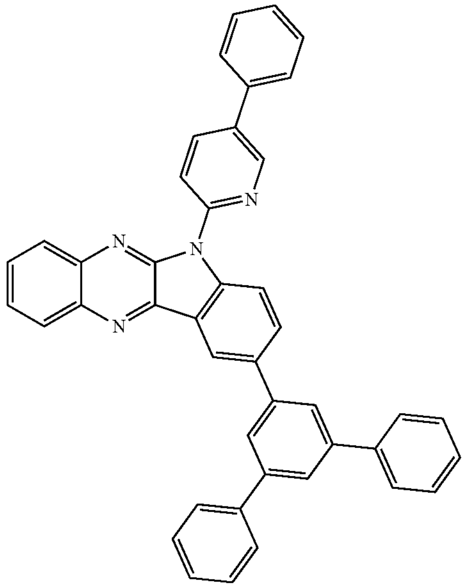
C-14
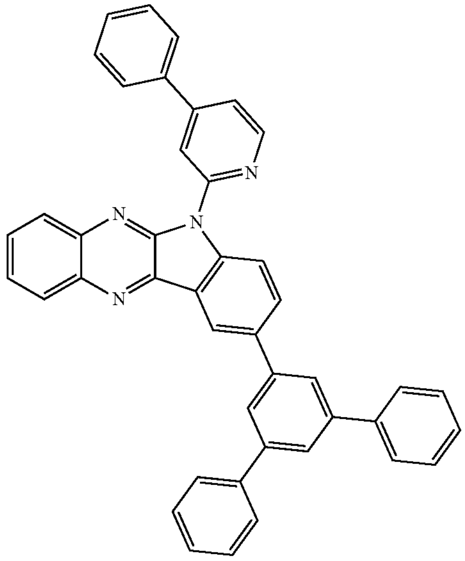
-continued
C-15
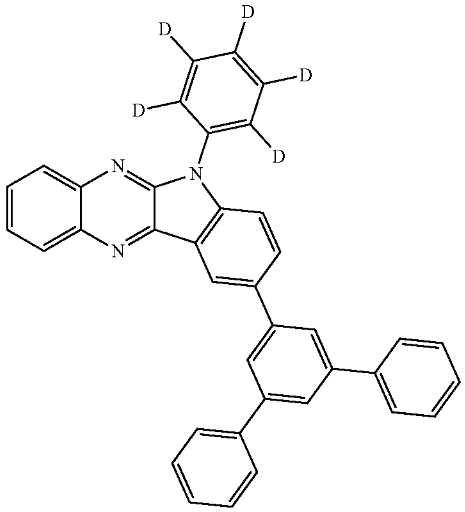
C-16
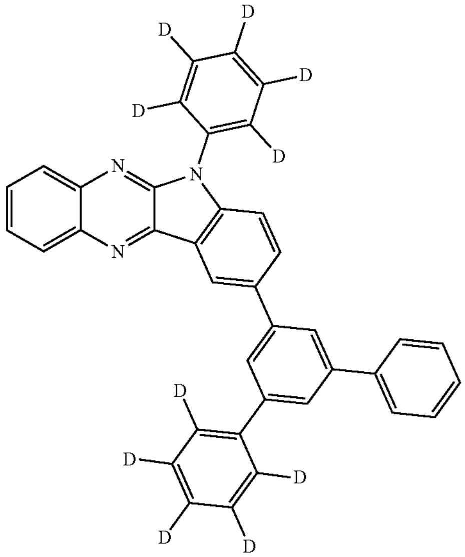
C-17
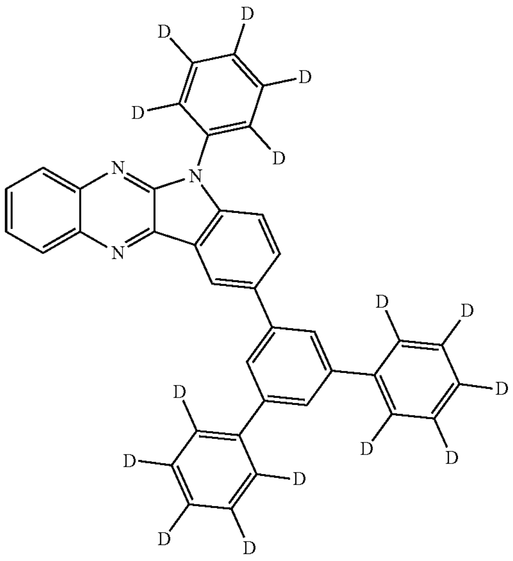

-continued
C-18
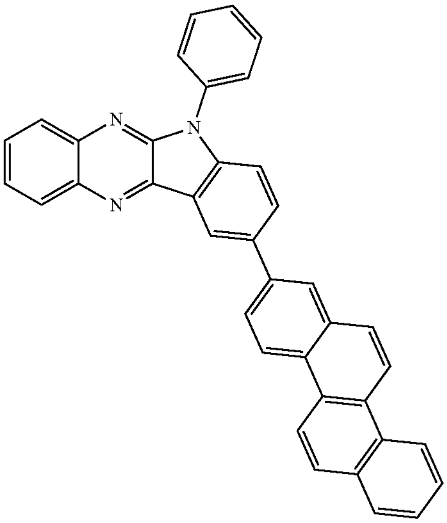
C-19
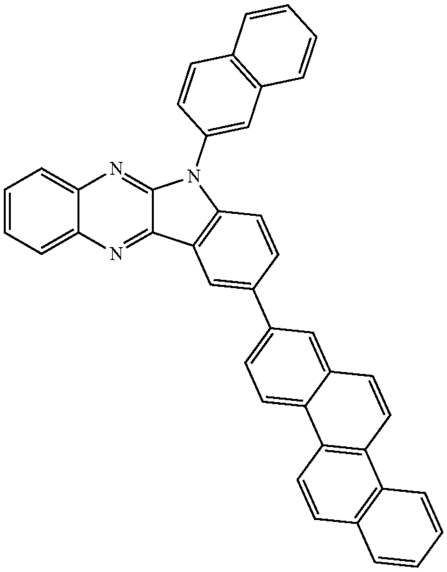
C-20
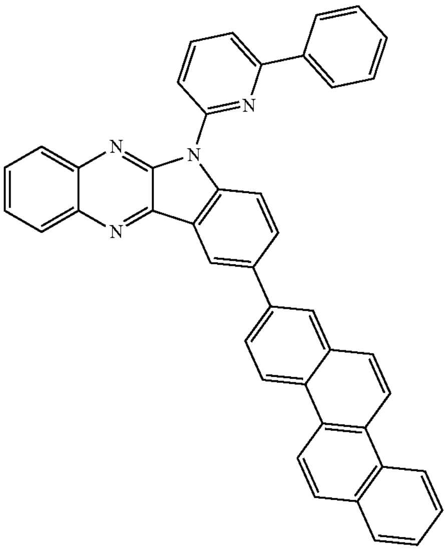
-continued
C-21
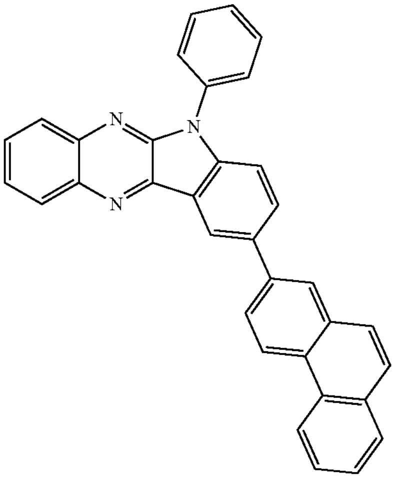
C-22
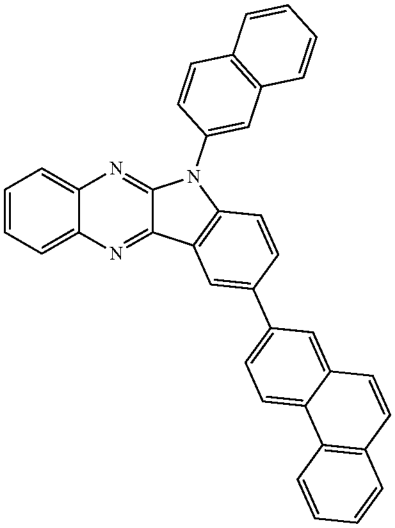
C-23
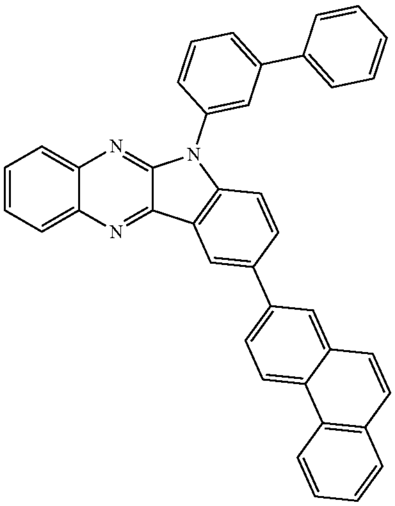

-continued
C-24
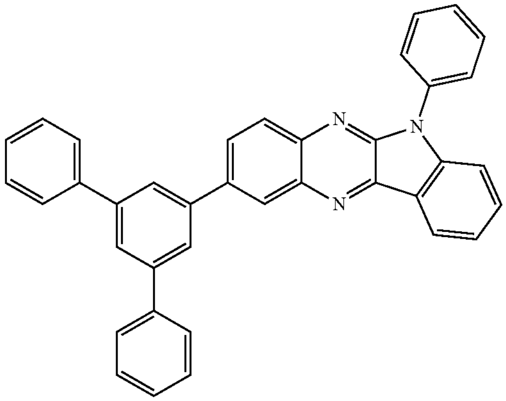
C-25
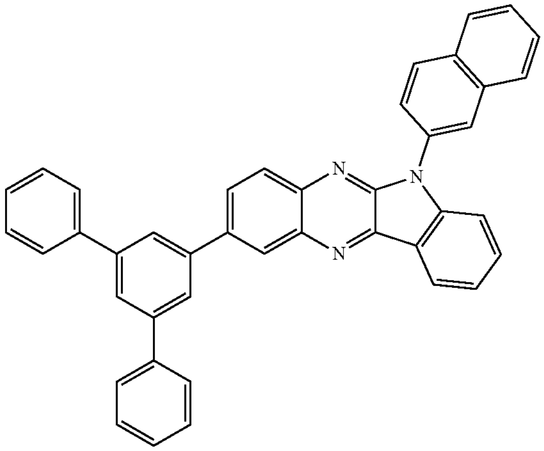
C-26
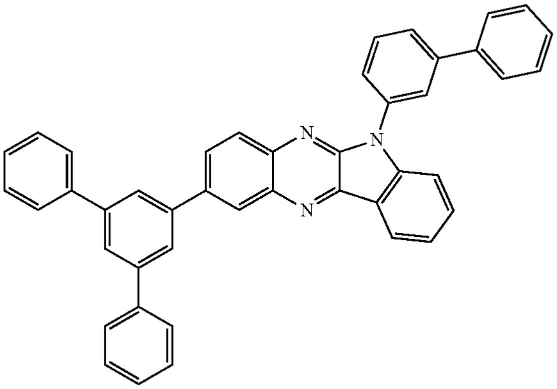
-continued
C-27
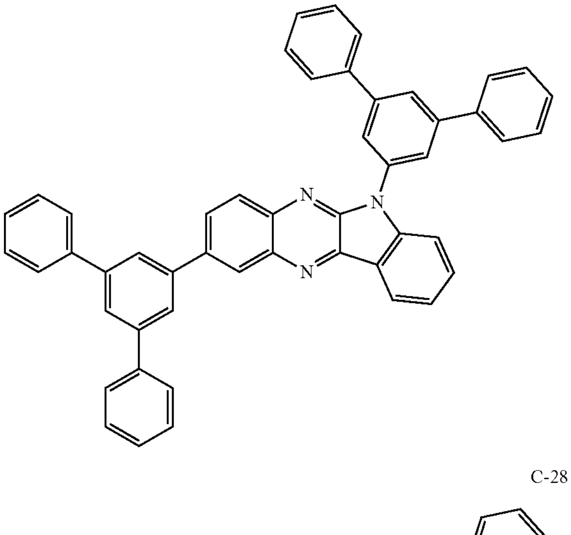
C-28
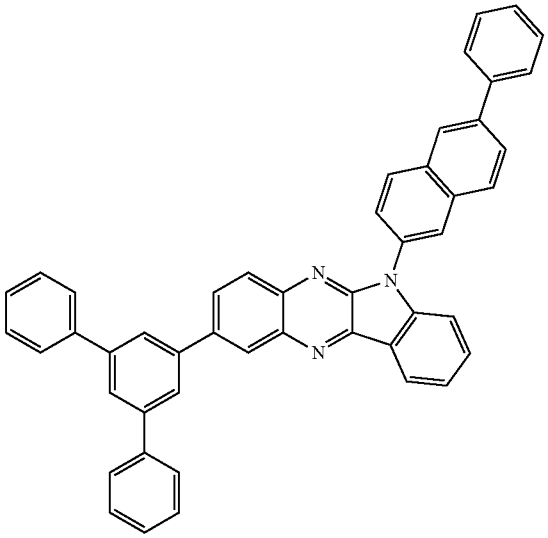
C-29
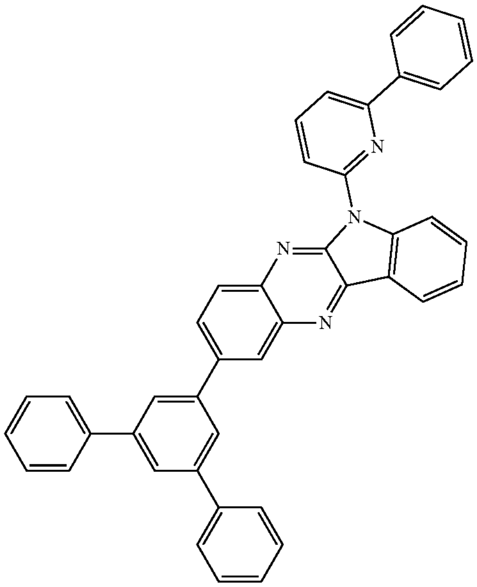

-continued
C-30
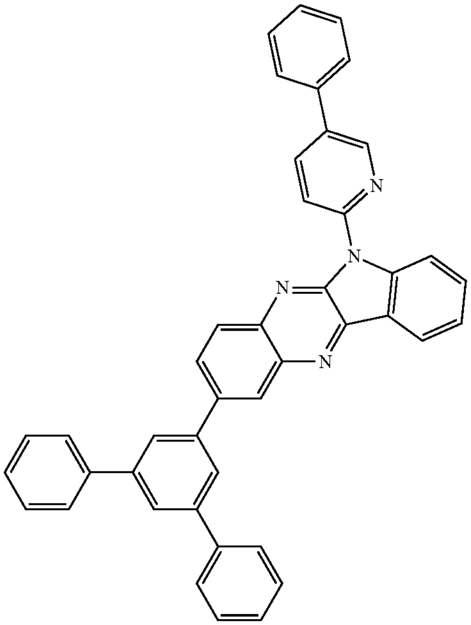
C-31
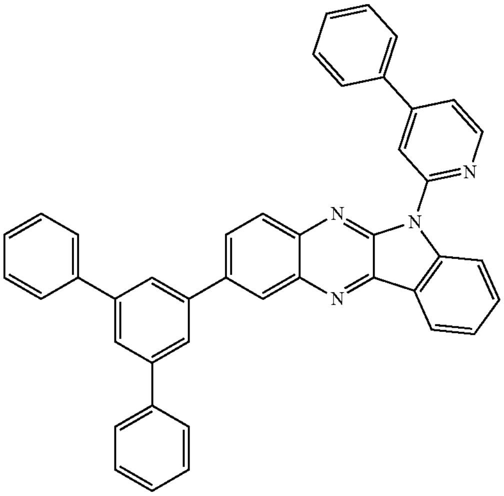
C-32
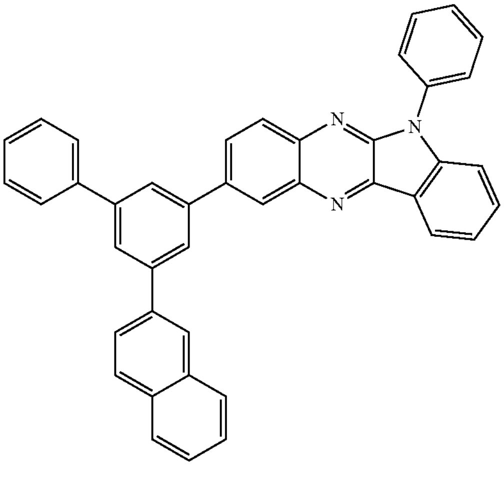
-continued
C-33
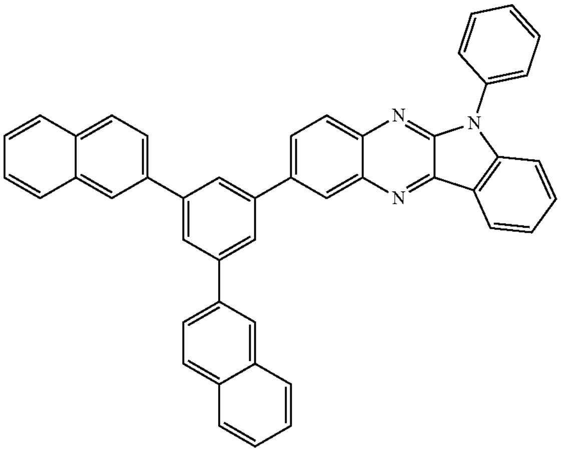
C-34
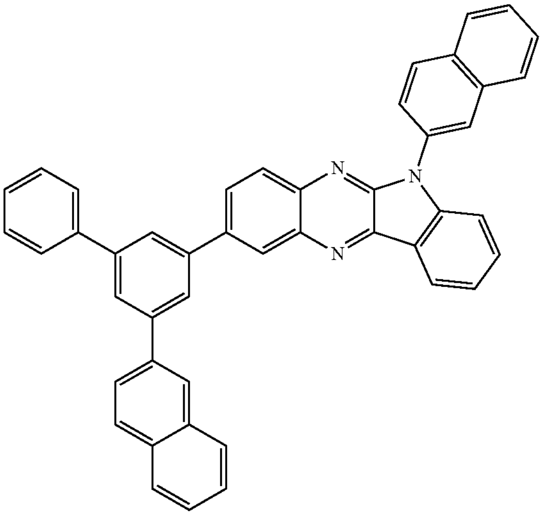
C-35
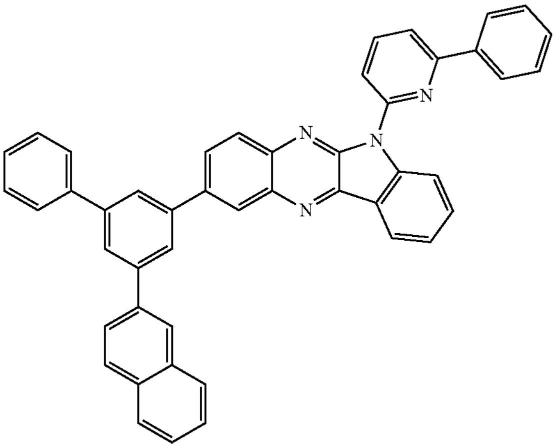

-continued
C-36
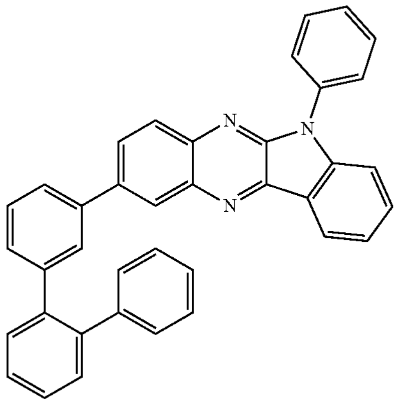
C-37
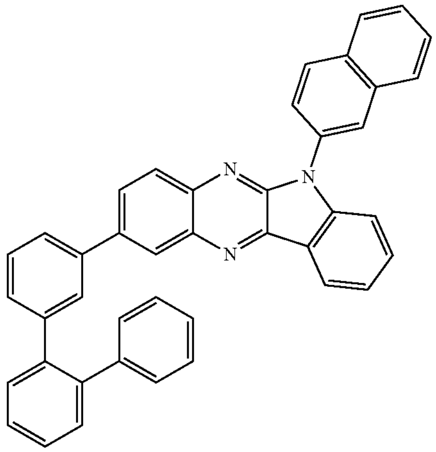
C-38
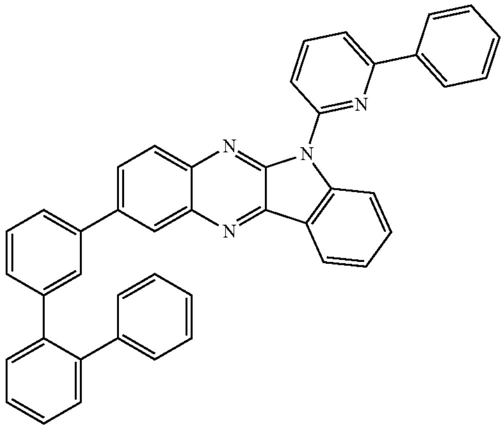
-continued
C-39
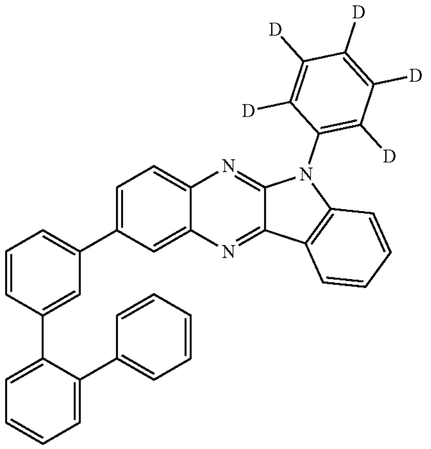
C-40
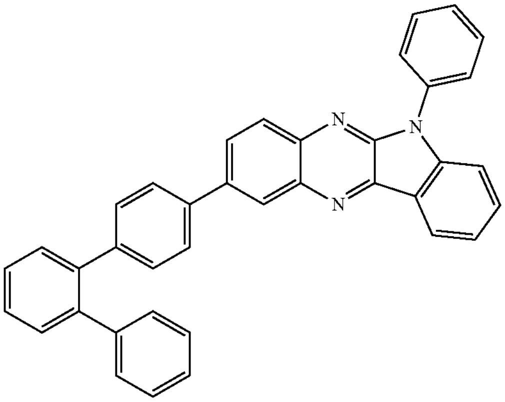
C-41
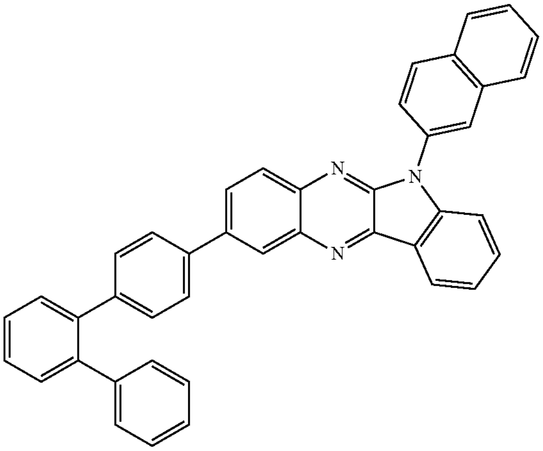

-continued
C-42
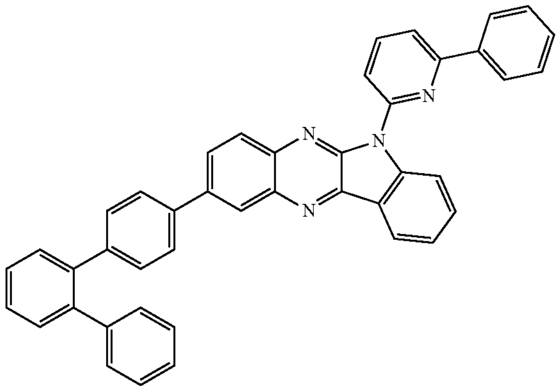
C-43
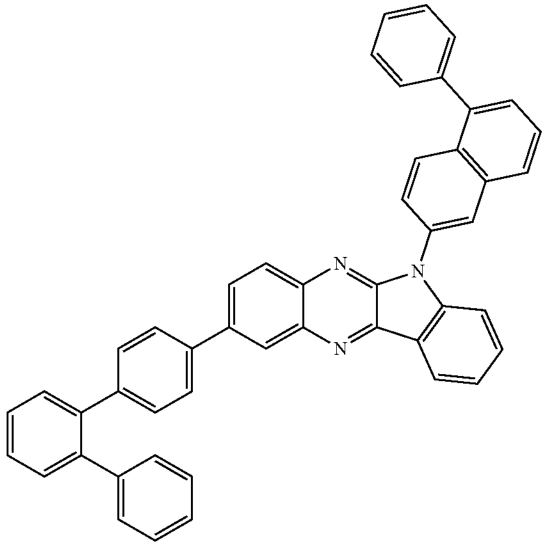
C-44
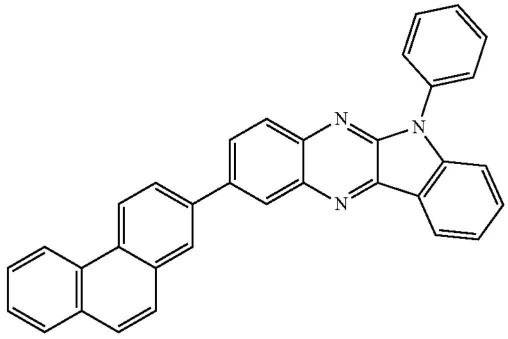
C-45
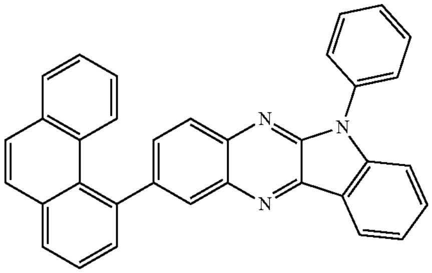
-continued
C-46
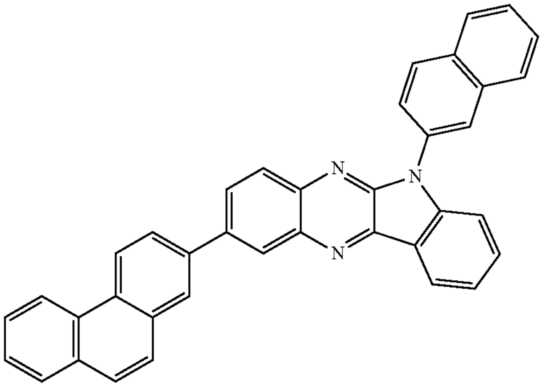
C-47
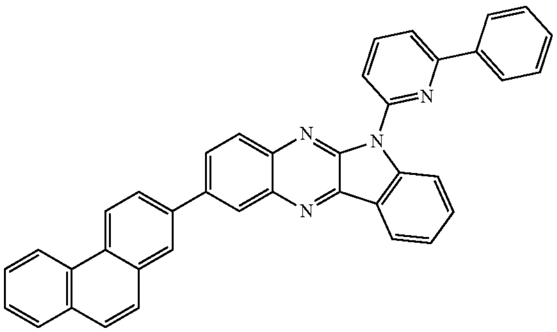
C-48
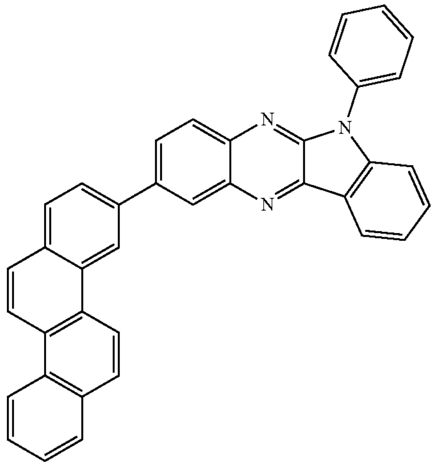
C-49
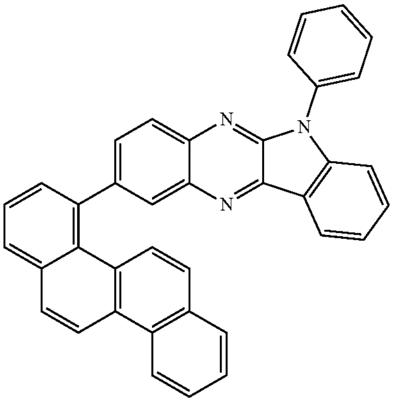

-continued
C-50
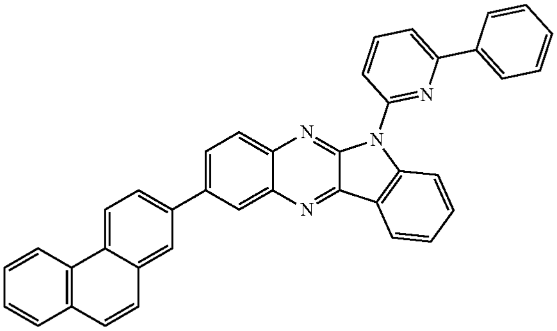
C-51
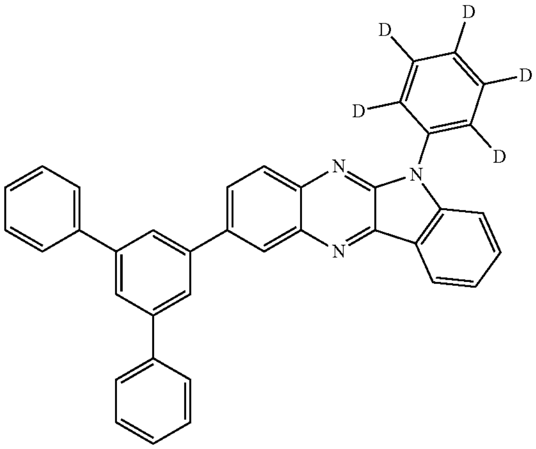
C-52
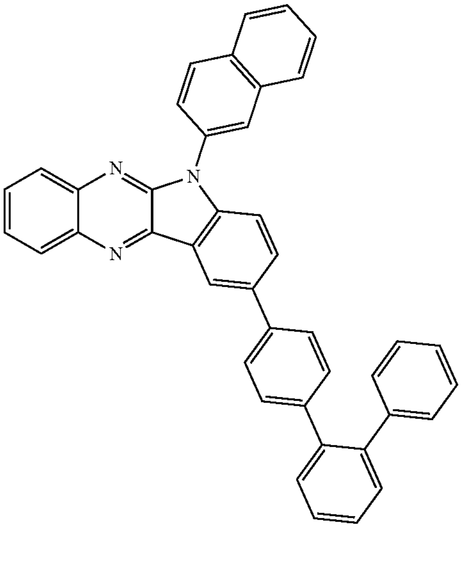
-continued
C-53
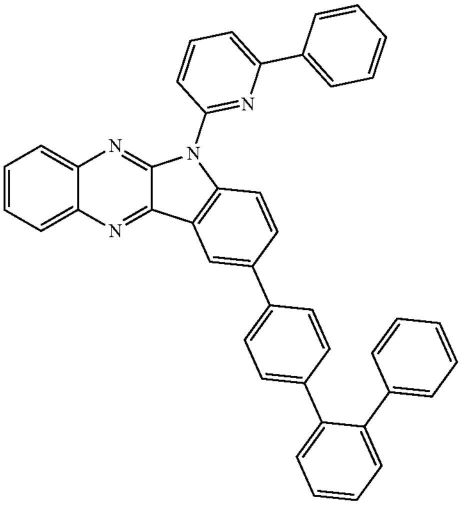
C-54
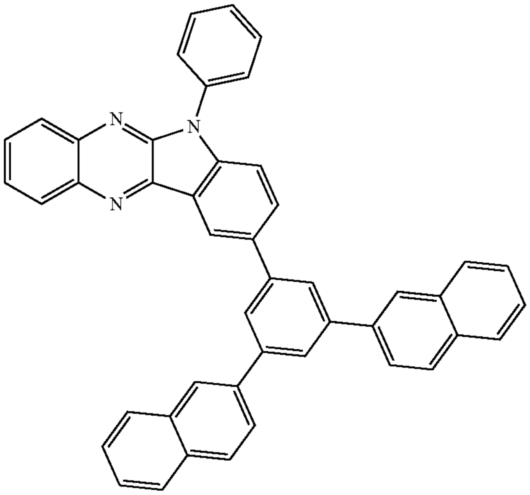
C-55
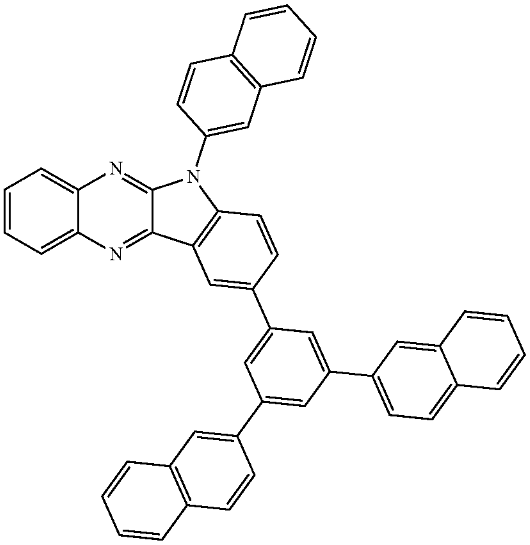

-continued
C-56
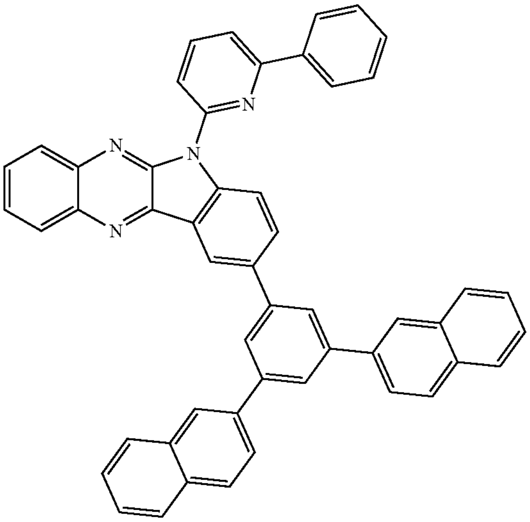
C-57
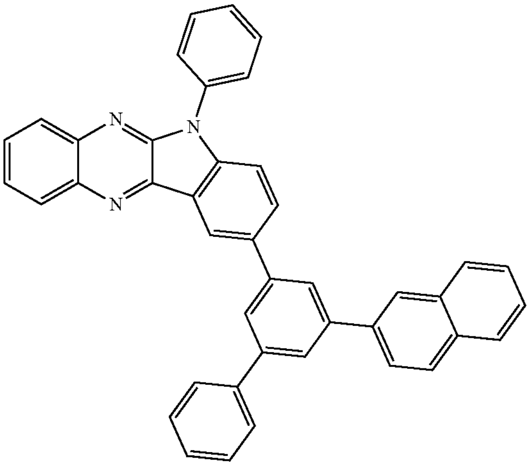
C-58
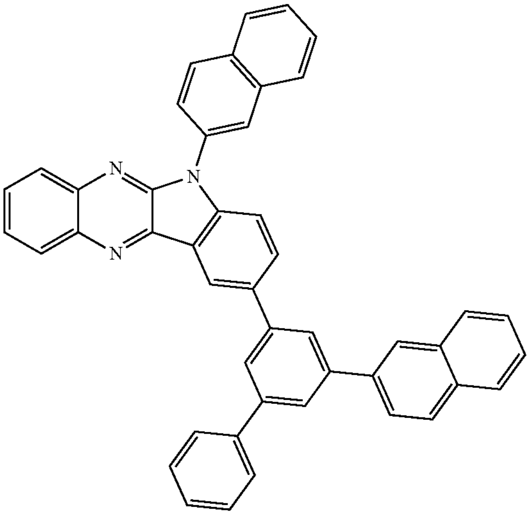
-continued
C-59
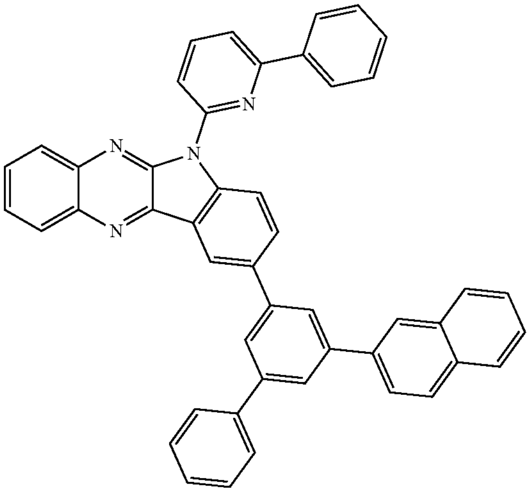
C-60
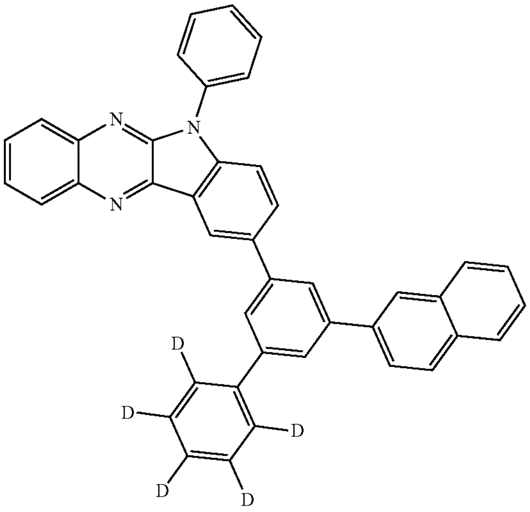
C-61
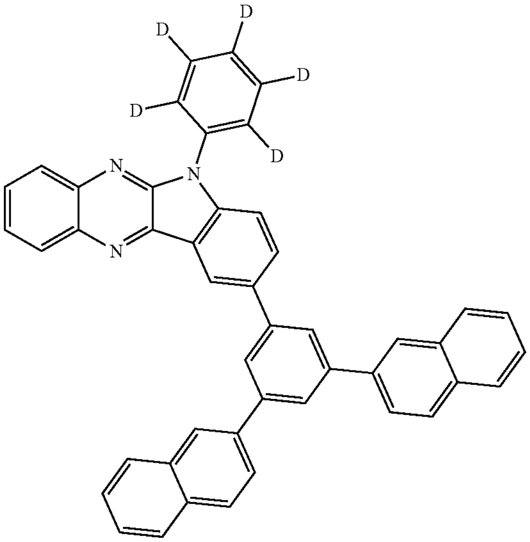

-continued
C-62
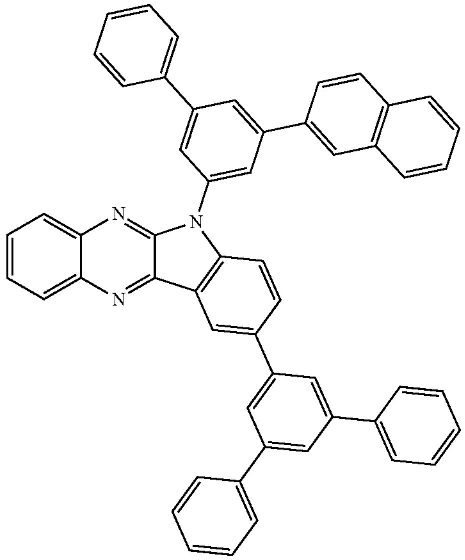
C-63
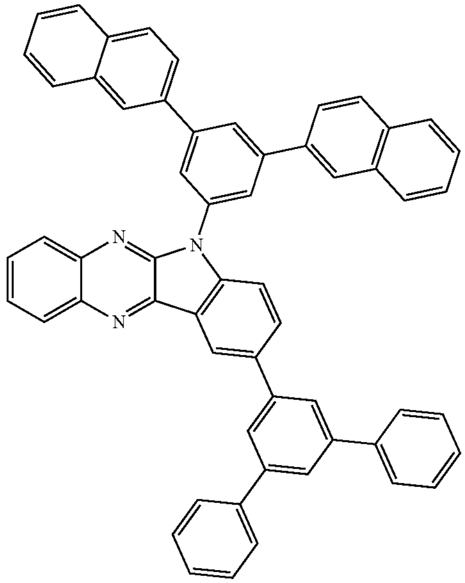
C-64
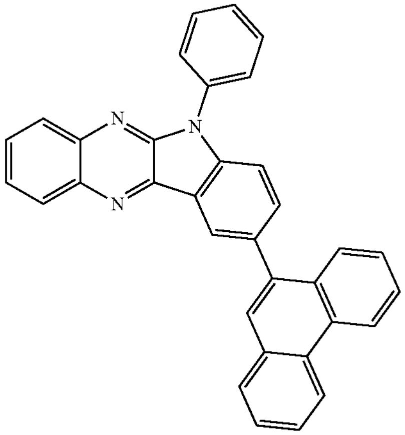
-continued
C-65
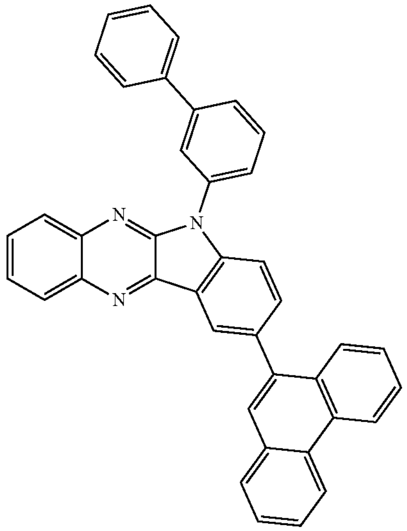
C-66
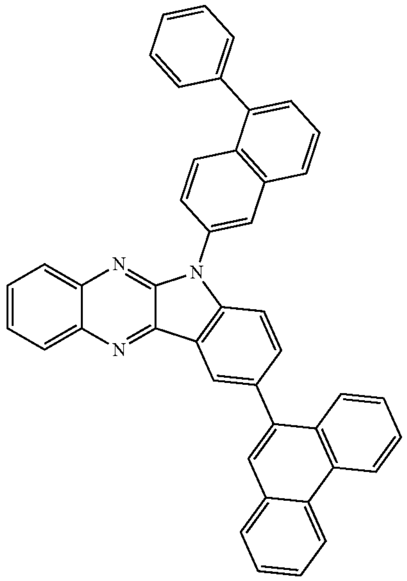
C-67
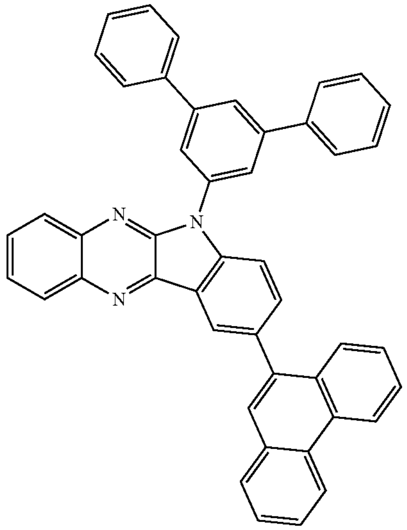

-continued
C-68
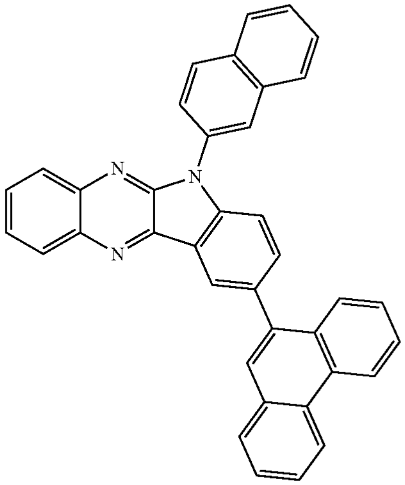
C-69
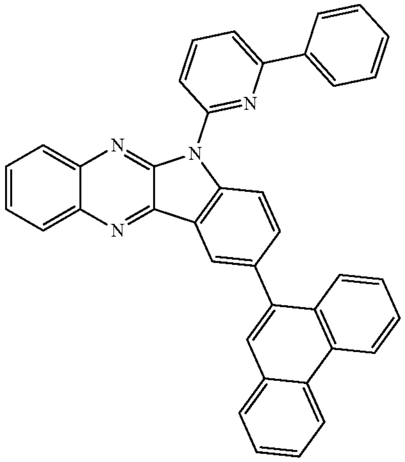
C-70
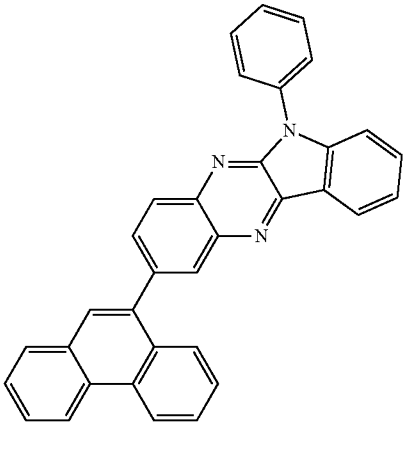
-continued
C-71
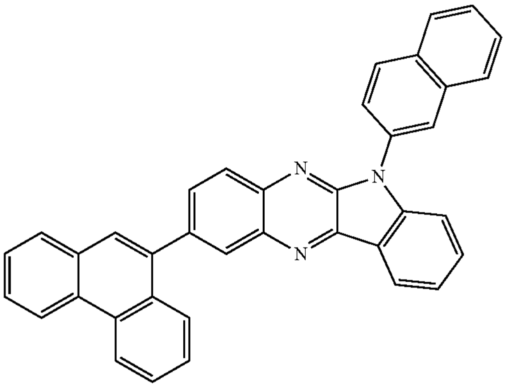
C-72
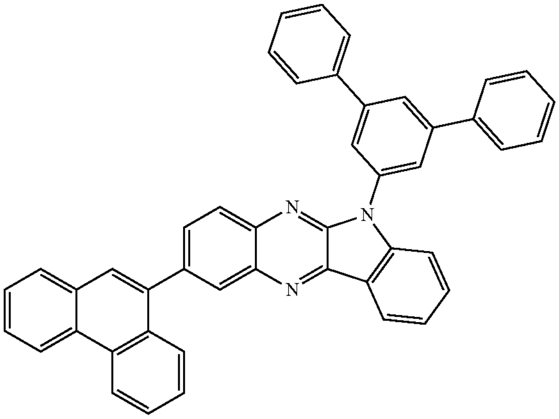
C-73
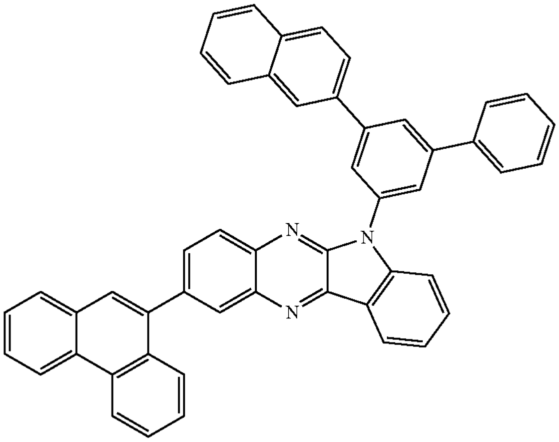

-continued
C-74
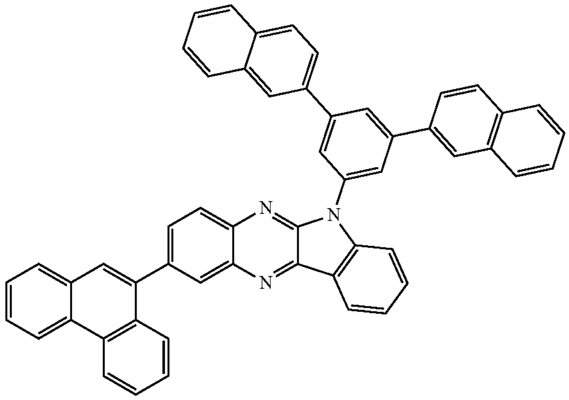
C-75
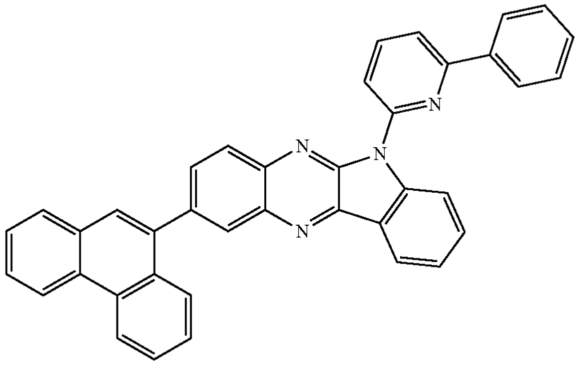
C-76
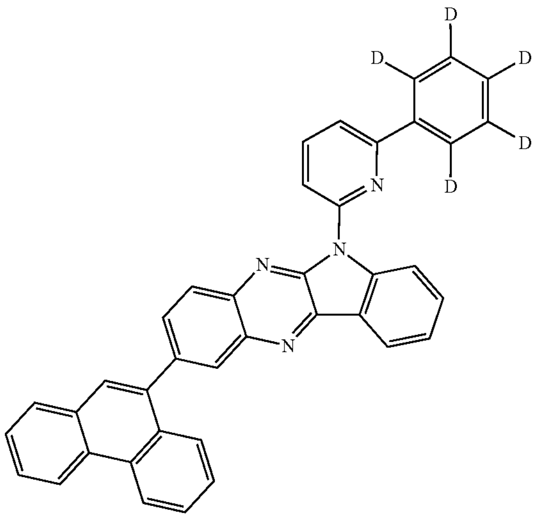
-continued
C-77
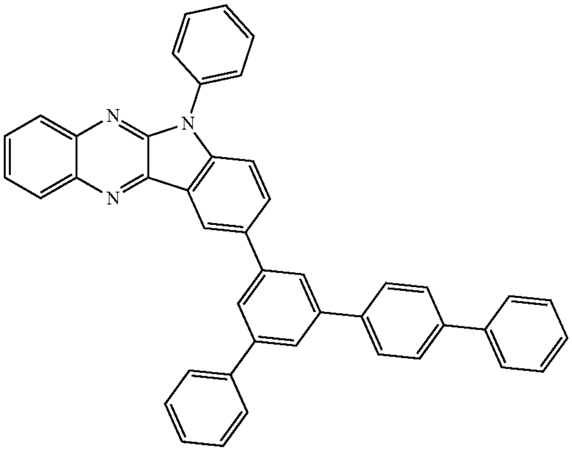
C-78
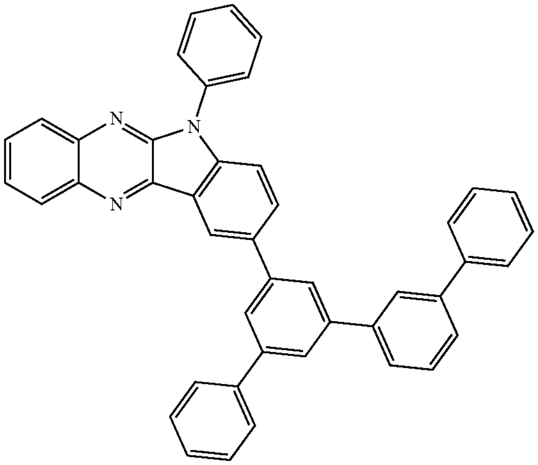
C-79
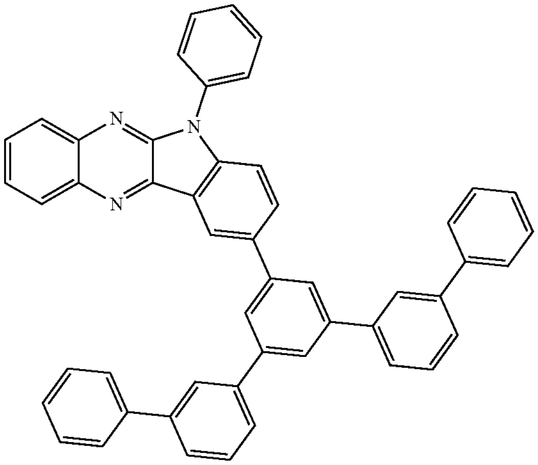

-continued
C-80
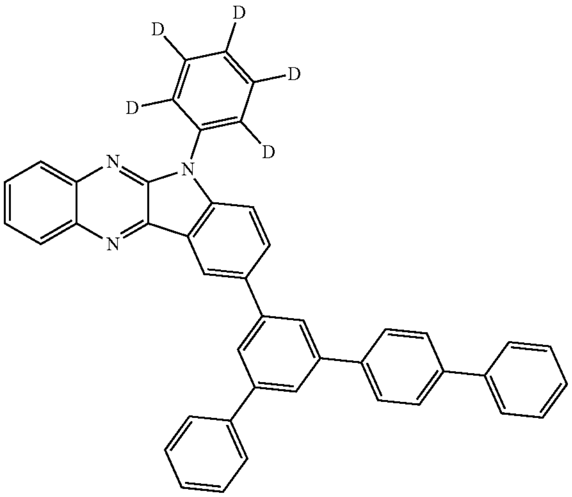
C-81
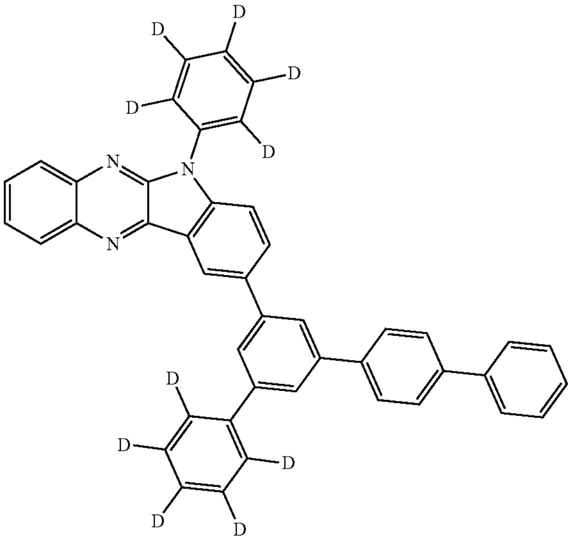
C-82
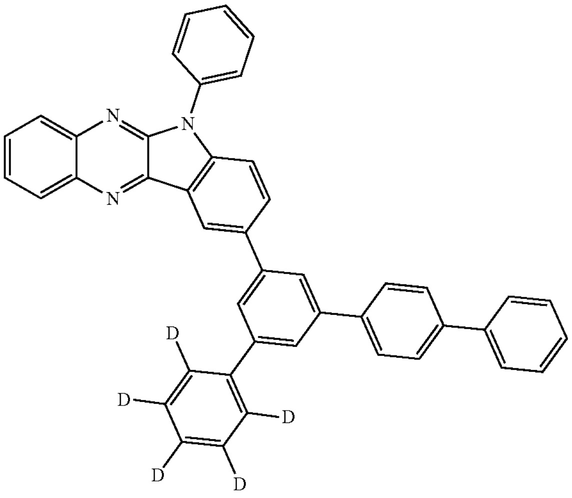
-continued
C-83
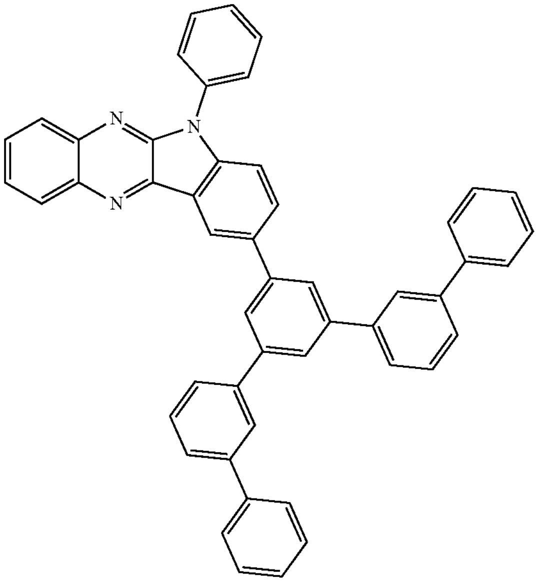
C-84
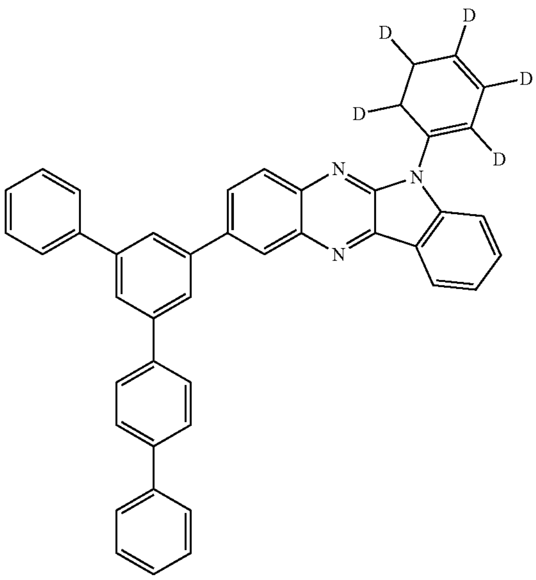

-continued
C-85
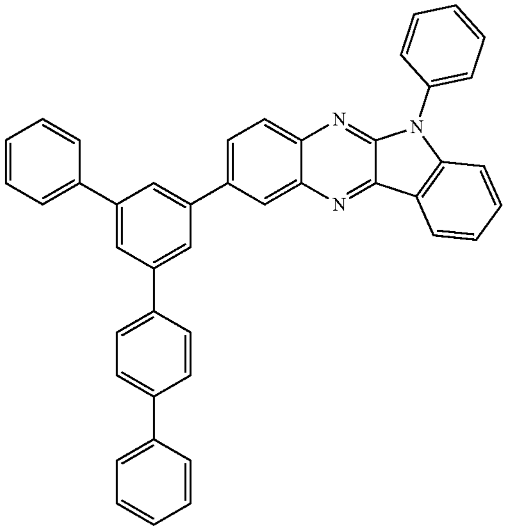
C-86
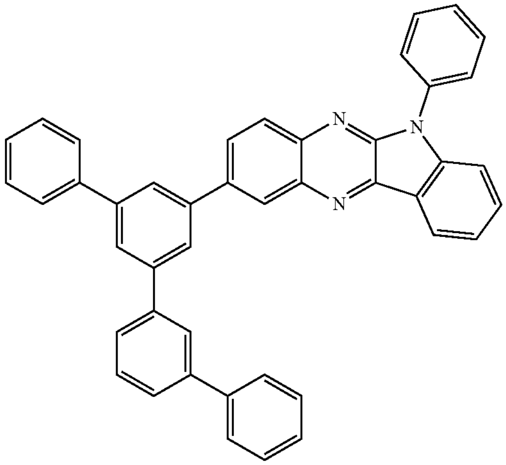
C-87
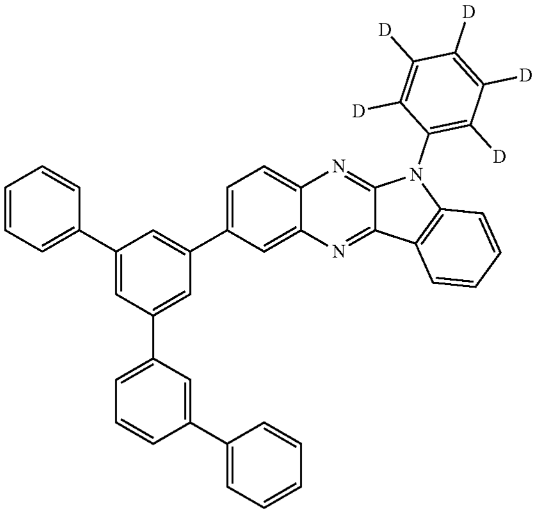
-continued
C-88
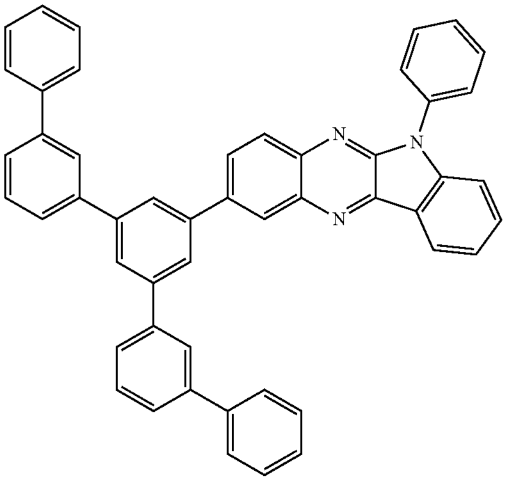
C-89
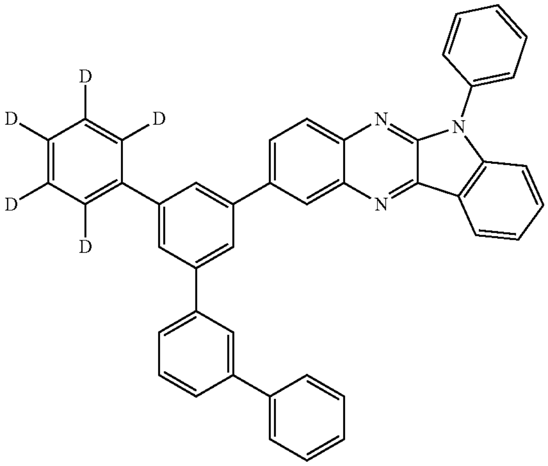
C-90
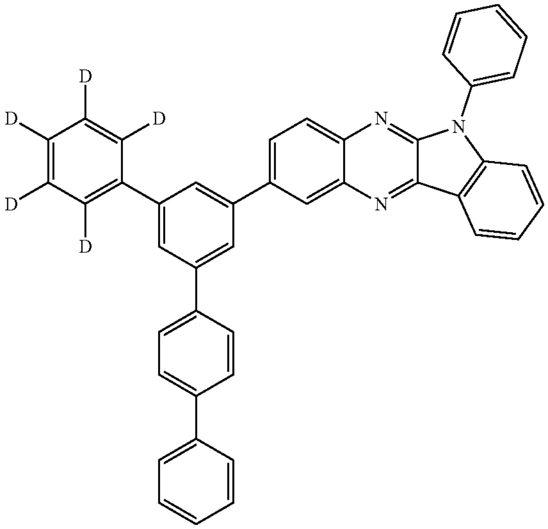

-continued
C-91
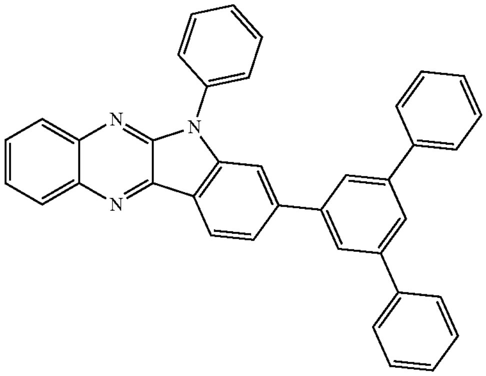
C-92
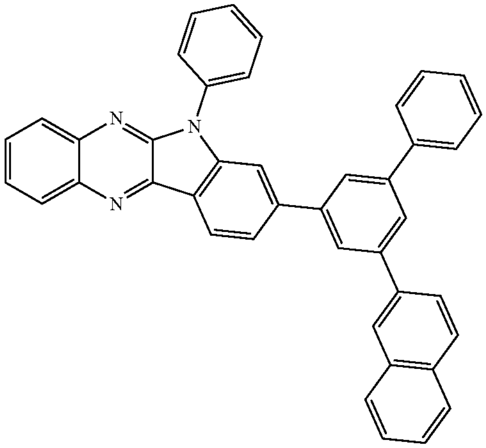
C-93
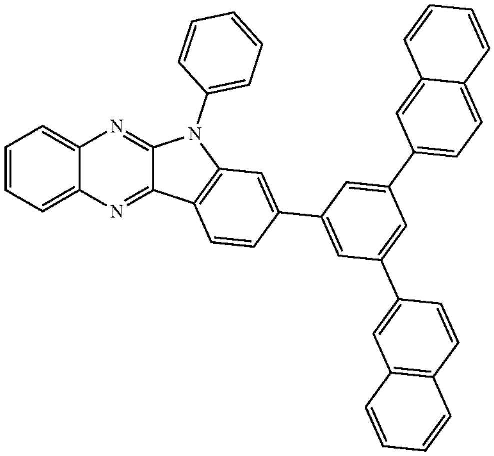
C-94
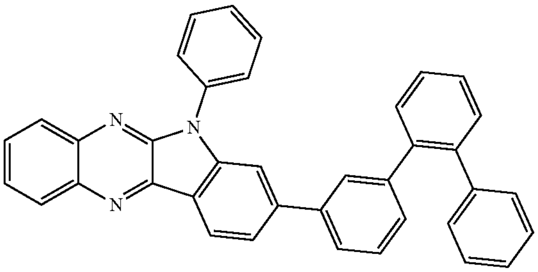
-continued
C-95
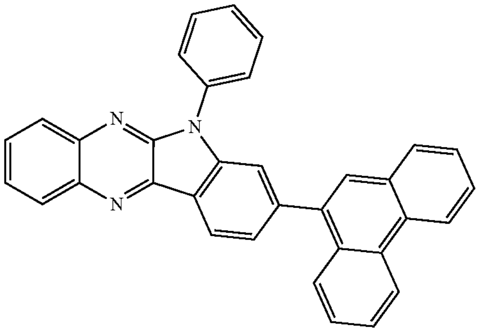
C-96
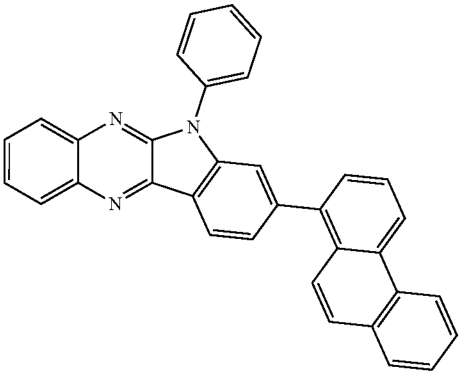
C-97
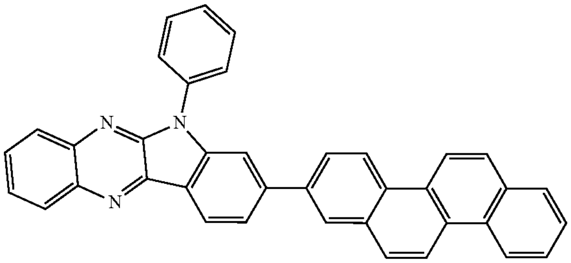
C-98
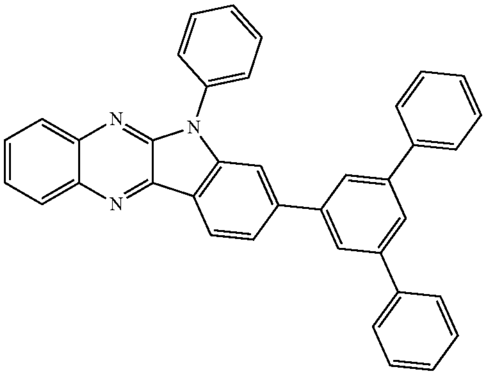

-continued
C-99
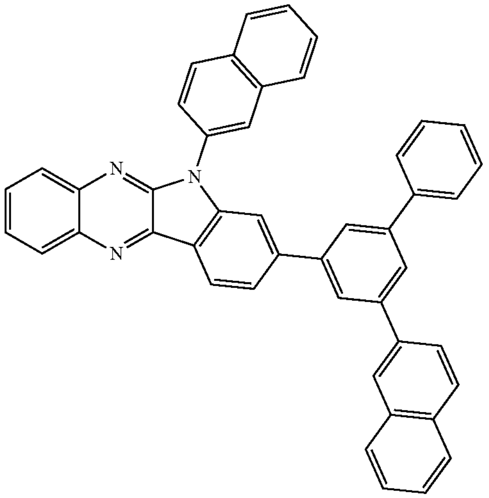
C-100
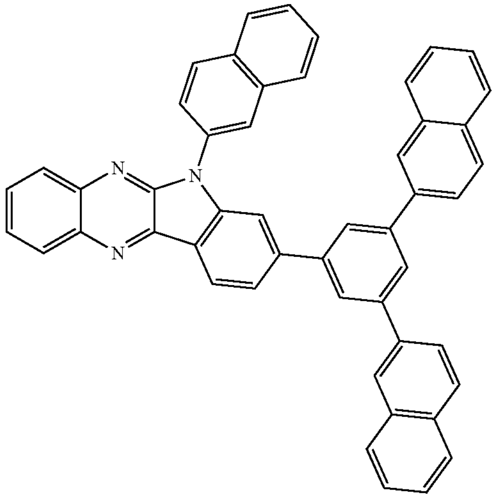
C-101
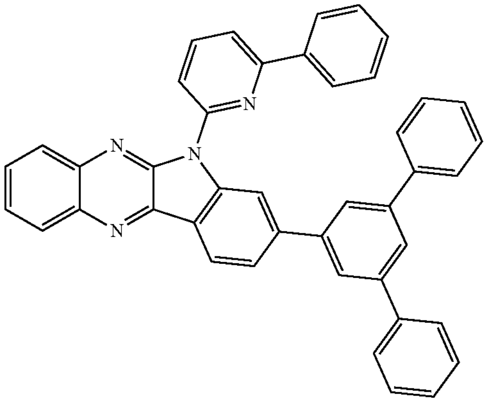
-continued
C-102
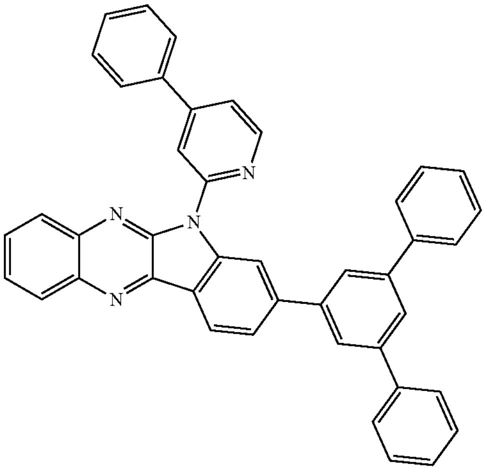
C-103
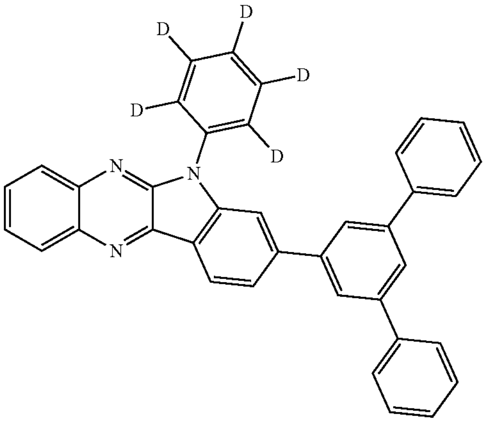
C-104
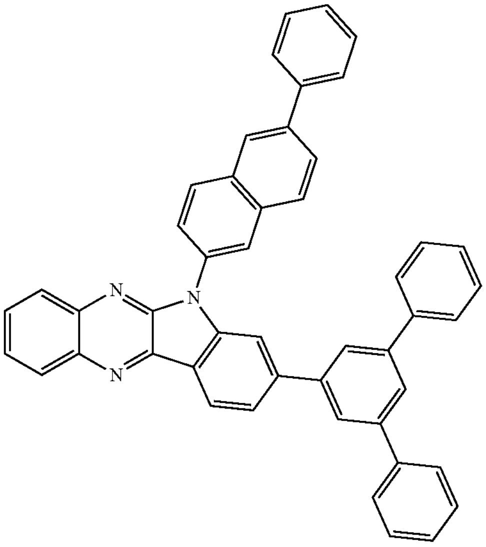

-continued
C-105
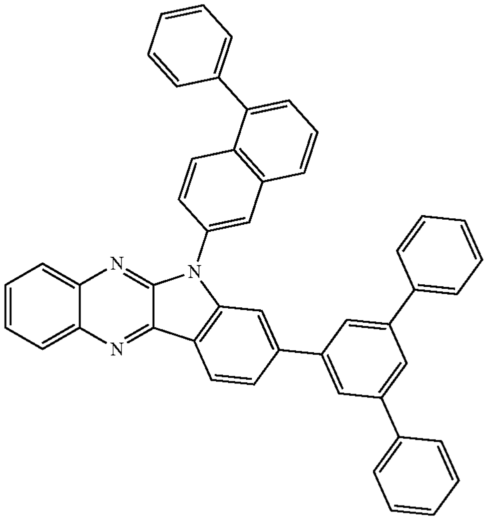
C-106
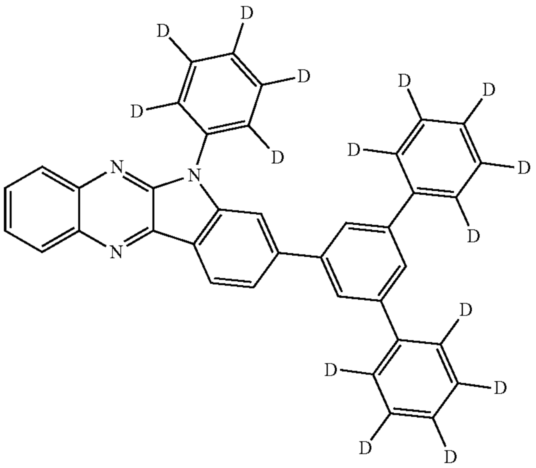
C-107
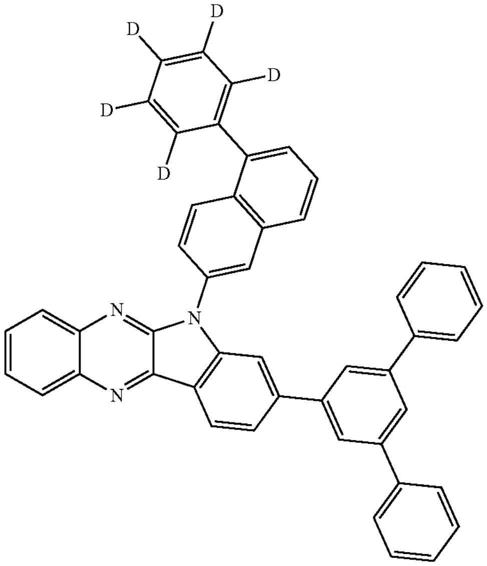
-continued
C-108
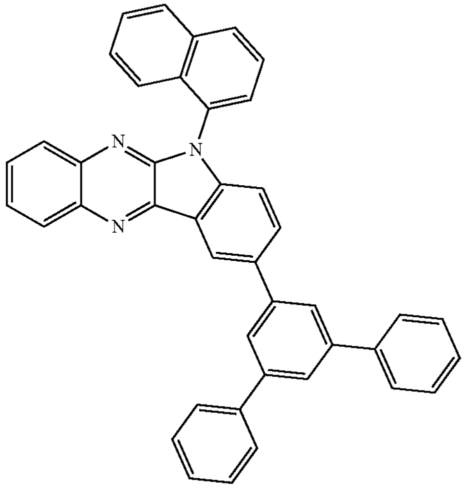
C-109
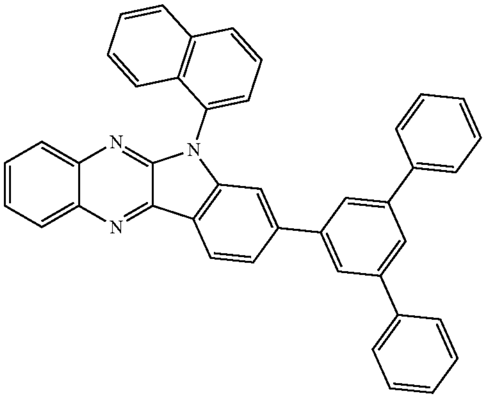
C-110
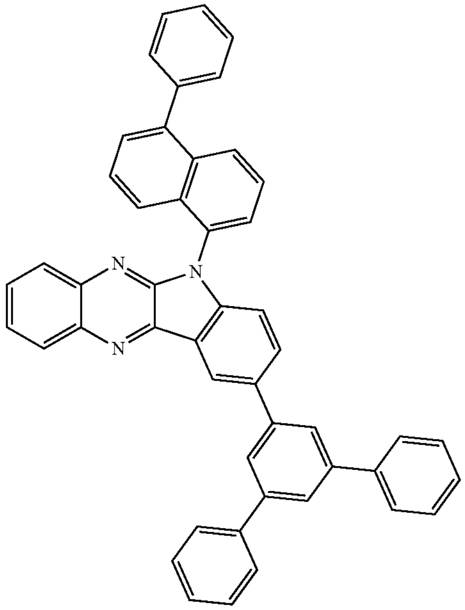

-continued
C-111
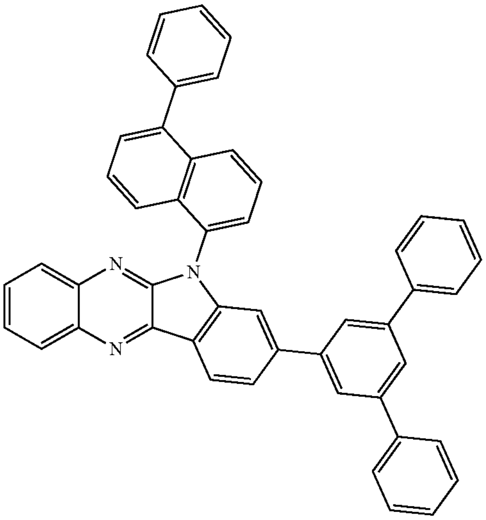
C-112
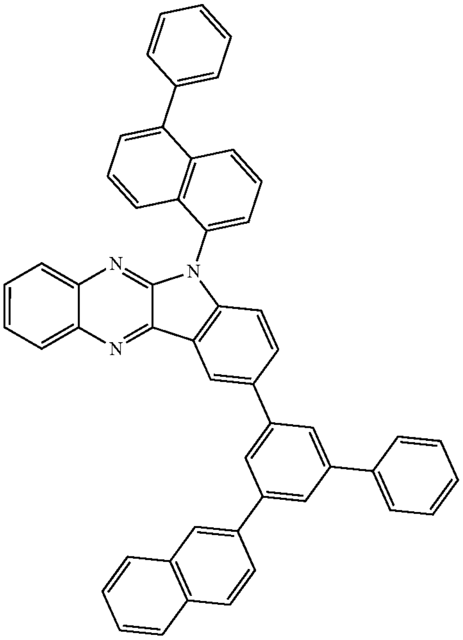
-continued
C-113
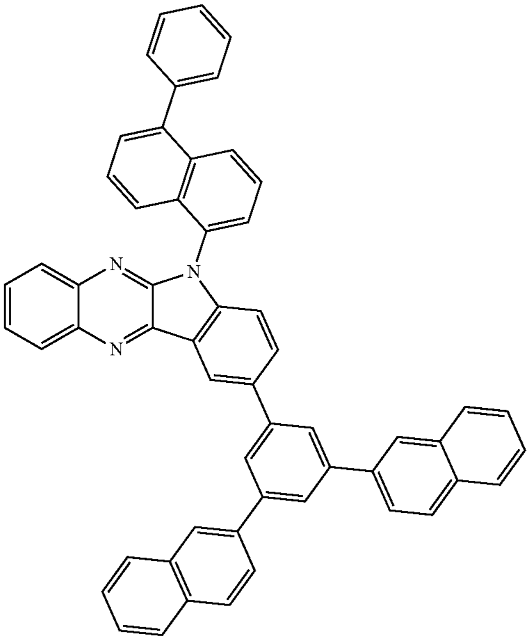
C-114
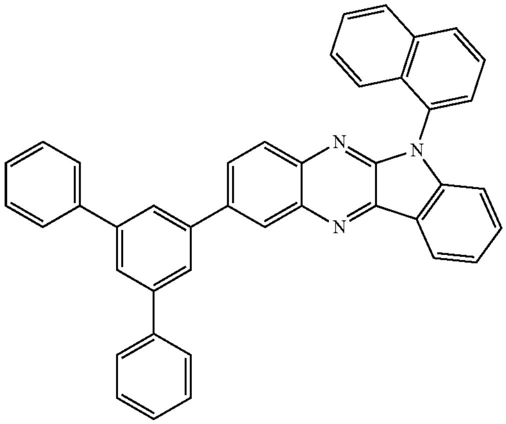

-continued
C-115
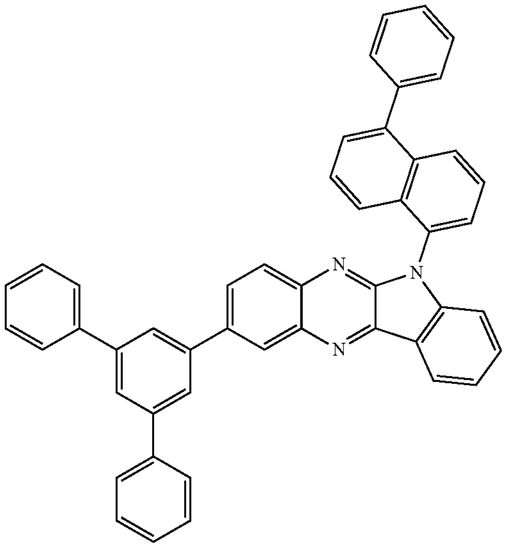
C-116
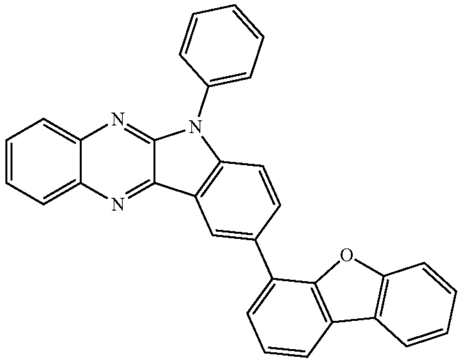
C-117
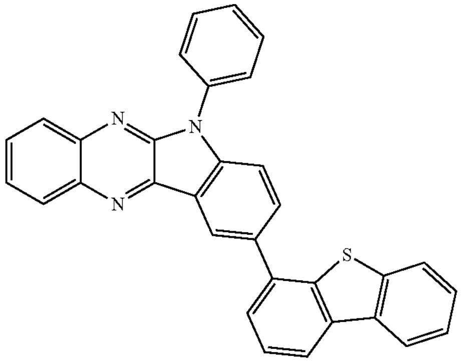
-continued
C-118
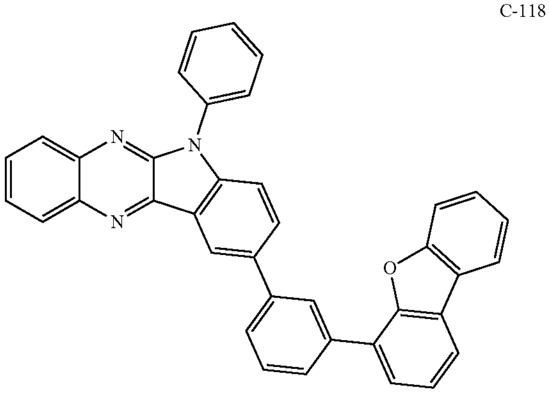
C-119
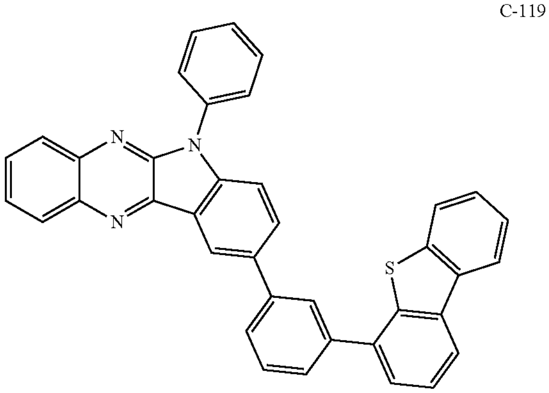
C-120
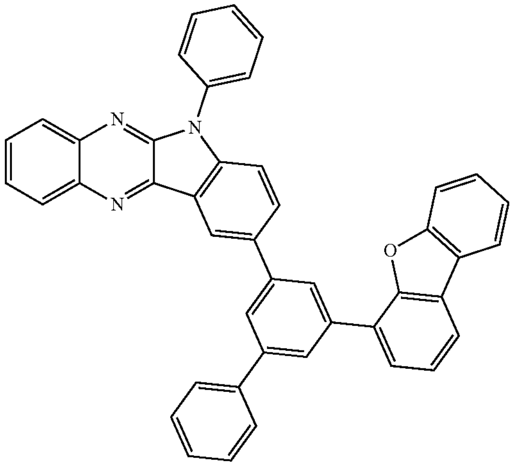

-continued
C-121
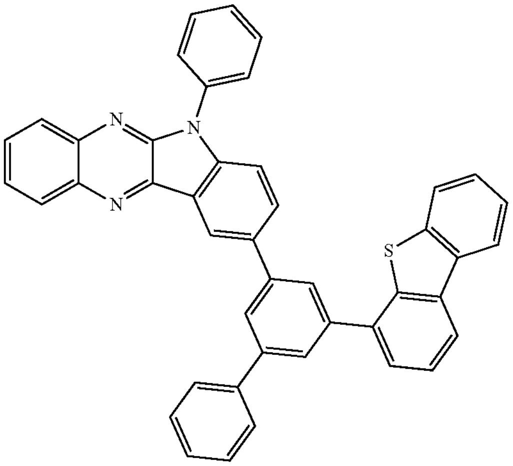
C-122
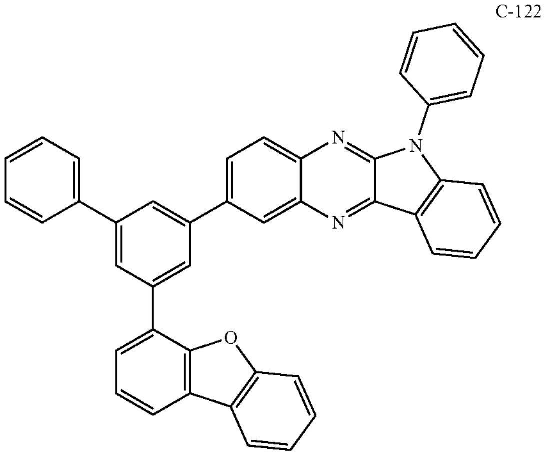
C-123
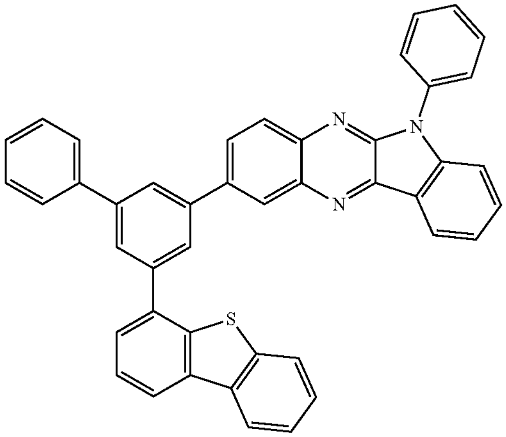
-continued
C-124
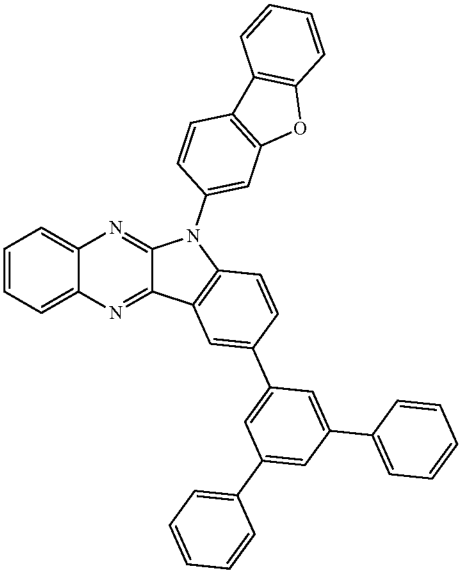
C-125
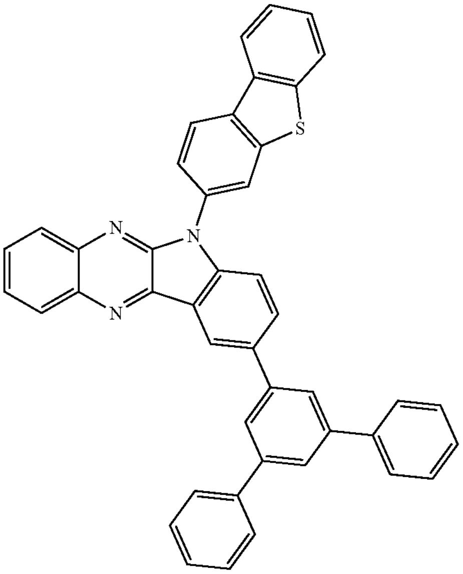

-continued
C-126
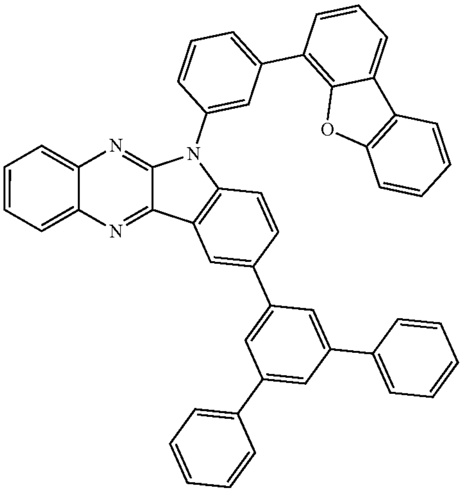
C-127
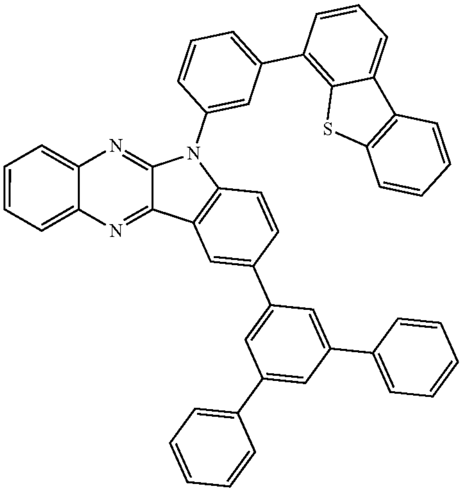
C-128
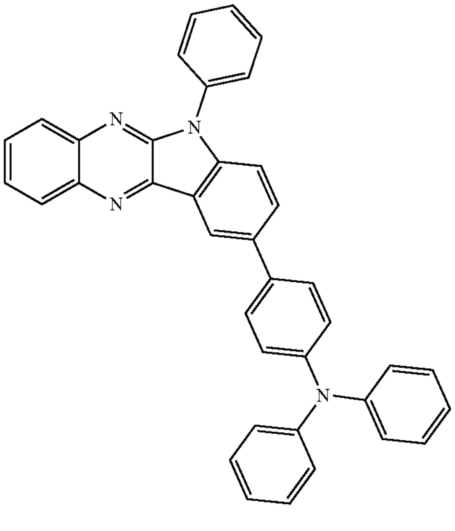
-continued
C-129
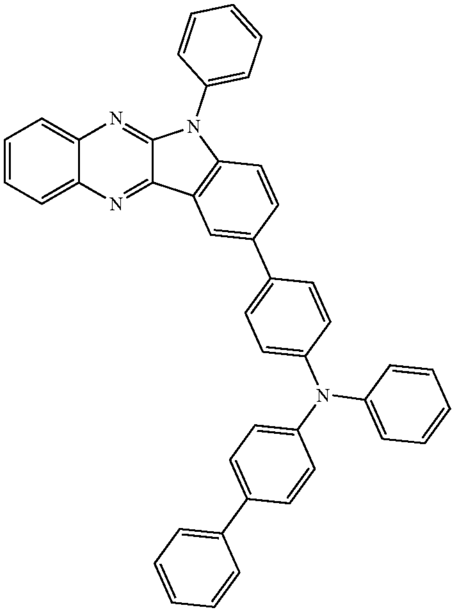
C-130
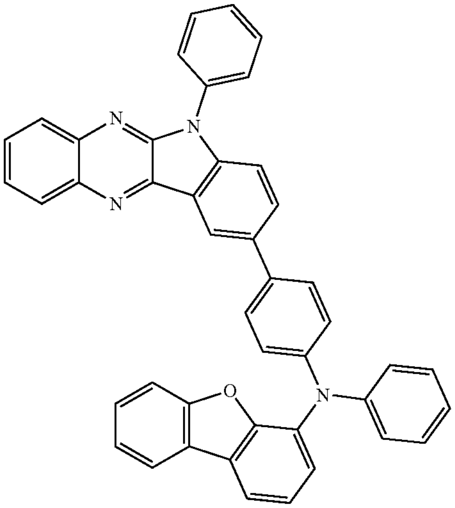
C-131
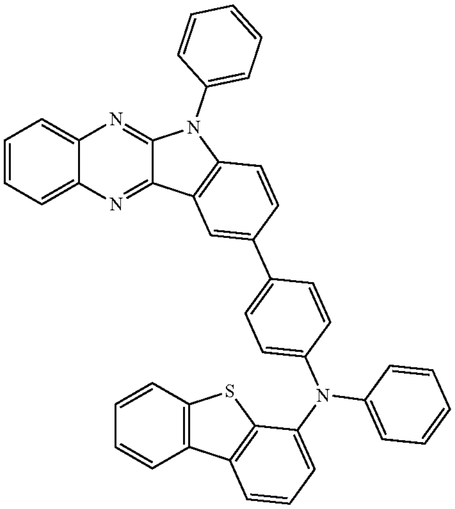

The compound represented by formula 1 of the present disclosure may be produced by a synthetic method known to a person skilled in the art. For example it may be prepared by referring to the following reaction scheme 1 or 2, but is not limited thereto.

[Reaction Scheme 1]

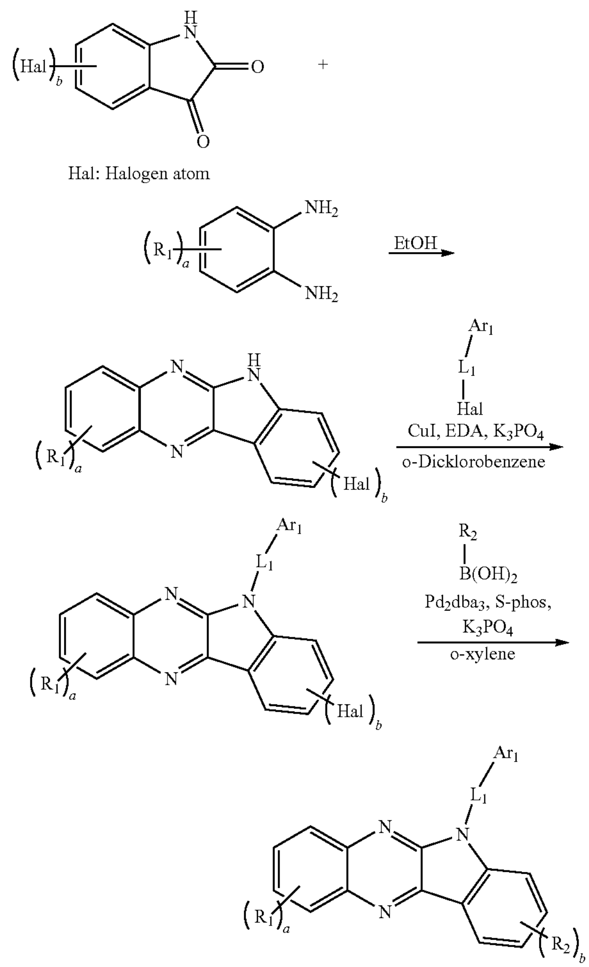

[Reaction Scheme 2]

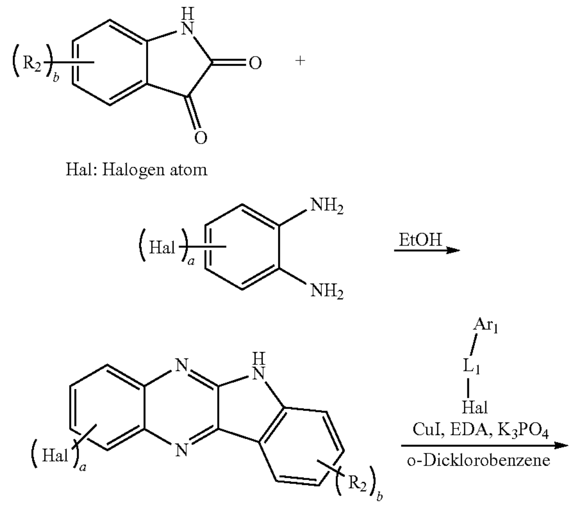

-continued

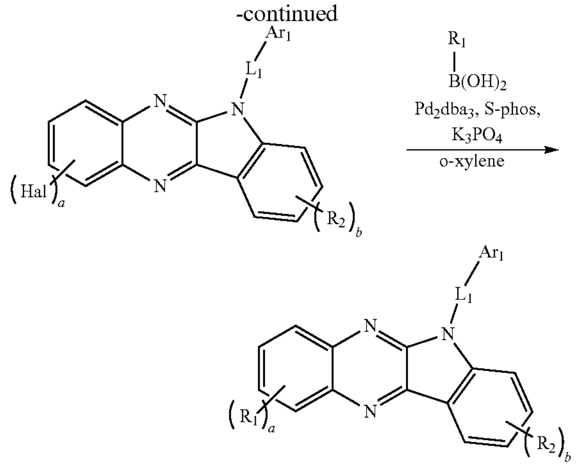

In reaction schemes 1 and 2 above, the definition of the substituents is as defined in formula 1, a and b are an integer of 1 to 4, and Hal represents a halogen atom.

As described above, exemplary synthesis examples of the compounds represented by formula 1 according to the present disclosure are described, but they are based on Buchwald-Hartwig cross coupling reaction, N-arylation reaction, H-mont-mediated etherification reaction, Miyaura borylation reaction, Suzuki cross-coupling reaction, Intramolecular acid-induced cyclization reaction. Pd(II)-catalyzed oxidative cyclization reaction. Grignard reaction, Heck reaction, Cyclic Dehydration reaction, SN1 substitution reaction, SN2 substitution reaction, and Phosphine-mediated reductive cyclization reaction, etc. It will be understood by one skilled in the art that the above reaction proceeds even if other substituents defined in the formula 1 other than the substituents described in the specific synthesis examples are bonded.

The second host material as another host material according to one embodiment may comprise a compound represented by the following formula 2, (2)

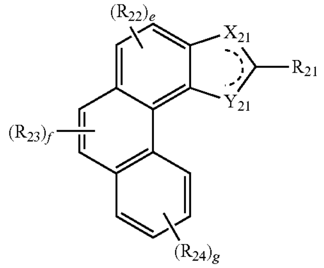

In formula 2, $X_{21}$ and $Y_{21}$ each independently represent —N=, —$NR_{25}$—, —O—, or —S—, provided that one of $X_{21}$ and $Y_{21}$ is —N=, and the other of $X_{21}$ and $Y_{21}$ is —$NR_{25}$—, —O—, or —S—;

$R_{21}$ represents a substituted or unsubstituted (C6-C30)aryl or a substituted or unsubstituted (3- to 30-membered)heteroaryl;

$R_{22}$ to $R_{25}$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to the adjacent substituents to form a ring(s);

provided that at least one of $R_{22}$ to $R_{24}$ is $-L_{21}-Ar_{21}$;

$L_{21}$ represents a single bond or a substituted or unsubstituted (C6-C30)arylene;

$Ar_{21}$ represents a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, or $—NR_{31}R_{32}$;

$R_{31}$ and $R_{32}$ each independently represent a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl;

e and f each independently represent an integer of 1 or 2, and g represents an integer of 1 to 4; and when e to g are an integer of 2 or more, each of $R_{22}$, each of $R_{23}$, and each of $R_{24}$ may be the same or different.

The second host material represented by the above formula 2 according to one embodiment may be represented by any one of the following formulas 2-1 to 2-3.

(2-1)

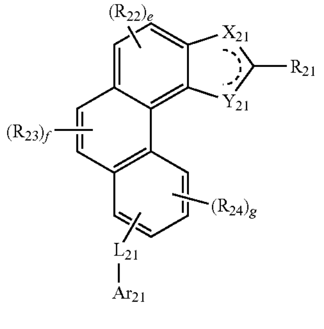

(2-2)

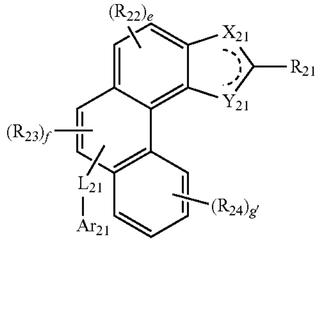

-continued (2-3)

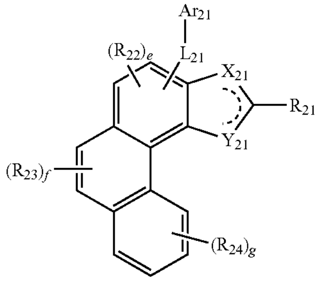

In formulas 2-1 to 2-3, $X_{21}$, $Y_{21}$, $L_{21}$, $Ar_{21}$, $R_{21}$ to $R_{24}$, e, f, and g are as defined in the formula 2;

g' represents an integer of 1 to 3; and when g' is an integer of 2 or more, each of $R_{24}$ may be the same or different.

In one embodiment, in the formulas 2-1 to 2-3, one of $X_{21}$ and $Y_{21}$ is —N═, and the other of $X_{21}$ and $Y_{21}$ may be —O— or —S—; $R_{21}$ may be a substituted or unsubstituted (C6-C30)aryl; all of $R_{22}$ to $R_{24}$ may be hydrogen; $L_{21}$ may be a single bond or a substituted or unsubstituted (C6-C30) arylene; $Ar_{21}$ may be a substituted or unsubstituted fused ring of (C3-C30) aliphatic ring and (C6-C30) aromatic ring, a substituted or unsubstituted (C6-C30)aryl, or $—NR_{31}R_{32}$, wherein $R_{31}$ and $R_{32}$ each independently may be a substituted or unsubstituted (C6-C30)aryl or a substituted or unsubstituted (3- to 30-membered)heteroaryl.

In one embodiment, $R_{21}$ may be a substituted or unsubstituted (C6-C30)aryl, preferably a substituted or unsubstituted (C6-C25)aryl, more preferably a substituted or unsubstituted (C6-C18)aryl. For example, $R_{21}$ may be unsubstituted phenyl or unsubstituted p-biphenyl.

In one embodiment, $L_1$ may be a single bond or a substituted or unsubstituted (C6-C30)arylene, preferably a single bond or a substituted or unsubstituted (C6-C25) arylene, more preferably a single bond or a substituted or unsubstituted (C6-C18)arylene. For example, $L_{21}$ may be a single bond, unsubstituted phenylene or unsubstituted naphthalenylene.

In one embodiment, $Ar_{21}$ may be a substituted or unsubstituted fused ring of (C5-C25) aliphatic ring and (C6-C25) aromatic ring; a substituted or unsubstituted (C6-C30)aryl, or $—NR_{31}R_{32}$, In one embodiment $R_{31}$ and $R_{32}$ each independently may be a substituted or unsubstituted (C6-C30) aryl or a substituted or unsubstituted (5- to 30-membered) heteroaryl, preferably a substituted or unsubstituted (C6-C25)aryl or a substituted or unsubstituted (5- to 25-membered)heteroaryl, more preferably a substituted or unsubstituted (C6-C18)aryl or a substituted or unsubstituted (5- to 18-membered)heteroaryl. For example, $Ar_{21}$ may be a substituted or unsubstituted phenyl, a substituted or unsubstituted naphthyl, a substituted or unsubstituted o-biphenyl, a substituted or unsubstituted m-biphenyl, a substituted or unsubstituted p-biphenyl, a substituted or unsubstituted o-terphenyl, a substituted or unsubstituted m-terphenyl, a substituted or unsubstituted p-terphenyl, a substituted or unsubstituted triphenylenyl, a substituted or unsubstituted phenanthrenyl, a substituted or unsubstituted chrysenyl, a substituted or unsubstituted fluoranthenyl, a substituted or unsubstituted fluorenyl, a substituted or unsubstituted benzofluorenyl, a substituted or unsubstituted spirobifluorenyl, a substituted or unsubstituted spiro[cyclopentane-fluoren]yl, a substituted or unsubstituted spiro[dihydroindene-fluoren]

yl, a substituted or unsubstituted spiro[benzofluoren-fluoren]yl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthathiophenyl, a substituted or unsubstituted dibenzofuranyl, a substituted or unsubstituted benzofuranyl, or a substituted or unsubstituted benzonaphthofuranyl; or amino substituted with at least one substituents selected from the group consisting of phenyl; naphthylphenyl; naphthyl; phenylnaphthyl; o-biphenyl; m-biphenyl; p-biphenyl; o-terphenyl; m-terphenyl; p-terphenyl; fluorenyl substituted with at least one of methyl or phenyl, e.g., 9,9-dimethylfluorenyl or 9,9-diphenylfluorenyl; benzofluorenyl substituted with at least one methyl, e.g., 7,7-dimethyl-7H-benzofluorenyl; phenanthrenyl; dibenzothiophenyl unsubstituted or substituted with phenyl; benzonaphthofuranyl; and dibenzofuranyl unsubstituted or substituted with phenyl.

In one embodiment; the second host material represented by the above formula 2 may be more specifically illustrated by the following compounds, but is not limited thereto.

H-1

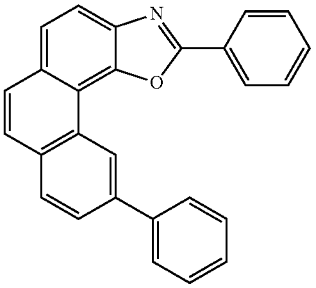

H-2

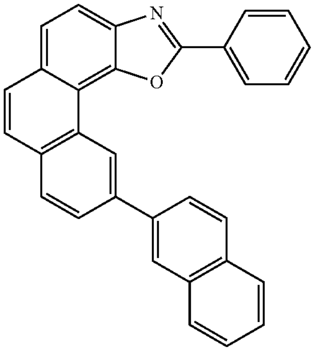

H-3

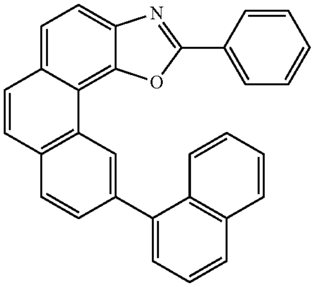

-continued

H-4

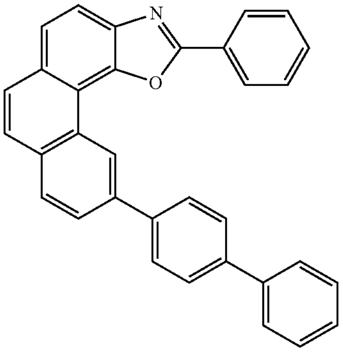

H-5

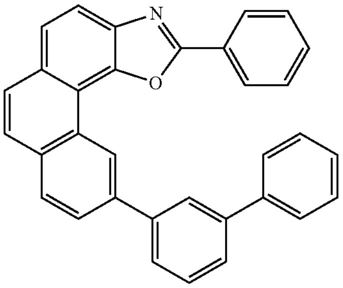

H-6

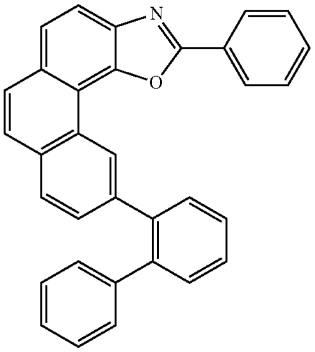

H-7

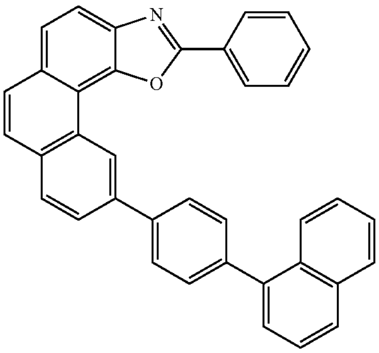

-continued
H-8
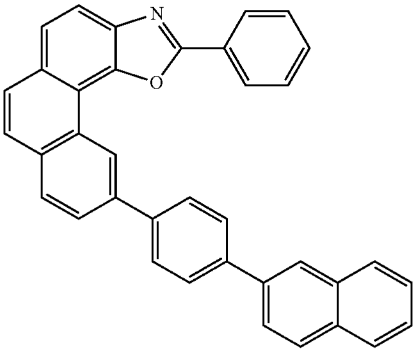
H-9
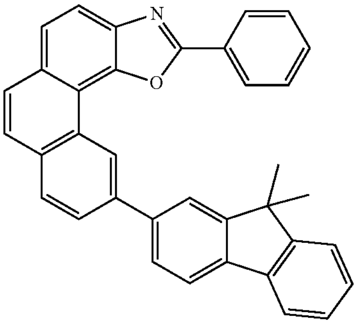
H-10
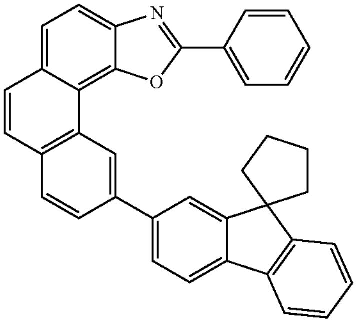
H-11
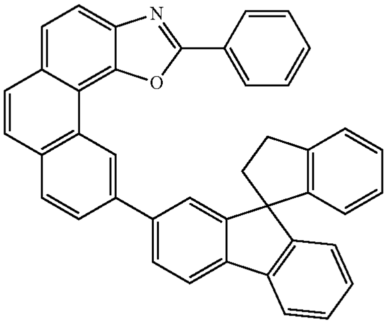
-continued
H-12
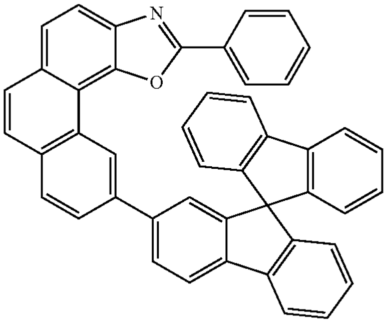
H-13
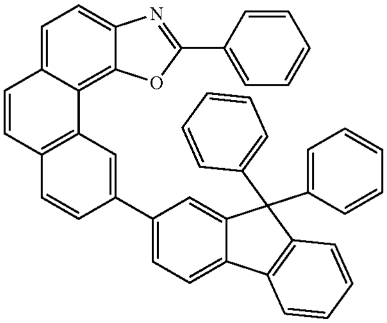
H-14
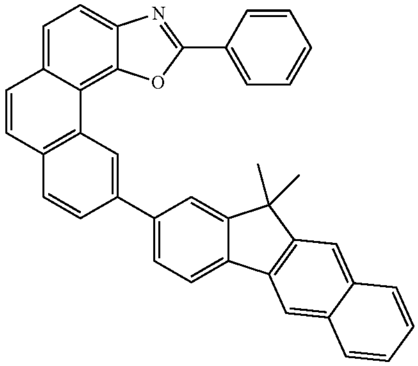
H-15
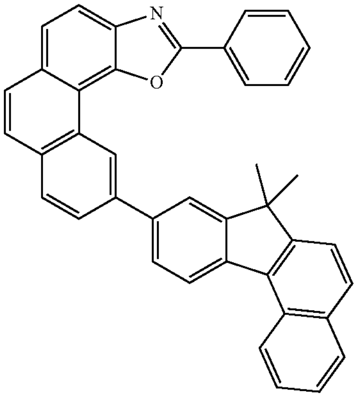

-continued
H-16
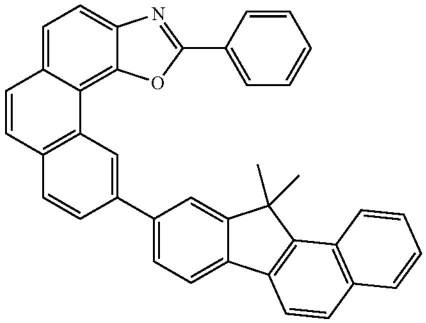
H-17
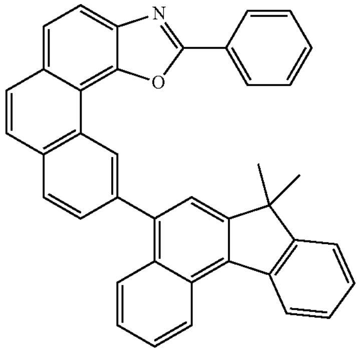
H-18
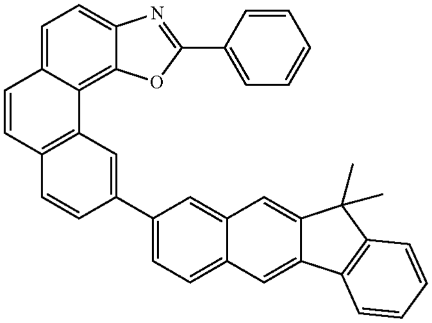
H-19
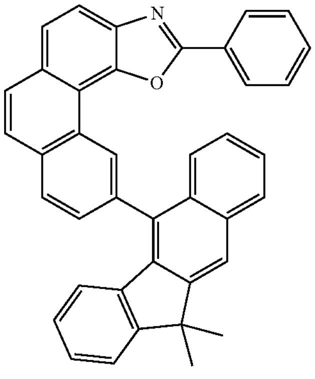
-continued
H-20
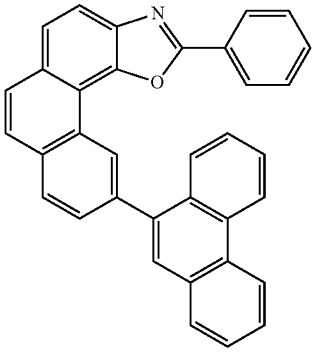
H-21
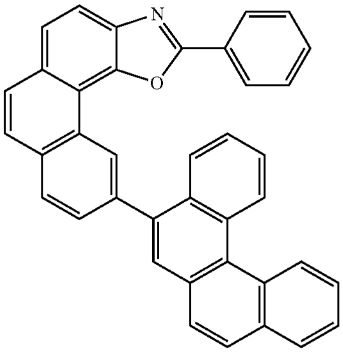
H-22
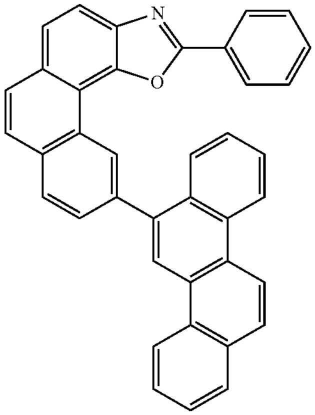
H-23
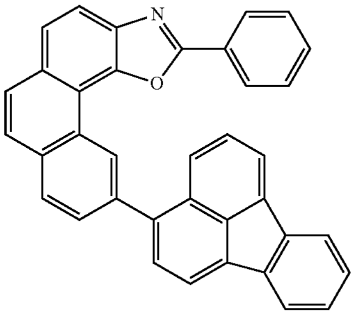

-continued
H-24
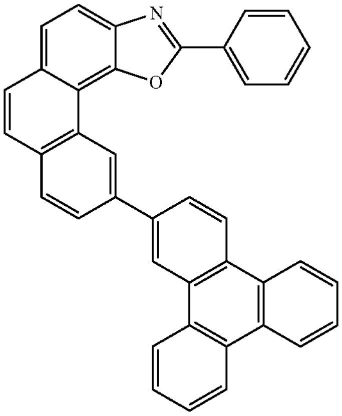
H-25
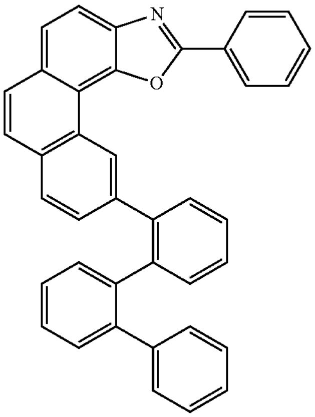
H-26
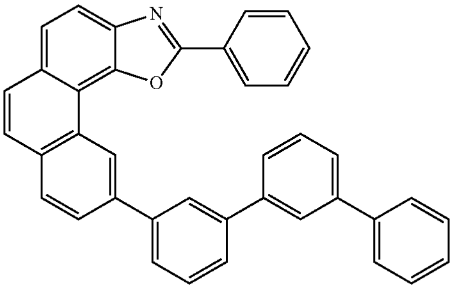
H-27
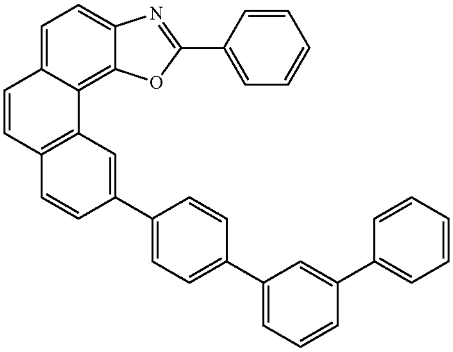
-continued
H-28
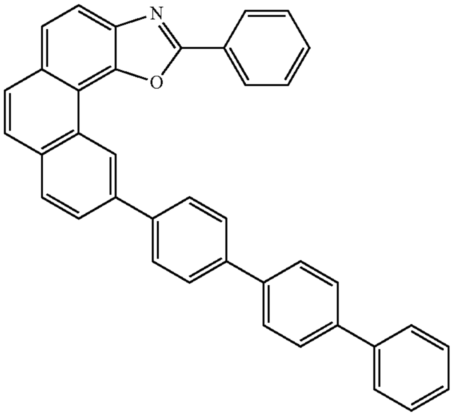
H-29
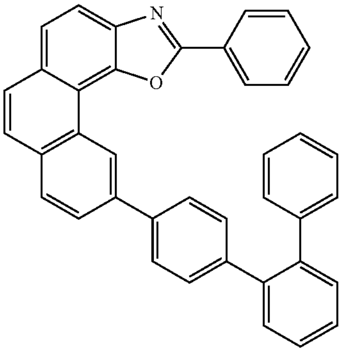
H-30
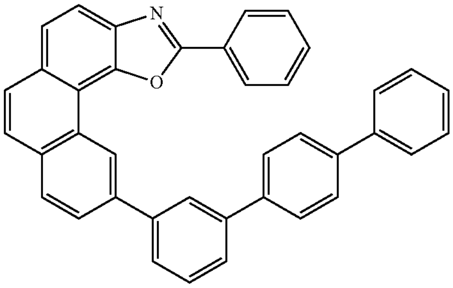
H-31
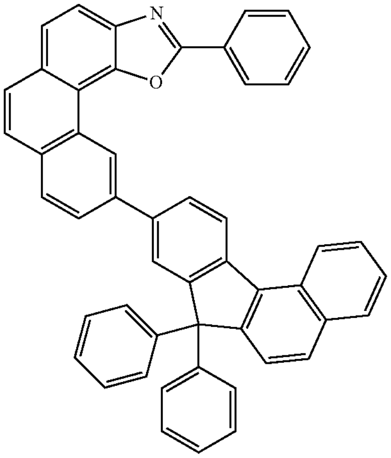

-continued
H-32
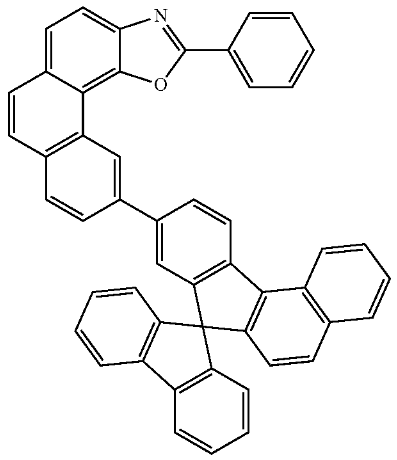
H-33
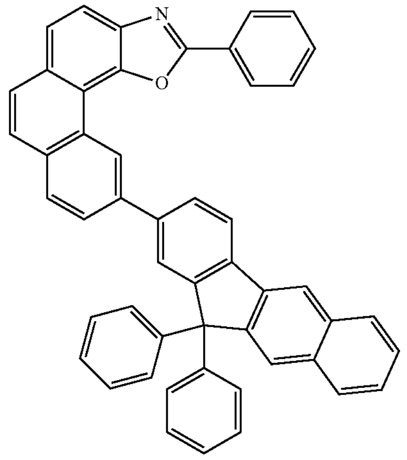
H-34
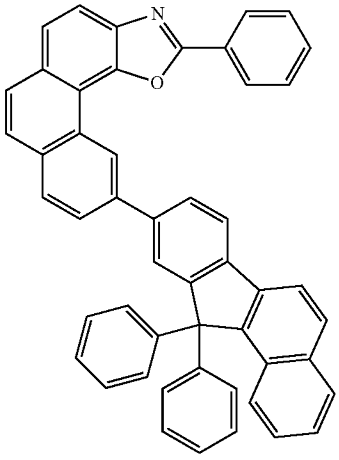
-continued
H-35
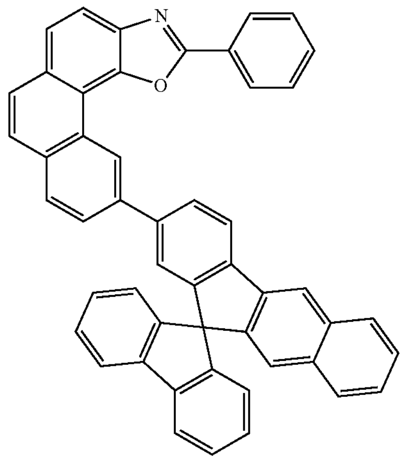
H-36
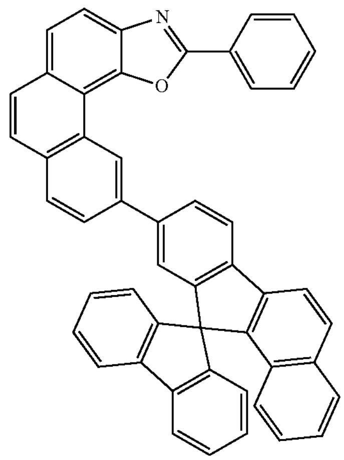
H-37
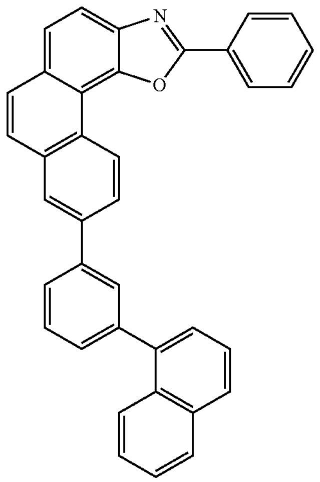

-continued
H-38
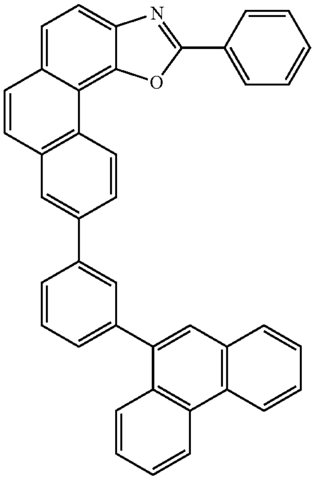
H-39
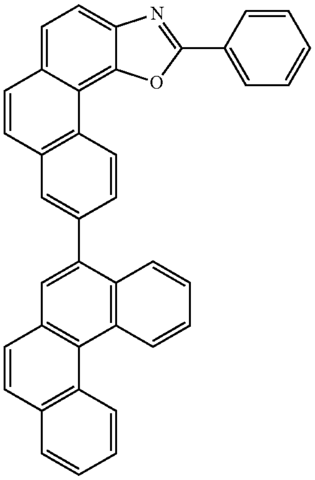
H-40
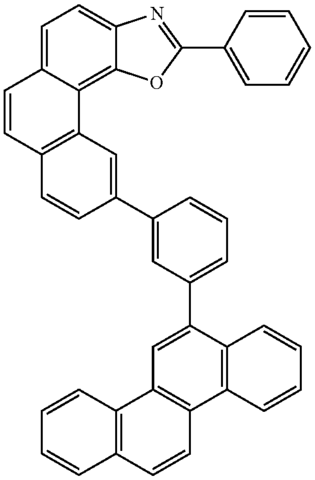
-continued
H-41
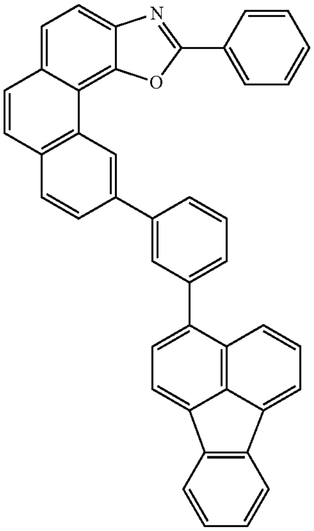
H-42
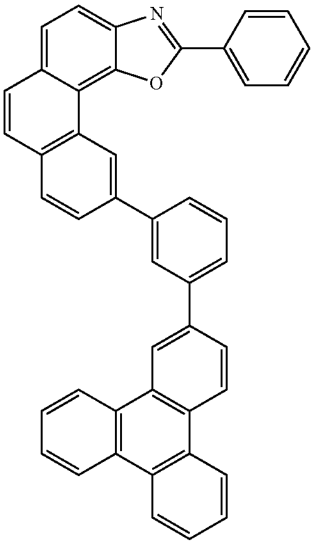
H-43
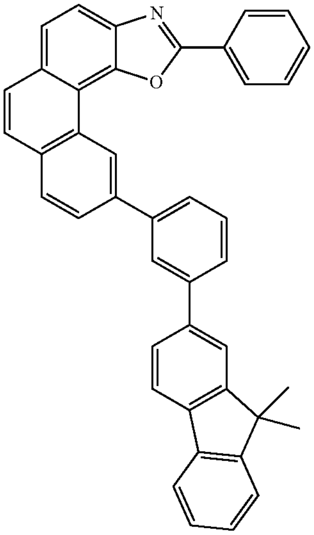

-continued
H-44
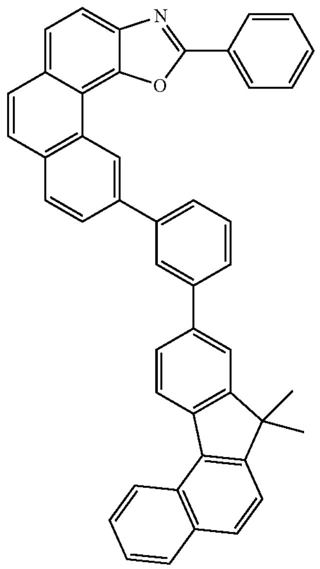
H-45
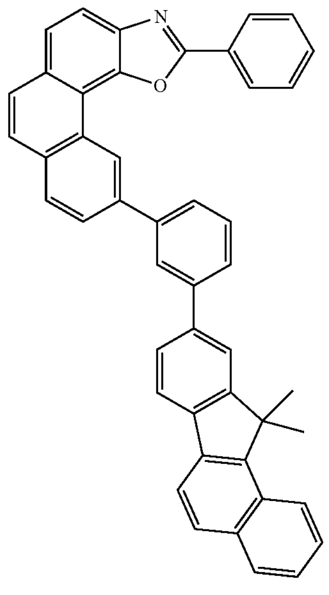
-continued
H-46
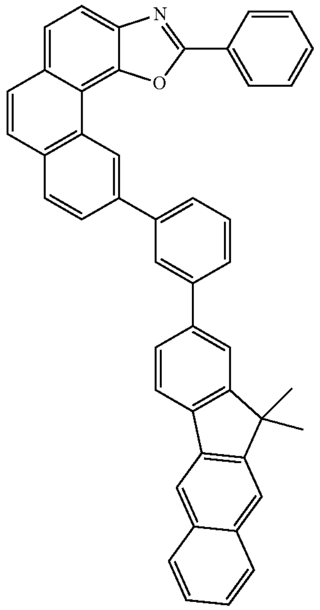
H-47
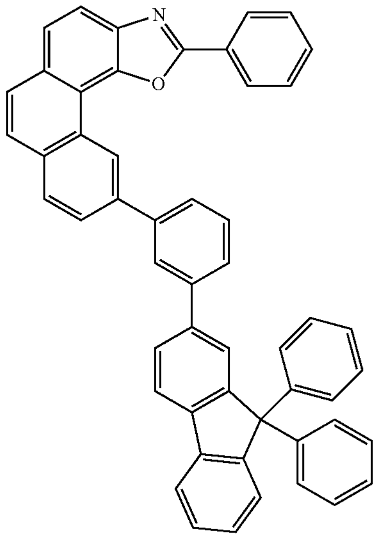

-continued
H-48
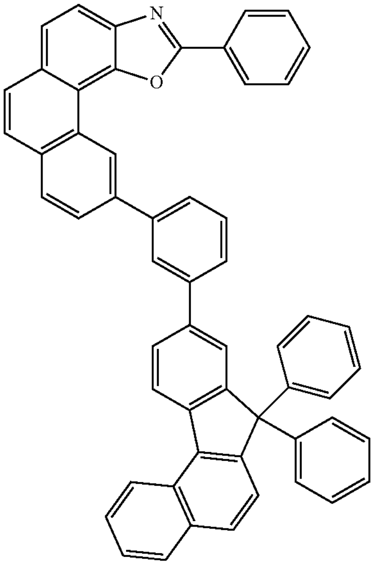
H-49
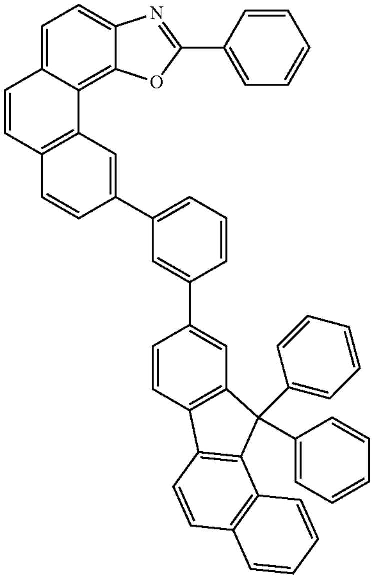
-continued
H-50
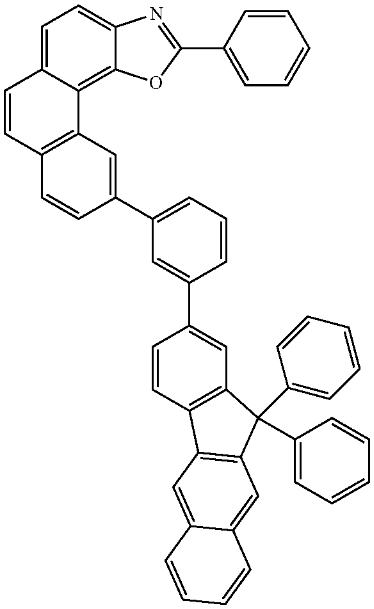
H-51
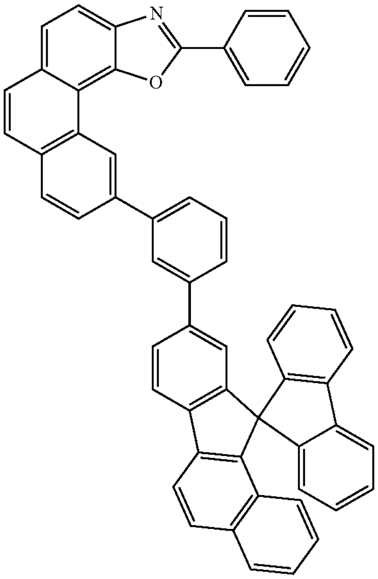

-continued
H-52
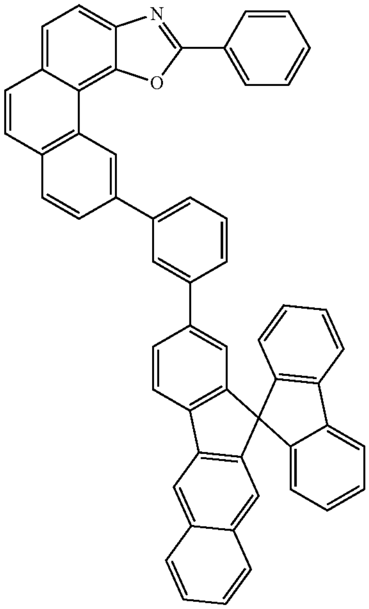
H-53
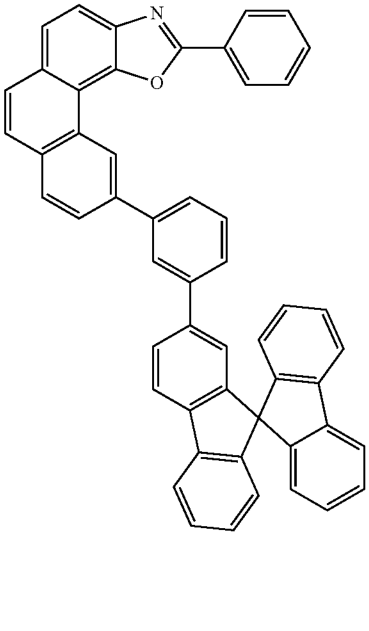
-continued
H-54
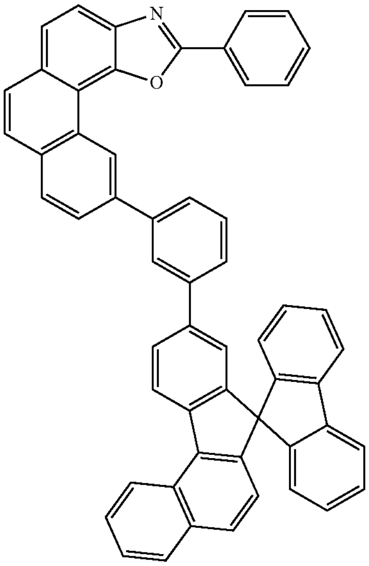
H-55
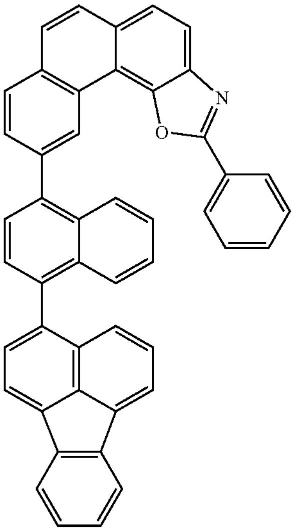
H-56
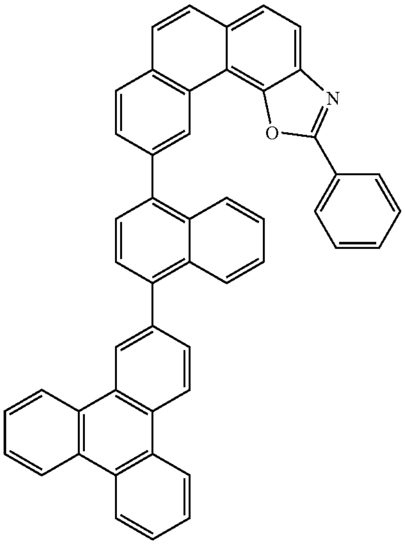

H-57
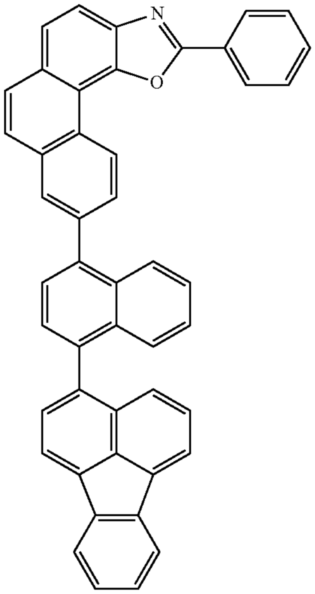
H-58
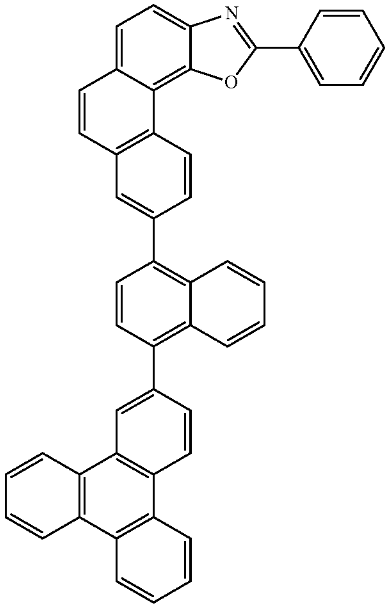
H-59
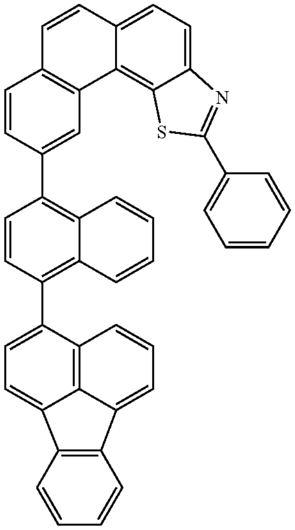
H-60
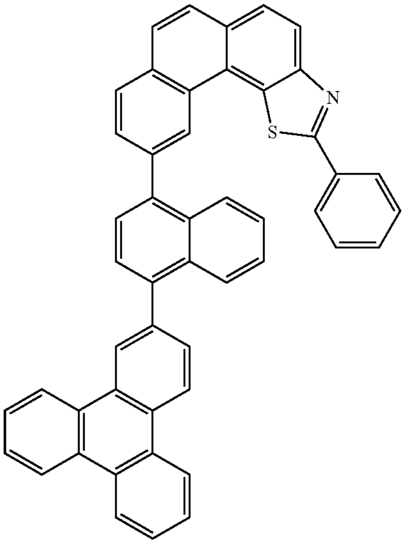

-continued
H-61
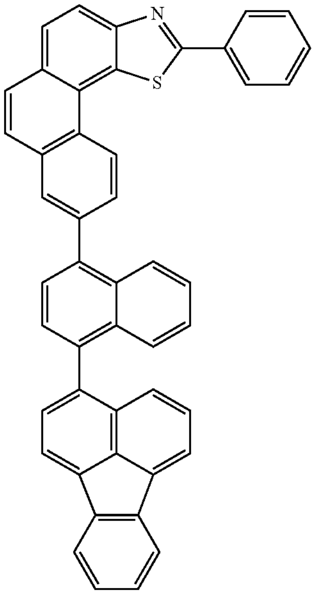
H-62
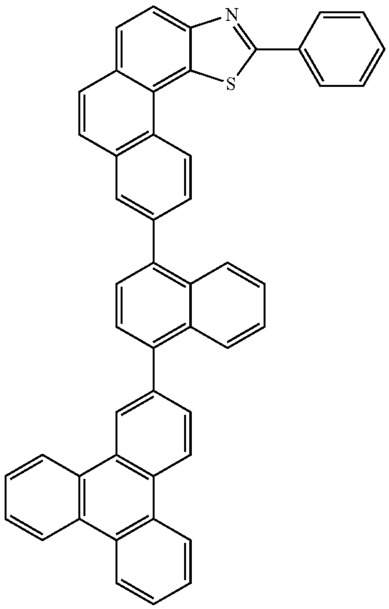
-continued
H-63
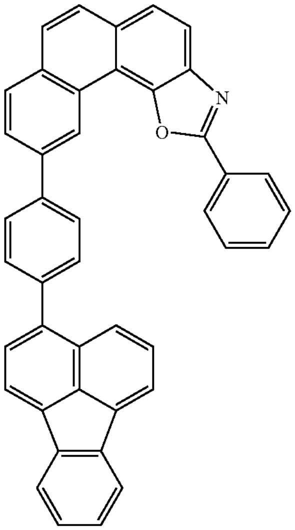
H-64
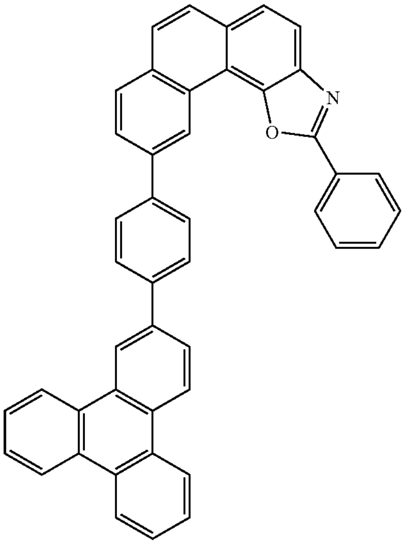
H-65
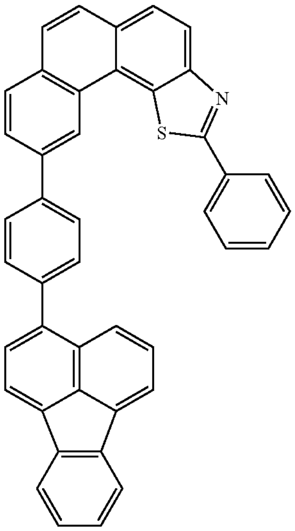

-continued
H-66
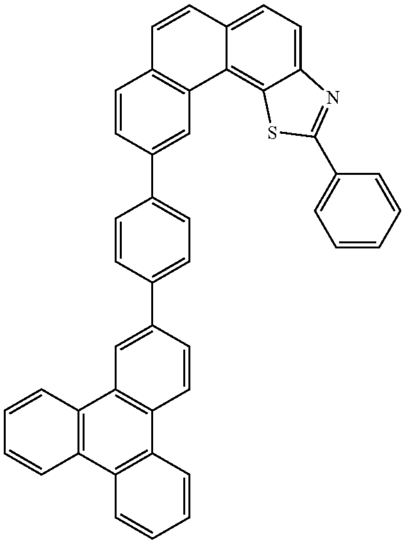
H-67
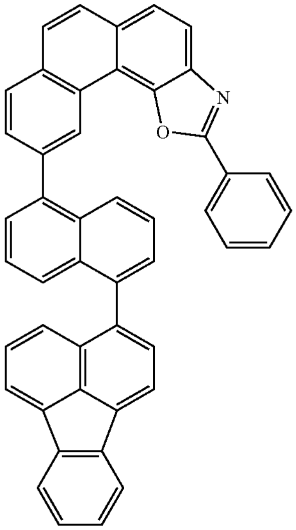
H-68
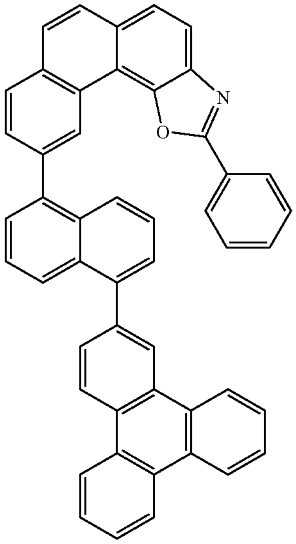
-continued
H-69
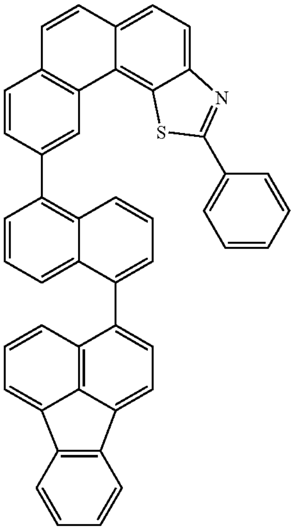
H-70
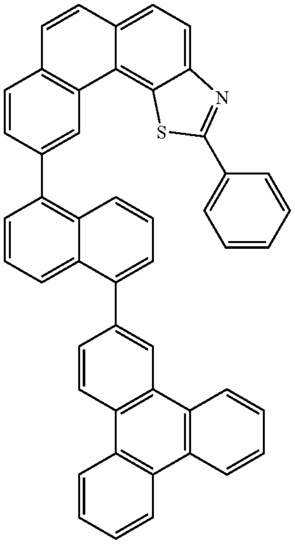
H-71
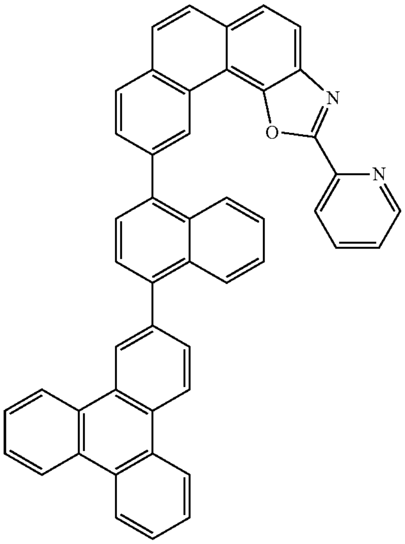

-continued
H-72
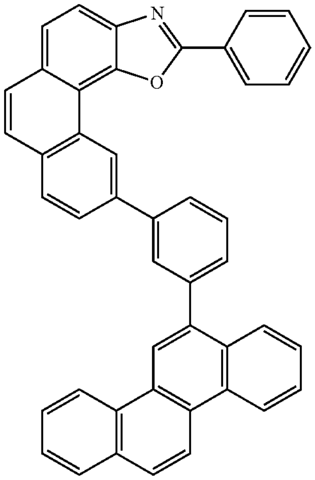
H-73
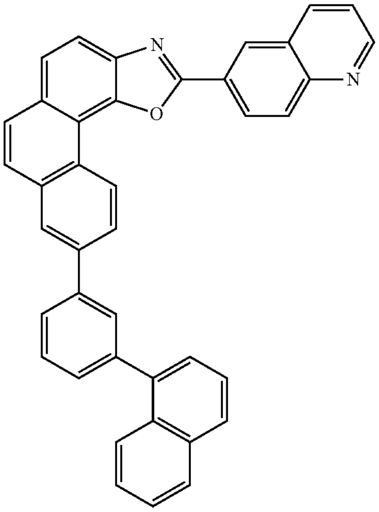
H-74
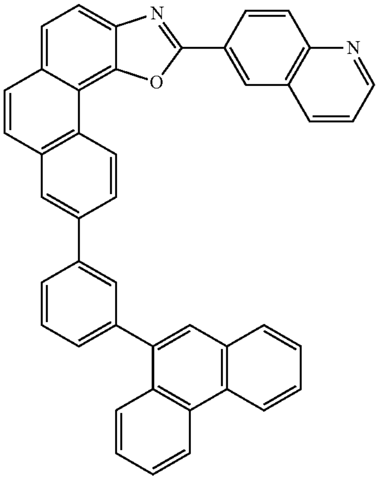
-continued
H-75
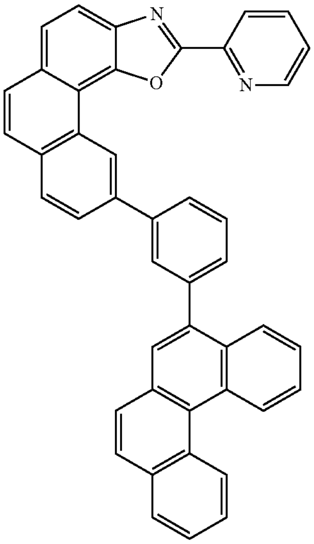
H-76
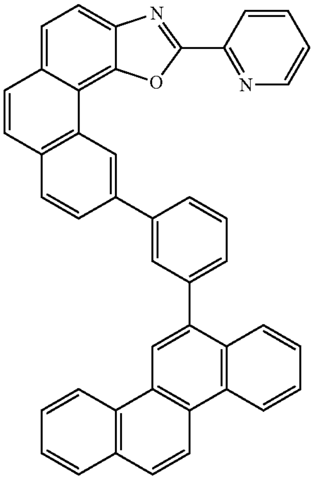
H-77
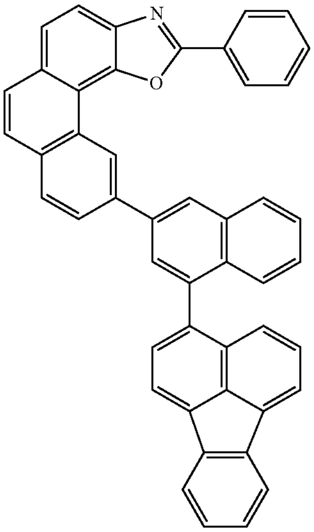

-continued
H-78
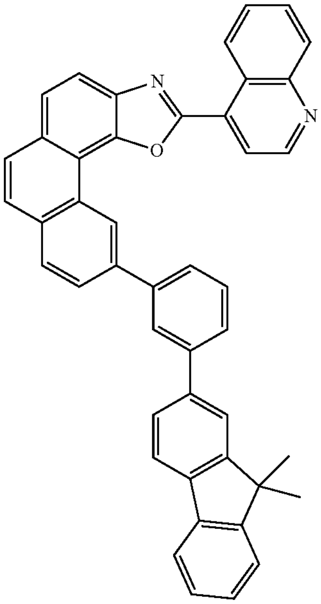
H-79
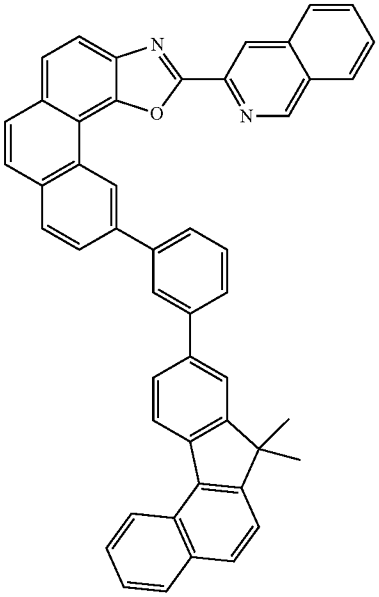
-continued
H-80
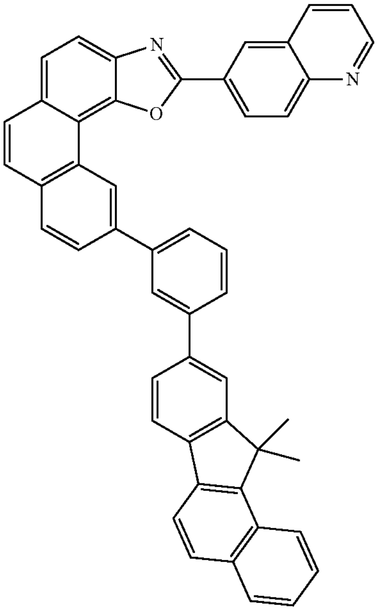
H-81
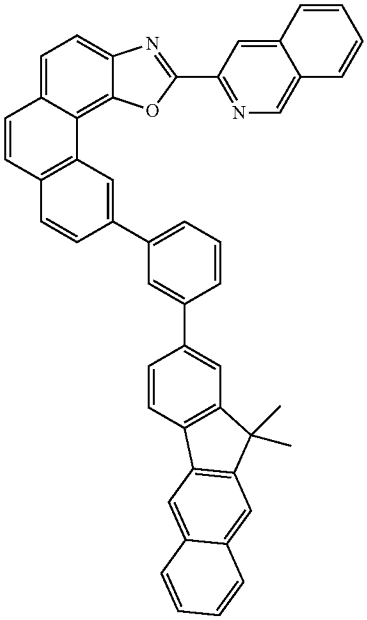

-continued
H-82
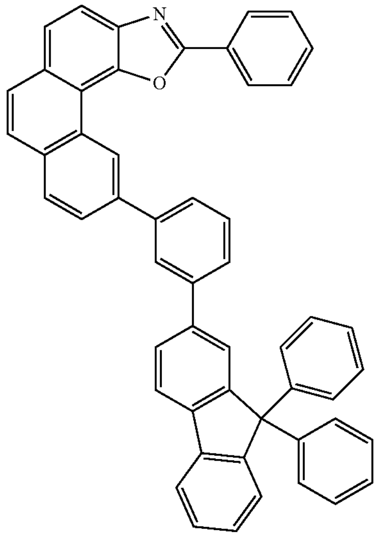
H-83
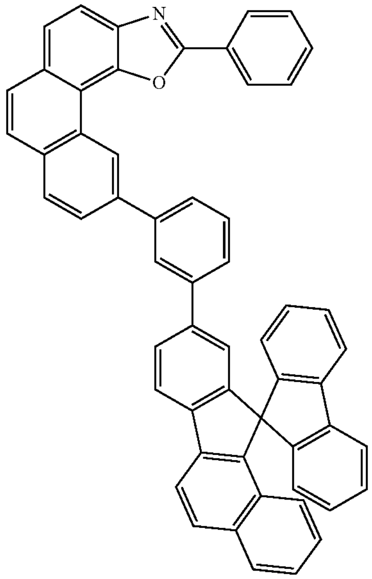
-continued
H-84
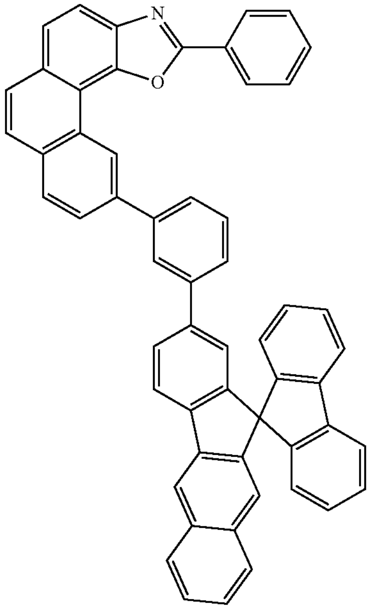
H-85
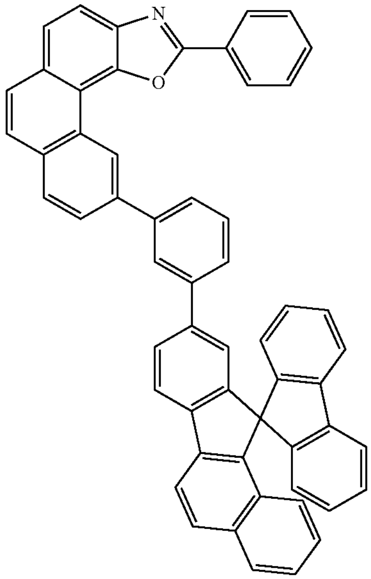
H-86
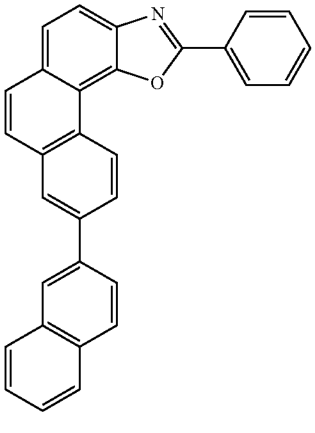

-continued
H-87
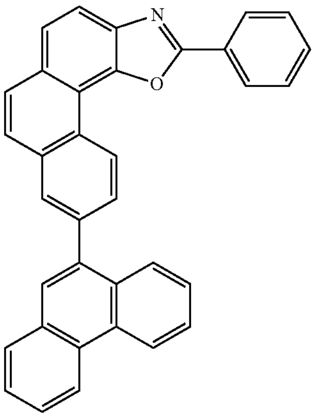
H-88
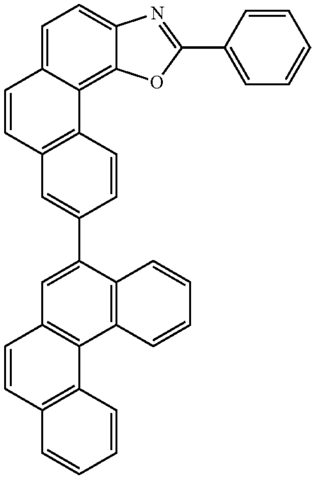
H-89
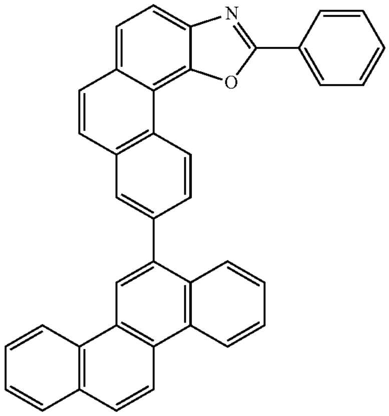
-continued
H-90
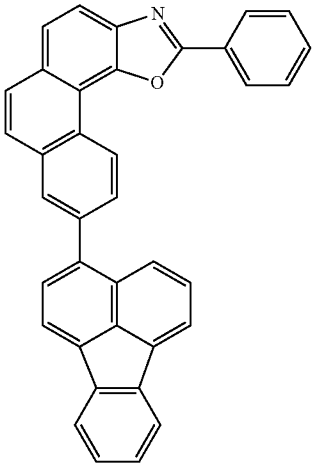
H-91
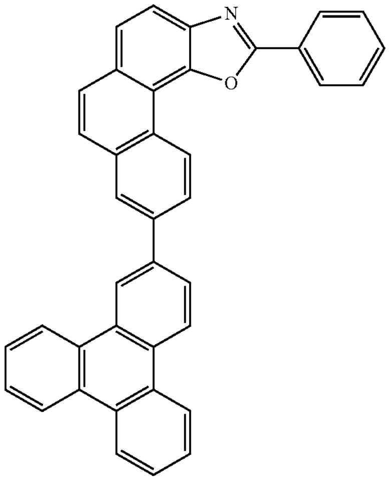
H-92
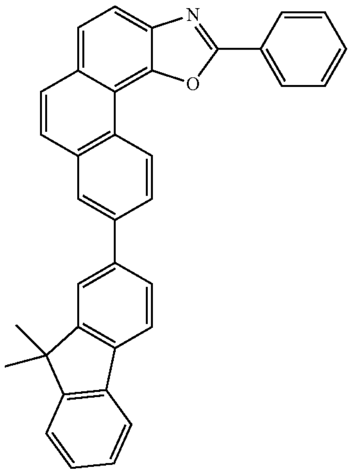

-continued
H-93
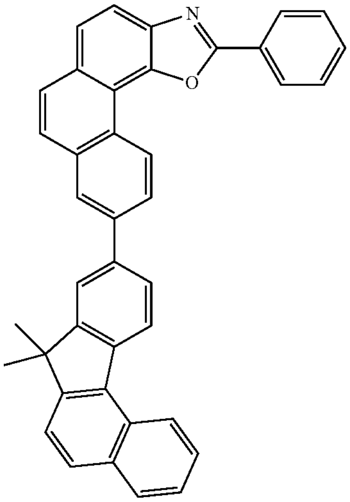
H-94
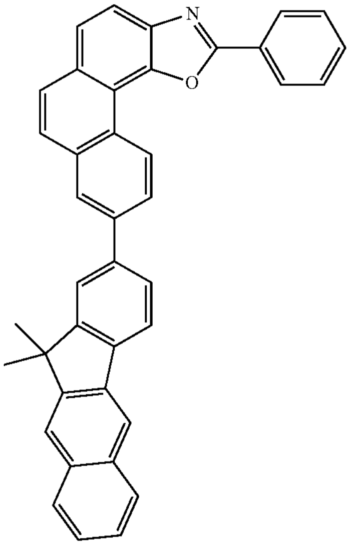
H-95
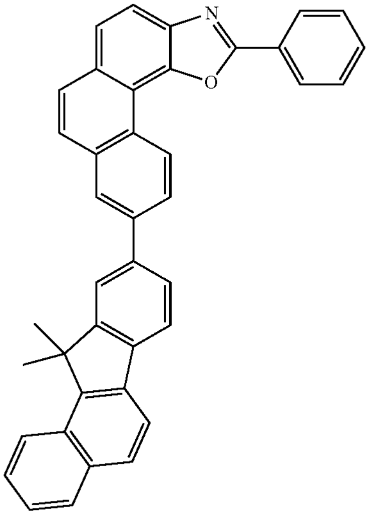
-continued
H-96
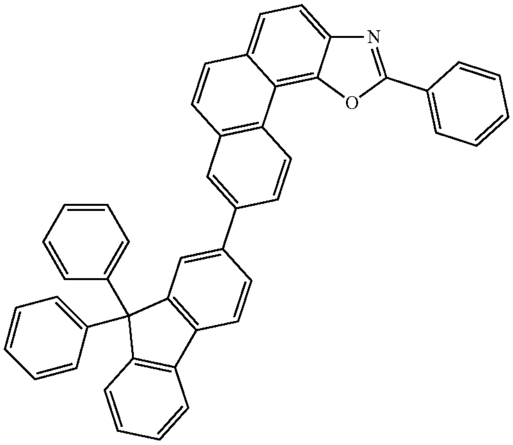
H-97
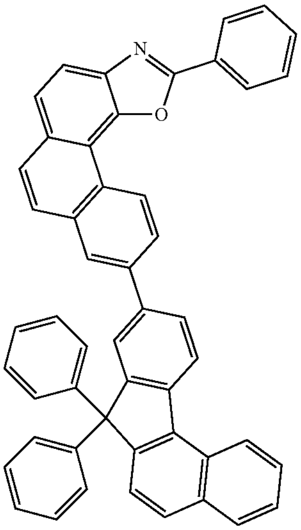
H-98
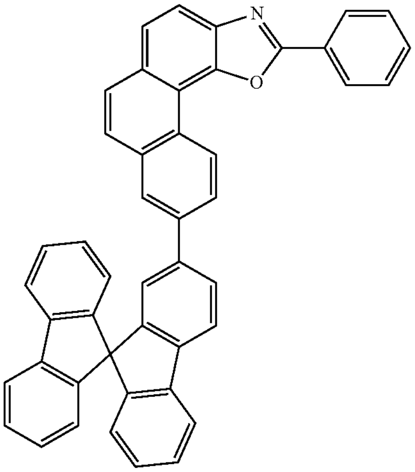

-continued
H-99
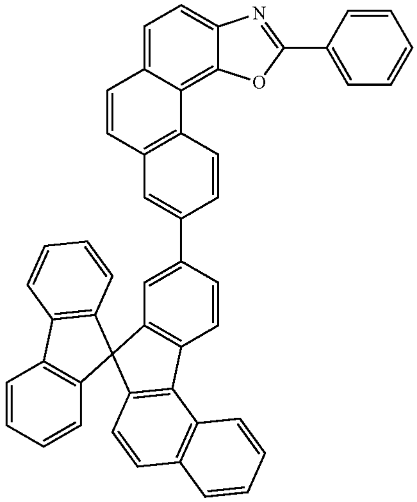
H-100
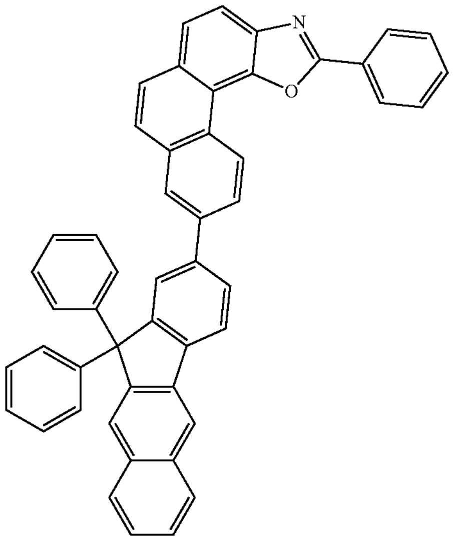
H-101
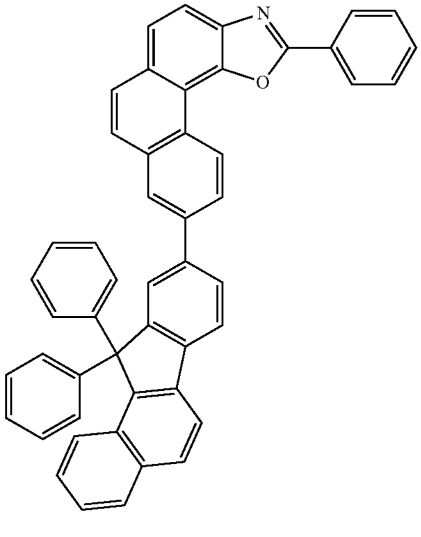
-continued
H-102
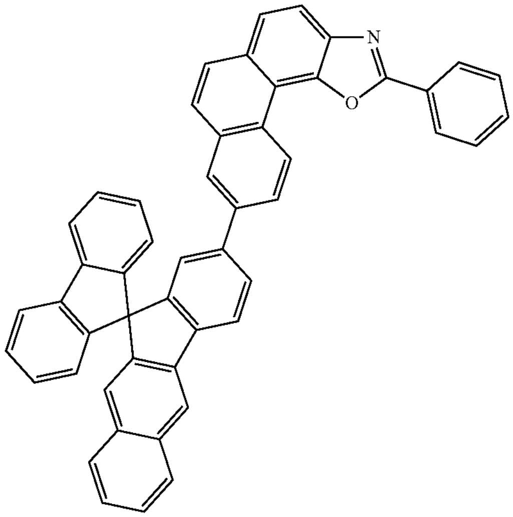
H-103
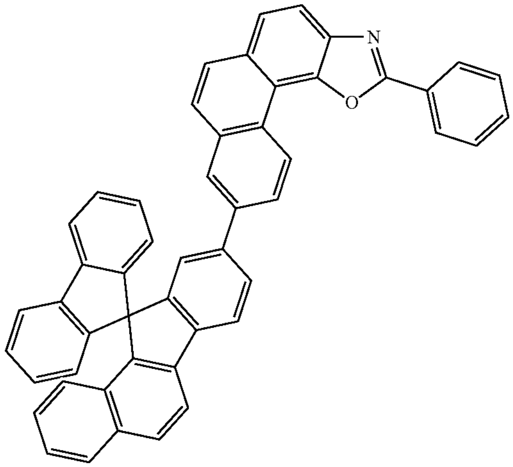
H-104
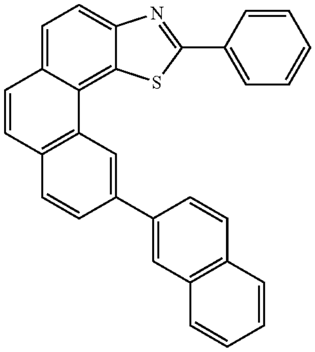

-continued
H-105
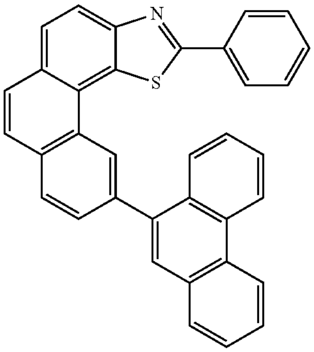
H-106
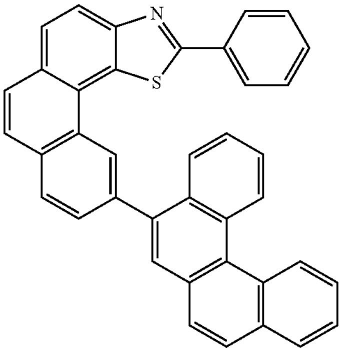
H-107
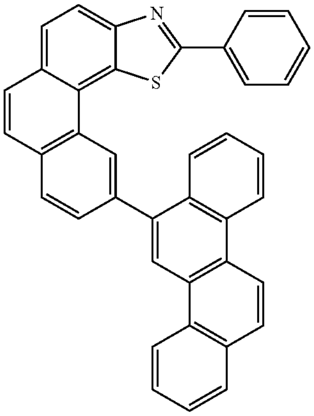
H-108
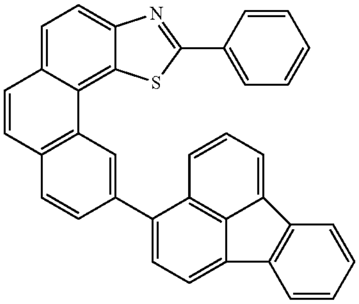
-continued
H-109
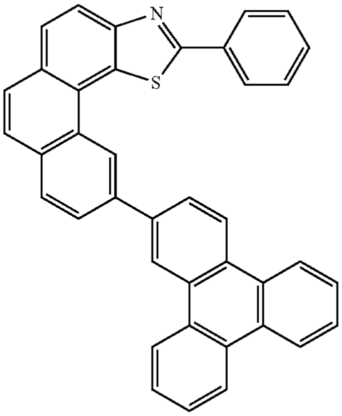
H-110
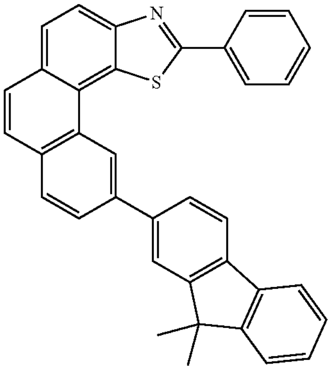
H-111
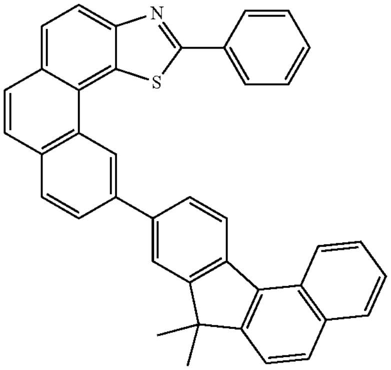
H-112
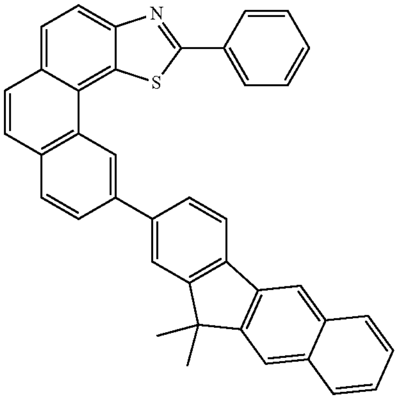

-continued
H-113
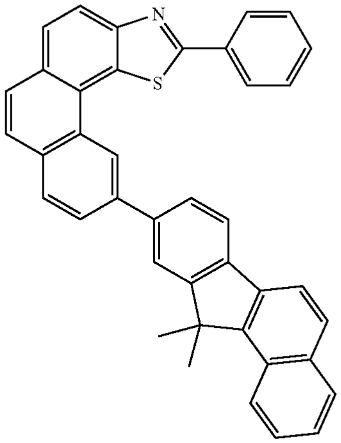
H-114
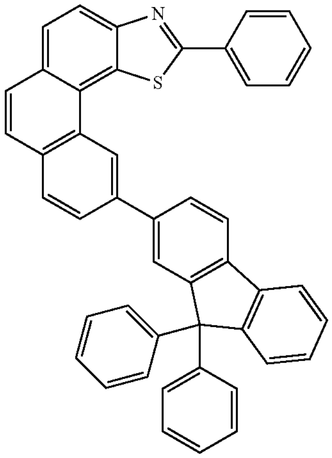
H-115
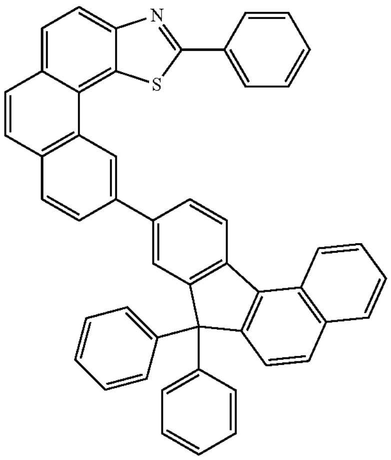
-continued
H-116
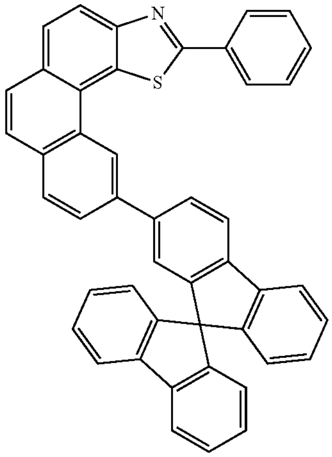
H-117
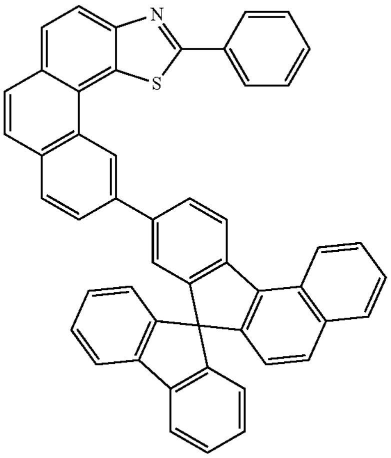
H-118
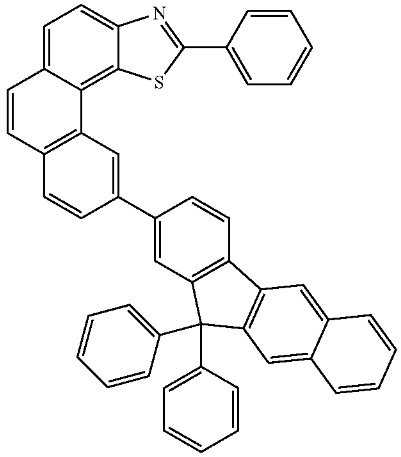

-continued
H-119
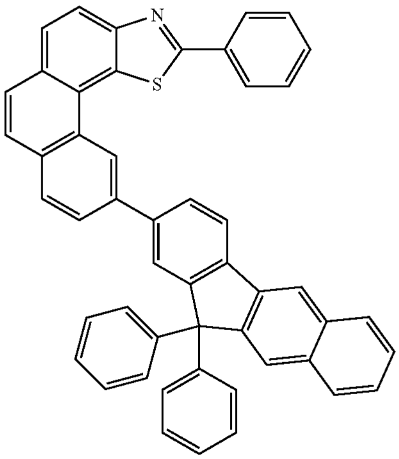
H-120
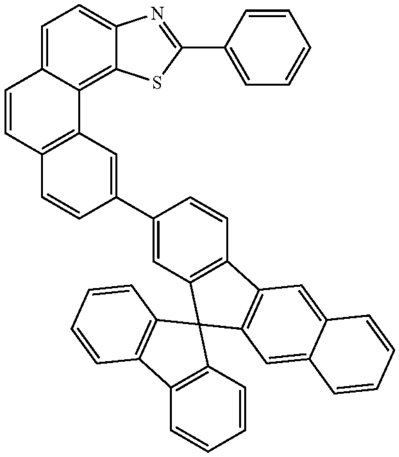
H-121
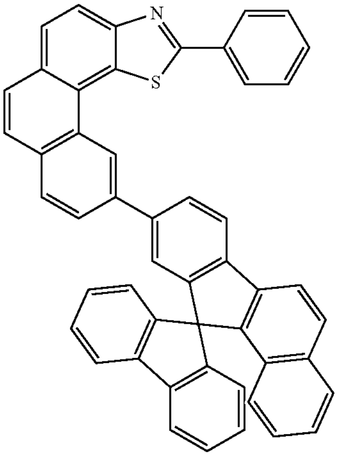
-continued
H-122
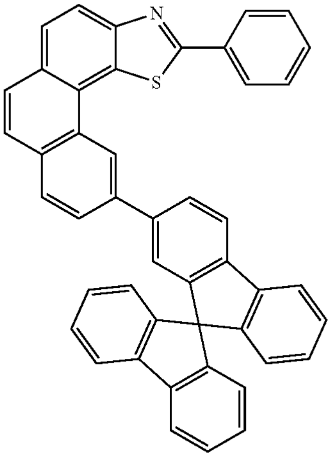
H-123
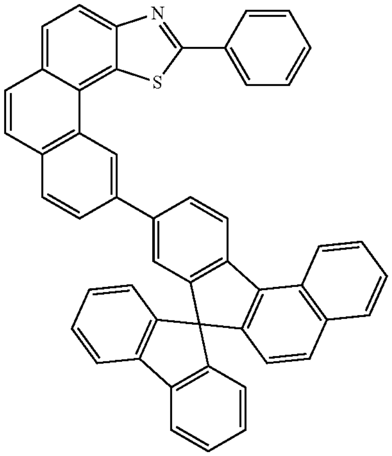
H-124
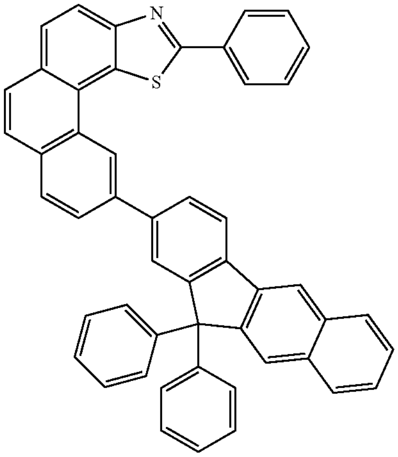

-continued
H-125
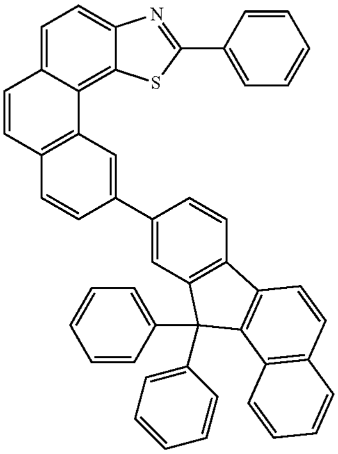
H-126
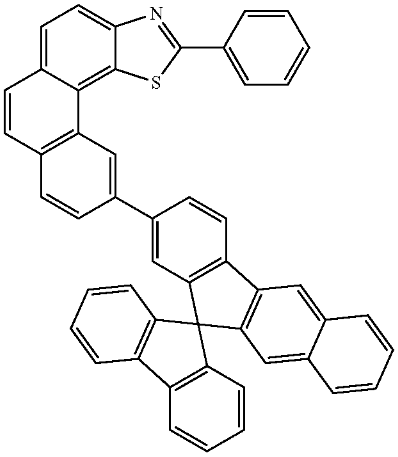
H-127
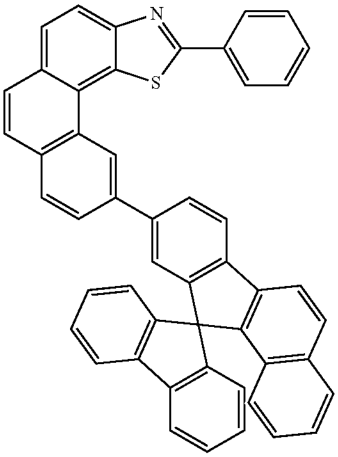
-continued
H-128
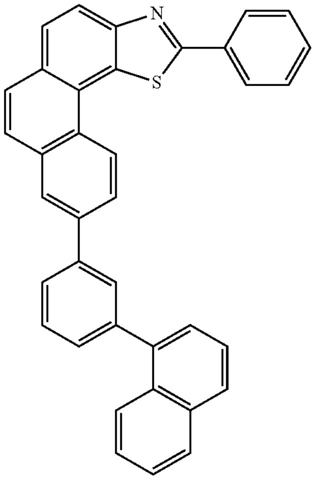
H-129
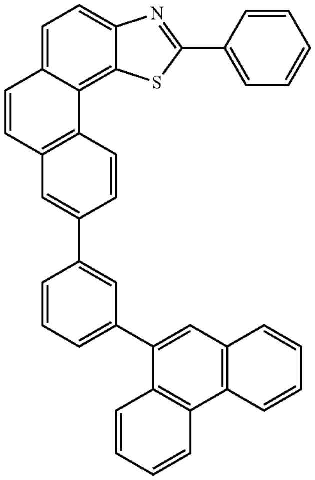
H-130
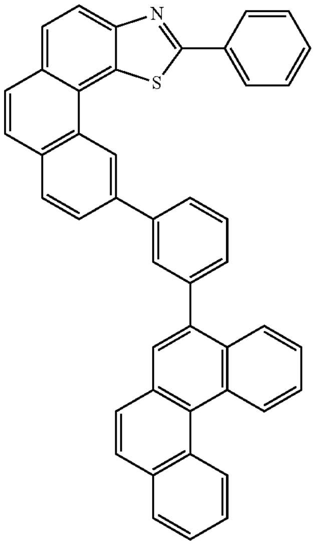

-continued
H-131
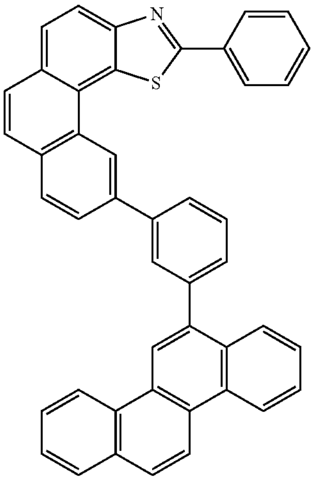
H-132
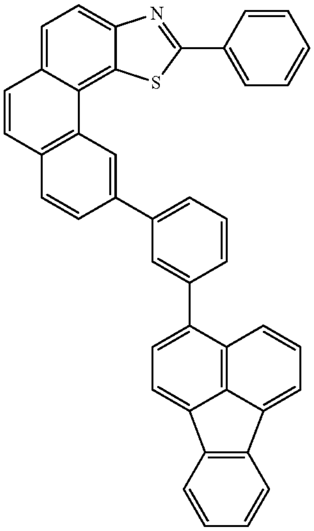
H-133
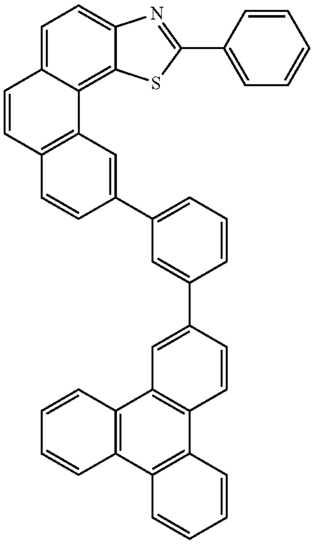
-continued
H-134
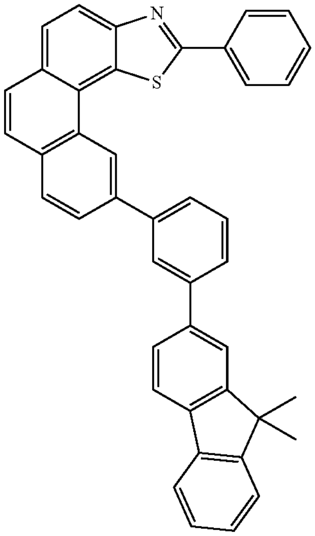
H-135
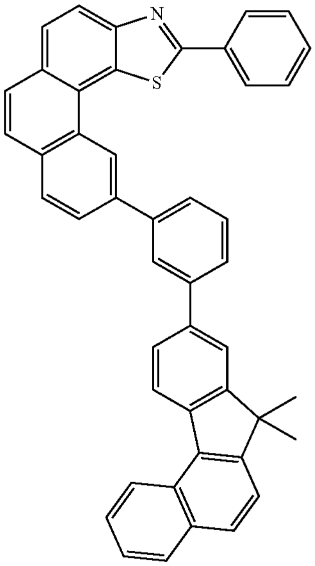

-continued
H-136
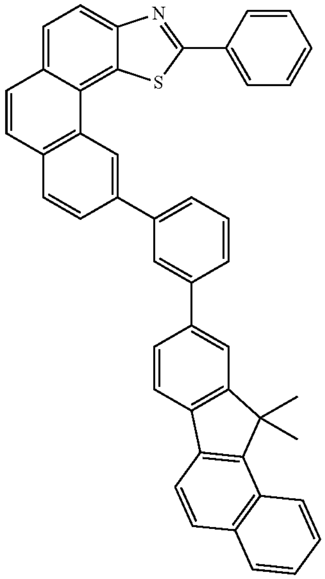
H-137
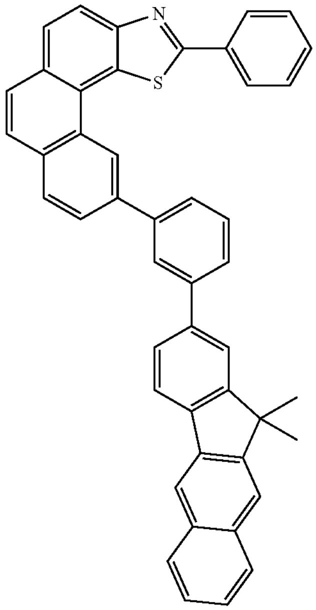
-continued
H-138
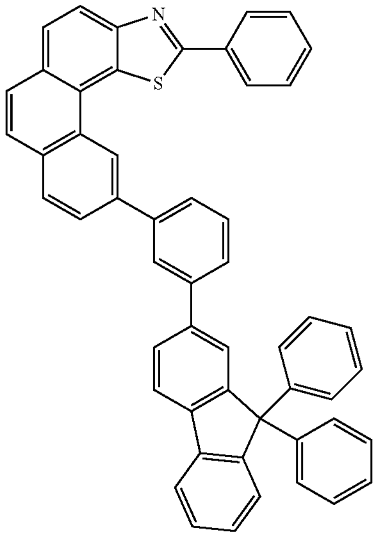
H-139
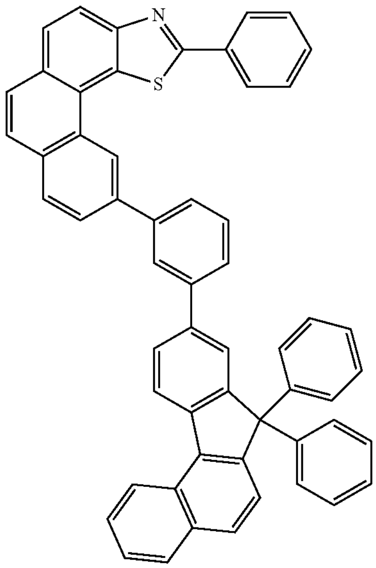

-continued
H-140
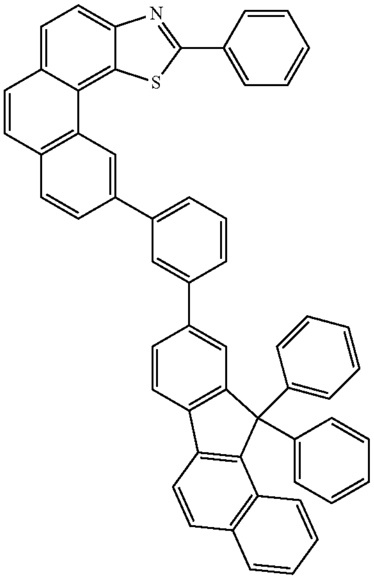
H-141
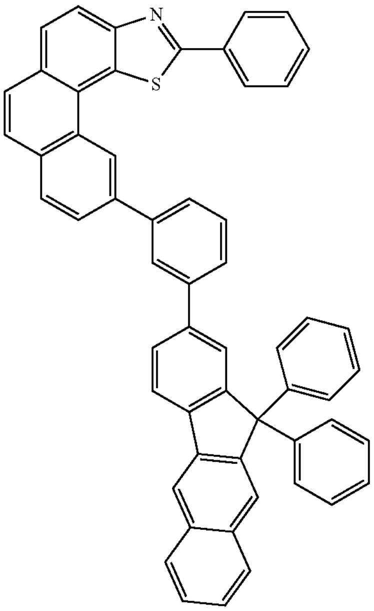
-continued
H-142
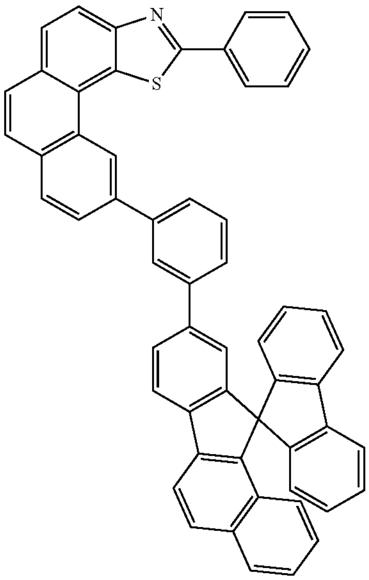
H-143
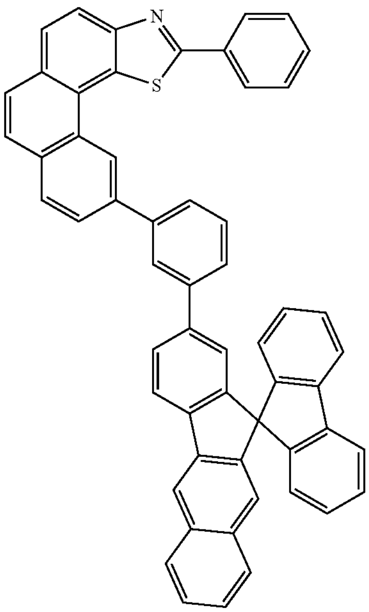

-continued
H-144
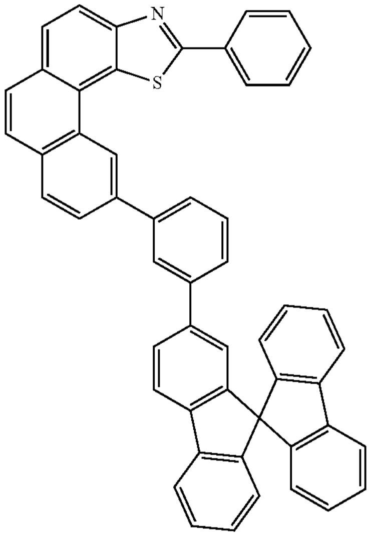
H-145
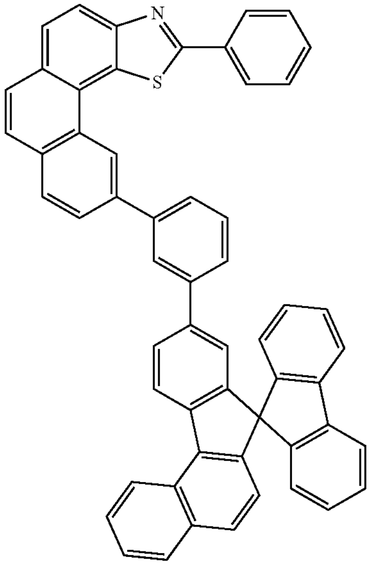
H-146
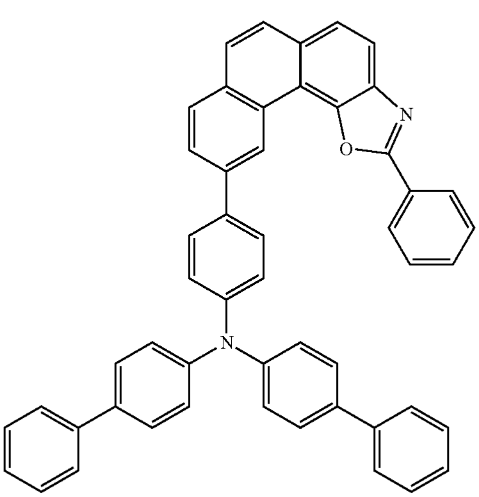
-continued
H-147
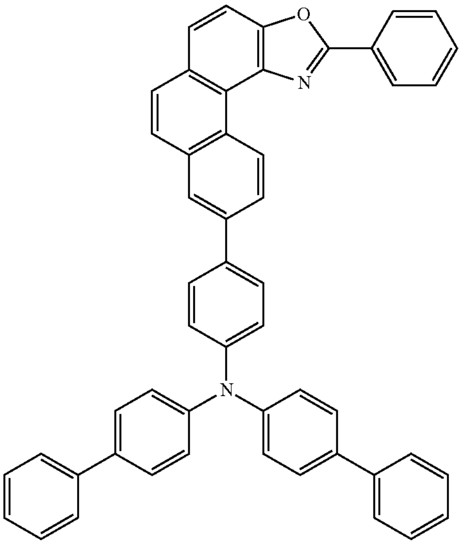
H-148
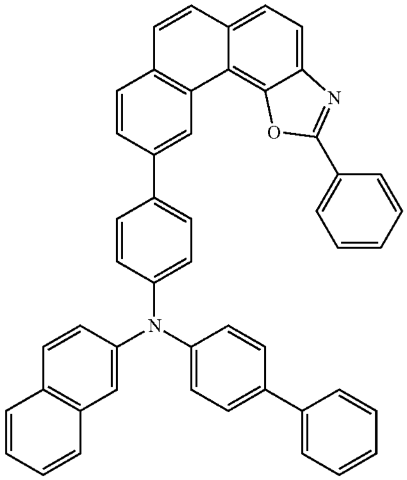
H-149
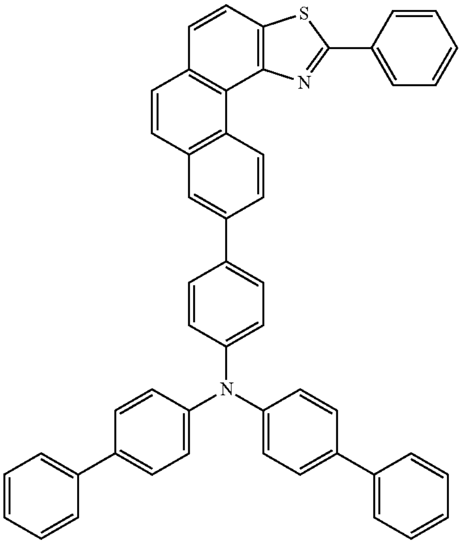

-continued
H-150
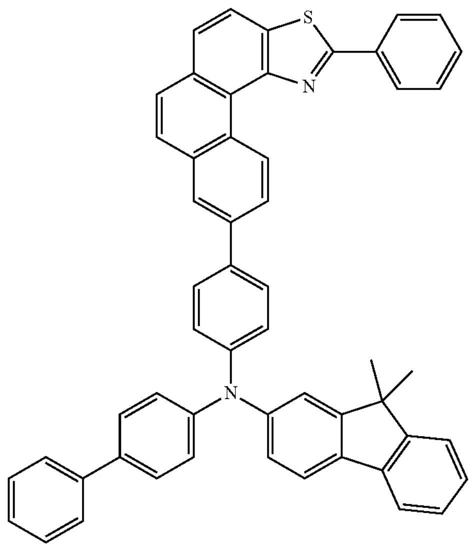
H-151
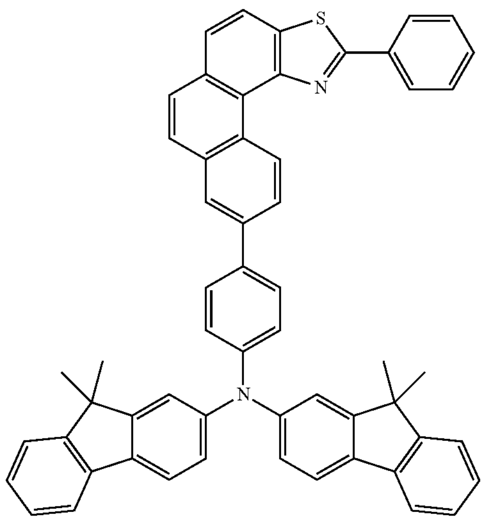
H-152
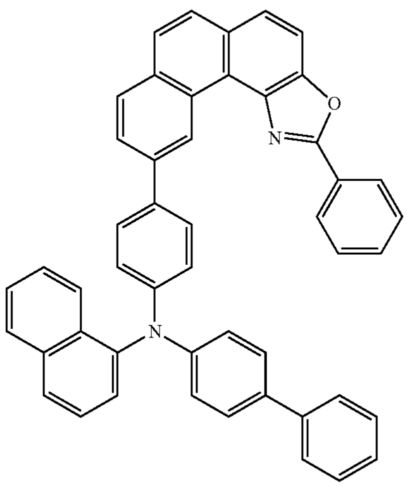
-continued
H-153
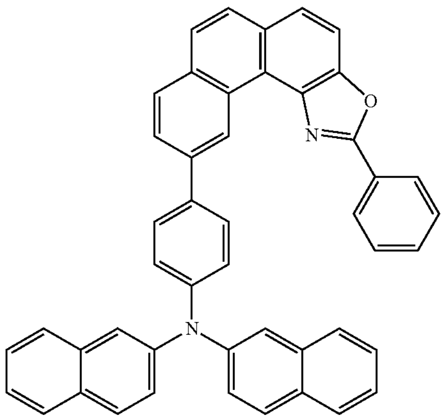
H-154
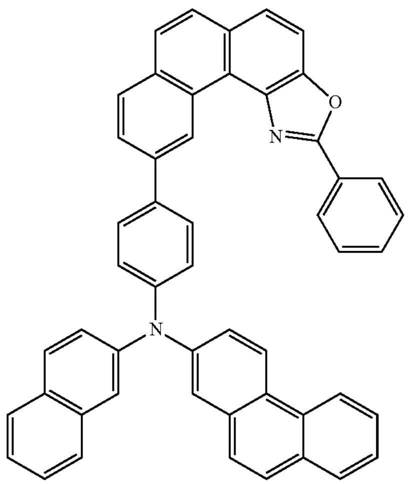
H-155
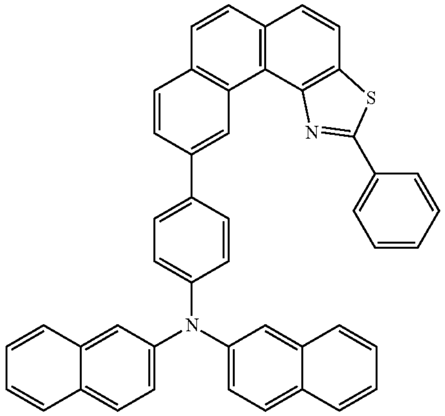

-continued
H-156
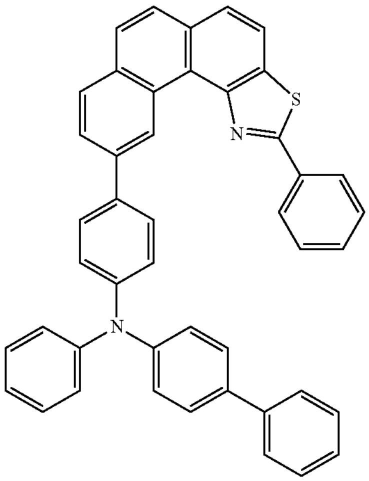
H-157
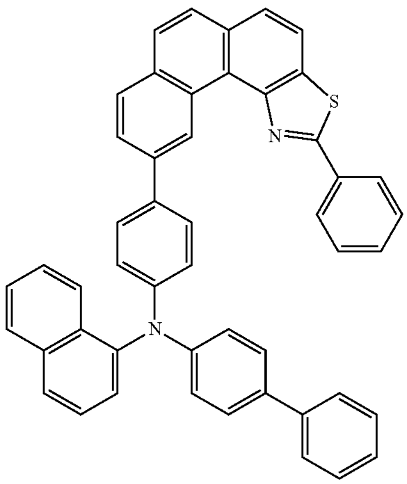
H-158
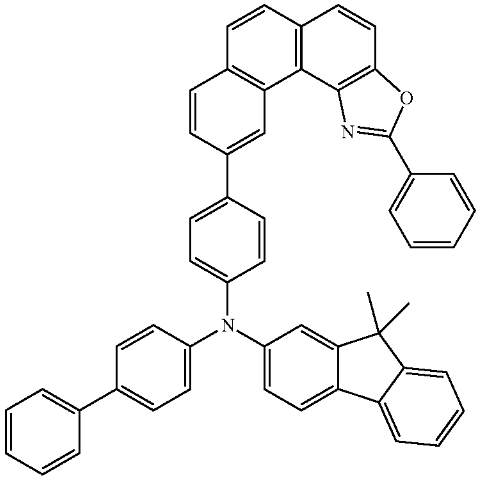
-continued
H-159
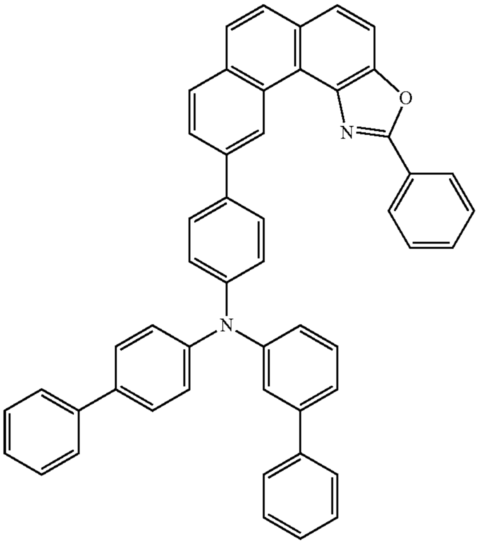
H-160
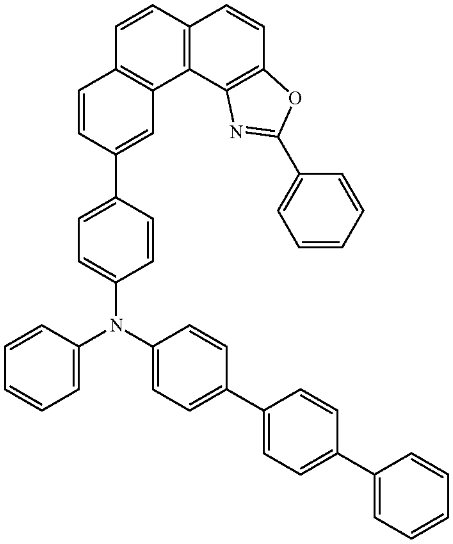
H-161
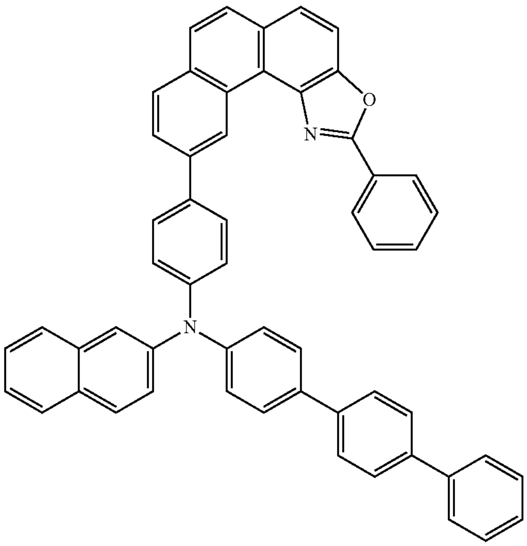

-continued
H-162
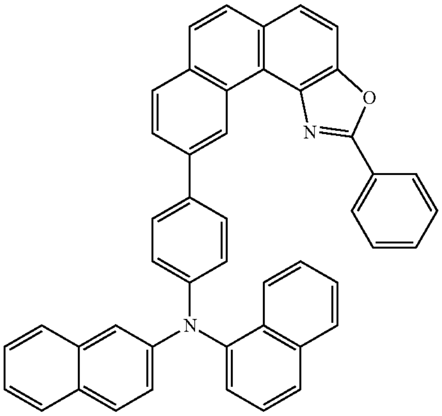
H-163
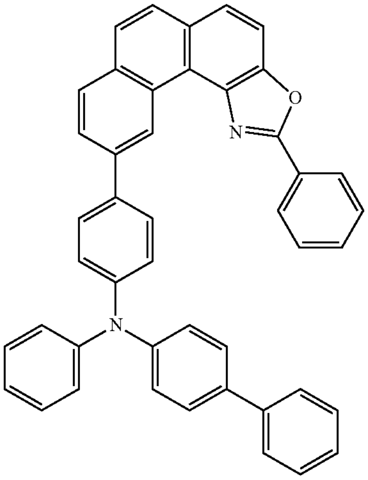
H-164
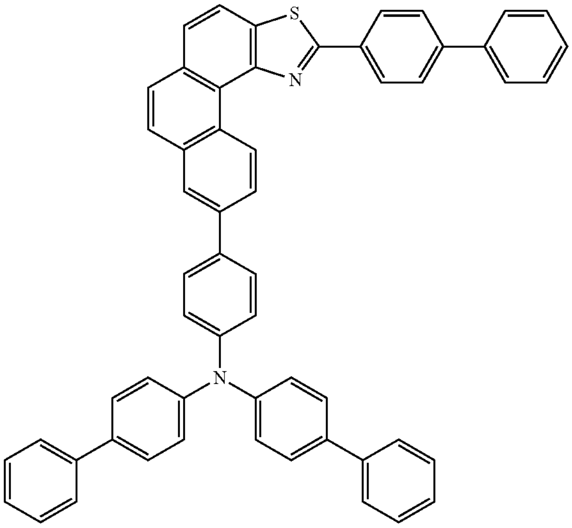
-continued
H-165
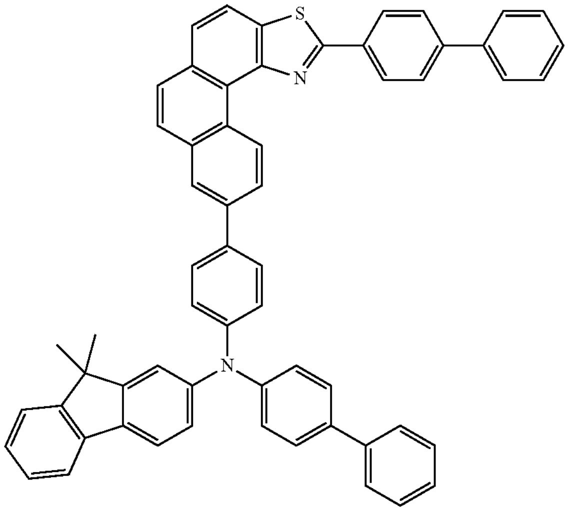
H-166
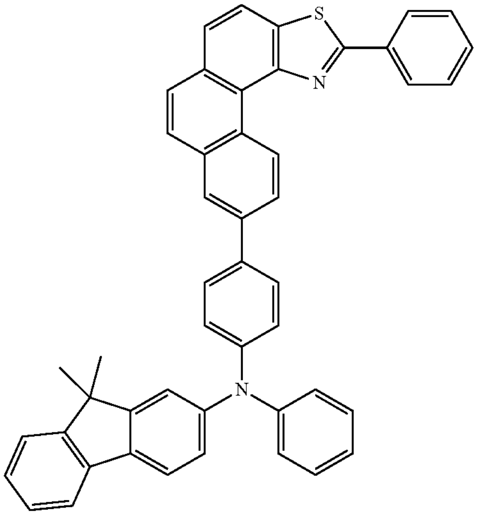
H-167
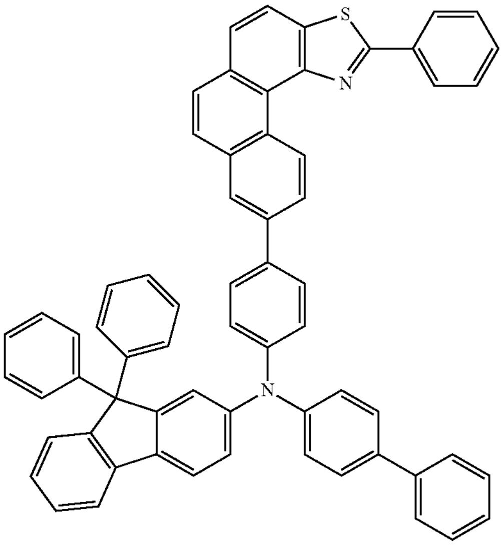

H-168
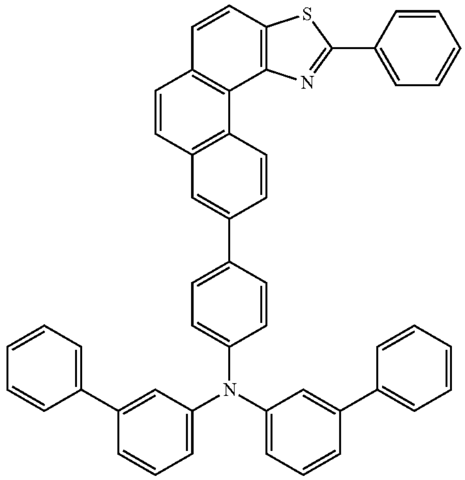
H-169
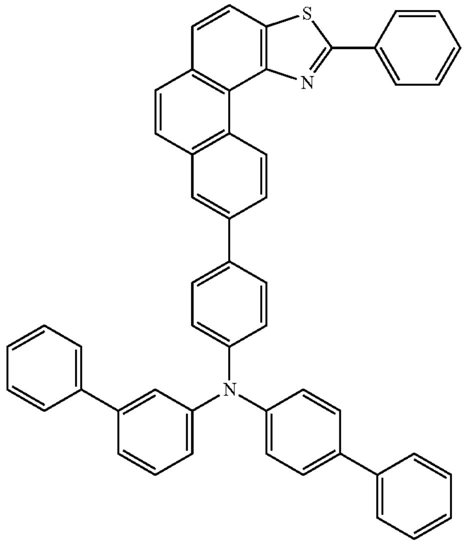
H-170
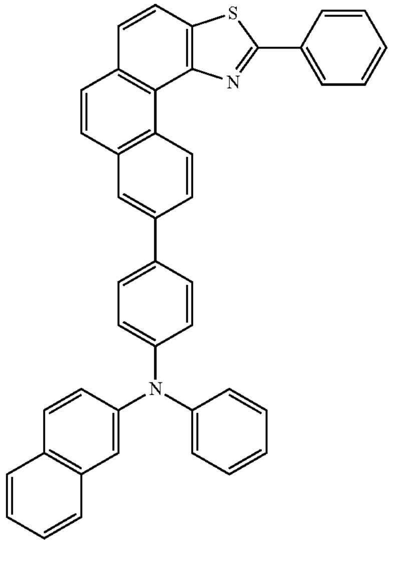
H-171
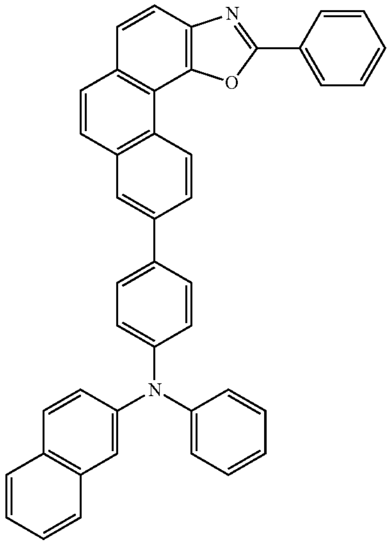
H-172
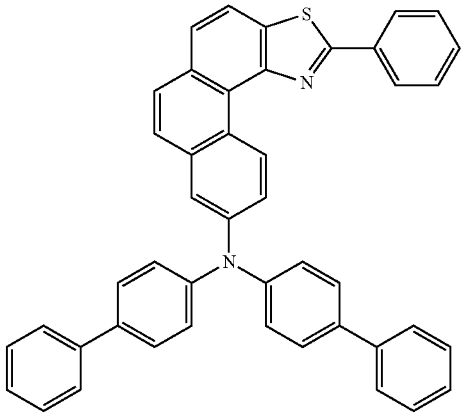
H-173
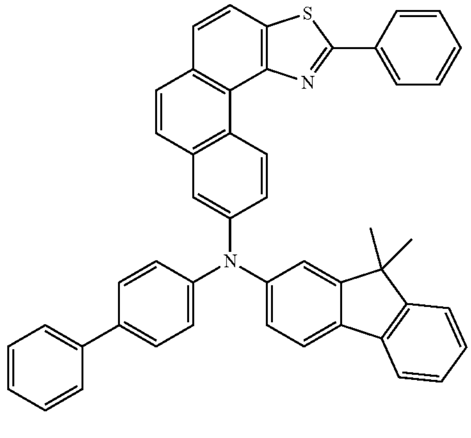

-continued
H-174
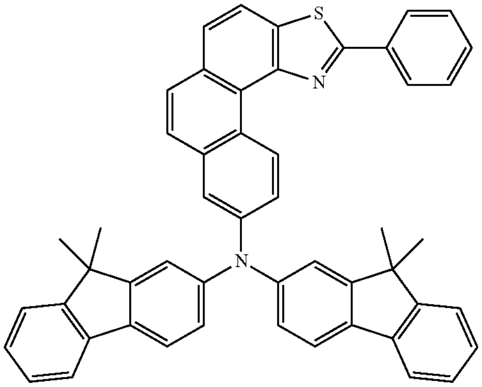
H-175
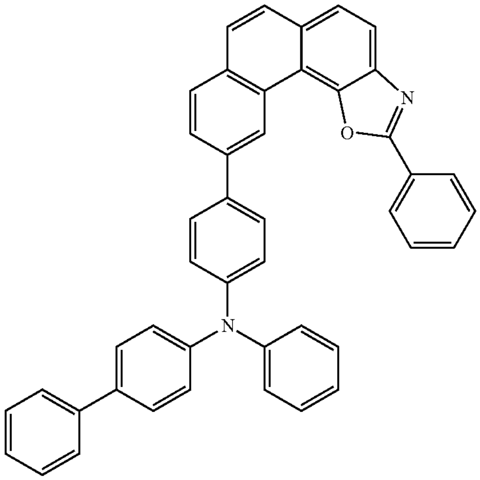
H-176
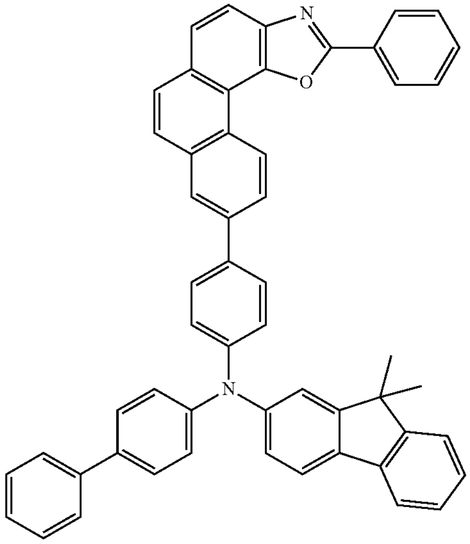
H-177
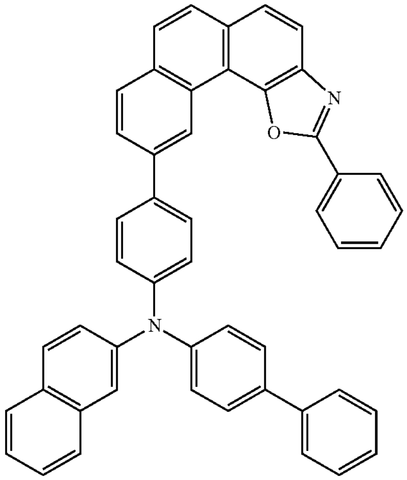
H-178
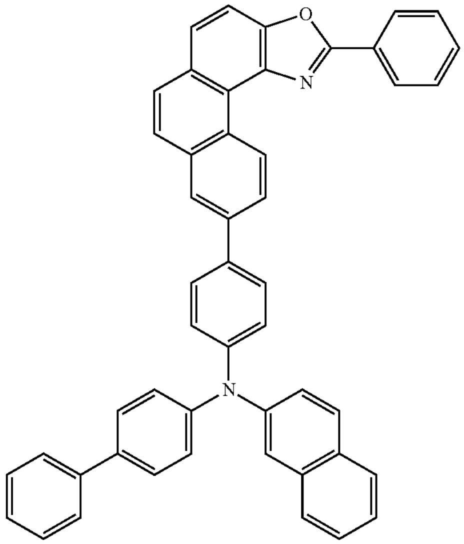
H-179
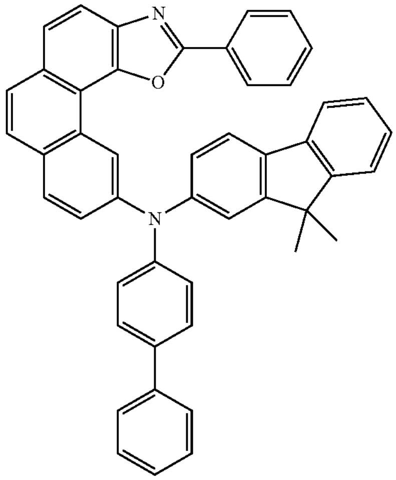

-continued
H-180
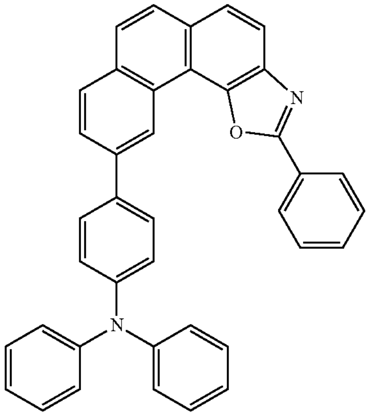
H-181
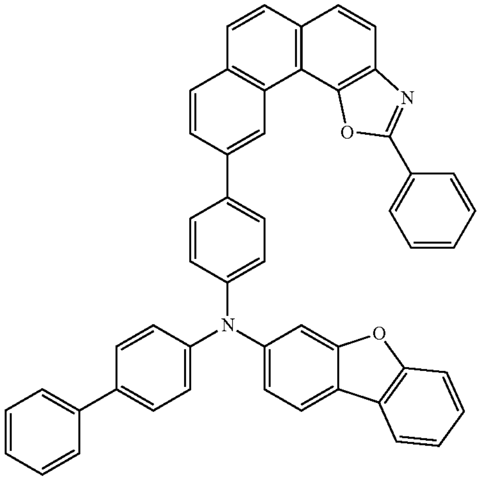
H-182
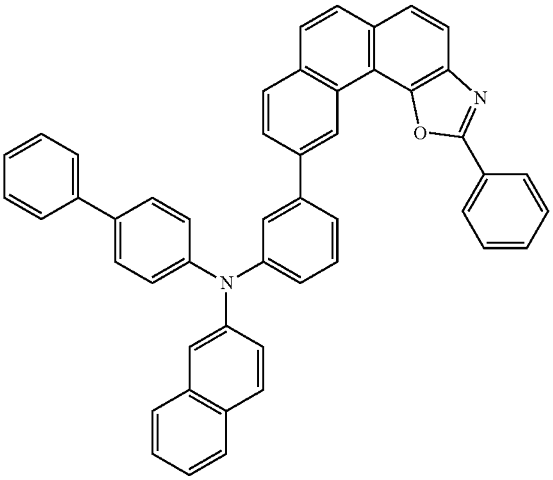
-continued
H-183
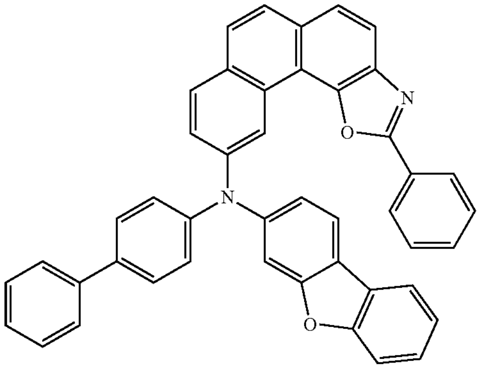
H-184
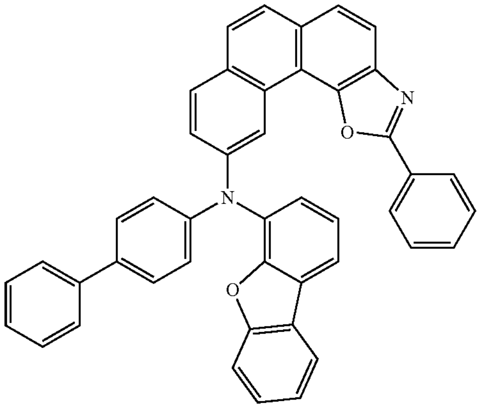
H-185
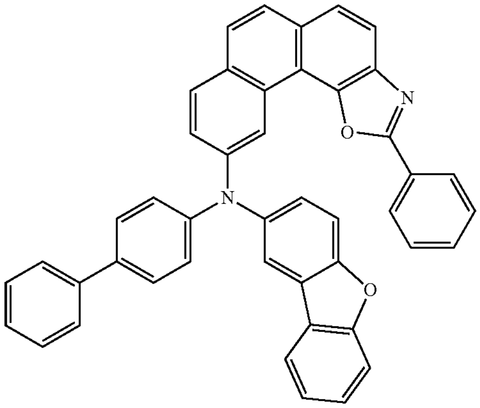
H-186
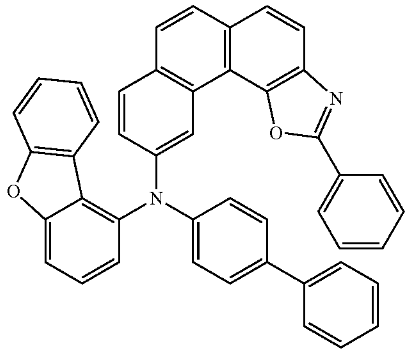

-continued
H-187
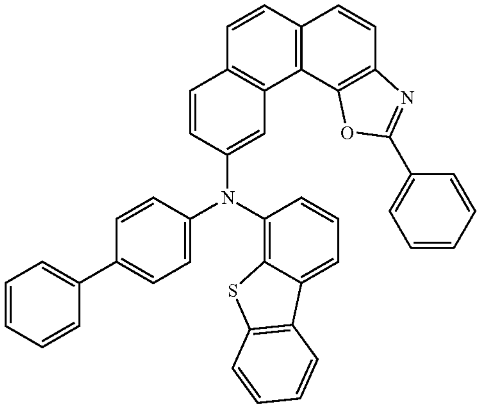
H-188
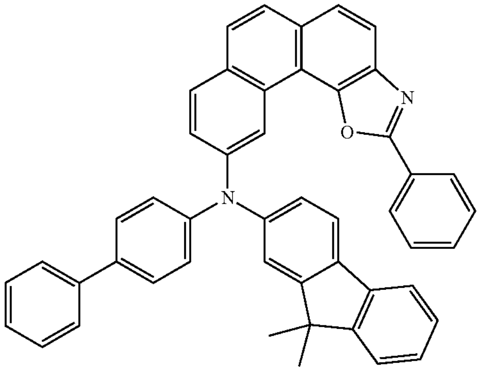
H-189
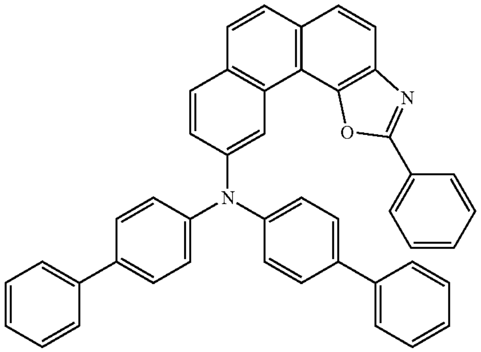
H-190
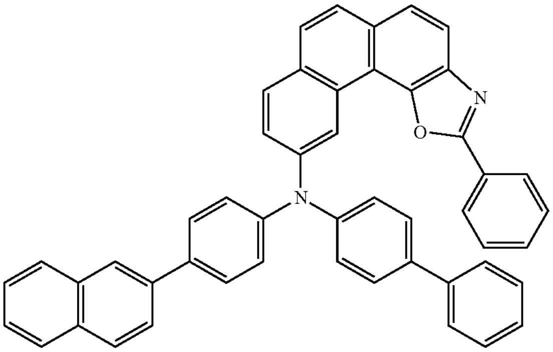
-continued
H-191
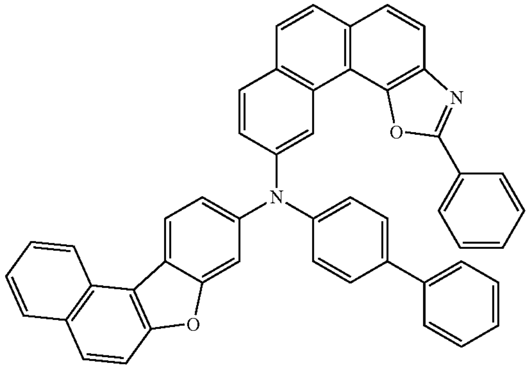
H-192
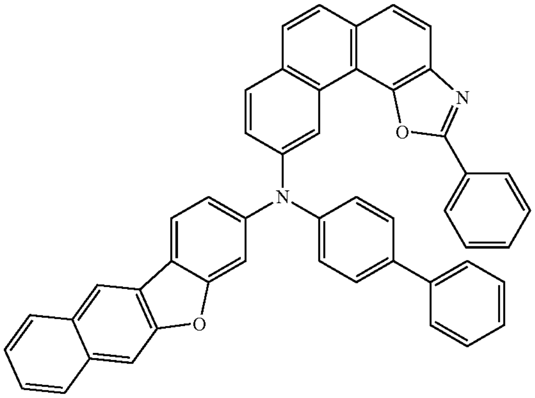
H-193
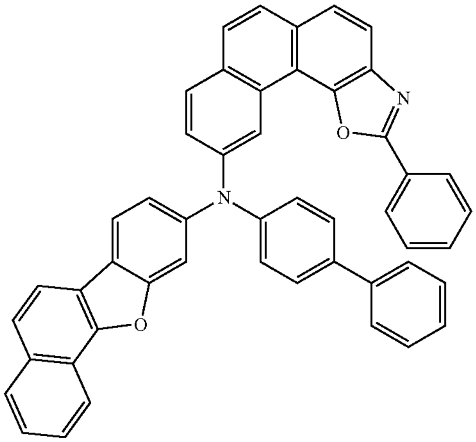

-continued
H-194
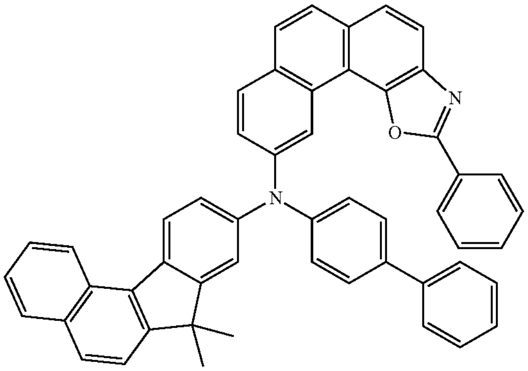
H-195
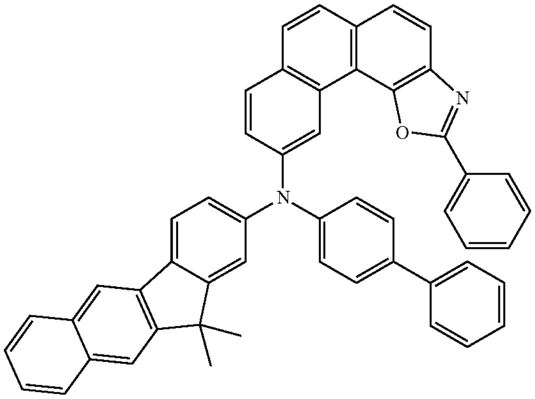
H-196
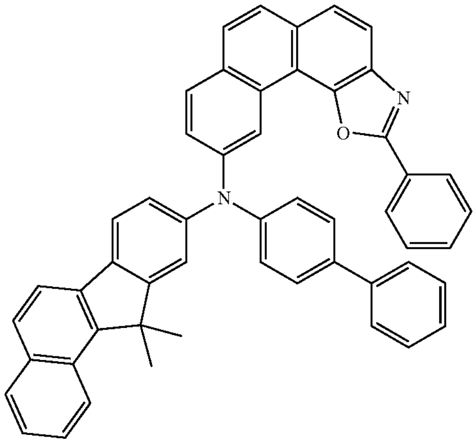
-continued
H-197
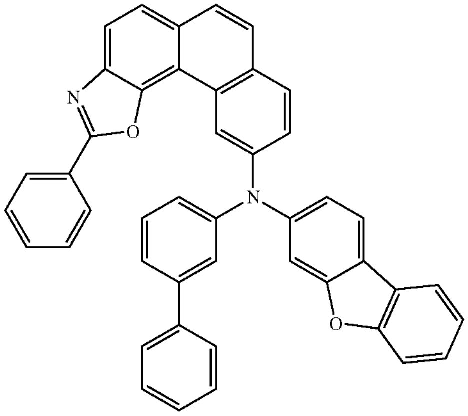
H-198
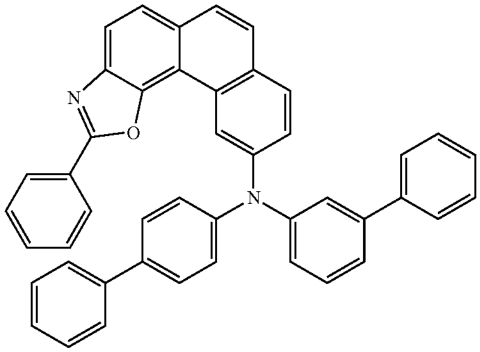
H-199
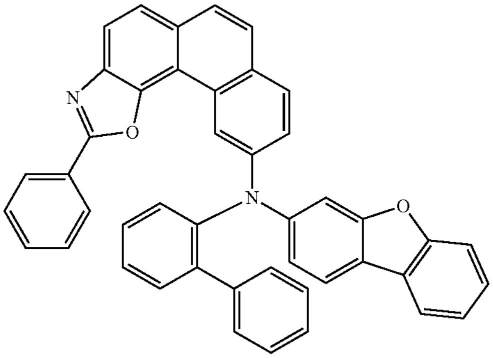
H-200
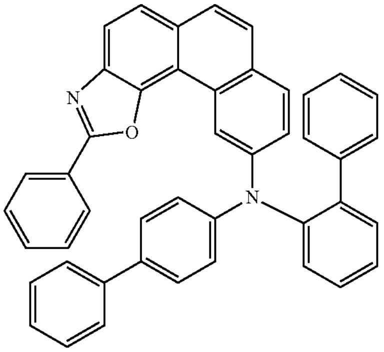

-continued
H-201
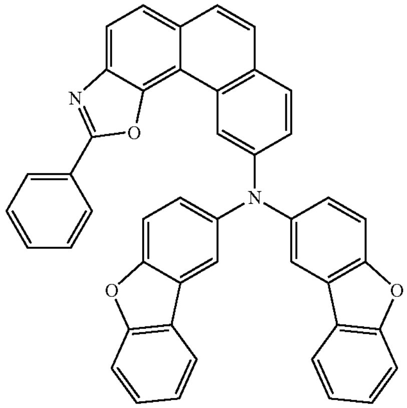
H-202
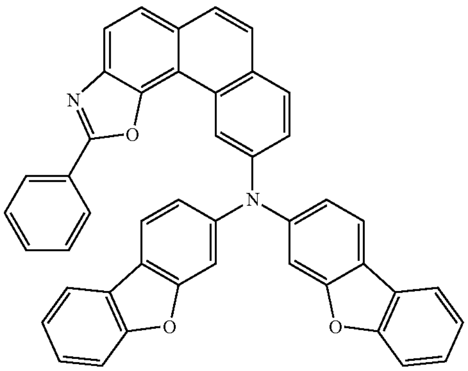
H-203
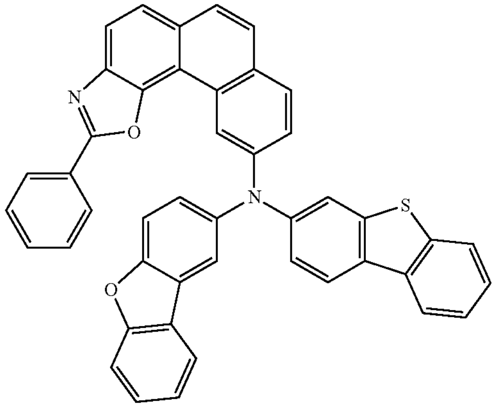
H-204
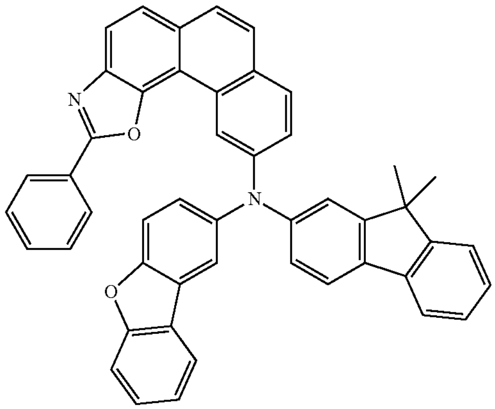
-continued
H-205
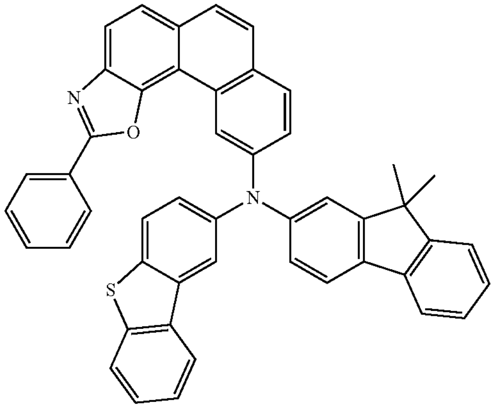
H-206
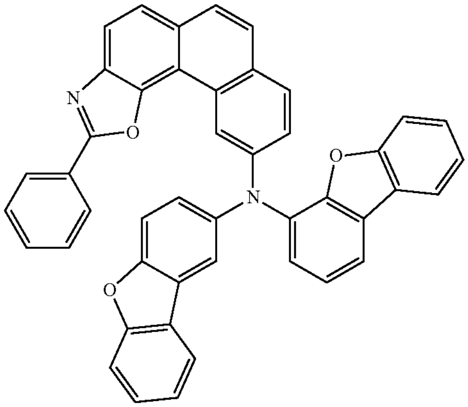
H-207
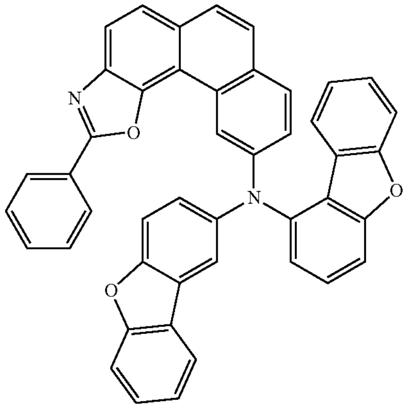
H-208
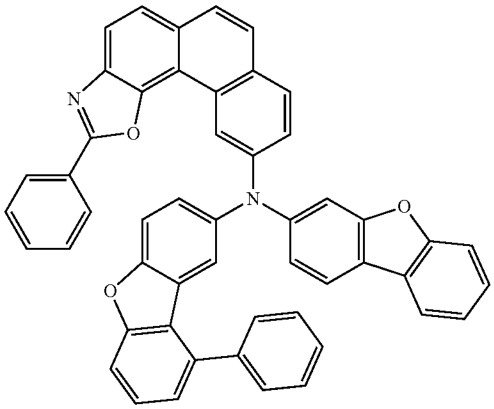

-continued
H-209
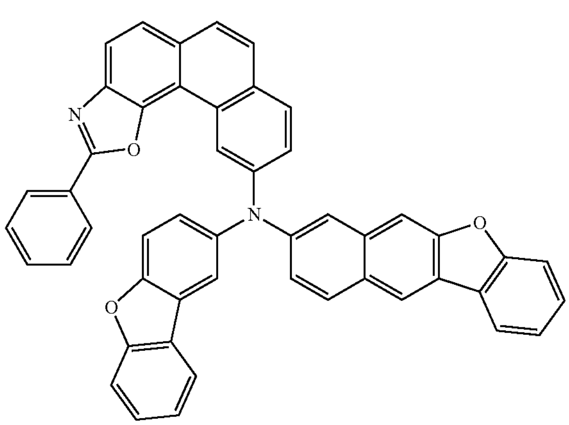
H-210
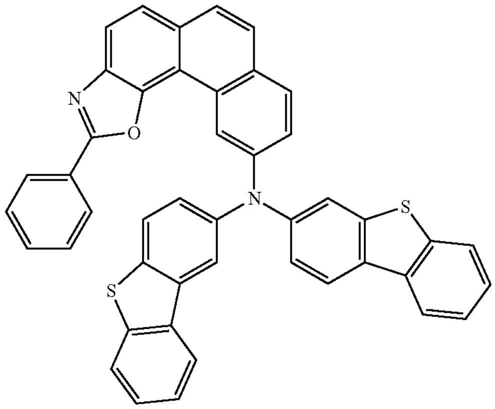
H-211
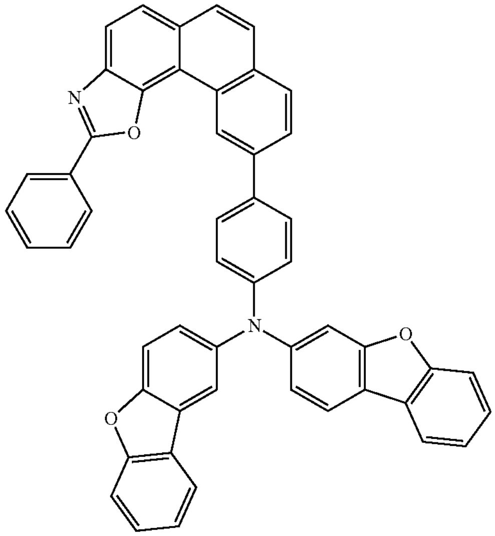
-continued
H-212
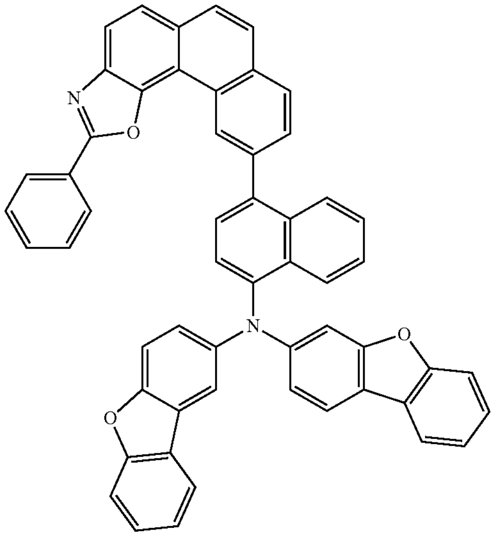
H-213
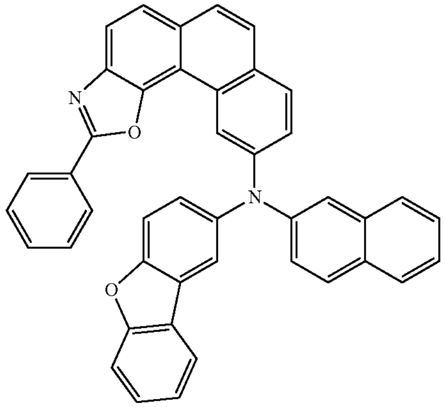
H-214
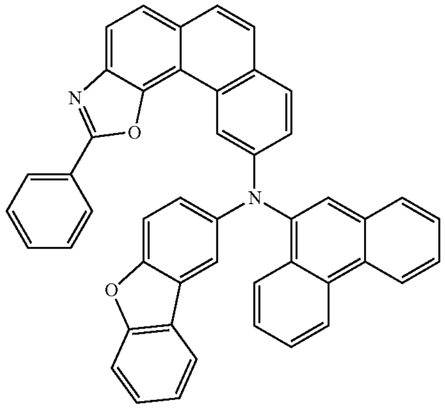

-continued

H-215

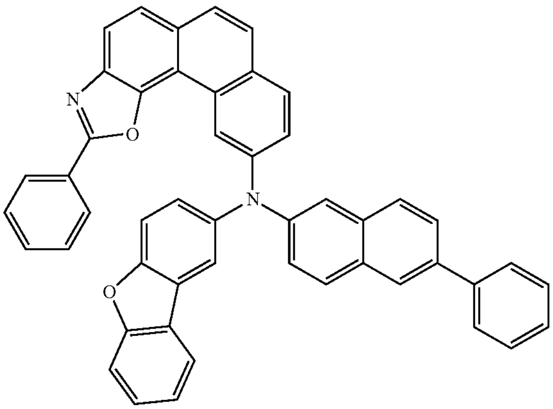

H-216

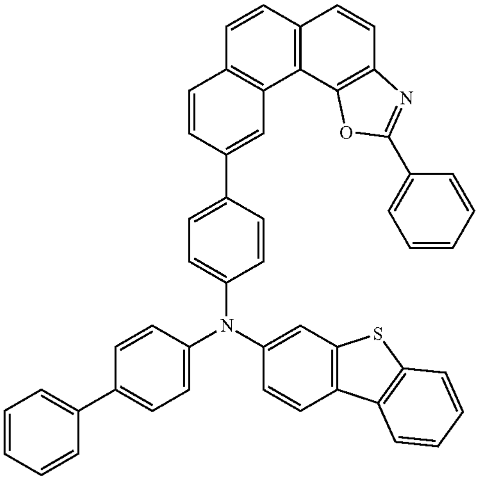

H-217

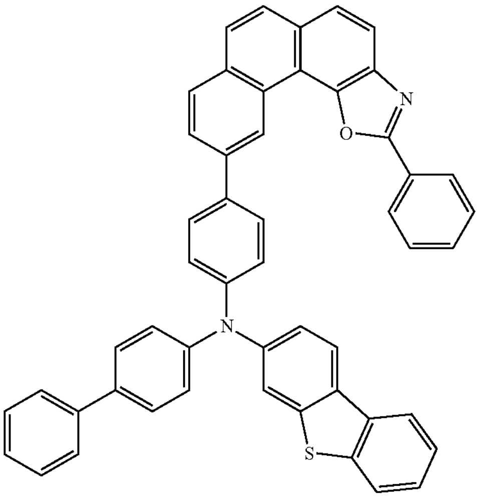

-continued

H-218

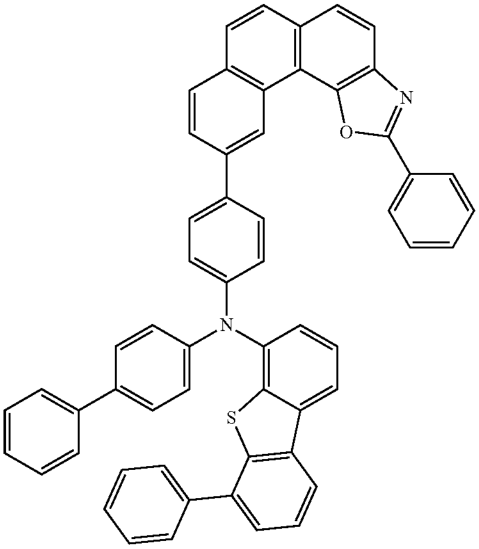

H-219

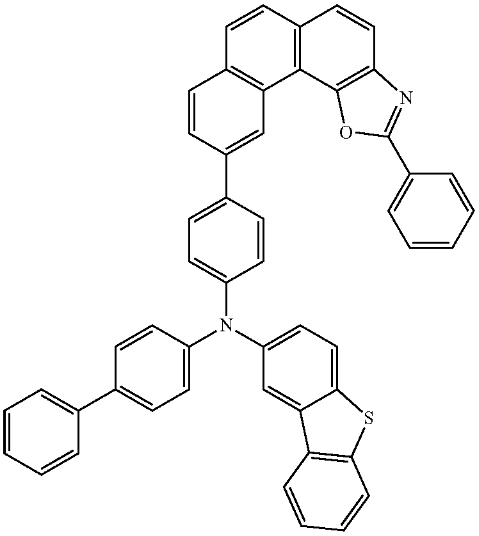

H-220

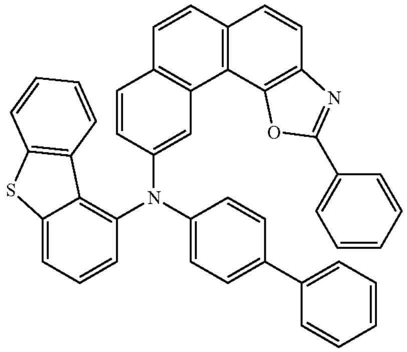

The compound represented by the formula 2 according to one embodiment may be produced by a synthetic method known to a person skilled in the art. In particular, preparation by using a synthesis method disclosed in a number of patent documents can be used. For example, it may be synthesized with reference to the method disclosed in Korean Patent Application Laid-Open No. 2017-0022865 (published on Mar. 2, 2017), but is not limited thereto.

An organic electroluminescent compound according to another embodiment of the present disclosure may be represented by the following formula 3.

(3)

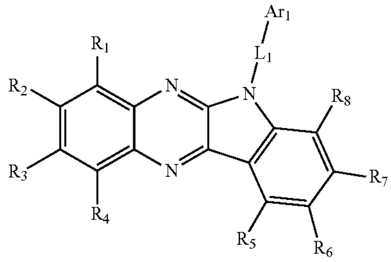

In formula 3, $L_1$ represents a single bond or a substituted or unsubstituted (C6-C30)arylene;

$Ar_1$ represents a substituted or unsubstituted (C6-C30) aryl, a substituted or unsubstituted pyridyl, a substituted or unsubstituted dibenzofuranyl, or a substituted or unsubstituted dibenzothiophenyl;

$R_1$ to $R_8$ each independently represent hydrogen, deuterium, halogen, cyano, a substituted or unsubstituted (C1-C30)alkyl, a substituted or unsubstituted (C6-C30)aryl excluding anthracene, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30) alkylamino, a substituted or unsubstituted mono- or di-(C2-C30)alkenylamino, a substituted or unsubstituted (C1-C30) alkyl(C2-C30)alkenylamino, a substituted or unsubstituted (C1-C30)alkyl(C6-C30)arylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl (3- to 30-membered)heteroarylamino; or may be linked to the adjacent substituents to form a ring(s);

provided that at least one of $R_1$ to $R_4$, or at least one of $R_5$ to $R_8$ represents $-L_{11}-(Ar_{11})_a$;

$L_{11}$ represents a single bond or a substituted or unsubstituted (C6-C30)arylene excluding anthracenylene;

$Ar_{11}$ represents a substituted or unsubstituted (C6-C30) aryl excluding anthracene, a substituted or unsubstituted pyridyl, a substituted or unsubstituted dibenzofuranyl, or a substituted or unsubstituted dibenzothiophenyl;

a is an integer of 1 or 2; and when a is an integer of 2, each of $Ar_{11}$ may be the same or different;

provided that when $Ar_1$, $R_1$ to $R_5$, $L_{11}$, and $Ar_{11}$ are substituted (C6-C30)aryl(ene), the case where (C6-C30)aryl (ene) is substituted with an amino group is excluded.

In one embodiment, $L_1$ may be a single bond or a substituted or unsubstituted (C6-C25)arylene, preferably a single bond or a substituted or unsubstituted (C6-C18) arylene, more preferably a single bond or a substituted or unsubstituted (C6-C12)arylene. For example, $L_1$ may be a single bond, phenylene unsubstituted or substituted with phenyl, or unsubstituted naphthylene.

In one embodiment, $Ar_1$ may be a substituted or unsubstituted (C6-C30)aryl, a substituted or unsubstituted pyridyl, a substituted or unsubstituted dibenzofuranyl, or a substituted or unsubstituted dibenzothiophenyl, preferably a substituted or unsubstituted (C6-C25)aryl, pyridyl unsubstituted or substituted with (C6-C30)aryl, a substituted or unsubstituted dibenzofuranyl, or a substituted or unsubstituted dibenzothiophenyl, more preferably a substituted or unsubstituted (C6-C18)aryl, pyridyl unsubstituted or substituted with (C6-C18)aryl, unsubstituted dibenzofuranyl, or unsubstituted dibenzothiophenyl. For example, $Ar_1$ may be phenyl unsubstituted or substituted with deuterium, phenyl unsubstituted or substituted with at least one of phenyl; naphthyl; dibenzofuranyl; and dibenzothiophenyl, unsubstituted m-biphenyl, unsubstituted m-terphenyl, naphthyl unsubstituted or substituted with phenyl unsubstituted or substituted with one or more deuterium, pyridyl unsubstituted or substituted with phenyl unsubstituted or substituted with one or more deuterium, unsubstituted dibenzofuranyl, or unsubstituted dibenzothiophenyl.

In one embodiment, $R_1$ to $R_5$ each independently may be hydrogen, deuterium, halogen, cyano, a substituted or unsubstituted (C1-C30)alkyl, a substituted or unsubstituted (C6-C30)aryl excluding anthracene, or a substituted or unsubstituted (5- to 30-membered)heteroaryl, preferably hydrogen, deuterium, or at least one (C6-C30)aryl-substituted or unsubstituted (C6-C25)aryl excluding anthracene, or a substituted or unsubstituted (5- to 25-membered)heteroaryl, more preferably hydrogen, deuterium, at least one (C6-C30)aryl-substituted or unsubstituted (C6-C18)aryl excluding anthracene, or a substituted or unsubstituted (5- to 25-membered)heteroaryl, with the proviso that at least one of $R_1$ to $R_4$, or at least one of $R_5$ to $R_8$ is $-L_{11}-(Ar_{11})_a$.

In one embodiment, $L_{11}$ may be a single bond, phenylene unsubstituted or substituted with phenyl unsubstituted or substituted with one or more deuterium, unsubstituted m-biphenylene, or unsubstituted p-biphenylene.

In one embodiment, when a is an integer of 2, $L_{11}$ may be a substituted or unsubstituted (C6-C30)arylene excluding anthracenylene, for example, unsubstituted phenylene.

In one embodiment, $Ar_{11}$ may be phenyl unsubstituted or substituted with at least one of one or more deuterium; phenyl unsubstituted or substituted with deuterium; naphthyl; dibenzofuranyl; and dibenzothiophenyl, unsubstituted naphthyl, unsubstituted o-biphenyl, unsubstituted m-biphenyl, p-biphenyl unsubstituted or substituted with phenyl, p-terphenyl unsubstituted or substituted with phenyl unsubstituted or substituted with one or more deuterium, m-terphenyl unsubstituted or substituted with phenyl unsubstituted or substituted with one or more deuterium, unsubstituted o-terphenyl, unsubstituted phenanthrenyl, unsubstituted chrysenyl, unsubstituted dibenzofuranyl, or unsubstituted dibenzothiophenyl.

In the formula 3, when $Ar_1$, $R_1$ to $R_3$, $L_{11}$, and $Ar_{11}$ are substituted (C6-C30)aryl(ene), the case where (C6-C30)aryl (ene) is substituted with an amino group is excluded.

The compound represented by the above formula 3 may be more specifically illustrated by the following compounds, but is not limited thereto.

C-1
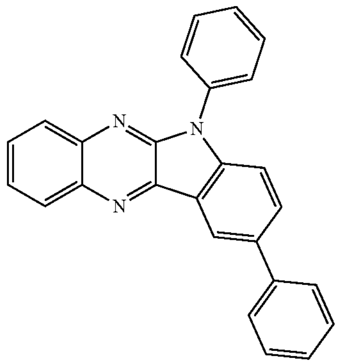
C-2
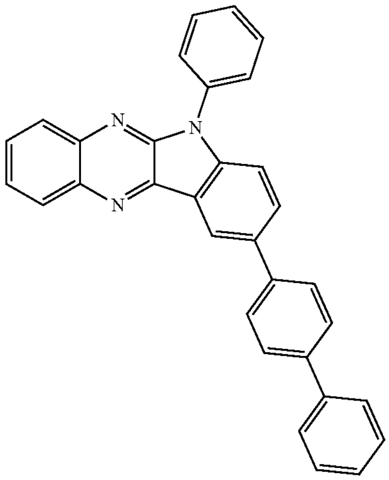
C-3
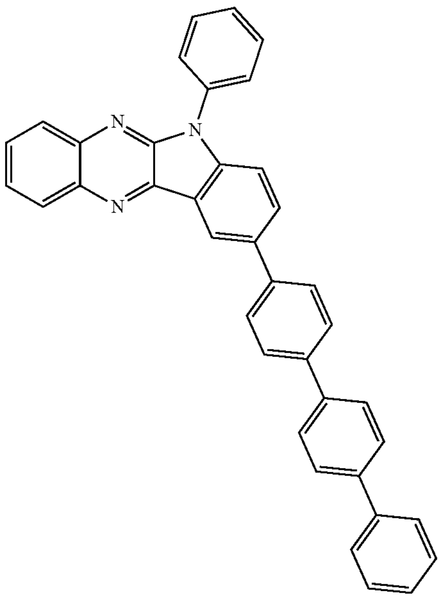
-continued
C-4
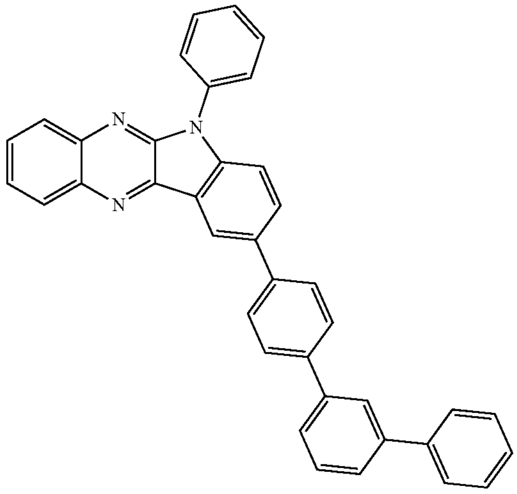
C-5
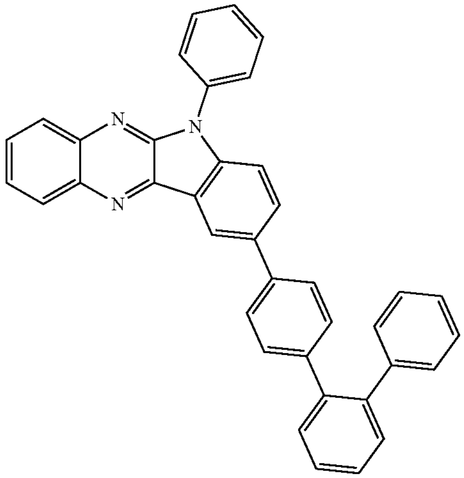
C-6
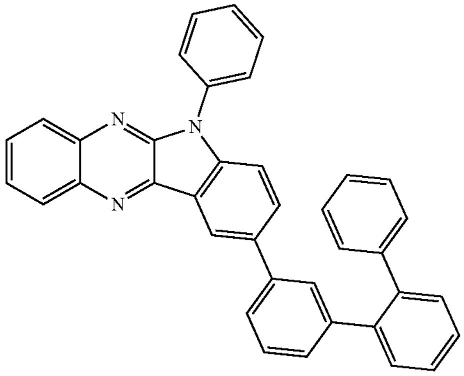

-continued
C-7
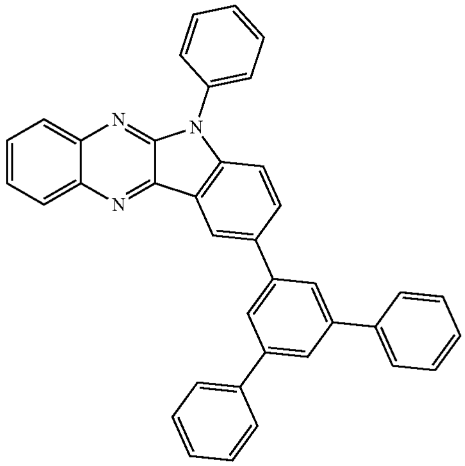
C-8
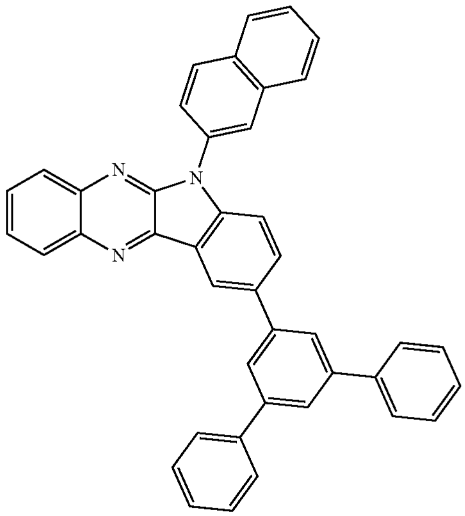
C-9
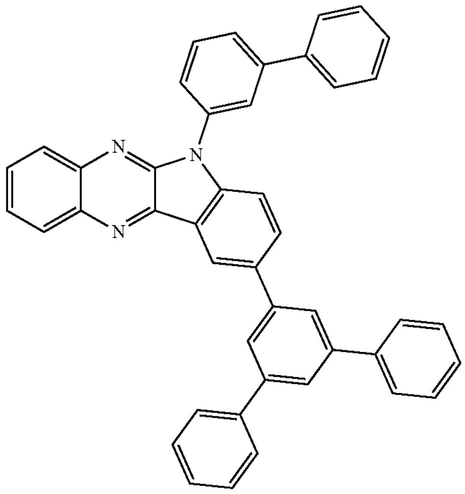
-continued
C-10
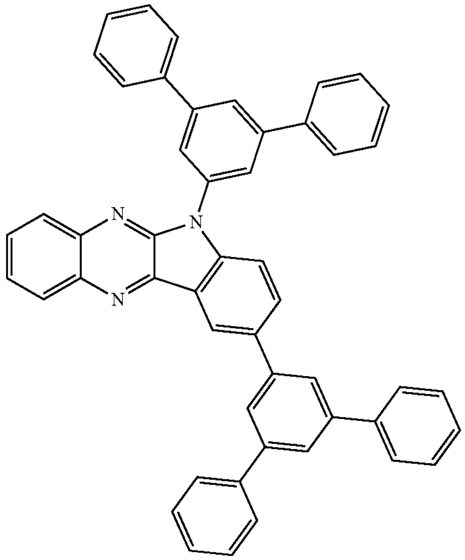
C-11
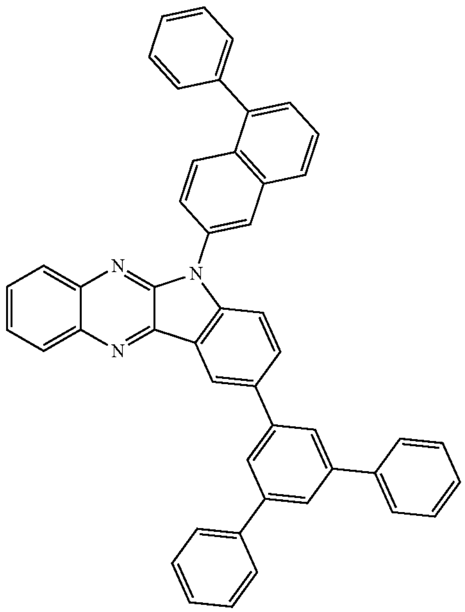
C-12
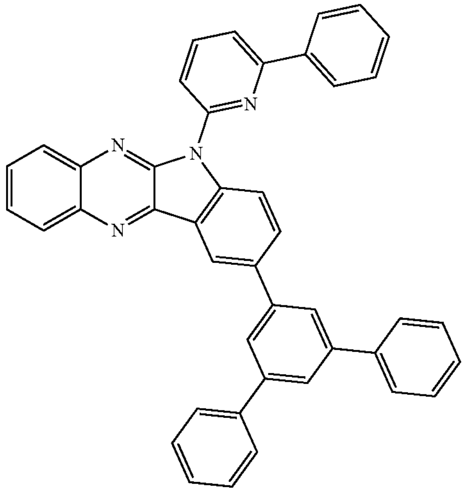

-continued
C-13
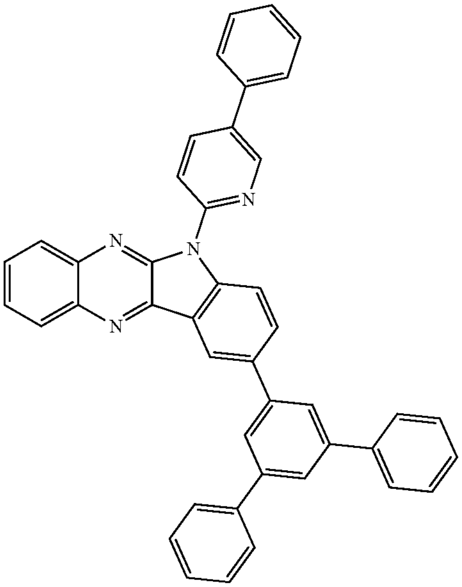
C-14
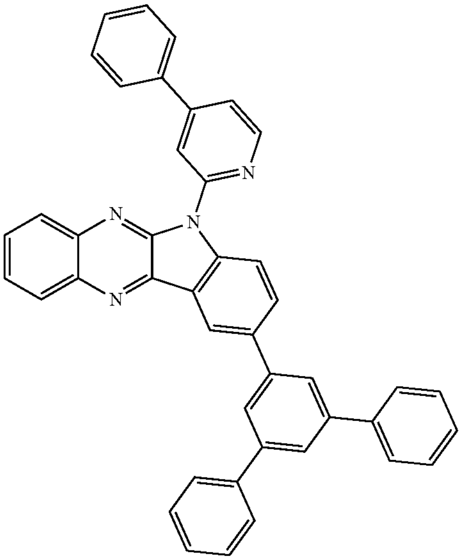
C-15
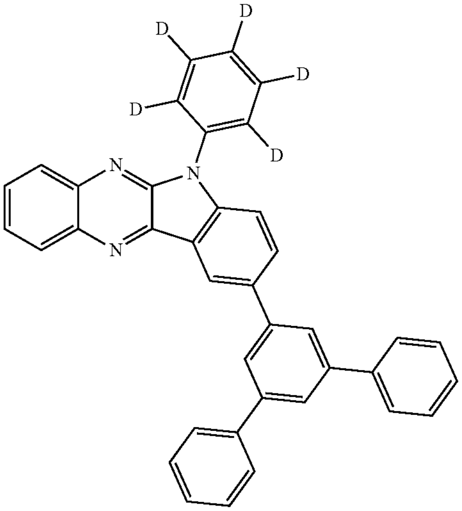
-continued
C-16
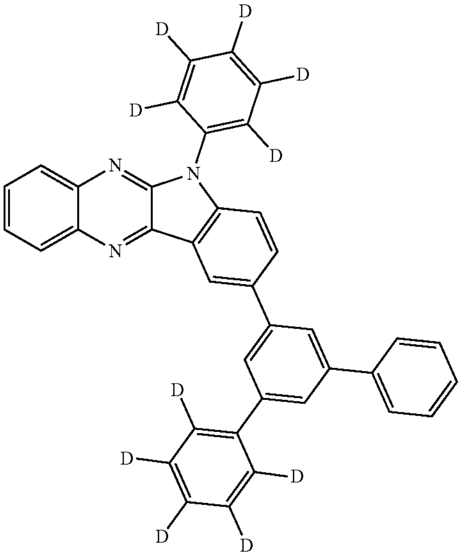
C-17
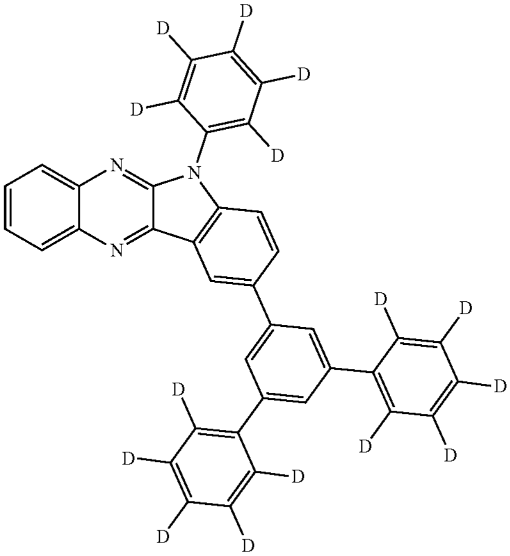
C-18
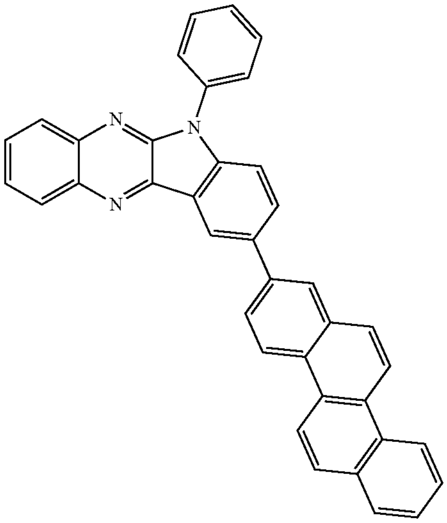

-continued
C-19
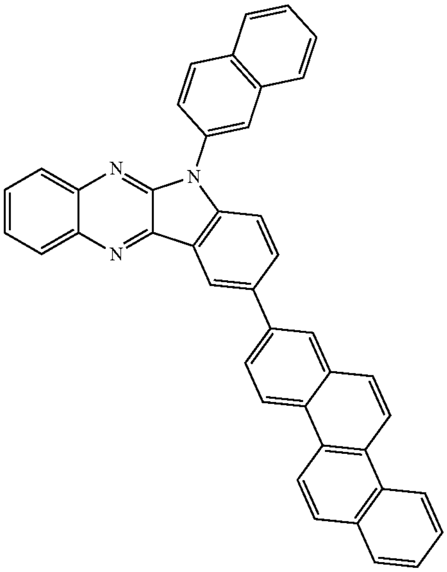
C-20
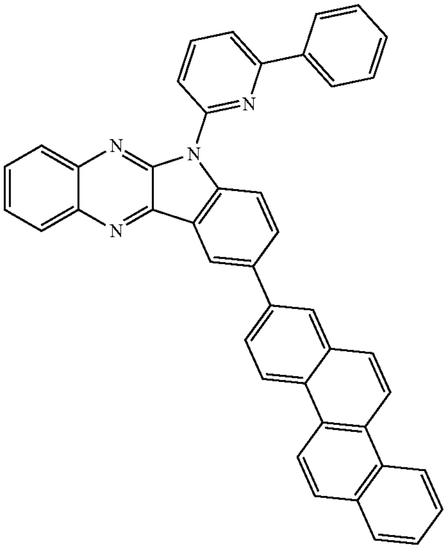
C-21
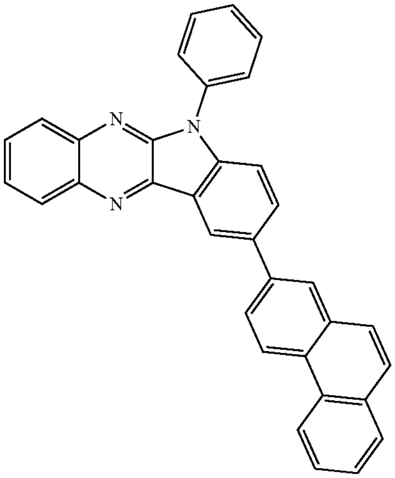
-continued
C-22
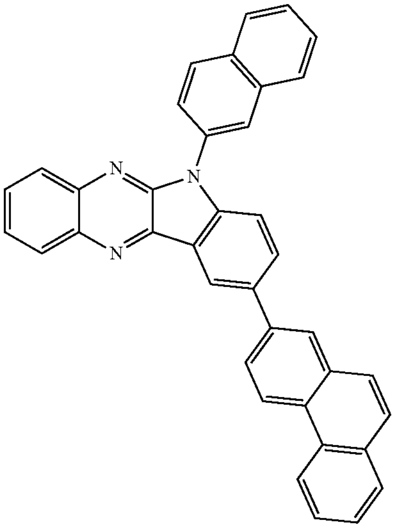
C-23
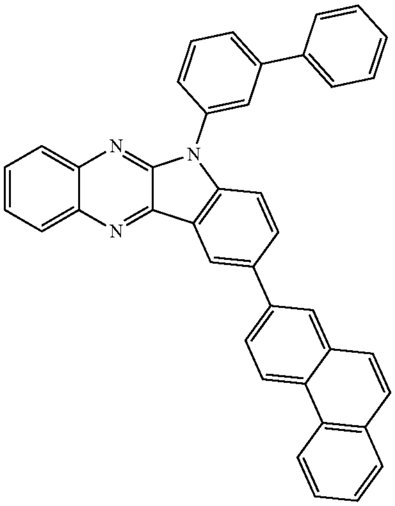
C-24
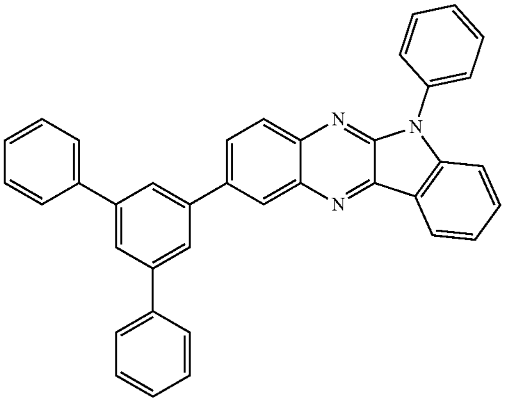

-continued
C-25
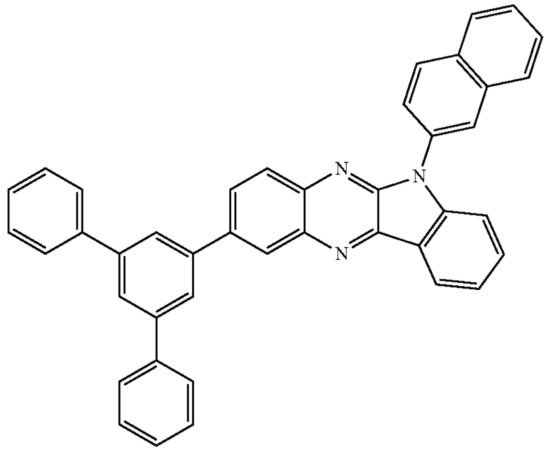
C-26
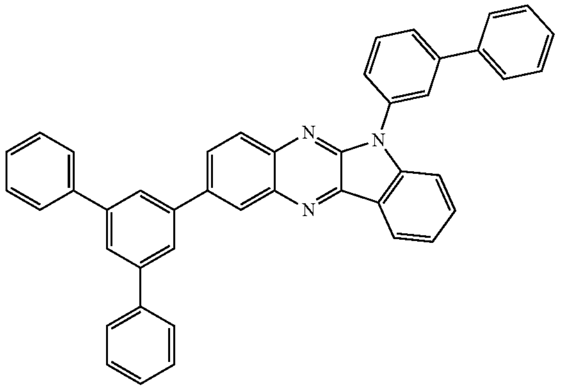
C-27
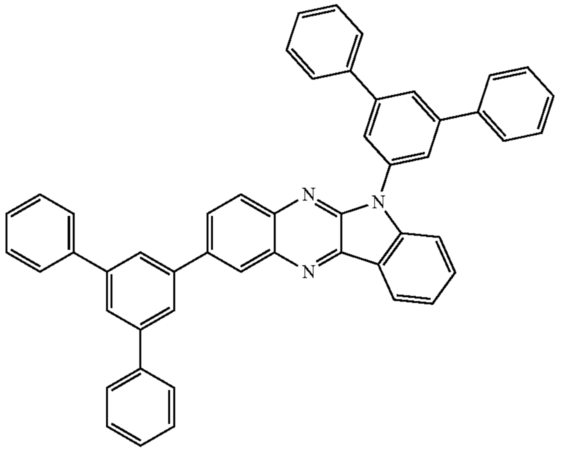
-continued
C-28
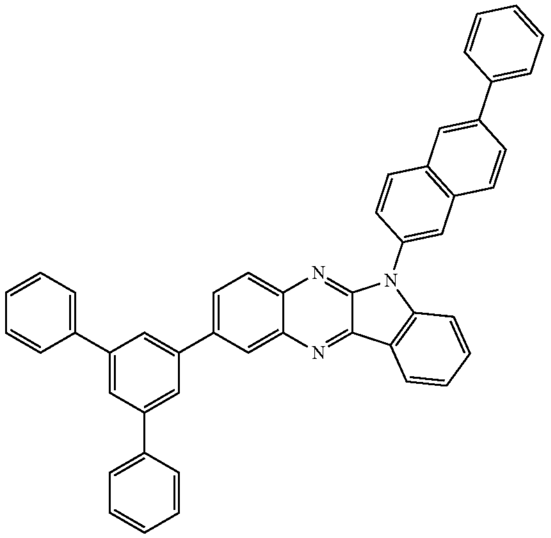
C-29
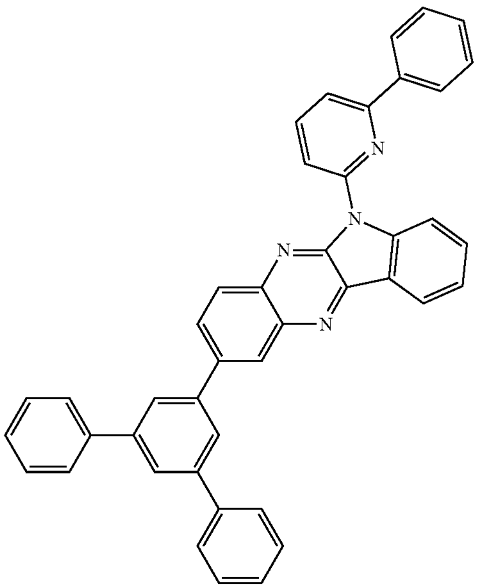

-continued
C-30
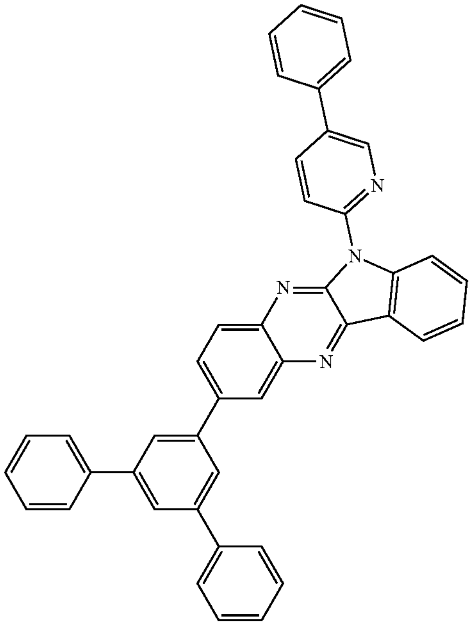
C-31
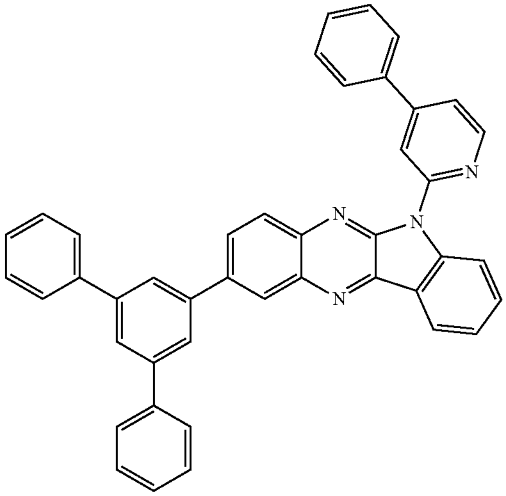
C-32
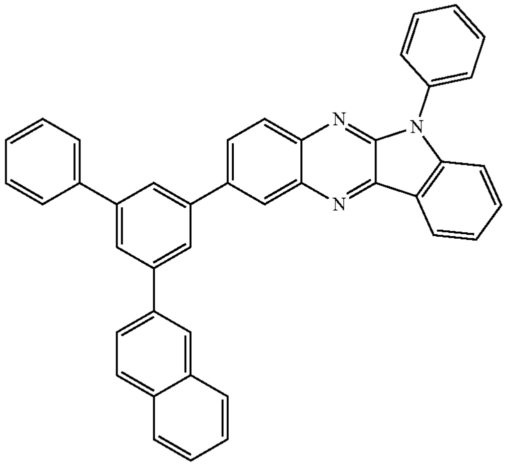
-continued
C-33
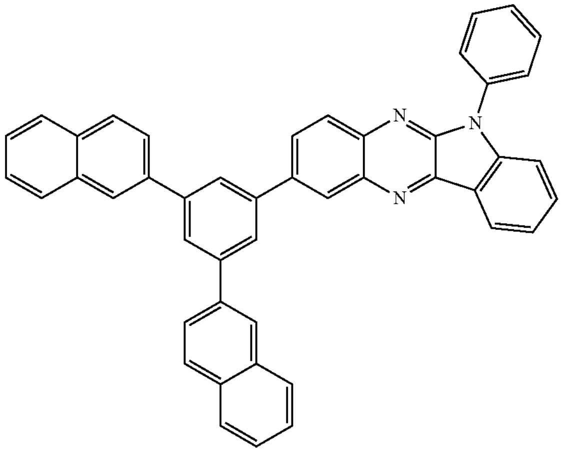
C-34
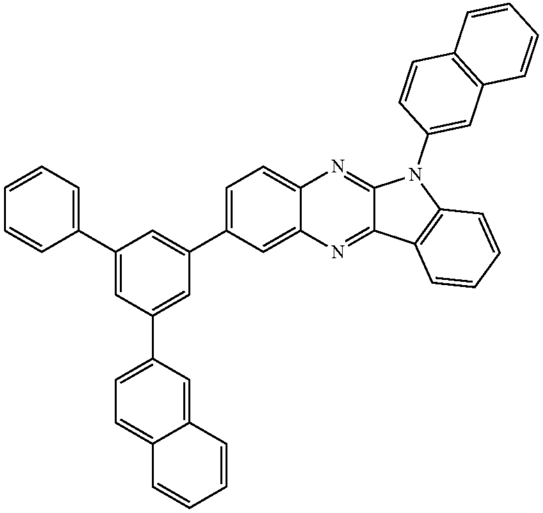
C-35
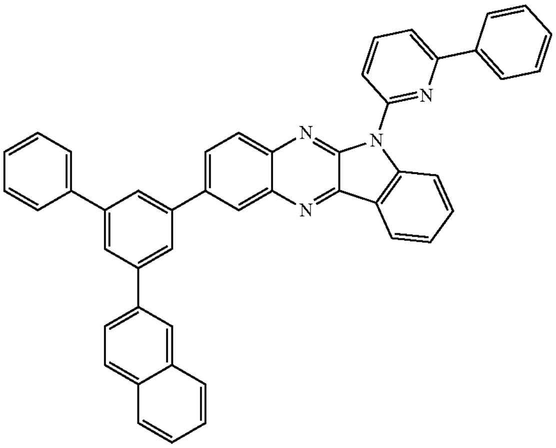

-continued
C-36
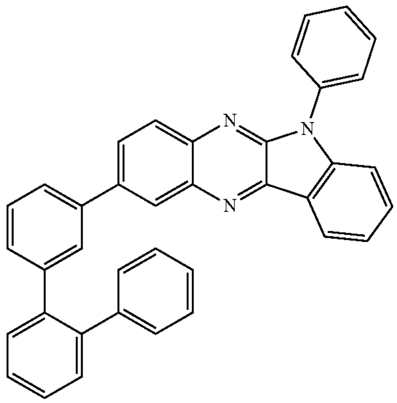
C-37
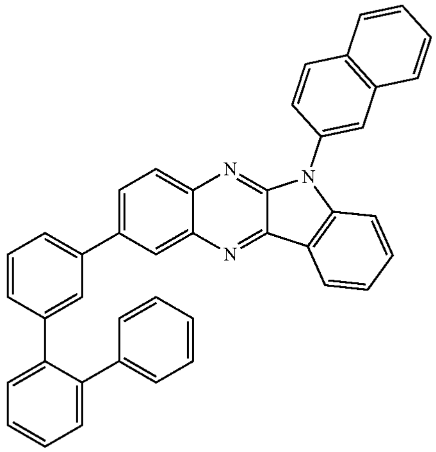
C-38
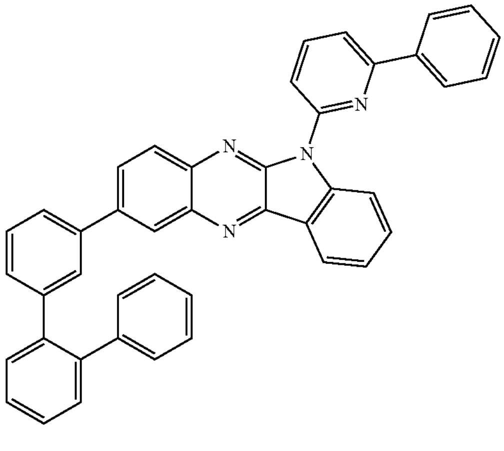
-continued
C-39
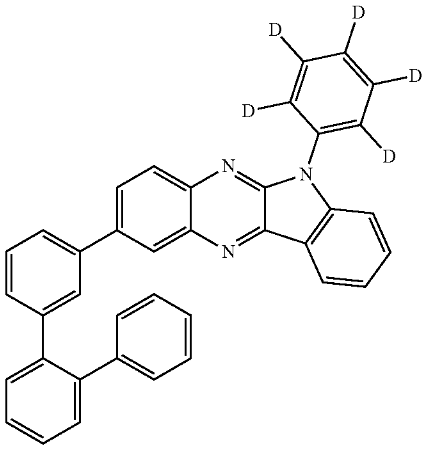
C-40
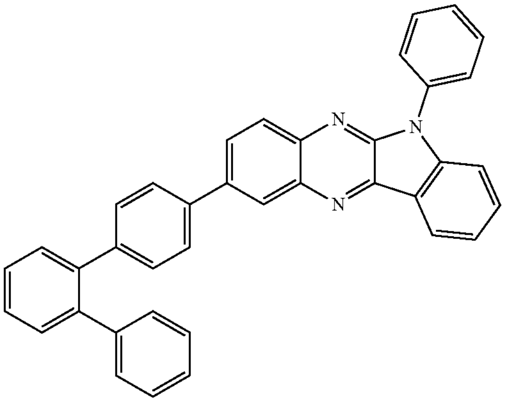
C-41
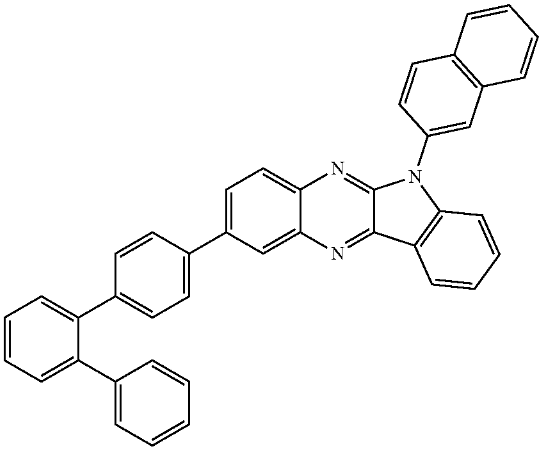

-continued
C-42
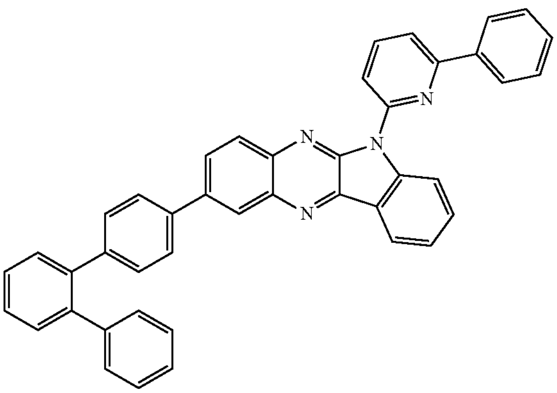
C-43
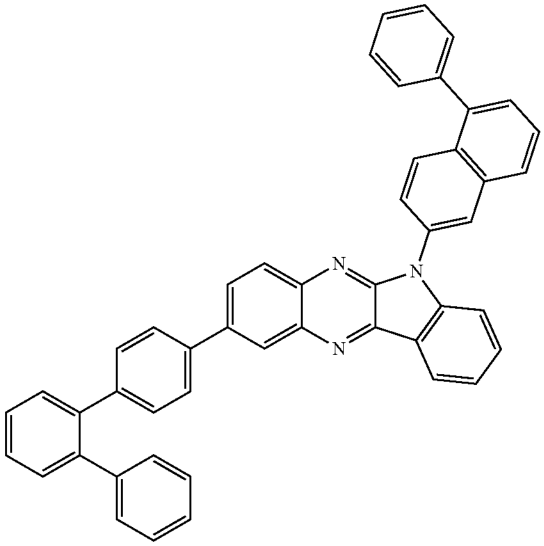
C-44
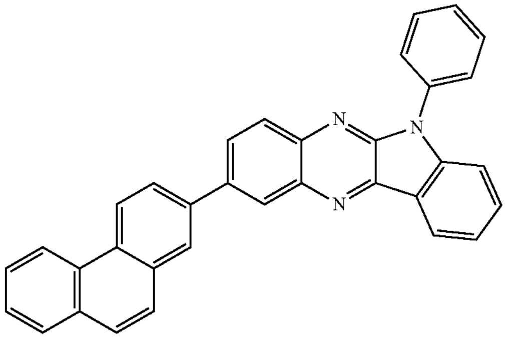
C-45
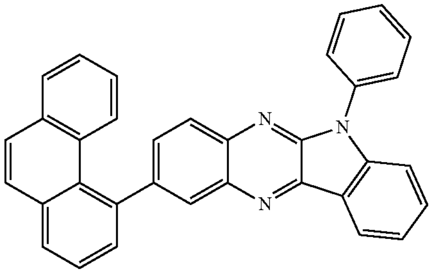
-continued
C-46
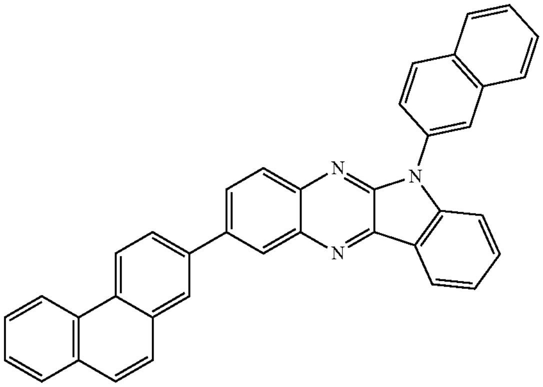
C-47
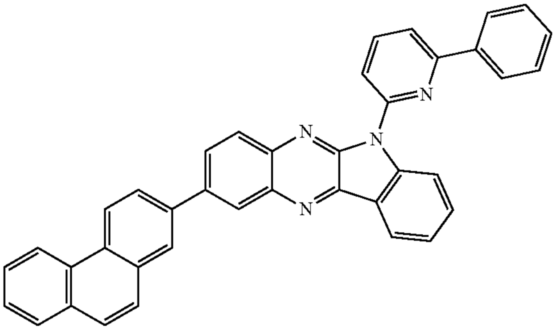
C-48
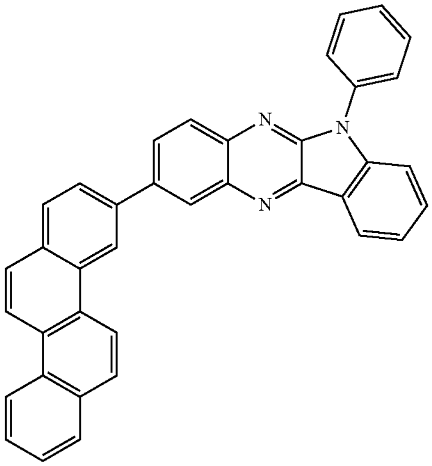
C-49
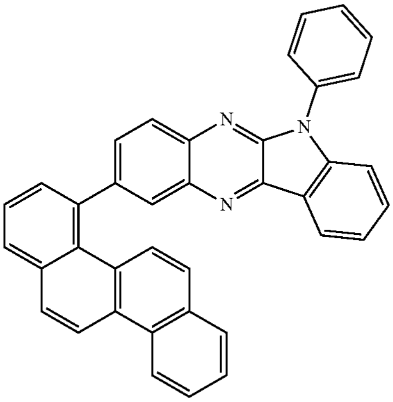

-continued
C-50
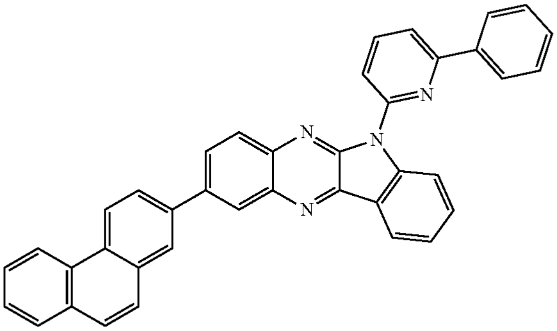
C-51
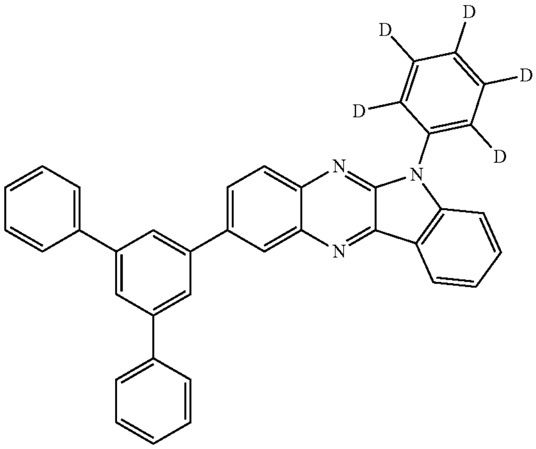
C-52
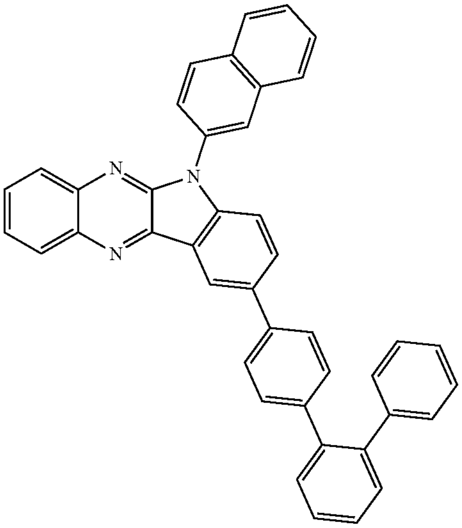
-continued
C-53
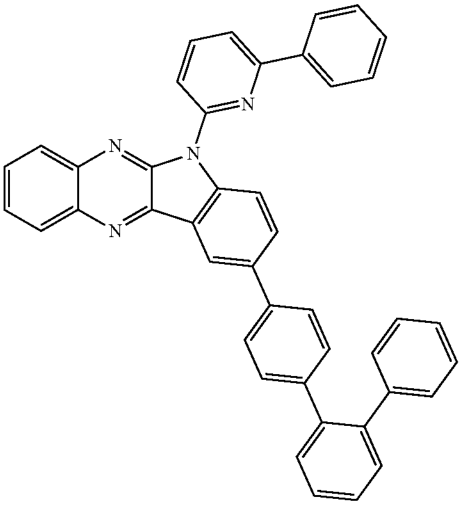
C-54
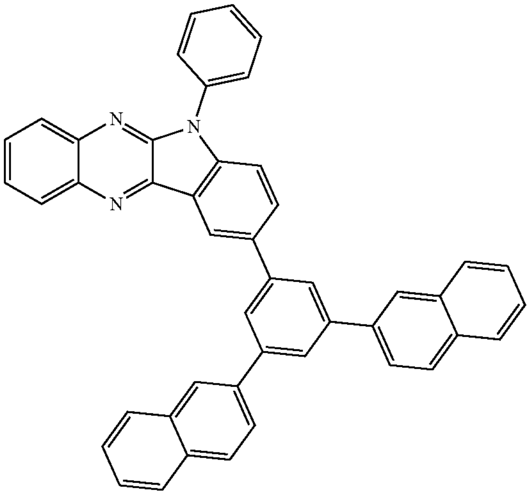
C-55
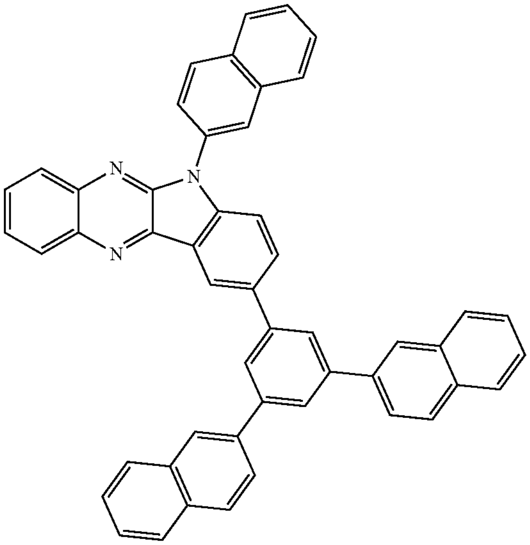

-continued
C-56
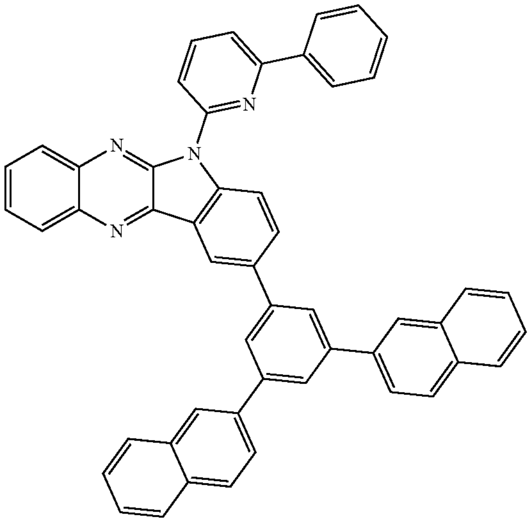
C-57
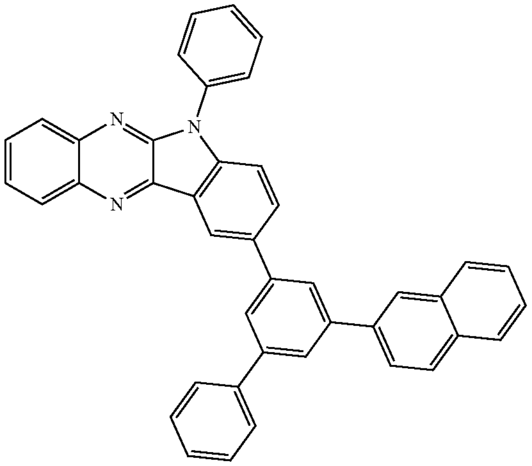
C-58
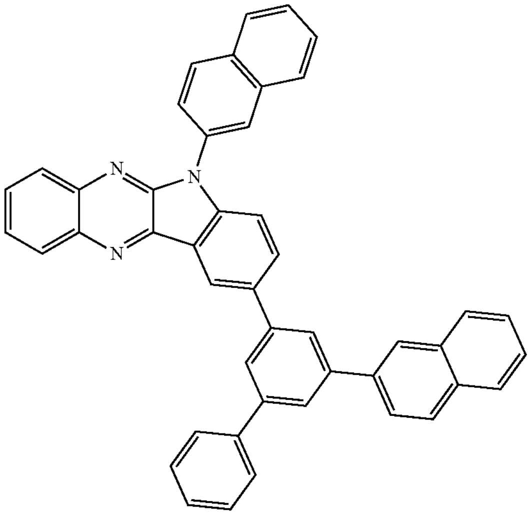
-continued
C-59
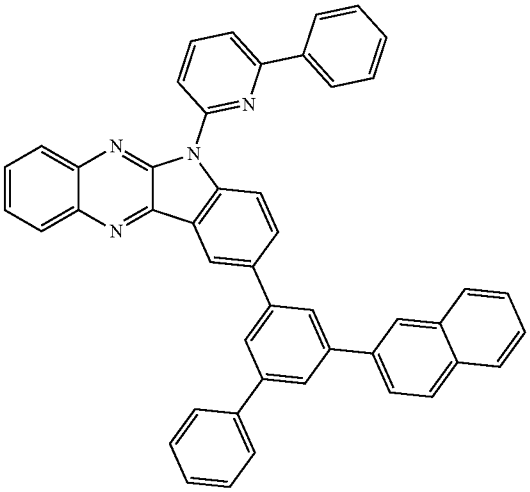
C-60
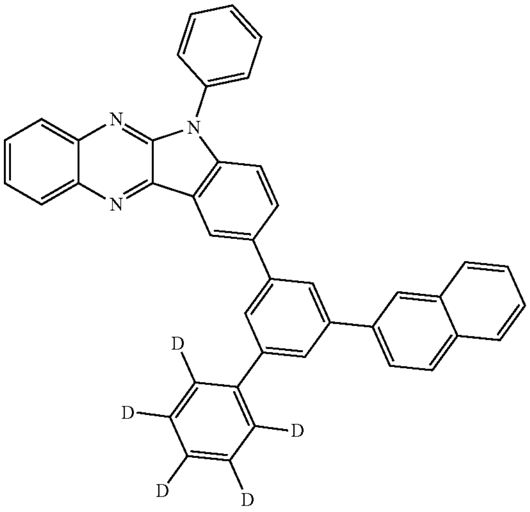
C-61
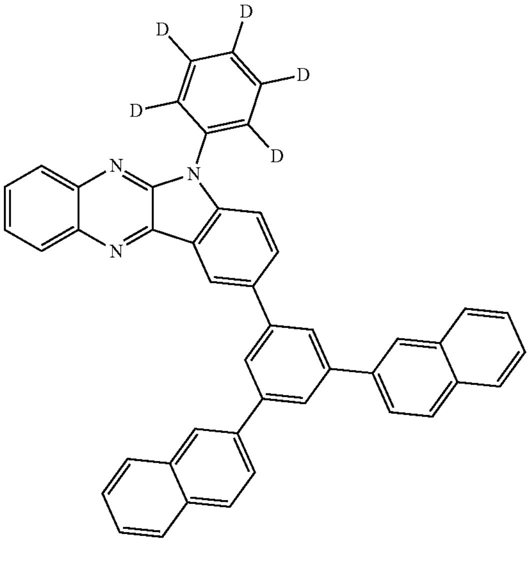

-continued
C-62
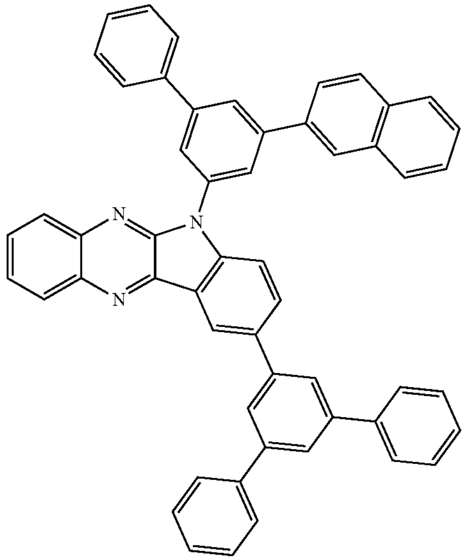
C-63
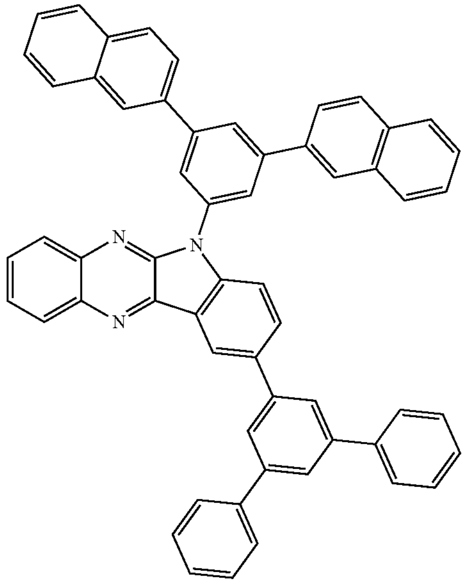
C-64
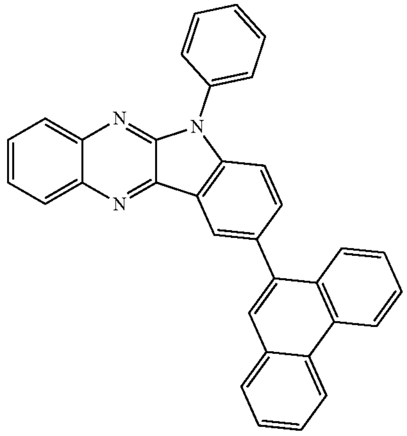
-continued
C-65
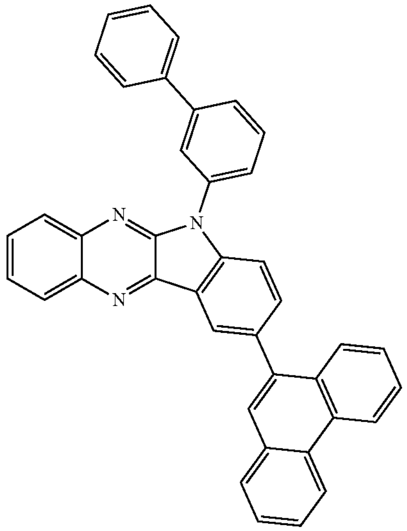
C-66
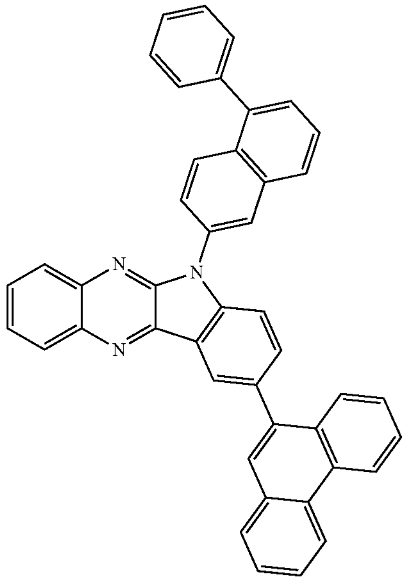
C-67
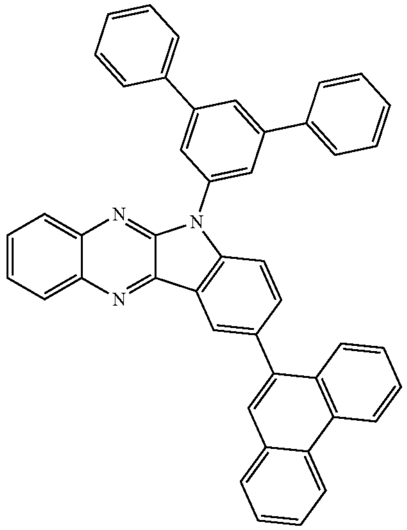

-continued
C-68
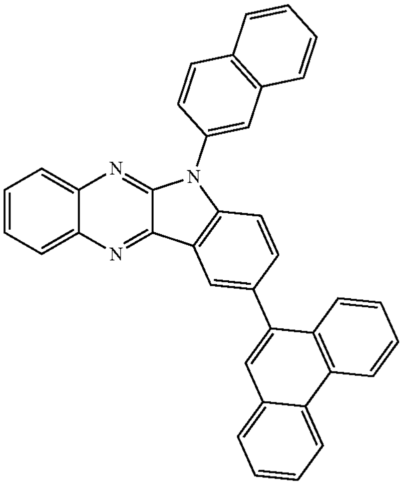
C-69
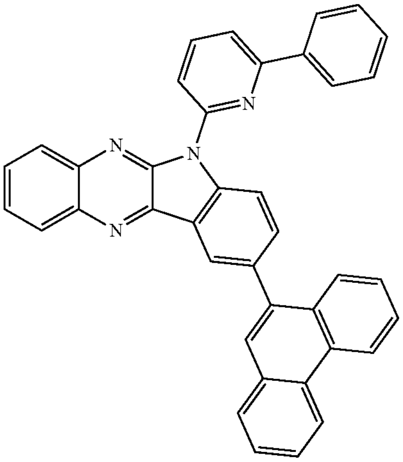
C-70
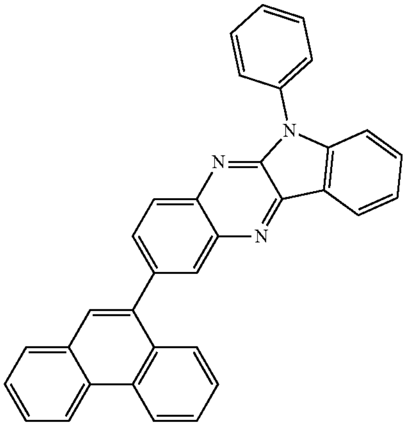
-continued
C-71
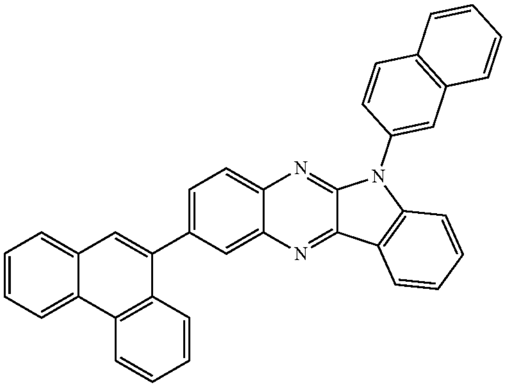
C-72
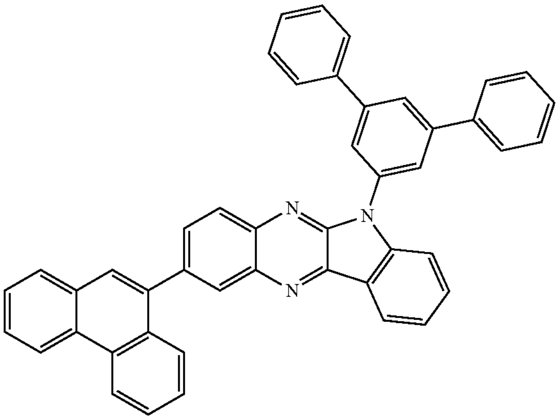
C-73
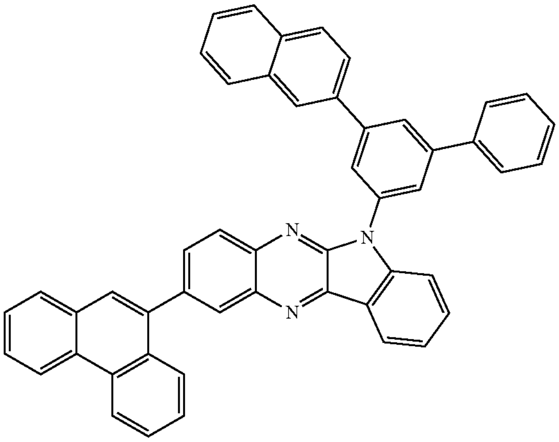

-continued
C-74
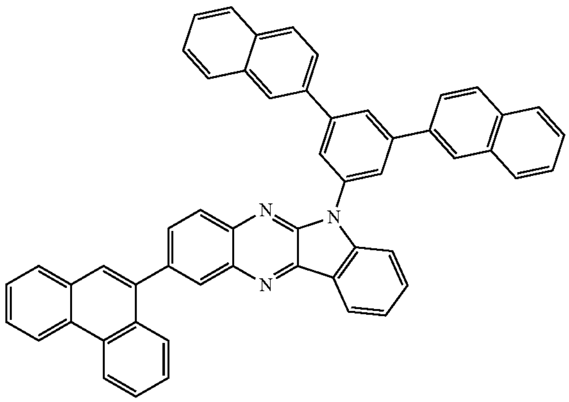
C-75
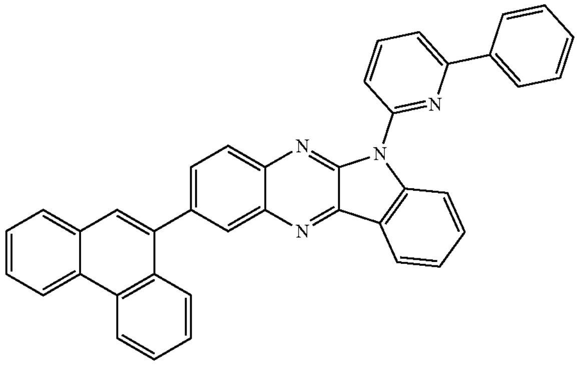
C-76
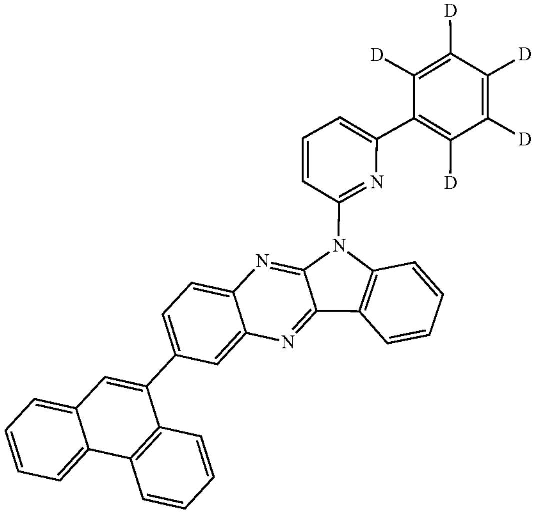
-continued
C-77
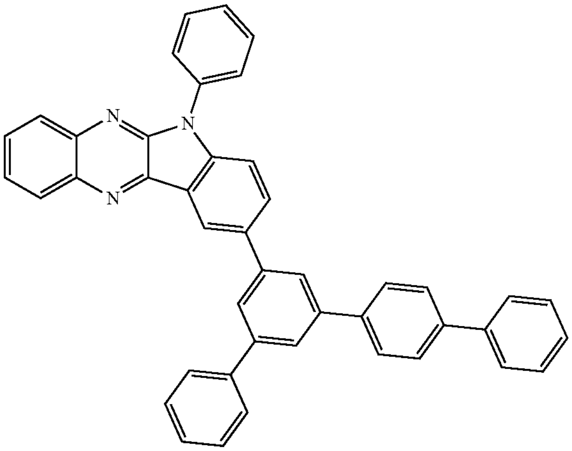
C-78
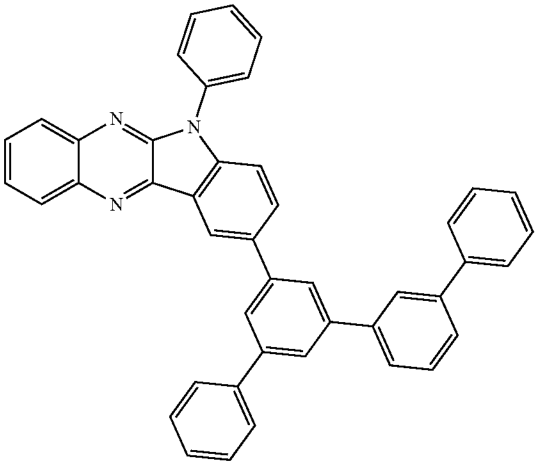
C-79
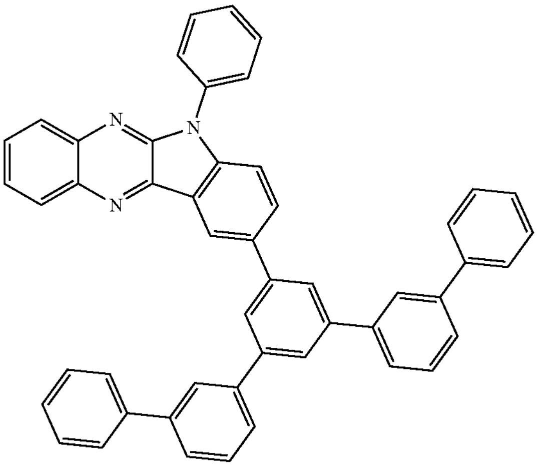

-continued
C-80
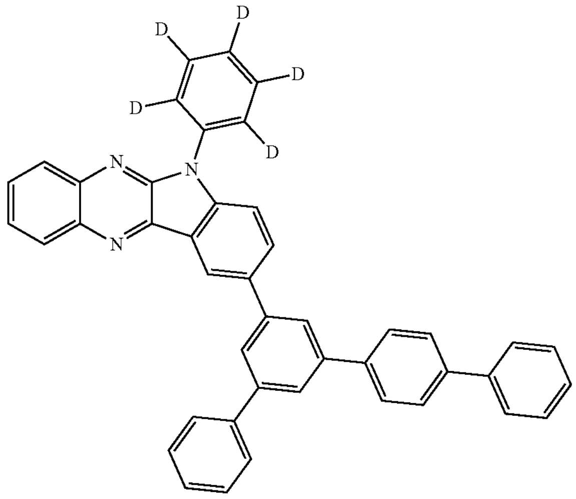
C-81
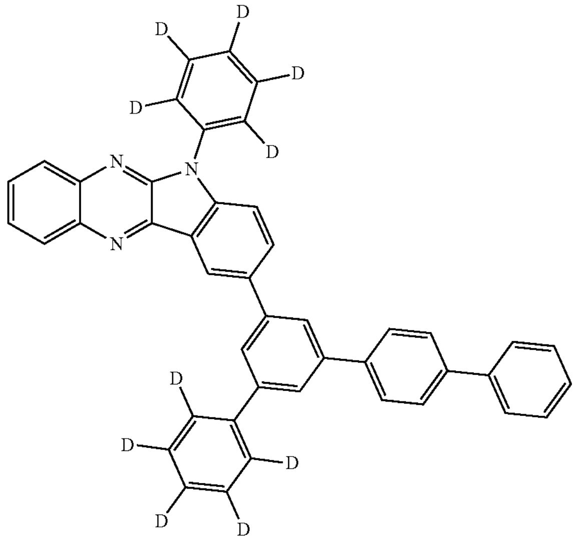
C-82
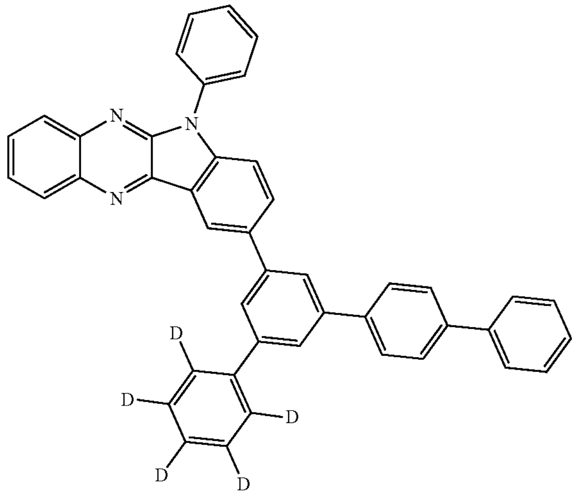
-continued
C-83
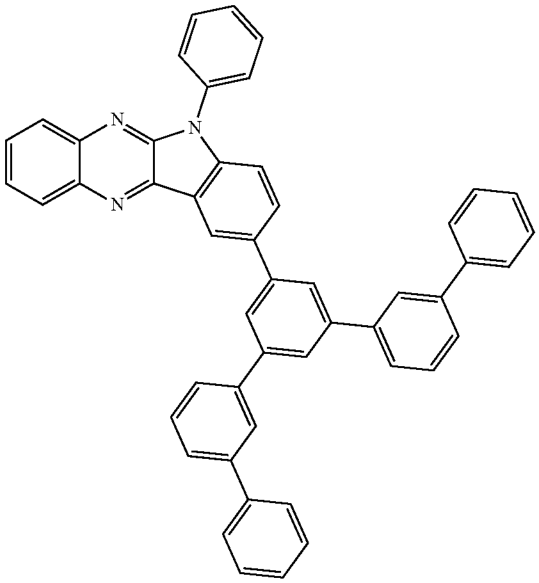
C-84
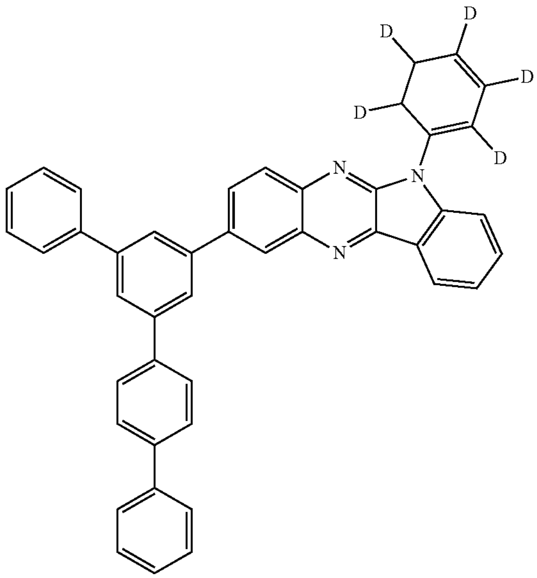

-continued
C-85
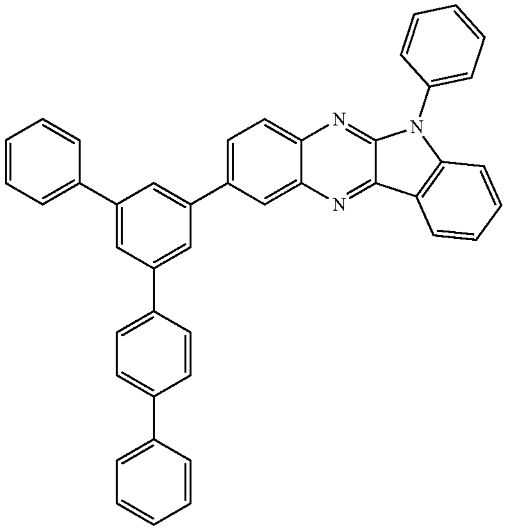
C-86
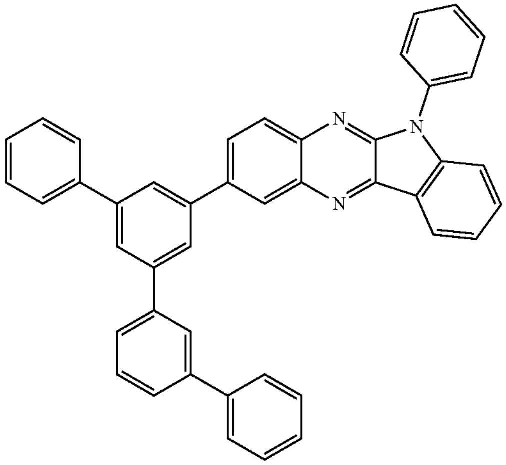
C-87
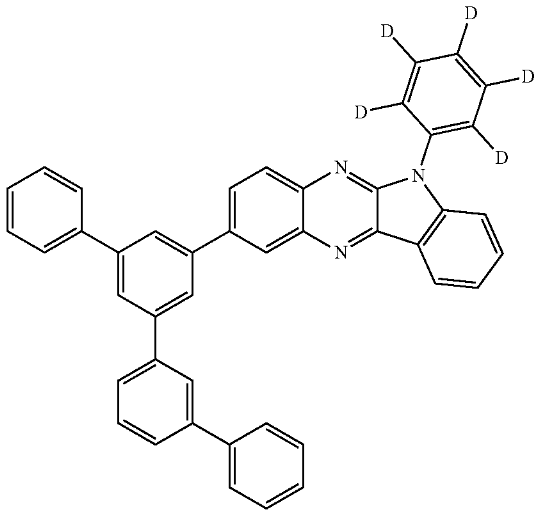
-continued
C-88
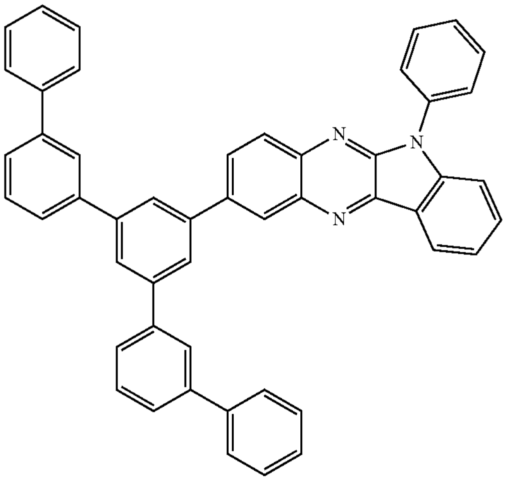
C-89
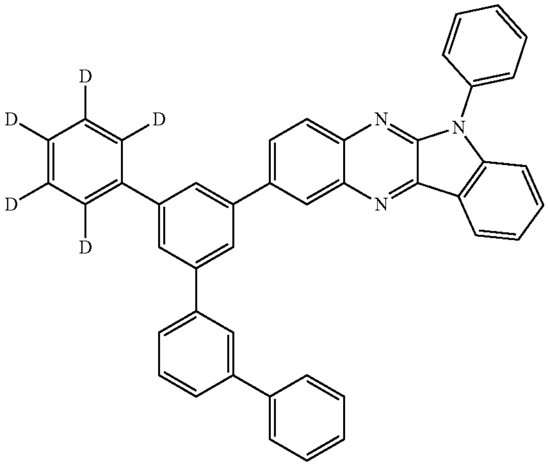
C-90
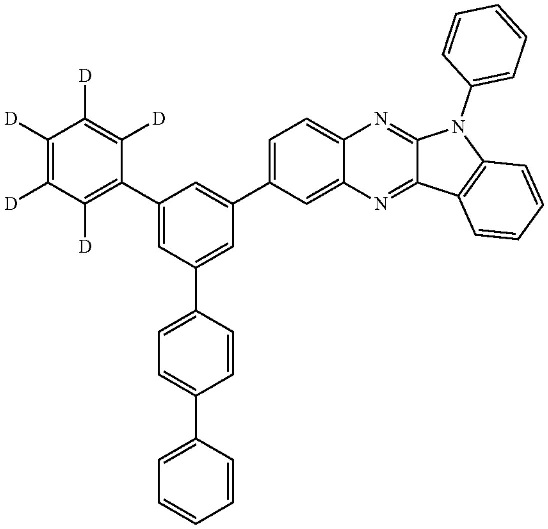

-continued
C-91
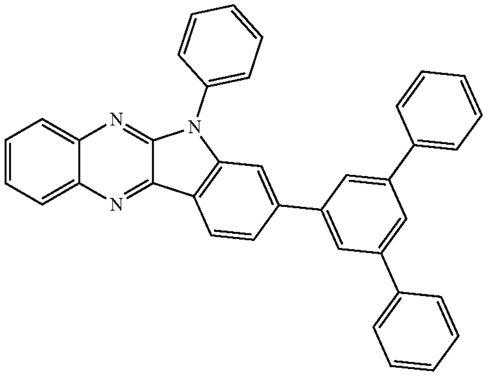
C-92
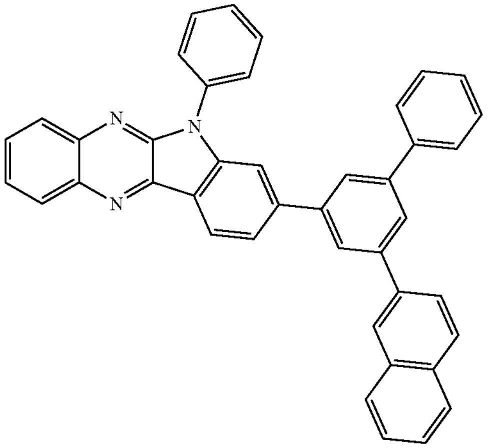
C-93
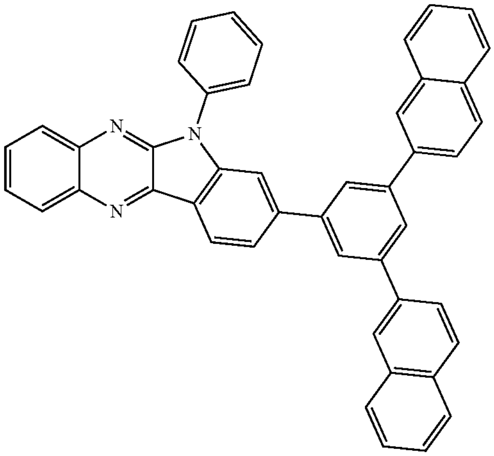
C-94
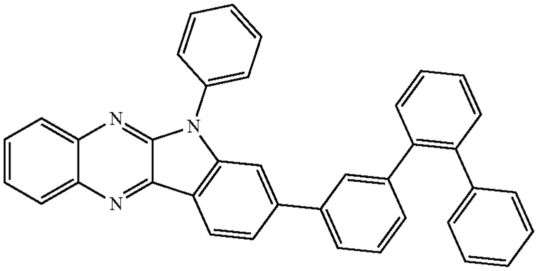
-continued
C-95
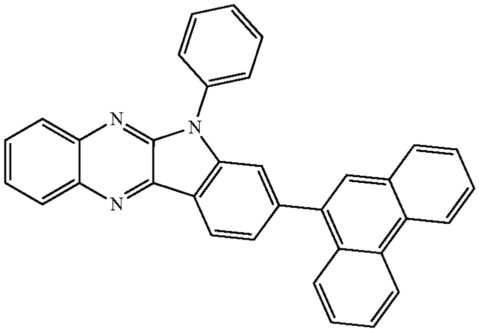
C-96
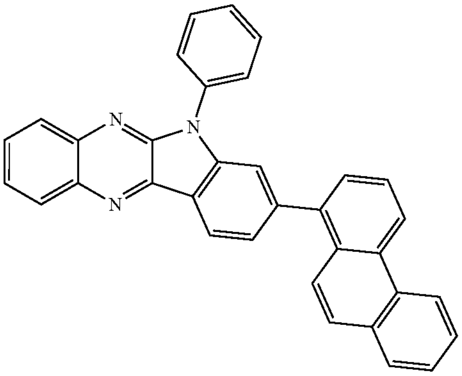
C-97
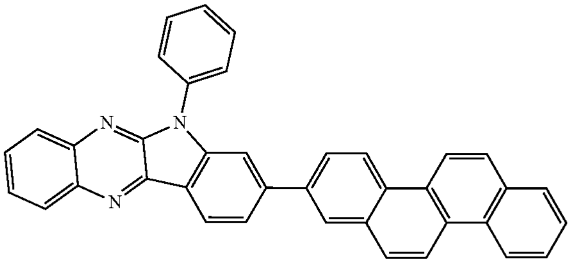
C-98
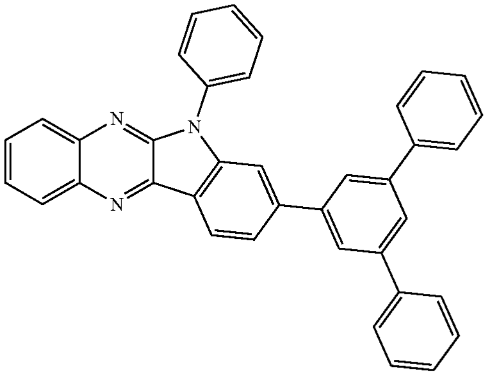

-continued
C-99
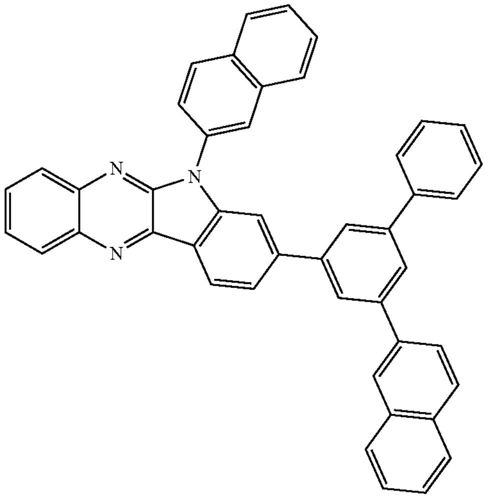
C-100
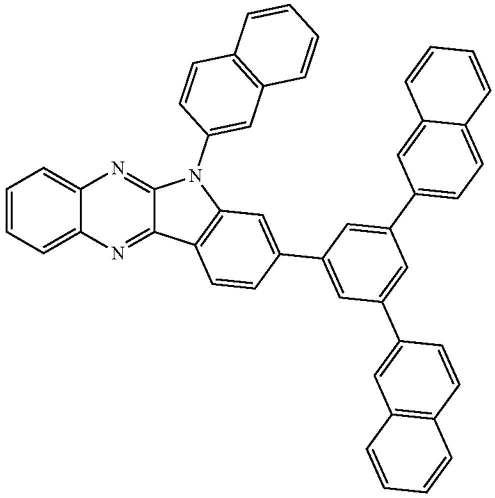
C-101
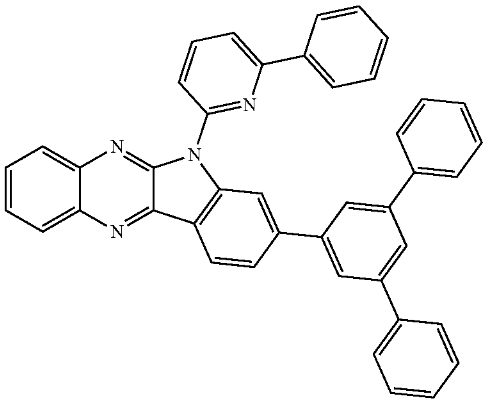
-continued
C-102
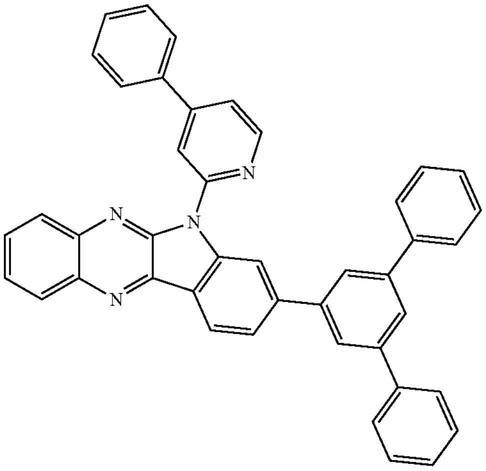
C-103
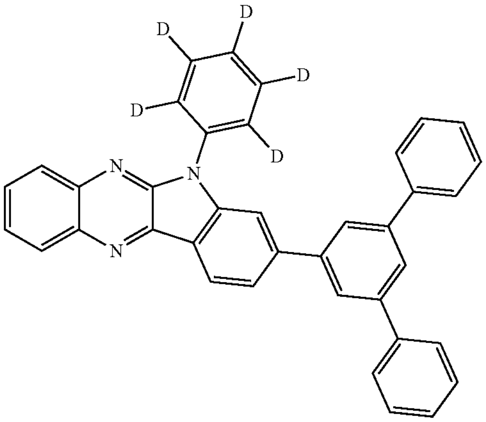
C-104
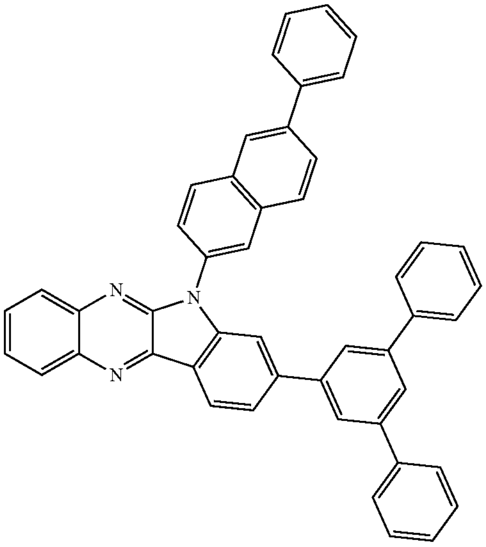

-continued
C-105
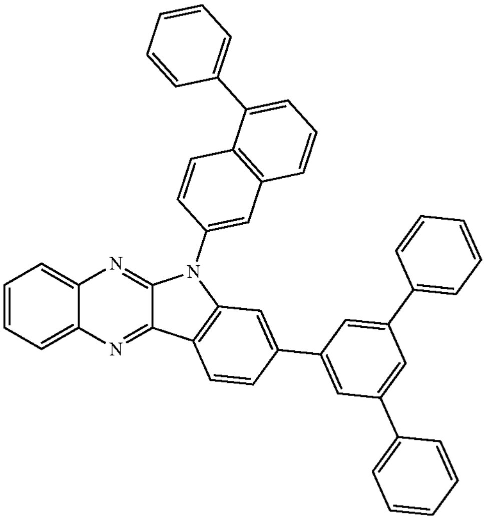
C-106
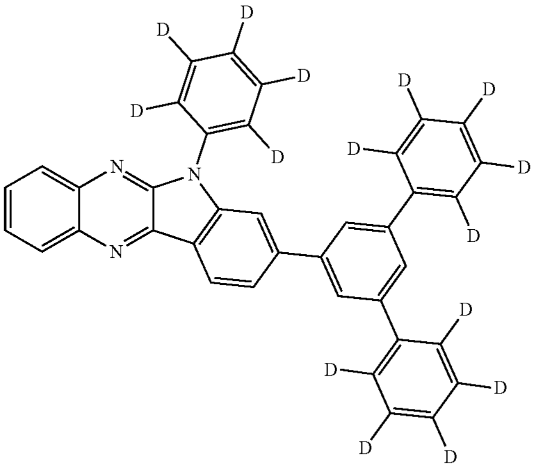
C-107
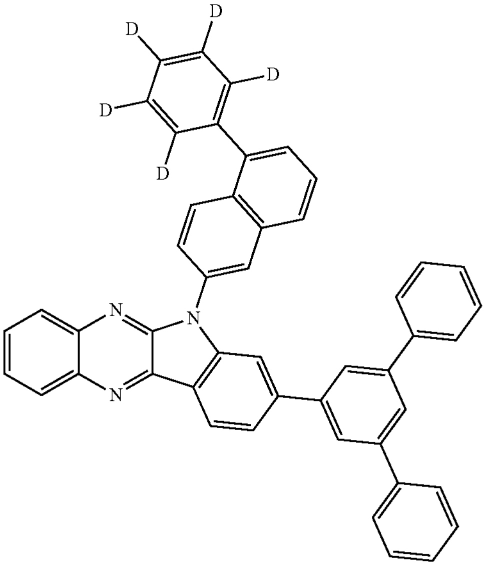
-continued
C-108
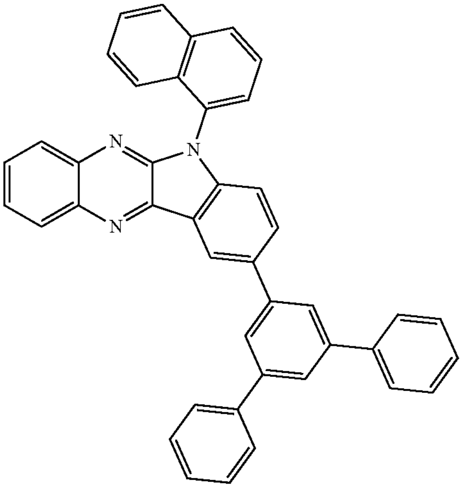
C-109
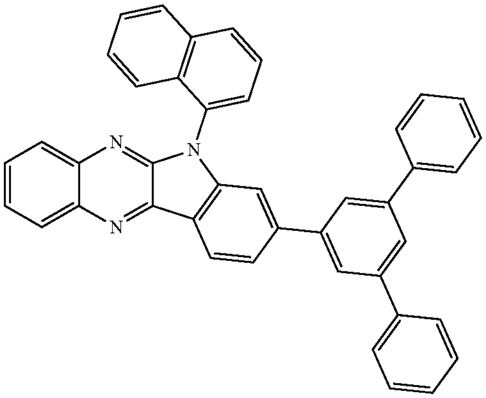
C-110
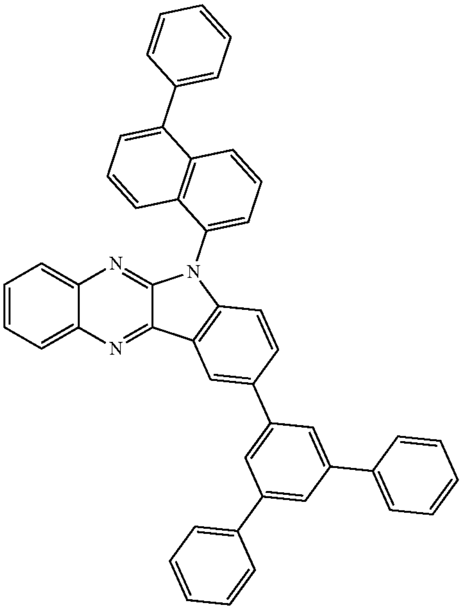

-continued
C-111
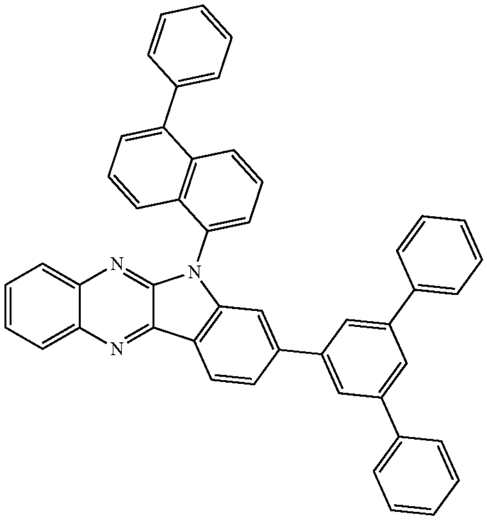
C-112
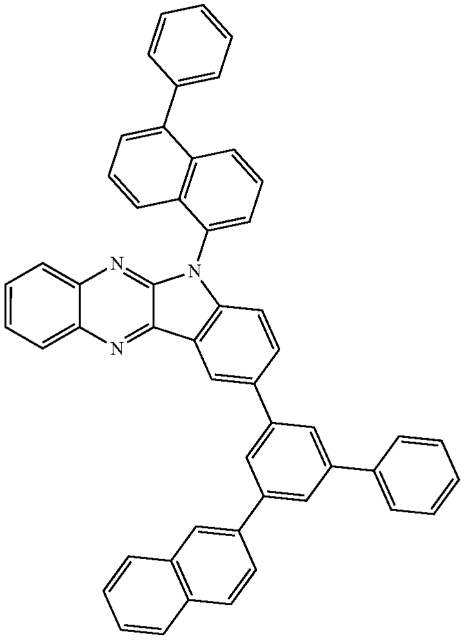
-continued
C-113
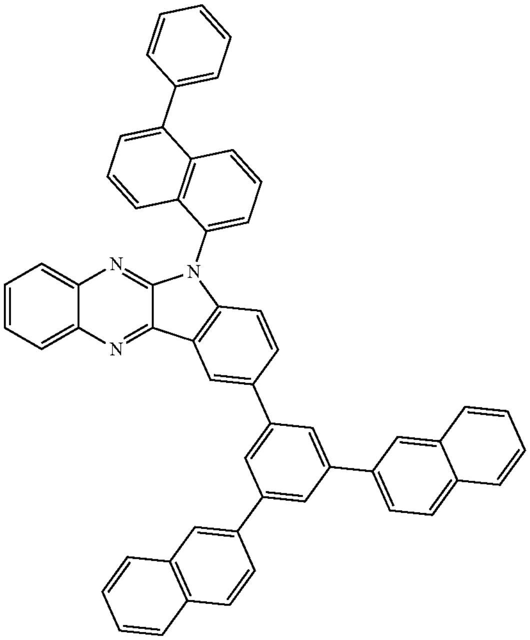
C-114
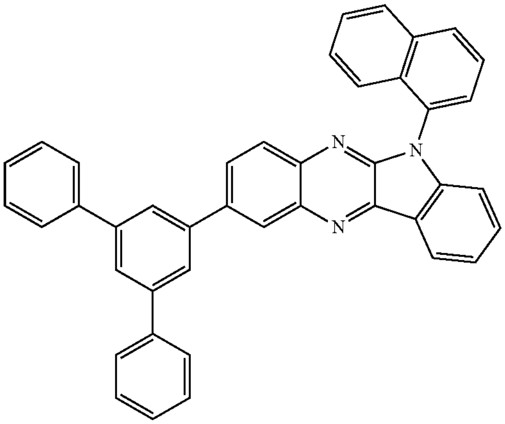

-continued
C-115
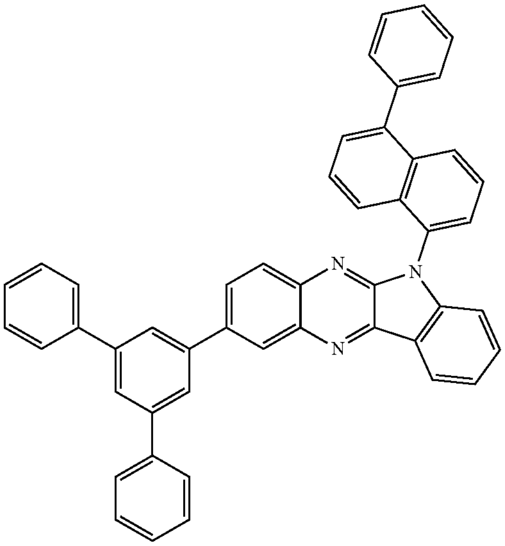
C-116
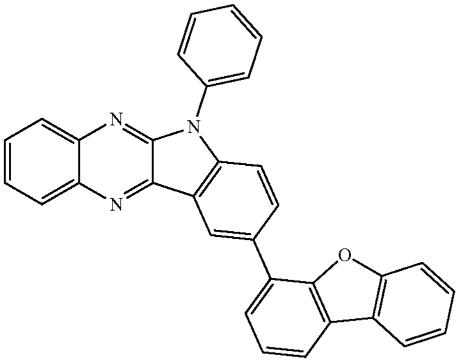
C-117
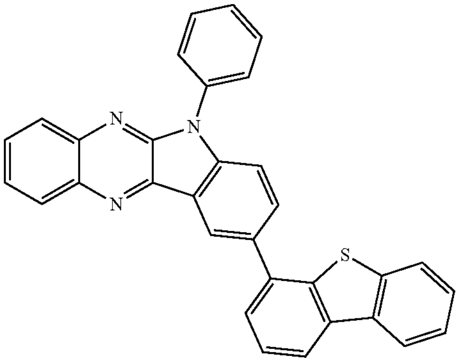
-continued
C-118
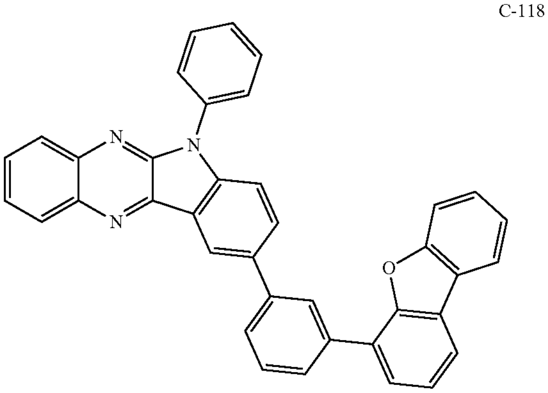
C-119
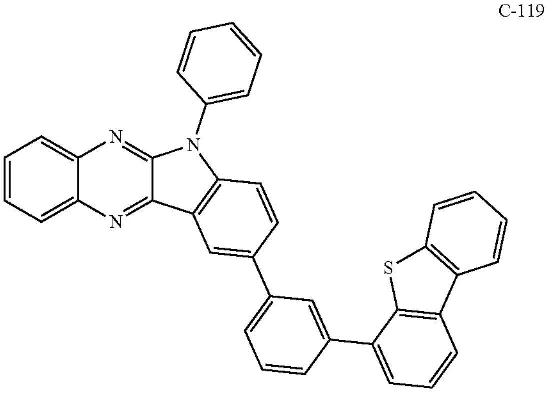
C-120
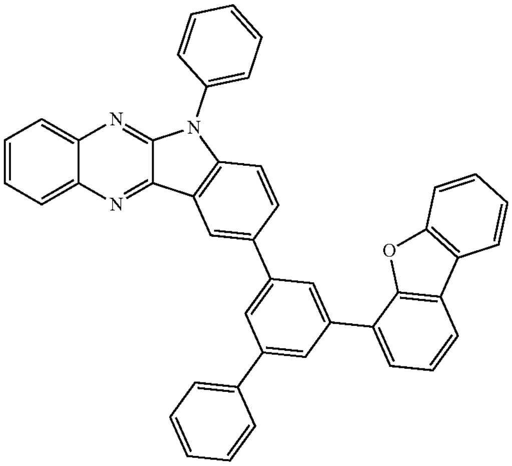

-continued
C-121
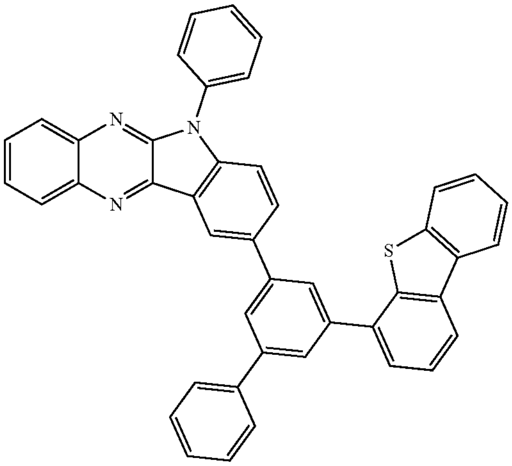
C-122
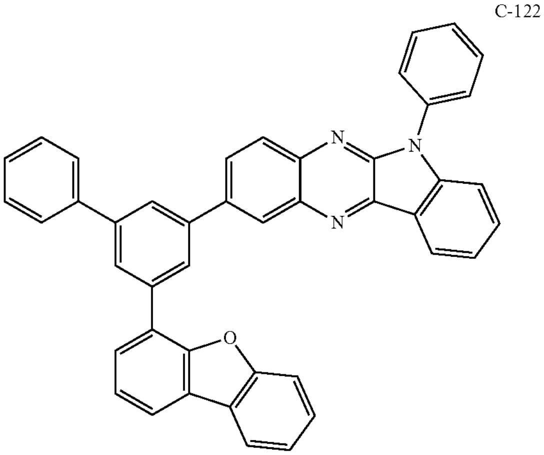
C-123
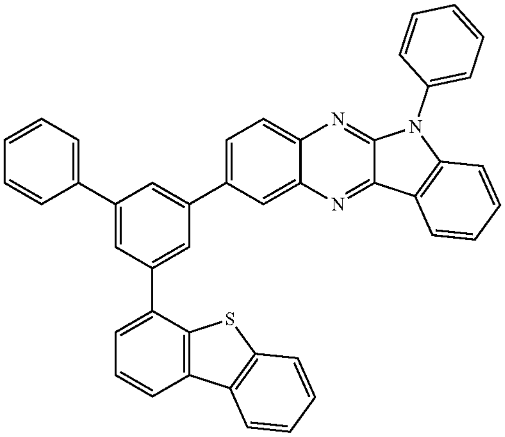
-continued
C-124
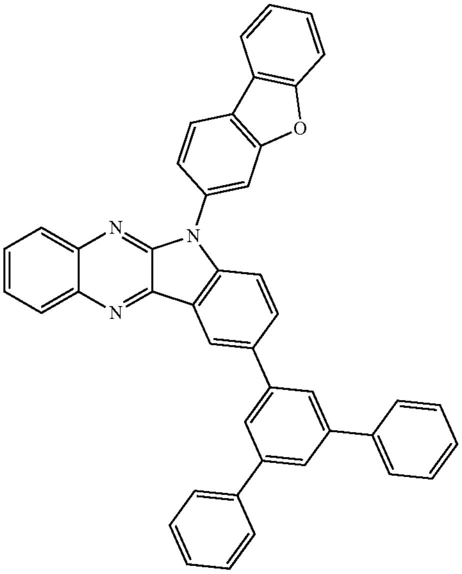
C-125
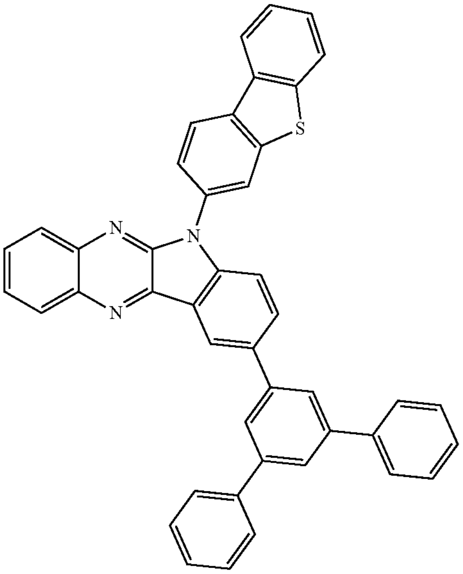

-continued

C-126

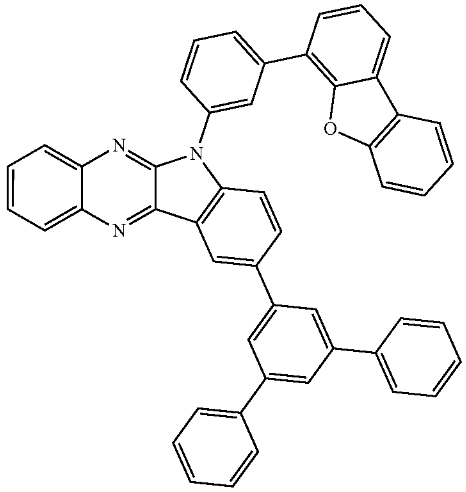

C-127

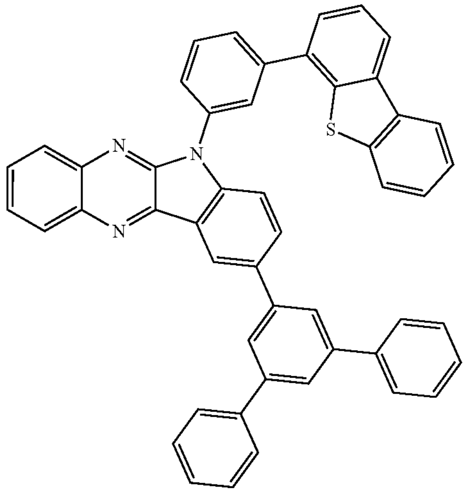

Hereinafter, an organic electroluminescent device to which the aforementioned plurality of host materials and/or the organic electroluminescent compound is(are) applied will be described.

The organic electroluminescent device according to one embodiment includes a first electrode; a second electrode; and at least one organic layer(s) interposed between the first electrode and the second electrode. The organic layer may include a light-emitting layer, and the light-emitting layer may comprise a plurality of host materials comprising a first host material comprising at least one compound represented by the above formula 1 and a second host material comprising at least one compound represented by the above formula 2. According to another embodiment of the present disclosure, the organic electroluminescent device according to the present disclosure includes a first electrode; a second electrode; and at least one light-emitting layer(s) interposed between the first electrode and the second electrode and the at least one light-emitting layer(s) may include a compound represented by the above formula 3.

According to one embodiment, the organic electroluminescent material of the present disclosure includes at least one of compounds C-1 to C-131 as the first host material represented by formula 1 and at least one of compounds H-1 to H-220 as the second host material represented by formula 2. The plurality of host materials may be included in the same organic layer, e.g., a light-emitting layer, or may be included in different light-emitting layers, respectively. According to another embodiment, the organic electroluminescent material of the present disclosure includes compounds C-1 to C-127 represented by formula 3 alone or in combination of two or more, and the organic electroluminescent material may be included in an organic layer, e.g., a light-emitting layer, of an organic electroluminescent device.

The organic layer may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer, in addition to a light-emitting layer. The organic layer may further comprise an amine-based compound and/or an azine-based compound, in addition to the light-emitting material of the present disclosure. Specifically, the hole injection layer, the hole transport layer, the hole auxiliary layer, the light-emitting layer, the light-emitting auxiliary layer, or the electron blocking layer may comprise an amine-based compound, for example, arylamine-based compound, a styrylarylamine-based compound, etc., as a hole injection material, a hole transport material, a hole auxiliary material, a light-emitting material, a light-emitting auxiliary material, or an electron blocking material. In addition, the electron transport layer, the electron injection layer, the electron buffer layer, and the hole blocking layer may comprise an azine-based compound as an electron transport material, an electron injection material, an electron buffer material, and a hole blocking material. In addition, the organic layer further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising such a metal.

The plurality of host materials according to one embodiment may be used as light-emitting materials for a white organic light-emitting device. The white organic electroluminescent device has suggested various structures such as a parallel side-by-side arrangement method, a stacking arrangement method, or color conversion material (CCM) method, etc., according to the arrangement of R (Red), G (Green), YG (yellowish green), or B (Blue) light-emitting units. In addition, the organic electroluminescent material according to one embodiment may also be applied to the organic electroluminescent device comprising a QD (quantum dot).

One of the first electrode and the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. In addition, the hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer may be placed between the electron transport layer (or electron injection layer) and the light-emitting layer, and blocks the arrival of holes to the cathode, thereby improving the probability of recombination of electrons and holes in the light-emitting layer. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_X$ ($1 \le X \le 2$), $AlO_X$ ($1 \le X \le 1.5$), SiON, SiAlON, etc.; the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

Further, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent device according to one embodiment may further include at least one dopant in the light-emitting layer.

The dopant comprised in the organic electroluminescent device of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compounds) of a metal atoms) selected from iridium (Ir), osmium (Os), copper (Cu), and platinum (Pt), as necessary; more preferably an ortho-metallated complex compound(s) of a metal atoms) selected from iridium (Ir), osmium (Os), copper (Cu), and platinum (Pt), as necessary; and even more preferably ortho-metallated iridium complex compound(s), as necessary.

The dopant comprised in the organic electroluminescent device of the present disclosure may use the compound represented by the following formula 101, but is not limited thereto.

(101)

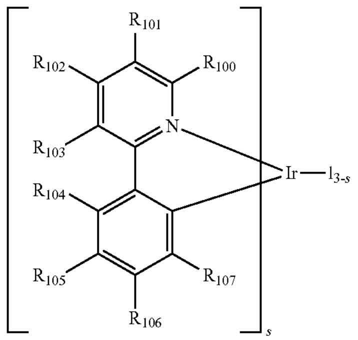

In formula 101,

L is selected from any one of the following structures 1 to 3;

structure (1)

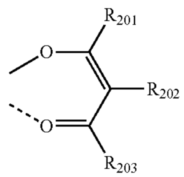

-continued structure (2)

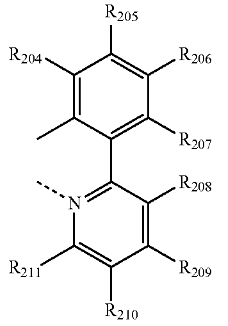

structure (3)

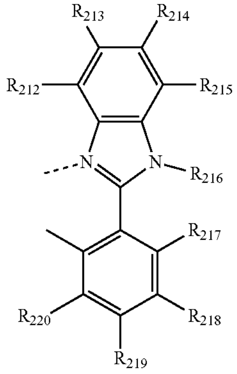

$R_{100}$ to $R_{103}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or may be linked to the adjacent substituents to form a ring(s), e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy, or may be linked to the adjacent substituents to form a ring(s), e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine, together with benzene;

$R_{201}$ to $R_{220}$ each independently represent hydrogen, deuterium, halogen, (C1-C30)alkyl unsubstituted or substituted with deuterium and/or halogen, a substituted or unsubstituted (C3-C30)cycloalkyl, or a substituted or unsubstituted (C6-C30)aryl; or may be linked to the adjacent substituents to form a substituted or unsubstituted ring(s); and s represents an integer of 1 to 3.

Specifically, the specific examples of the dopant compound include the following, but are not limited thereto.

D-1

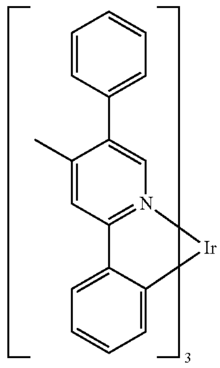

D-2

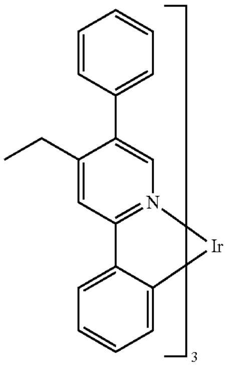

D-3

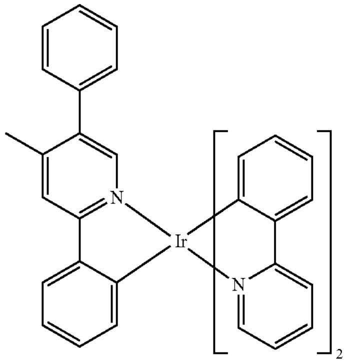

D-4

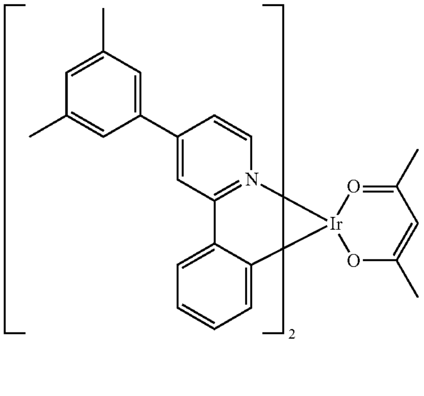

-continued
D-5
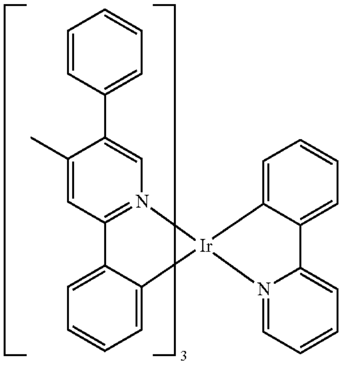
D-6
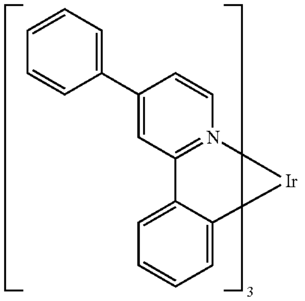
D-7
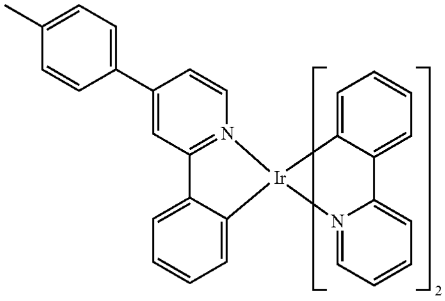
D-8
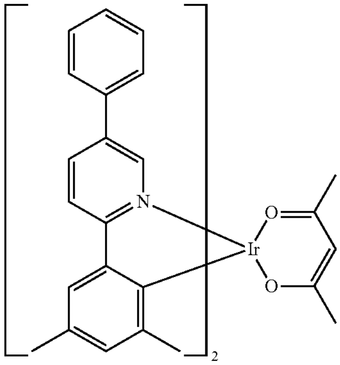
-continued
D-9
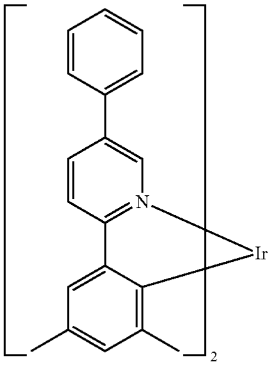
D-10
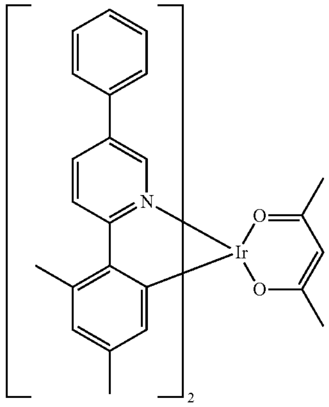
D-11
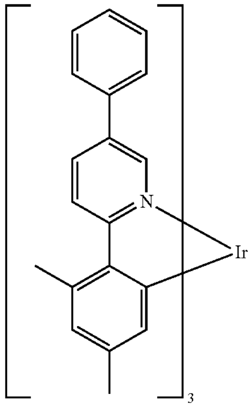
D-12
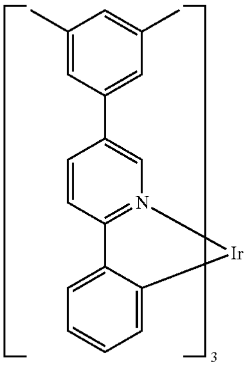

-continued
D-13
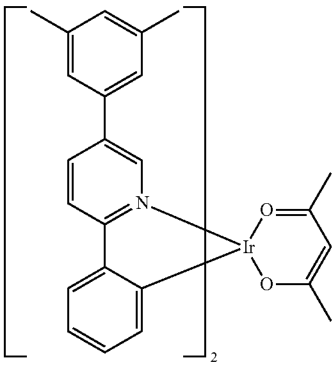
D-14
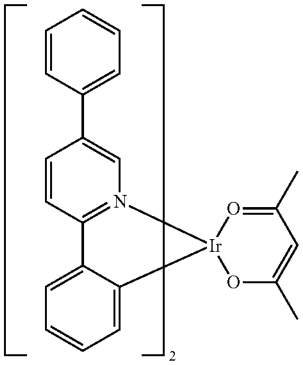
D-15
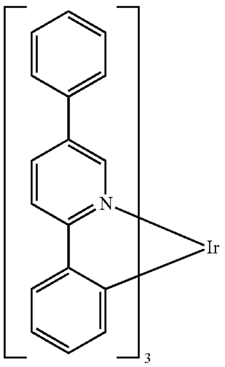
D-16
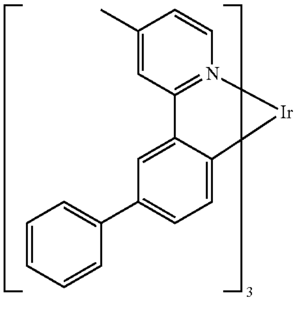
-continued
D-17
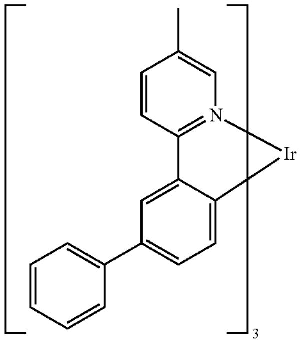
D-18
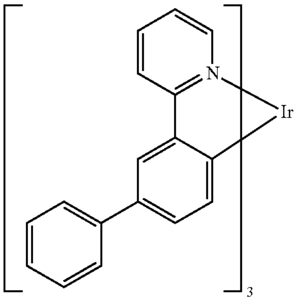
D-19
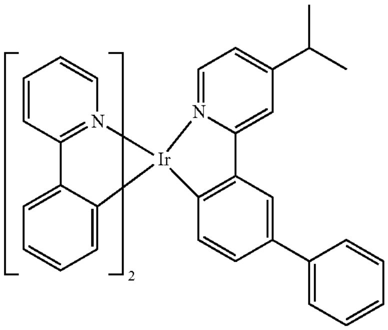
D-20
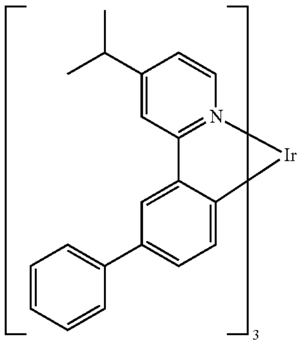

-continued
D-21
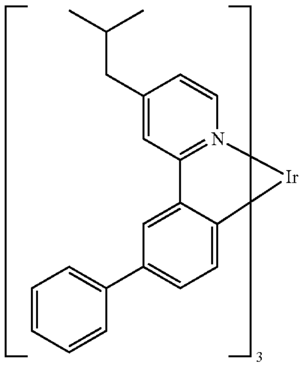
D-22
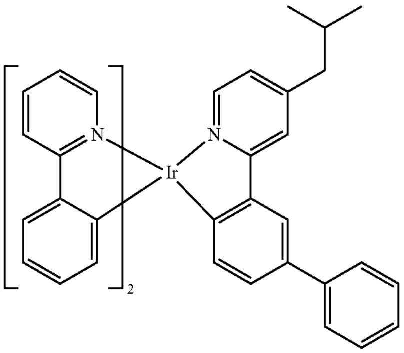
D-23
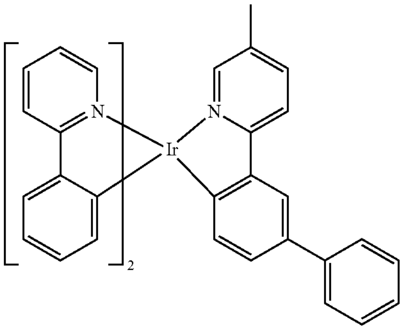
D-24
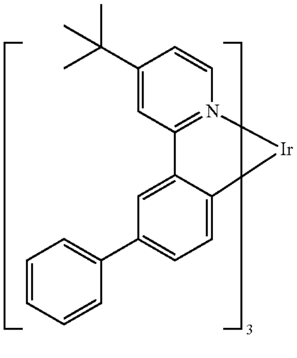
-continued
D-25
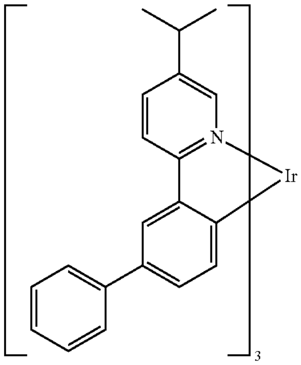
D-26
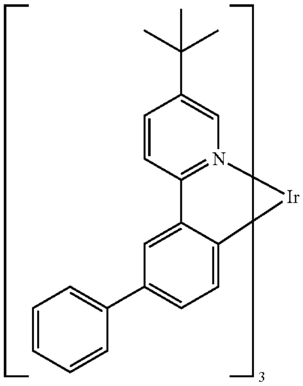
D-27
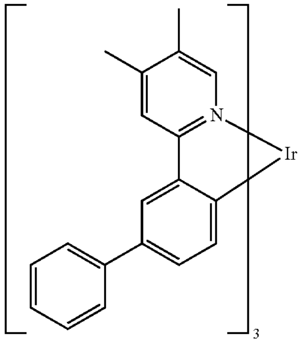
D-28
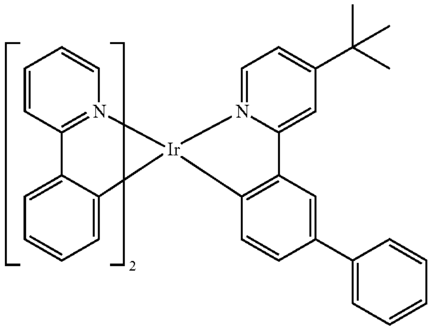

-continued
D-29
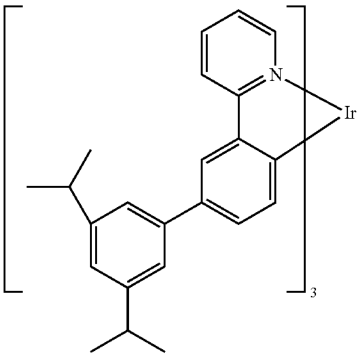
D-30
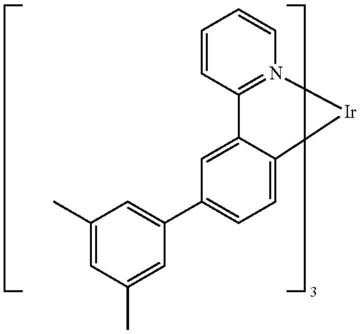
D-31
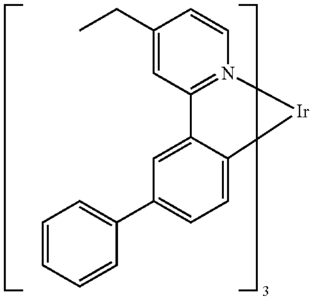
D-32
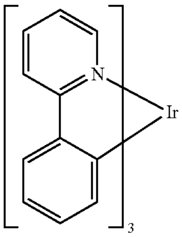
D-33
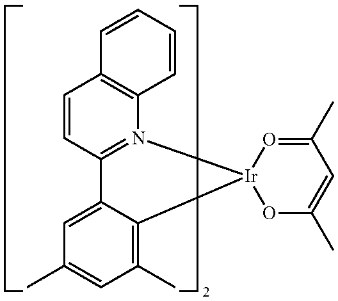
-continued
D-34
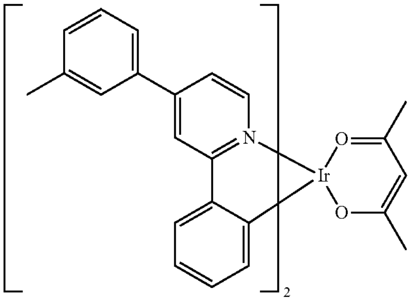
D-35
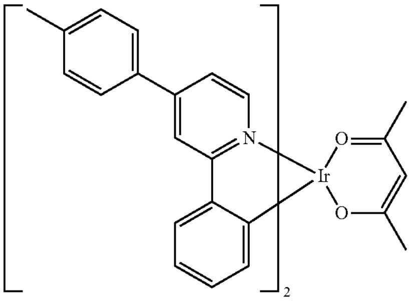
D-36
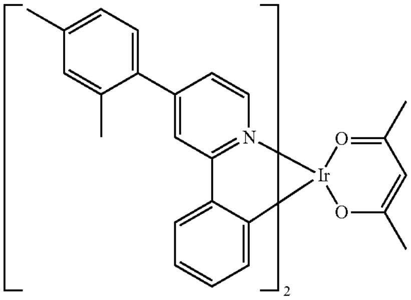
D-37
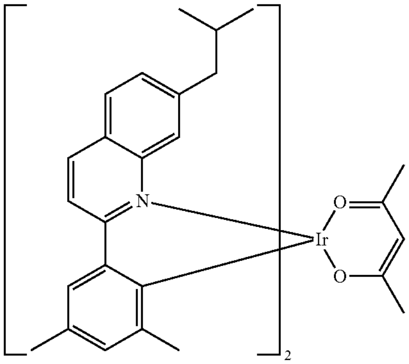
D-38
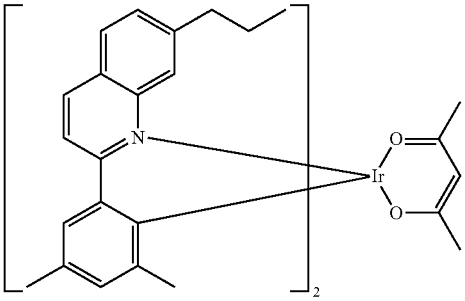

-continued
D-39
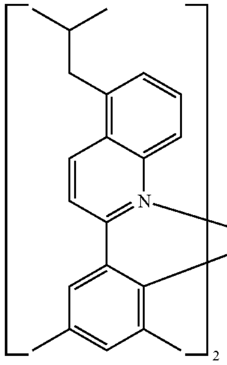
D-40
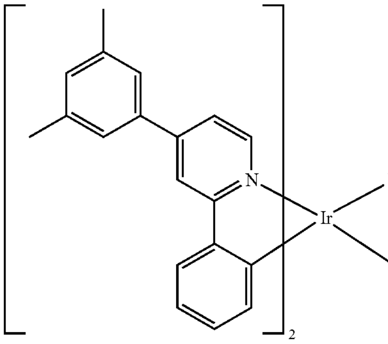
D-41
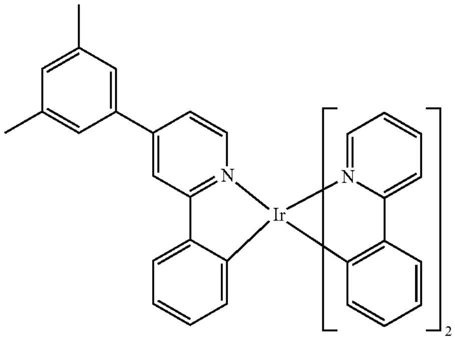
D-42
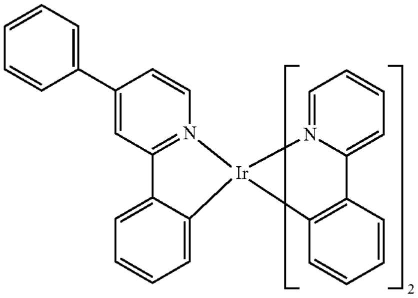
-continued
D-43
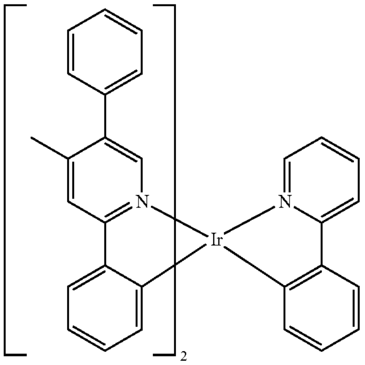
D-44
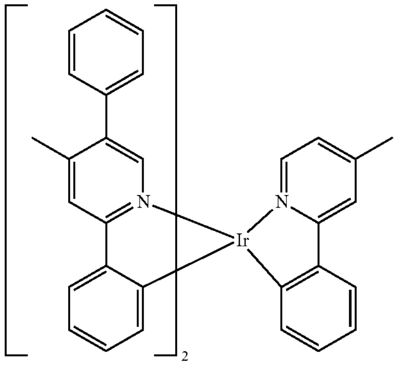
D-45
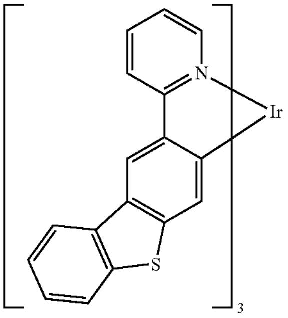
D-46
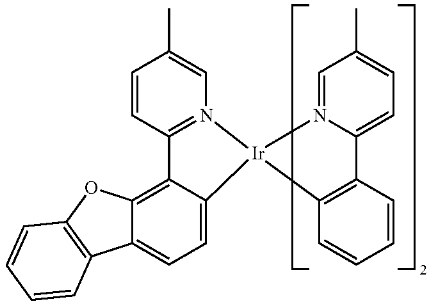

-continued
D-47
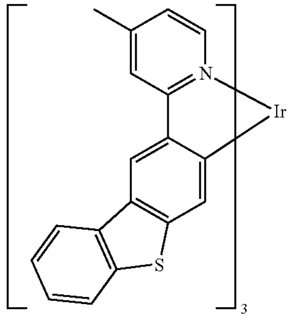
D-48
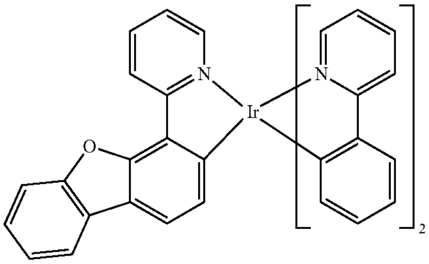
D-49
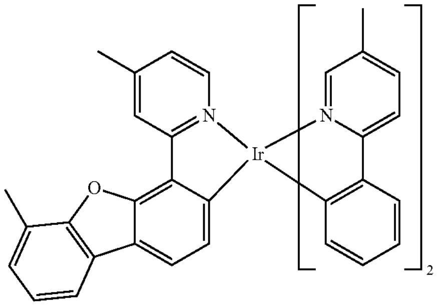
D-50
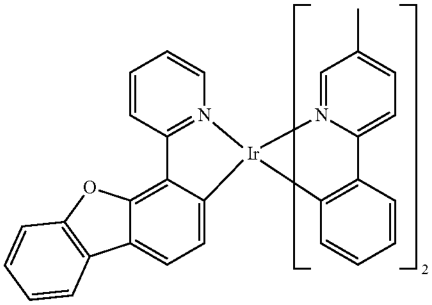
D-51
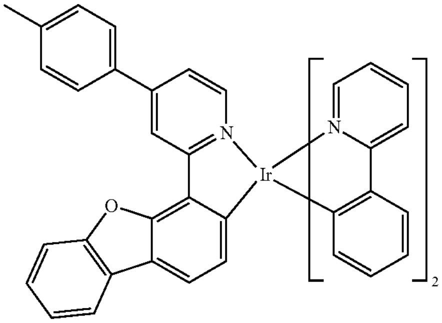
-continued
D-52
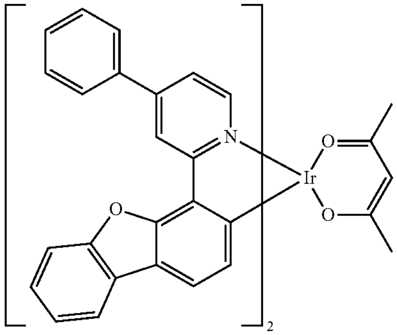
D-53
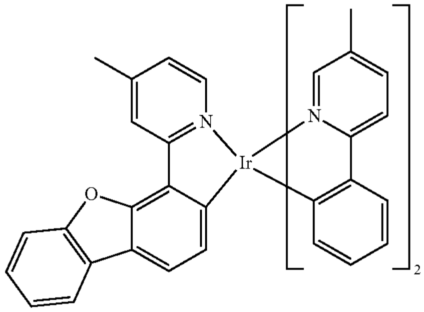
D-54
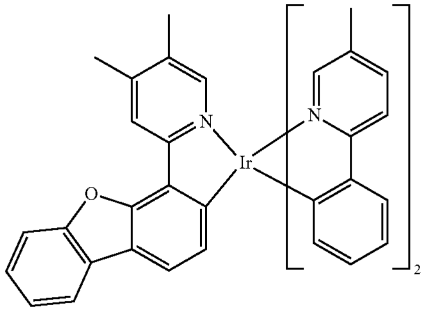
D-55
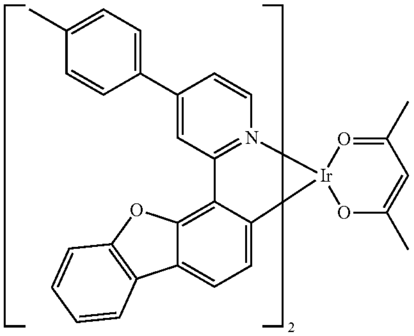
D-56
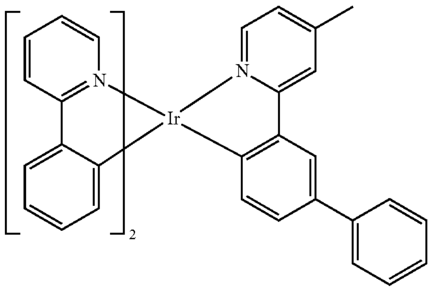

-continued
D-57
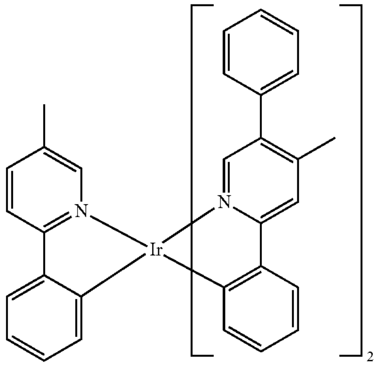
D-58
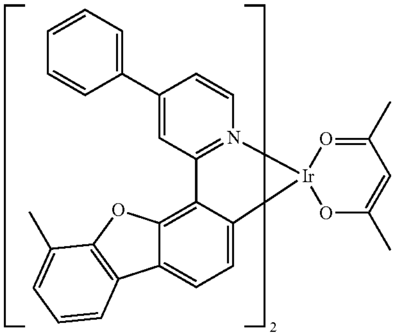
D-59
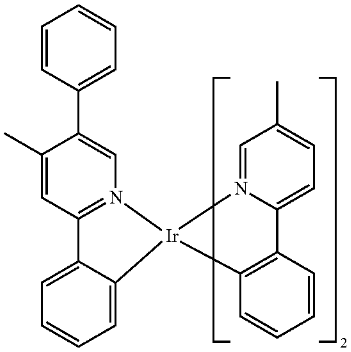
D-60
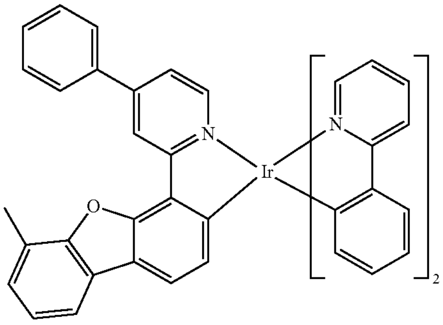
-continued
D-61
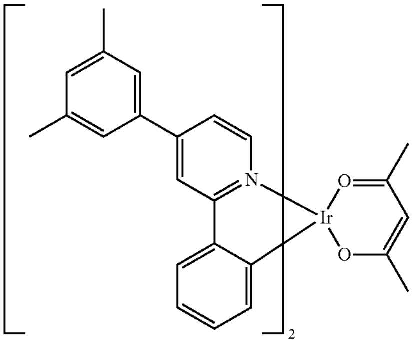
D-62
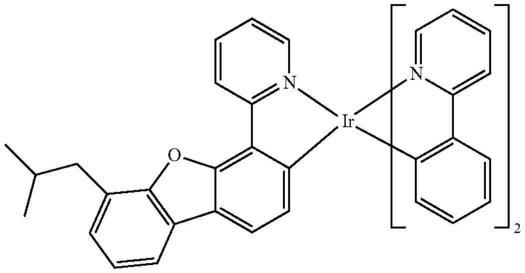
D-63
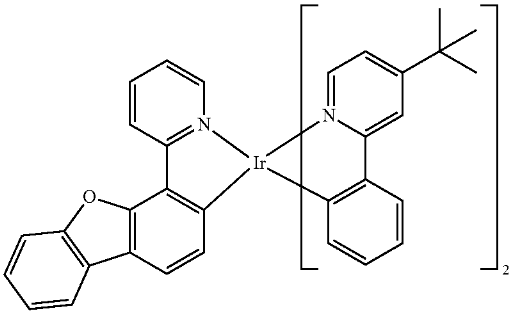
D-64
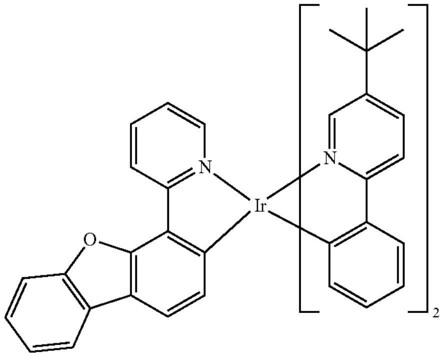

-continued
D-65
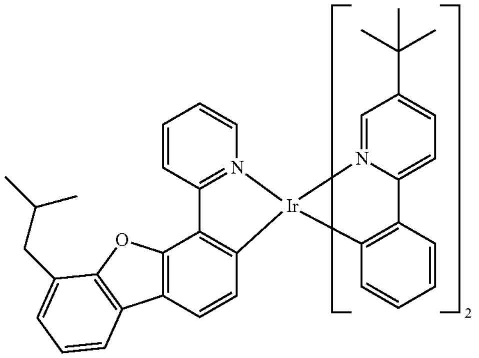
D-66
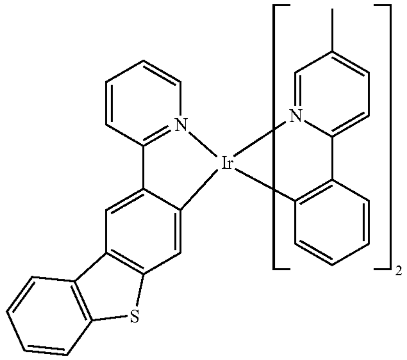
D-67
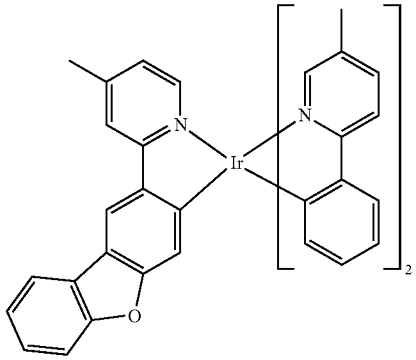
D-68
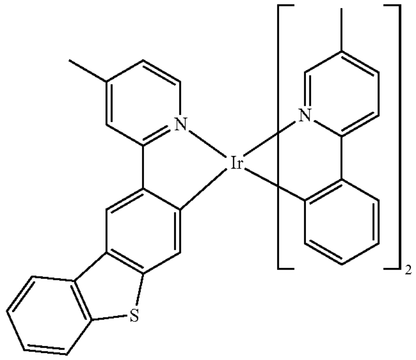
-continued
D-69
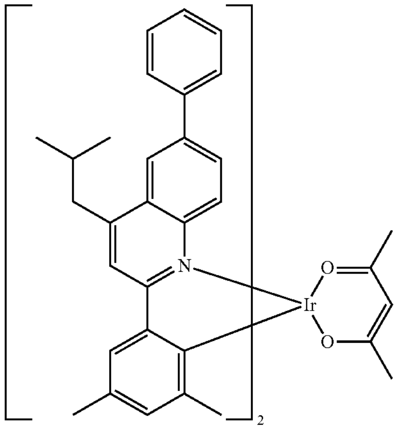
D-70
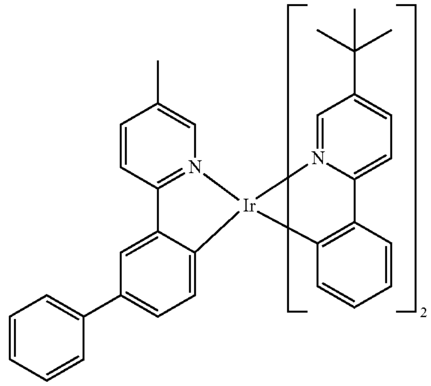
D-71
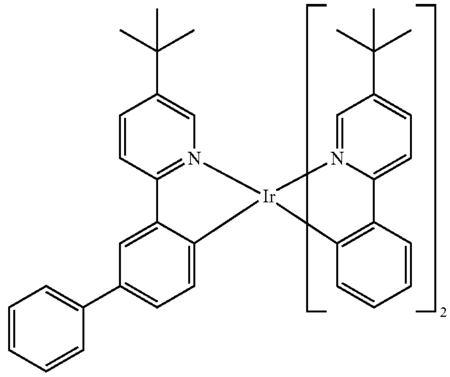
D-72
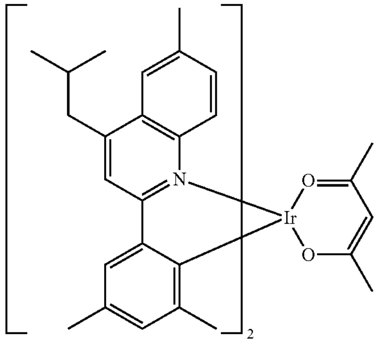

-continued
D-73
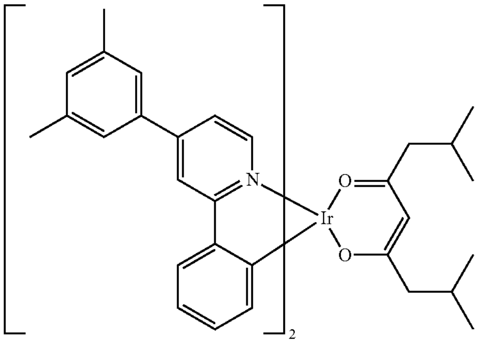
D-74
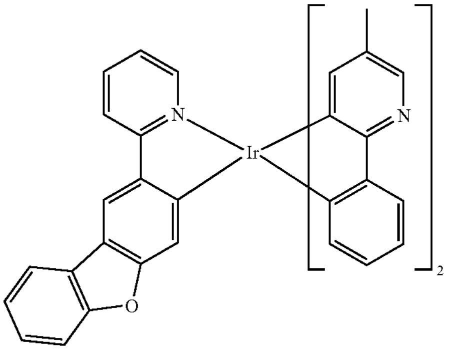
D-75
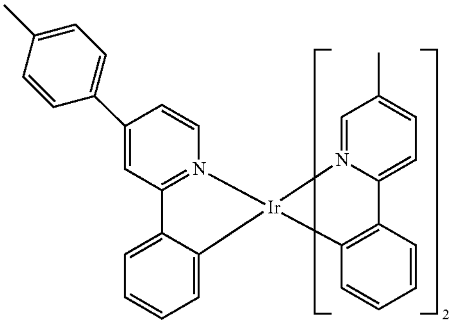
D-76
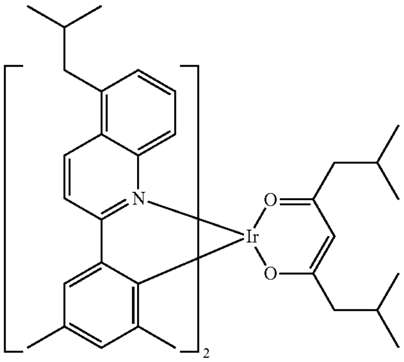
-continued
D-77
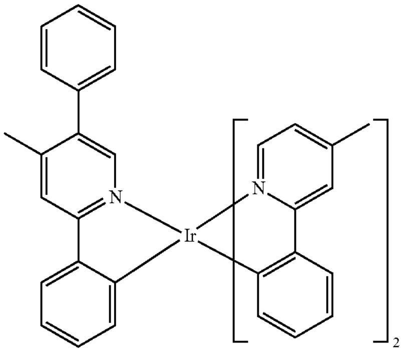
D-78
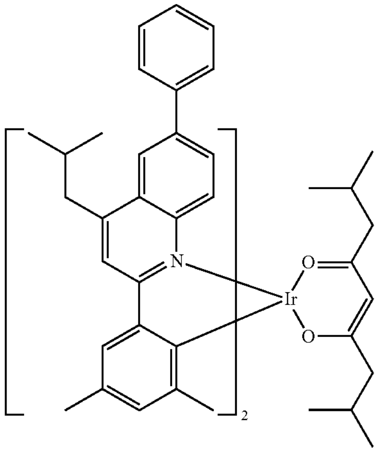
D-79
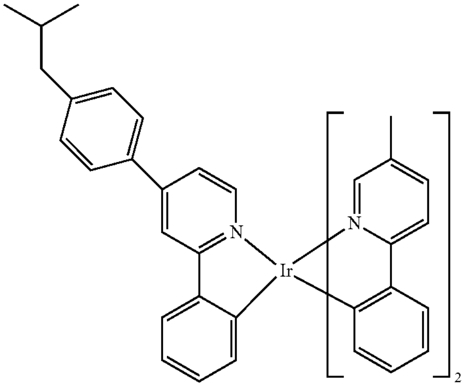
D-80
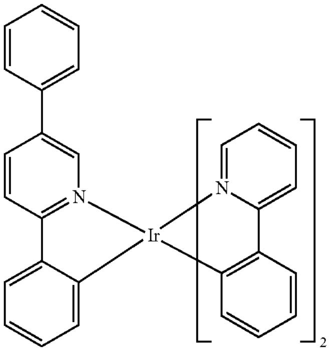

-continued
D-81
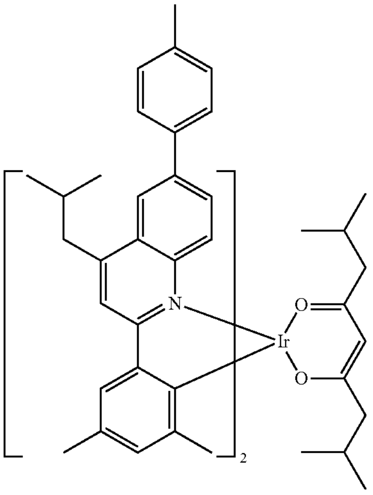
D-82
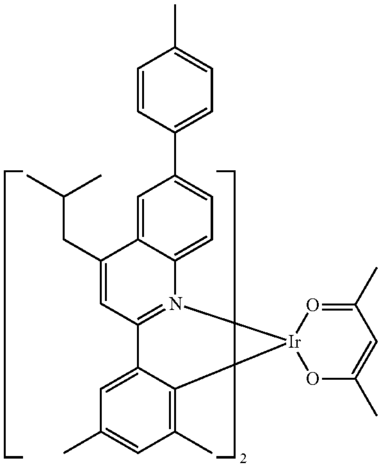
D-83
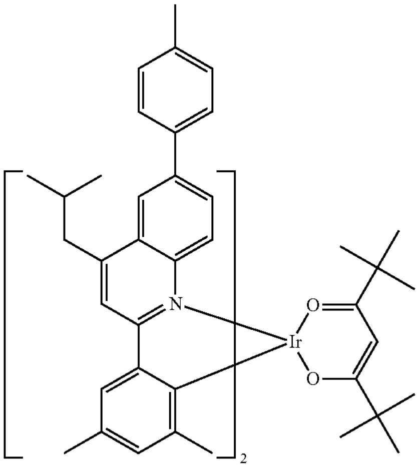
-continued
D-84
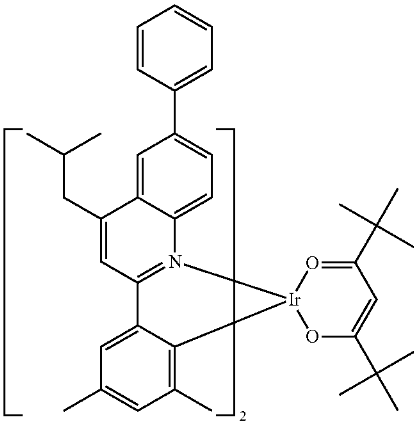
D-85
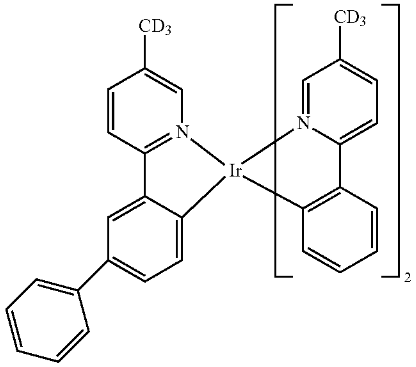
D-86
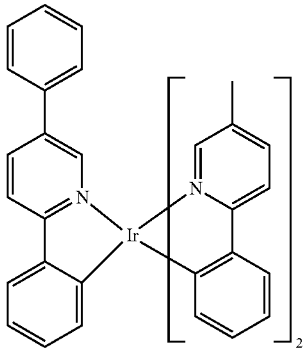
D-87
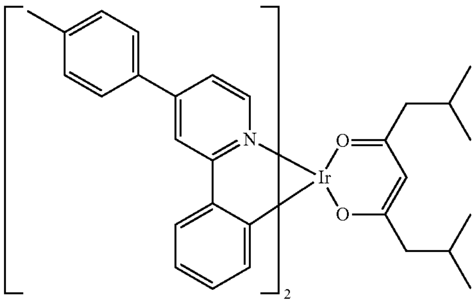

-continued
D-88
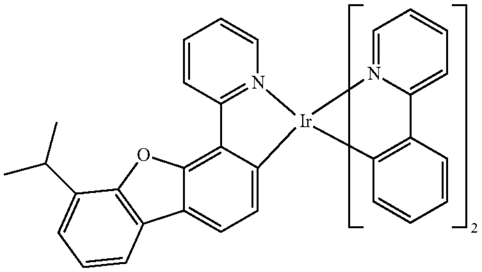
D-89
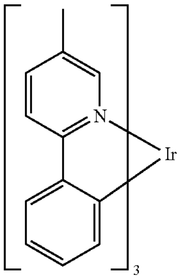
D-90
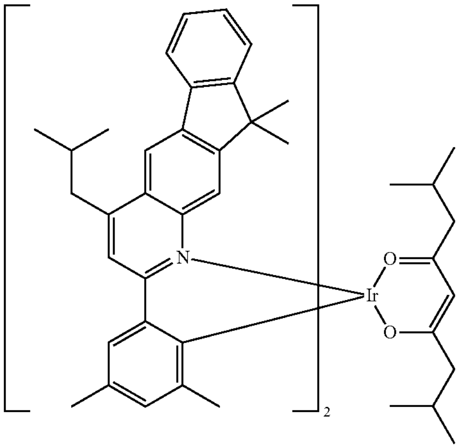
D-91
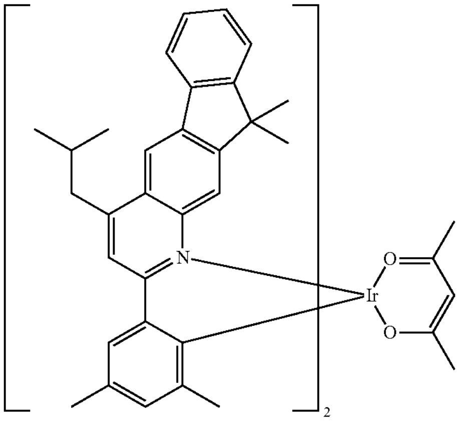
-continued
D-92
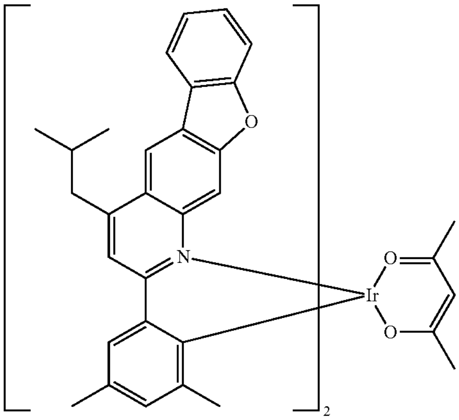
D-93
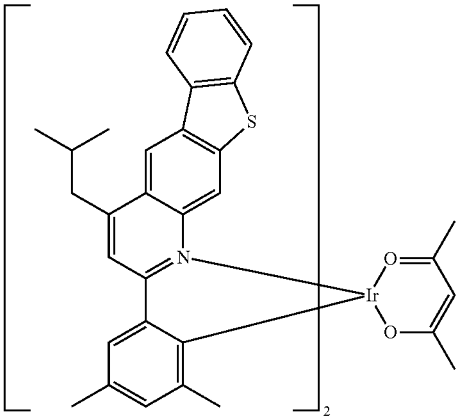
D-94
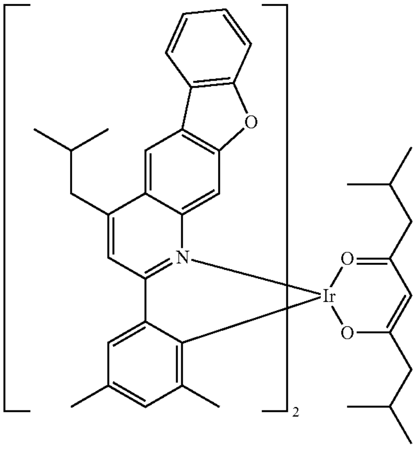

-continued
D-95
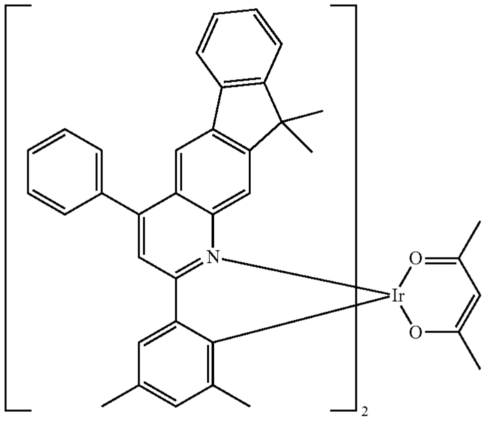
D-96
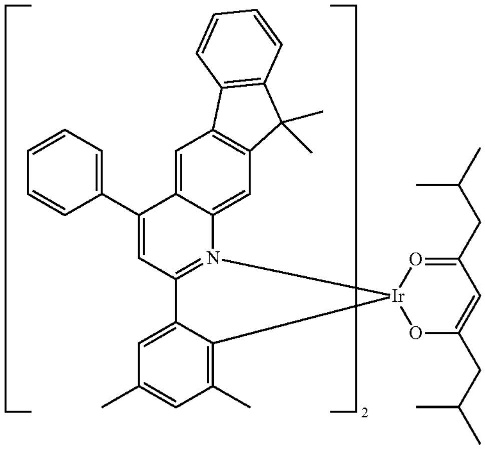
D-97
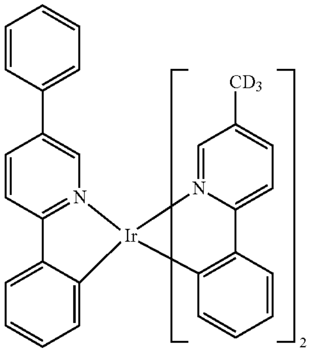
D-98
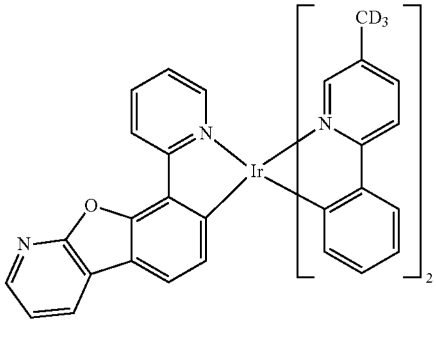
-continued
D-99
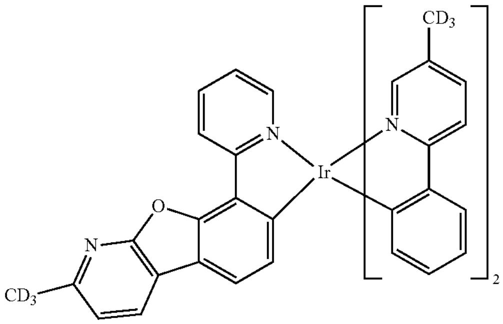
D-100
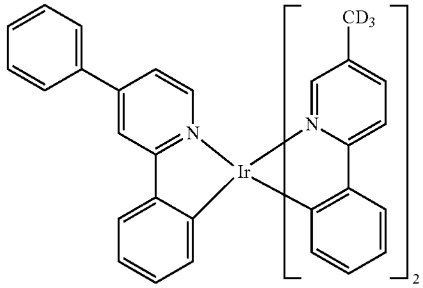
D-101
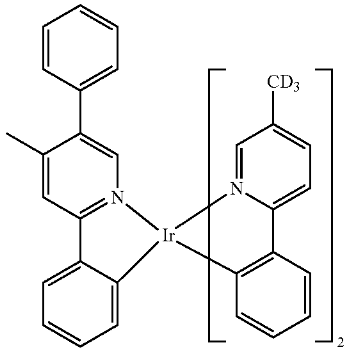
D-102
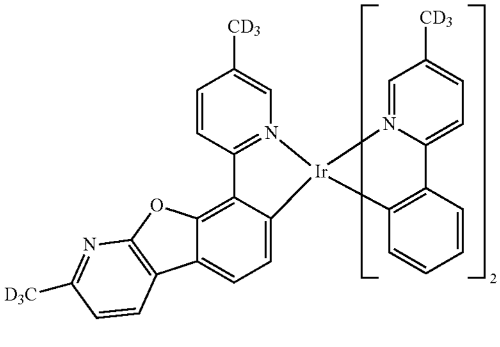

-continued
D-103
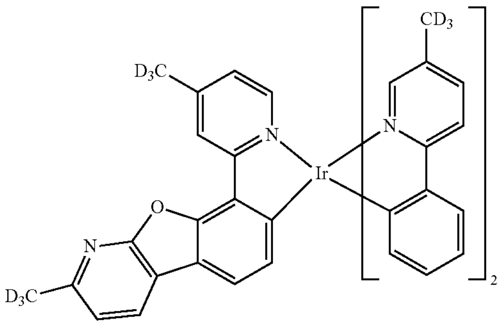
D-104
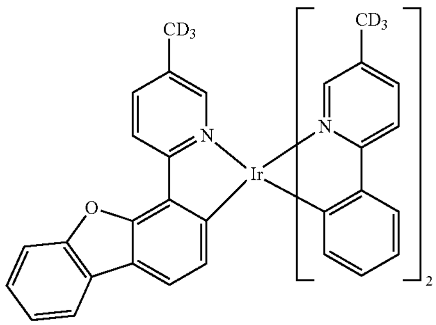
D-105
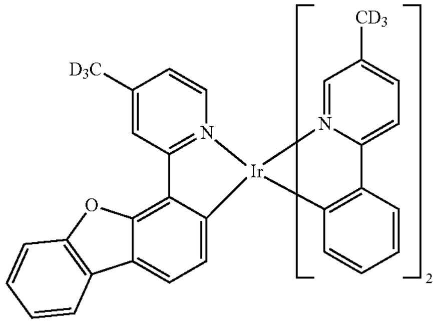
D-106
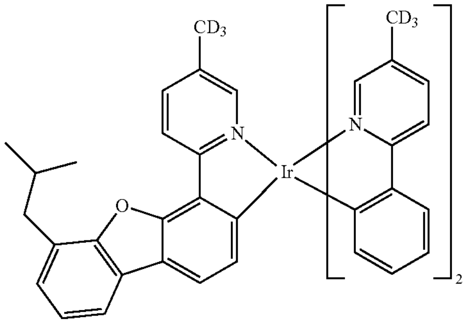
-continued
D-107
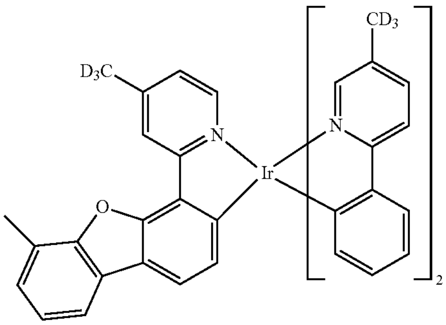
D-108
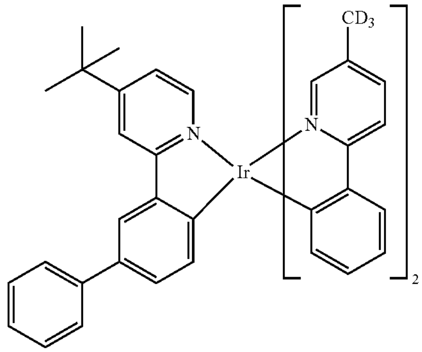
D-109
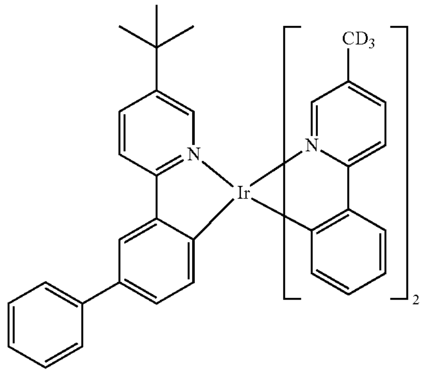
D-110
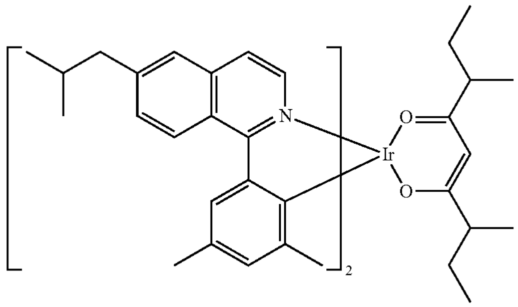

-continued
D-111
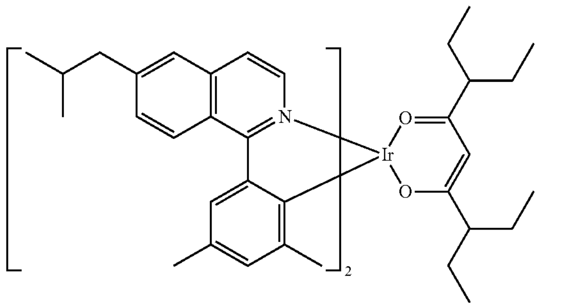
D-112
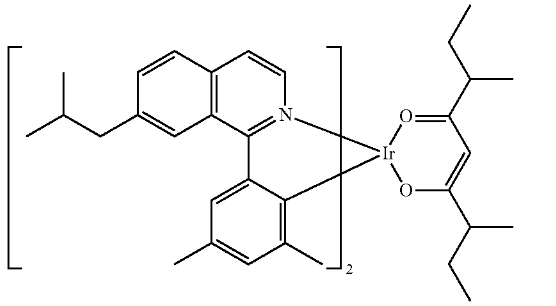
D-113
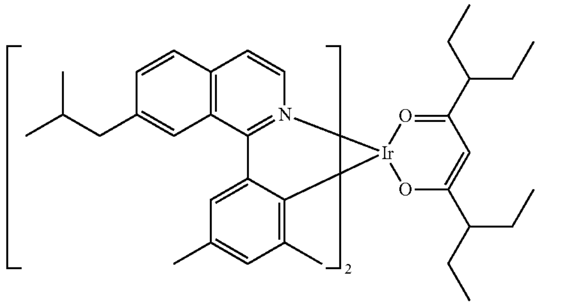
D-114
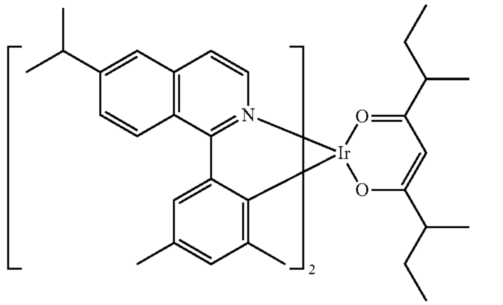
-continued
D-115
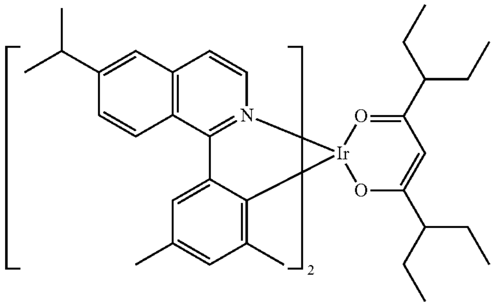
D-116
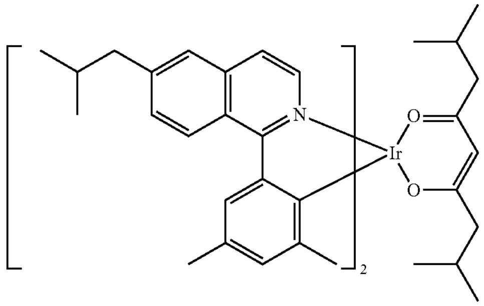
D-117
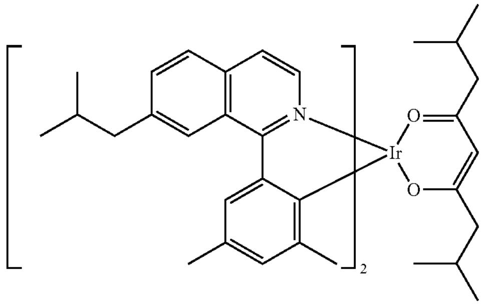
D-118
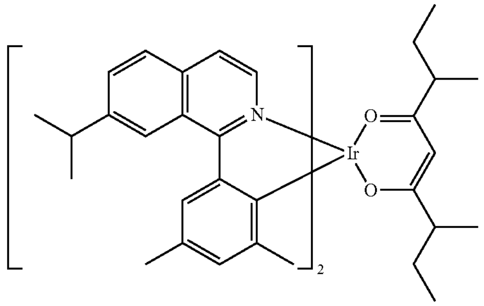
D-119
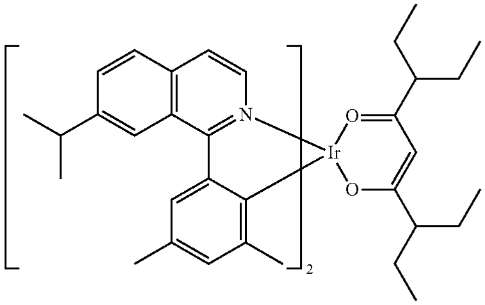

-continued
D-120
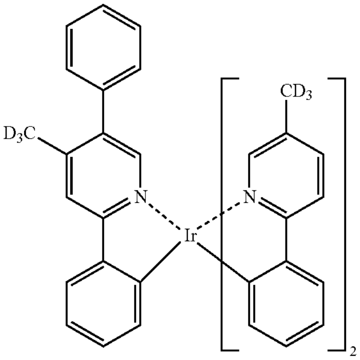
D-121
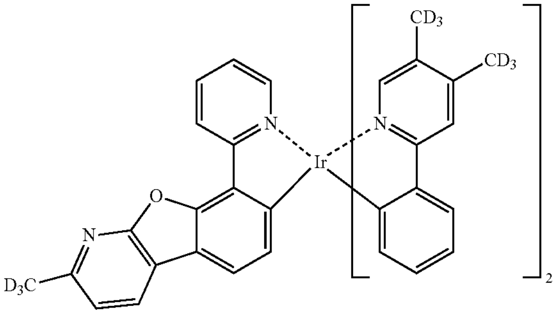
D-122
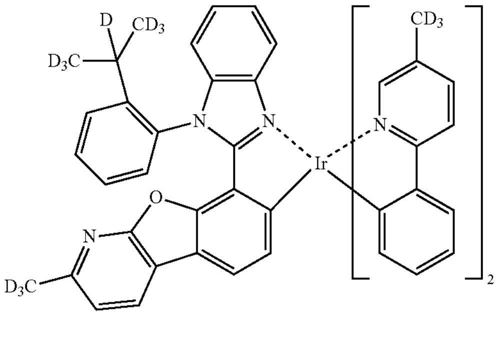
D-123
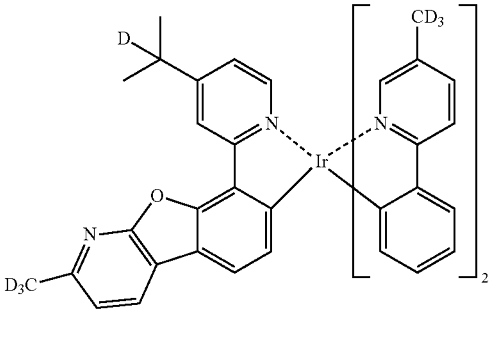
-continued
D-124
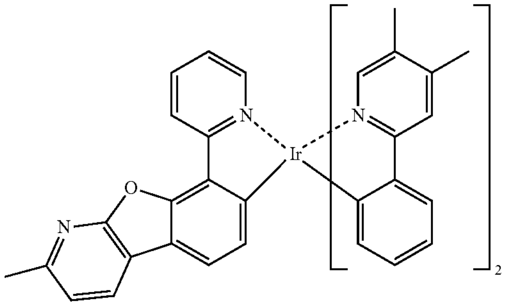
D-125
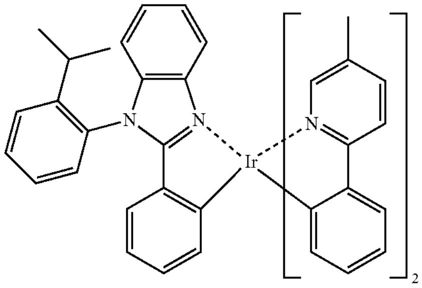
D-126
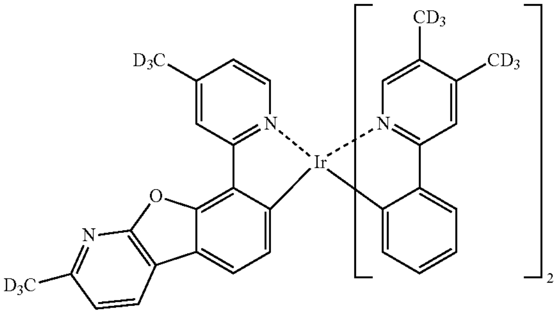
D-127
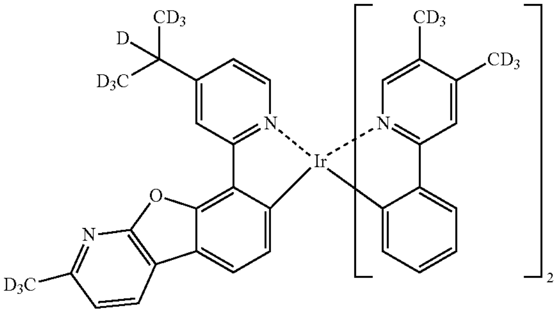
D-128
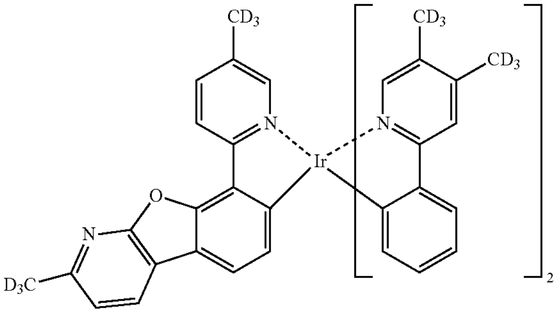

-continued
D-129
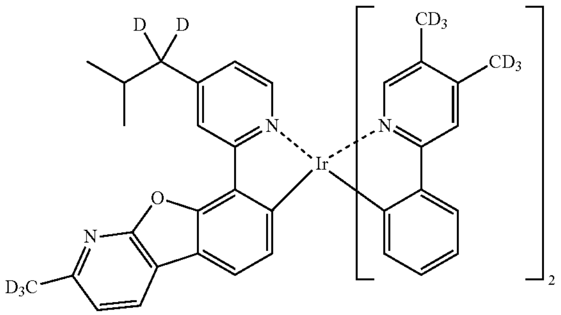
D-130
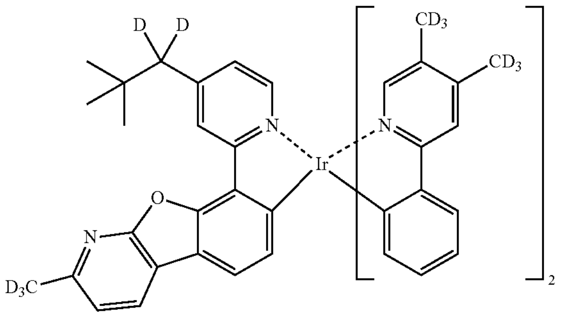
D-131
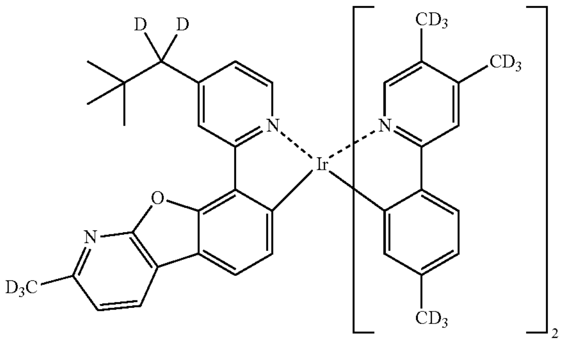
D-132
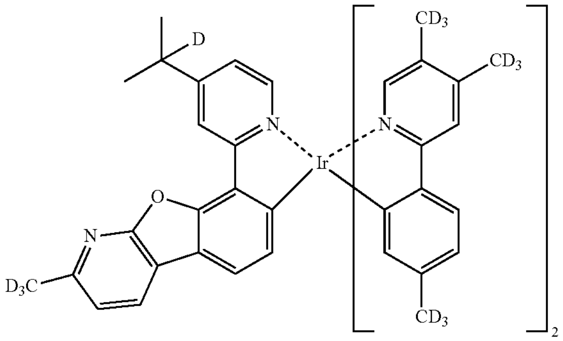
-continued
D-133
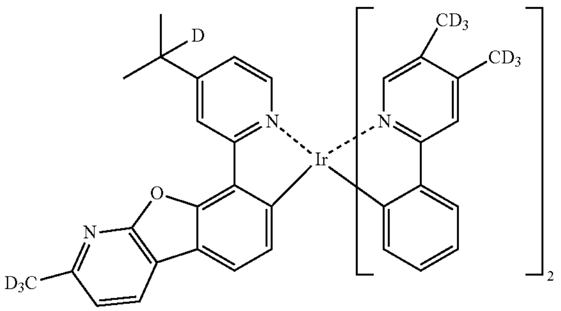
D-134
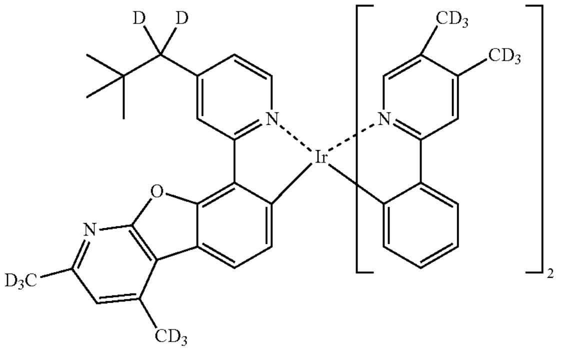
D-135
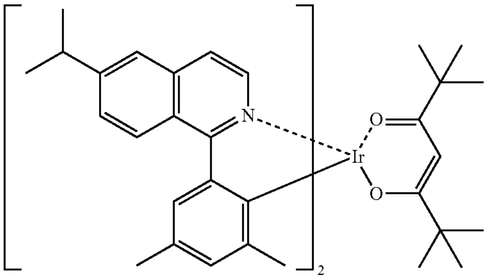
D-136
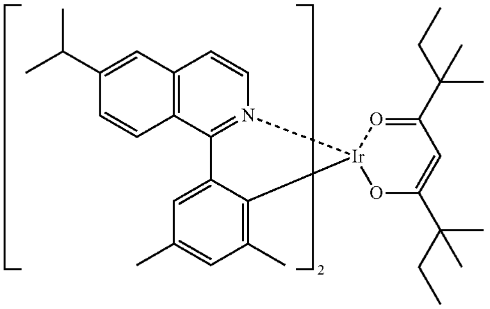
D-137
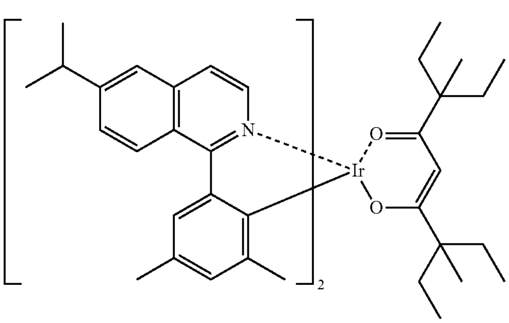

-continued
D-138
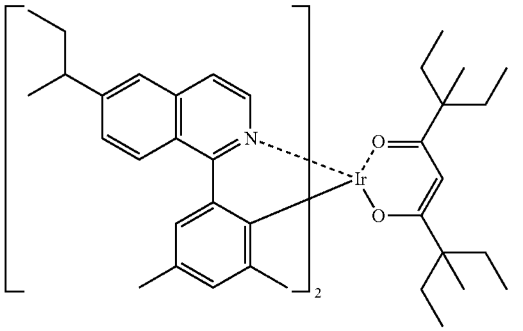
D-139
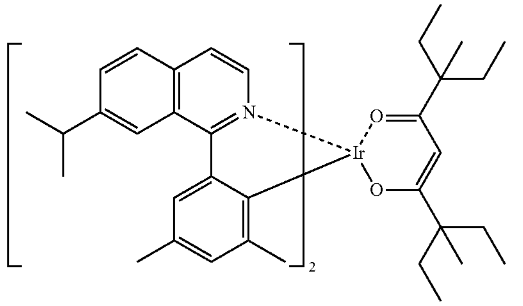
D-140
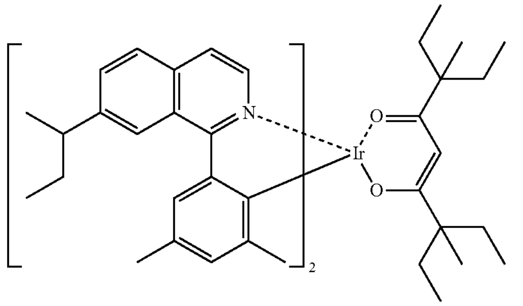
D-141
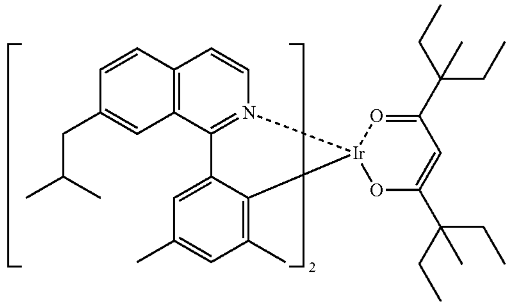
-continued
D-142
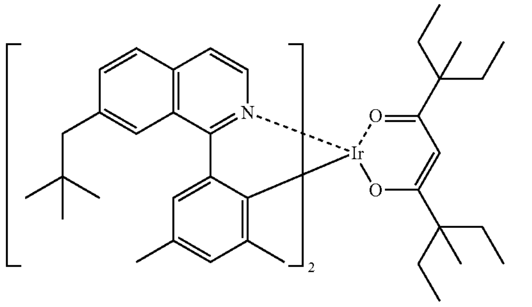
D-143
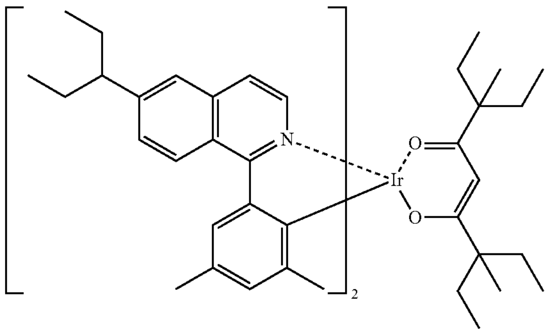
D-144
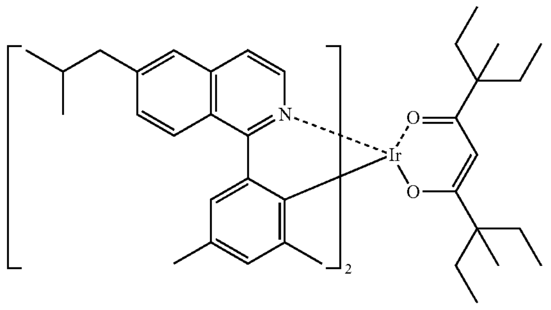
D-145
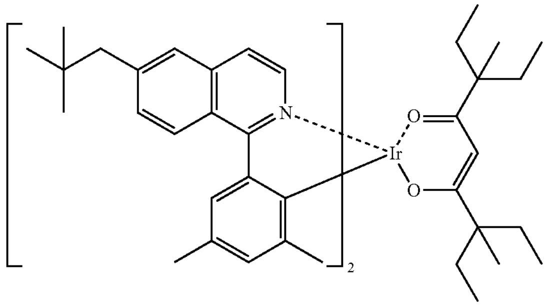

-continued

D-146

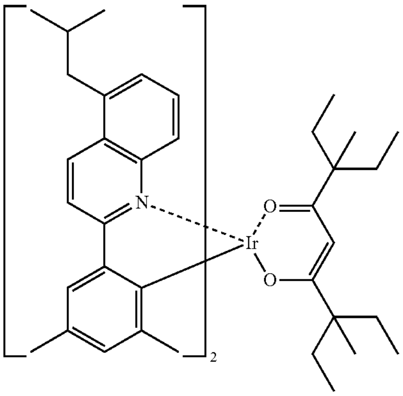

D-147

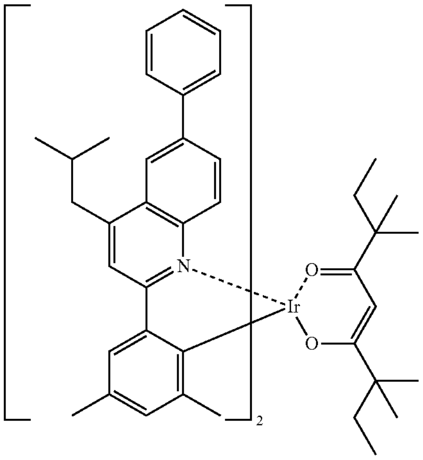

D-148

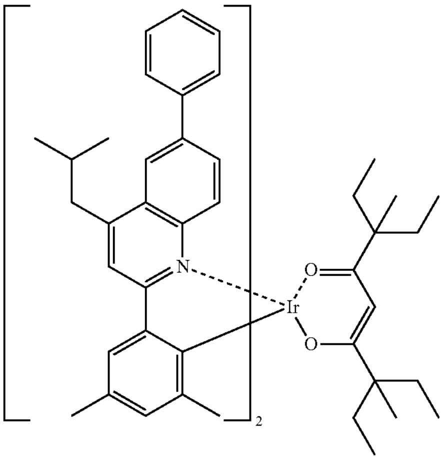

-continued

D-149

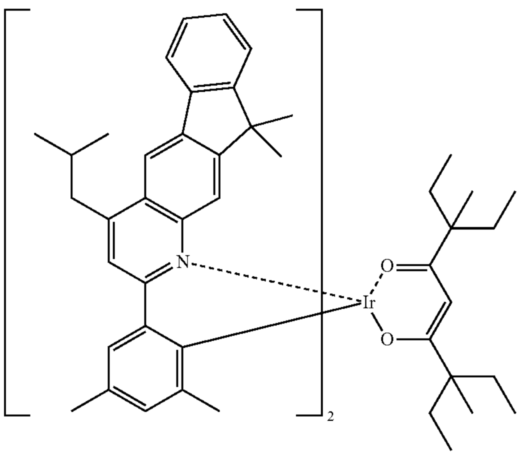

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the first host material and the second host material according to one embodiment, the layer can be formed by the above-listed methods, and can often be formed by co-deposition or mixture-deposition. The co-deposition is a mixed deposition method in which two or more materials are put into respective individual crucible sources and a current is applied to both cells simultaneously to evaporate the materials and to perform mixed deposition; and the mixed deposition is a mixed deposition method in which two or more materials are mixed in one crucible source before deposition, and then a current is applied to one cell to evaporate the materials.

According to one embodiment, when the first host material and the second host material exist in the same layer or different layers in the organic electroluminescent device, the layers by the two host compounds may be separately formed. For example, after depositing the first host material, a second host material may be deposited.

According to one embodiment, the present disclosure can provide display devices comprising a plurality of host materials including a first host material comprising the compound represented by formula 1 and a second host material comprising the compound represented by formula 2, or comprising an organic electroluminescent compound represented by formula 3 as a single host. In addition, by using the organic electroluminescent device of the present disclosure, display devices such as smartphones, tablets, notebooks, PCs, TVs, or display devices for vehicles, or lighting devices such as outdoor or indoor lighting can be prepared.

Hereinafter, the preparation method of compounds according to the present disclosure will be explained with reference to the synthesis method of a representative compound or intermediate compound in order to understand the present disclosure in detail.

[Example 1] Synthesis of Compound H-201

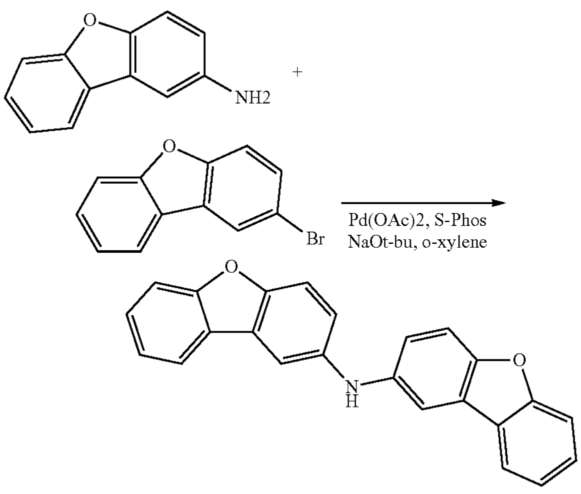

1

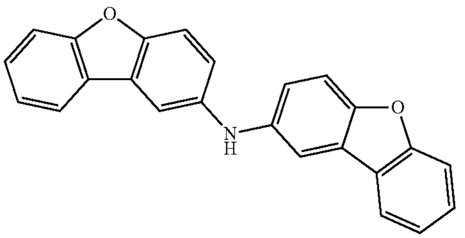

1

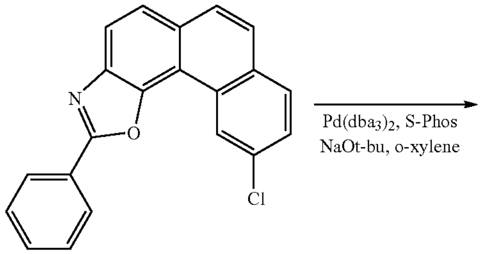

2

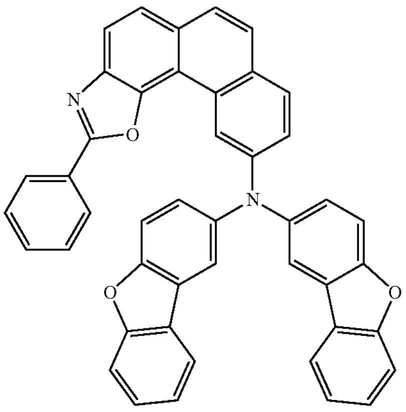

H-201

1) Synthesis of Compound 1

Dibenzofuran-2-amine (20 g, 144.7 mmol), 2-bromodibenzofuran (23.8 g, 96.47 mmol), $Pd(OAc)_2$ (1.1 g, 4.82 mmol), S-Phos (3.9 g, 9.65 mmol), NaOt-Bu (13.9 g, 144.7 mmol), and 485 mL, of o-xylene were added to the flask, and then stirred at 160° C. for 3 hours. After completion of the reaction, the mixture was cooled to room temperature, and then the organic layer was extracted with ethyl acetate, and the residual water was removed with magnesium sulfate followed by drying. Next, it was separated by column chromatography to obtain compound 1 (4.9 g, yield: 10%).

2) Synthesis of Compound H-201

Compound 1 (4.9 g, 12.76 mmol), compound 2 (4.2 g, 14.0 mmol), $Pd(dbas)_2$ (0.584 g, 0.638 mmol). S-Phos (0.523 g, 1.276 mmol), NaOt-Bu (1.8 g, 19.14 mmol), and 65 mL of o-xylene were added to the flask, and then stirred at 160° C. for 2 hours. After completion of the reaction, the mixture was cooled to room temperature, and then the organic layer was extracted with ethyl acetate, and the residual water was removed with magnesium sulfate followed by drying. Next, it was separated by column chromatography to obtain compound H-201 (5.6 g, yield: 68.3%).

| | MW | M.P |
|---|---|---|
| H-201 | 642.19 | 237° C. |

[Example 2] Synthesis of Compound H-183

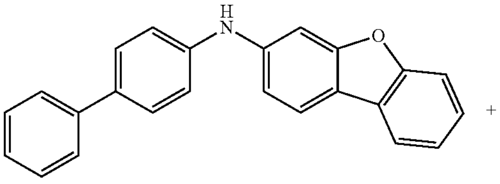

3

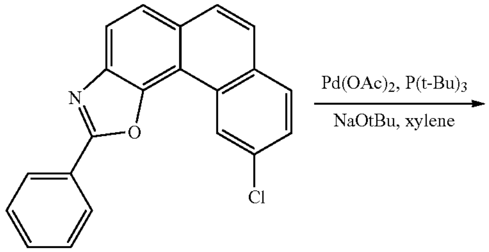

2

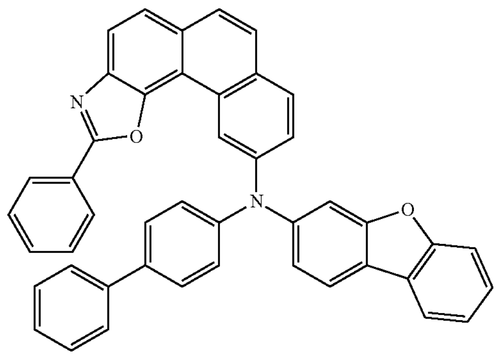

H-183

Compound 3 (25 g, 74.48 mmol), compound 2 (42.58 g, 81.93 mmol), $Pd(OAc)_2$ (0.16 g, 7.5 mmol), $P(t\text{-}Bu)_3$ (0.28 g, 7.5 mmol), NaOt-Bu (14.31 g, 150 mmol), and 284.09 mL of o-xylene were added to the flask, and then stirred at 160° C. for 2 hours. After completion of the reaction, the mixture was cooled to room temperature, and then the organic layer was extracted with ethyl acetate, and the residual water was removed with magnesium sulfate followed by drying. Next, it was separated by column chromatography to obtain compound H-183 (23.4 g, yield: 50%).

| | MW | M.P |
|---|---|---|
| H-183 | 628.22 | 256.5° C. |

[Example 3] Synthesis of Compound H-217

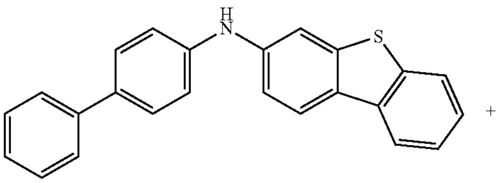

4

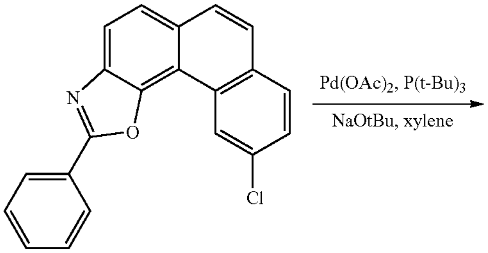

2

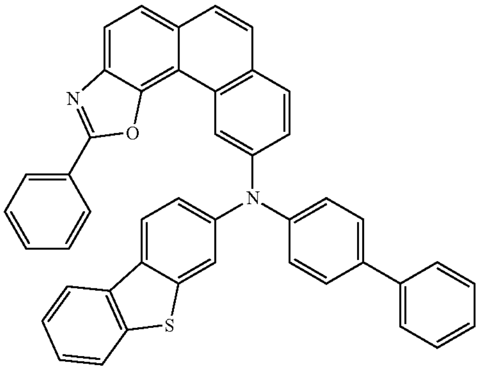

H-217

Compound 4 (20 g, 56.96 mmol), compound 2 (18.8 g, 57.13 mmol), $Pd(OAc)_2$ (0.13 g, 5.7 mmol), $P(t\text{-}Bu)_3$ (0.22 g, 5.7 mmol), NaOt-Bu (11 g, 113.92 mmol), and 227.27 mL of o-xylene were added to the flask, and then stirred at 160° C. for 2 hours. After completion of the reaction, the mixture was cooled to room temperature, and then the organic layer was extracted with ethyl acetate, and the residual water was removed with magnesium sulfate followed by drying. Next, it was separated by column chromatography to obtain compound H-217 (12.5 g, yield: 34%).

| | MW | M.P |
|---|---|---|
| H-217 | 644.19 | 249° C. |

[Example 4] Synthesis of Compound H-199

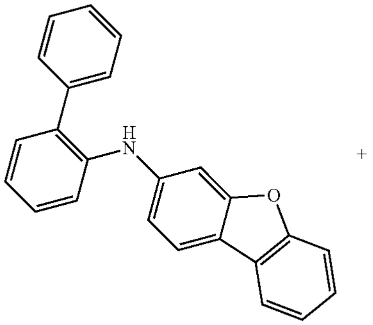

S1

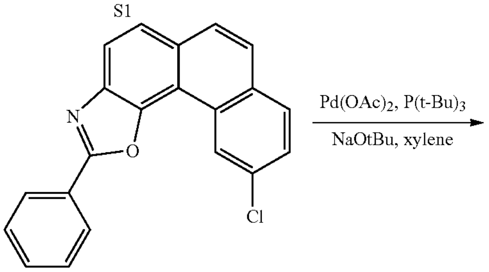

2

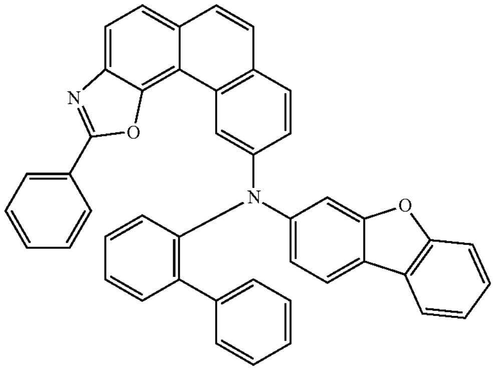

H-199

Compound S1 (25 g, 74.48 mmol), compound 2 (42.58 g, 81.93 mmol), $Pd(OAc)_2$ (0.16 g, 7.5 mmol), $P(t\text{-}Bu)_3$ (0.28 g, 7.5 mmol), NaOt-Bu (14.31 g, 150 mmol), and 284.09 mL of o-xylene were added to the flask, and then stirred at 160° C. for 2 hours. After completion of the reaction, the mixture was cooled to room temperature, and then the organic layer was extracted with ethyl acetate, and the residual water was removed with magnesium sulfate followed by drying. Next, it separated by column chromatography to obtain compound H-199 (23.4 g, yield: 50%).

| | MW | M.P |
|---|---|---|
| H-199 | 628.22 | 252° C. |

[Example 5] Synthesis of Compound C-8

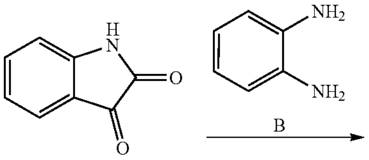

A

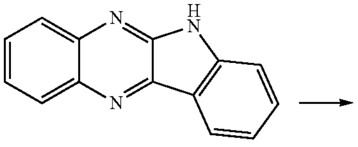

1-1

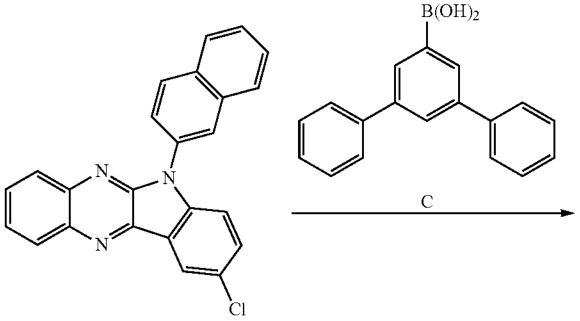

1-2

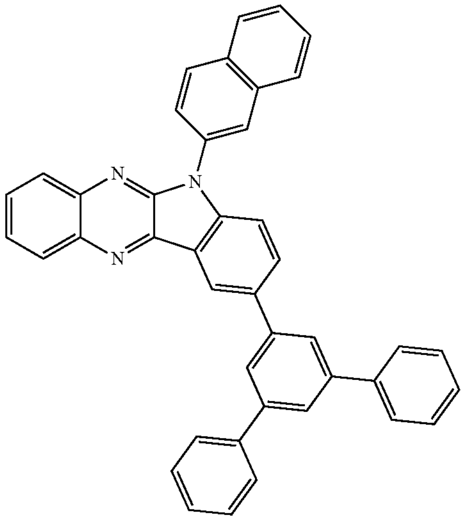

C-8

1) Synthesis of Compound 1-1

Compound A (25 g, 137.68 mmol), compound B (12.4 g, 114.73 mmol), and 300 mL of ethanol were added to the flask and dissolved, and then refluxed at 120° C. for 6 hours. After completion of the reaction, the resulting solid was filtered with methanol to obtain compound 1-1 (21.5 g, yield: 74%).

2) Synthesis of Compound 1-2

Compound 1-1 (10 g, 39.41 mmol) and 2-iodonaphthalene (15 g, 59.12 mmol), CuI (3.7 g, 19.70 mmol), EDA (3 mL, 39.41 mmol), and $Cs_2CO_3$ (25 g, 78.82 mmol) in the flask were dissolved in 200 mL of o-DCB, and then refluxed at 180° C. for 6 hours. Next, the reaction mixture was stirred at room temperature for 1 hour, and then methanol and distilled water were added thereto. After completion of the reaction, the resulting solid was filtered with methanol, and then the filtrate was distilled under reduced pressure. Next, it was separated by column chromatography to obtain compound 1-2 (4:7 g, yield: 48%).

3) Synthesis of Compound C-8

Compound 1-2 (3 g, 7.89 mmol), compound C (2.6 g, 9.47 mmol), $Pd_2(dba)_3$ (360 mg, 0.394 mmol), S-phos (323 mg, 0.789 mmol), NaOtBu (1.8 g, 19.72 mmol) and 50 mL of o-xylene 50 mL were added to the flask and dissolved, and then stirred under reflux for 5 hours. After completion of the reaction, the mixture was cooled to room temperature, and then distilled water was added thereto. Next, the organic layer was extracted with methylene chloride (MC), and then the residual water was removed with magnesium sulfate followed by drying. Next, it was distilled under reduced pressure, and then separated by column chromatography to obtain compound C-8 (2.0 g, yield: 44%).

| | MW | MP |
|---|---|---|
| C-8 | 573.68 | 274° C. |

Hereinafter, the preparation method of an organic electroluminescent device comprising the plurality of host materials according to the present disclosure, and the property thereof will be explained in order to understand the present disclosure in detail.

[Device Example 1] Preparation of an OLED Comprising the Plurality of Host Materials According to the Present Disclosure An OLED according to the present disclosure was produced. First, a transparent electrode indium tin oxide (ITO) thin film (10 n/sg) on a glass substrate for an OLED (GEOMATEC CO., LTD., Japan) was subjected to an ultrasonic washing with acetone and isopropyl alcohol, sequentially, and thereafter was stored in isopropanol and then used. Thereafter, the ITO substrate was mounted on a substrate holder of a vacuum vapor deposition apparatus. Then, compound HI-1 was introduced into a cell of the vacuum vapor deposition apparatus, and compound HT-1 was introduced into another cell of the vacuum vapor deposition apparatus. The two materials were evaporated at different rates and compound HI-1 was deposited in a doping amount of 3 wt % based on the total amount of compound HI-1 and compound HT-1 to form a first hole injection layer having a thickness of 10 nm. Next, compound HT-1 was introduced into a cell of the vacuum vapor deposition apparatus and was evaporated by applying an electric current to the cell, thereby forming a first hole transport layer having a thickness of 80 nm on the first hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: the first host material and the second host material described in the following Table 1 were introduced into two cells of the vacuum vapor deposition apparatus as hosts of the light-emitting layer, respectively, and compound D-39 was introduced into another cell as a dopant. The two host materials were evaporated at a rate of 1:1 and the dopant material was evaporated at a different rate, simultaneously, and was deposited in a doping amount of 3 wt % based on the total amount of the hosts and dopant to form a light-emitting layer having a thickness of 40 nm on the second hole transport layer. Next, compounds ET-1 and EI-1 in another two cells of the vacuum vapor deposition apparatus were evaporated at a rate of 1:1 to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced.

[Comparative Example 1] Preparation of an OLEO Comprising a Conventional Compound as a Host An OLED was produced in the same manner as in Device Example 1, except that compound C-8 was used alone as a host of the light-emitting layer.

The driving voltage, the luminous efficiency, and the light-emitting color at a luminance of 1,000 nits, and the time taken for luminance to decrease from 100% to 95% at a luminance of 5,000 nits (lifespan; T95) of the organic electroluminescent devices according to Device Example 1 and Comparative Example 1 produced as described above, are measured, and the results thereof are shown in Table 1 below:

TABLE 1

| | First host material | Second host material | Driving voltage (V) | Luminous Efficiency (cd/A) | Light-Emitting Color | Lifespan (T95) (hr) |
|---|---|---|---|---|---|---|
| Device Example 1 | C-8 | H-199 | 3.2 | 33.2 | Red | 226 |
| Comparative Example 1 | C-8 | — | 3.5 | 29.3 | Red | 7.9 |

Referring to Table 1 above, by comprising a specific combination of compounds according to the present disclosure as host materials, an organic electroluminescent device having high luminous efficiency and significantly improved lifespan properties can be provided, compared to the organic electroluminescent device comprising a single host material.

The compounds used in Device Example 1 and Comparative Example 1 above are shown in the following Table 2:

TABLE 2

| | |
|---|---|
| Hole Injection Layer/ Hole Transport Layer | 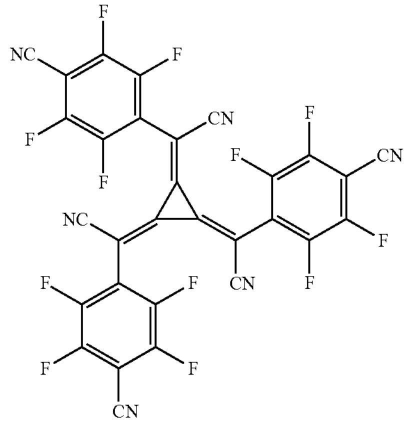 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F] HI-1 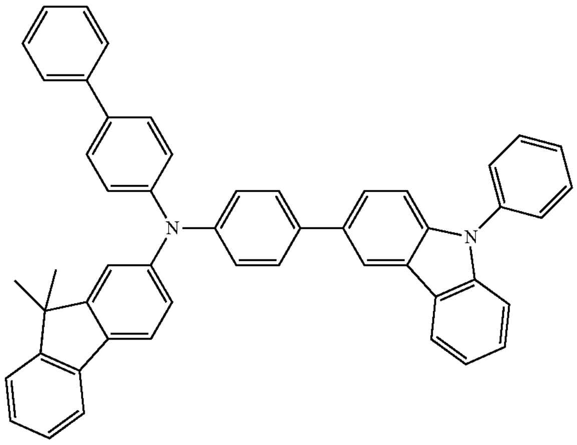 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21] HT-1 |

TABLE 2-continued
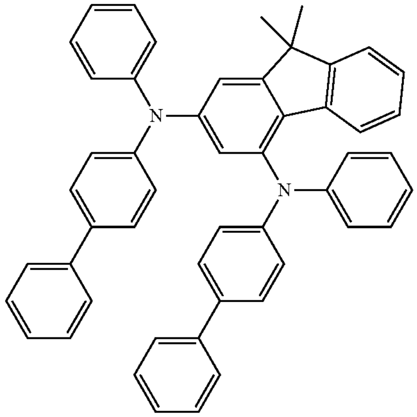 [SMILES: CC1(C)c2ccccc2-c2c(N(c3ccccc3)c3ccc(-c4ccccc4)cc3)cc(N(c3ccccc3)c3ccc(-c4ccccc4)cc3)cc21]
HT-2
Light-Ernitting Layer
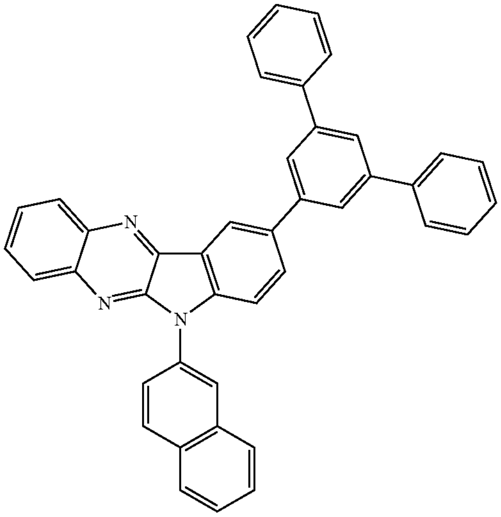 [SMILES: c1ccc(-c2cc(-c3ccccc3)cc(-c3ccc4c(c3)c3nc5ccccc5nc3n4-c3ccc4ccccc4c3)c2)cc1]
C-8
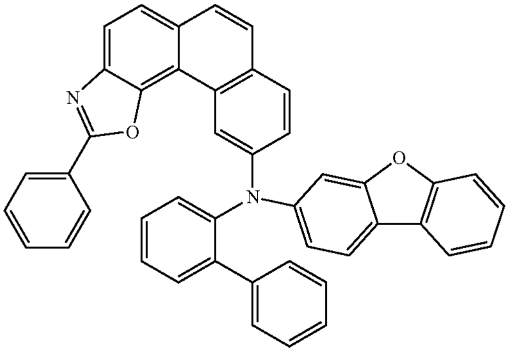 [SMILES: c1ccc(-c2nc3ccc4ccc5ccc(N(c6ccc7c(c6)oc6ccccc67)c6ccccc6-c6ccccc6)cc5c4c3o2)cc1]
H-199

TABLE 2-continued

| | |
|---|---|
| | 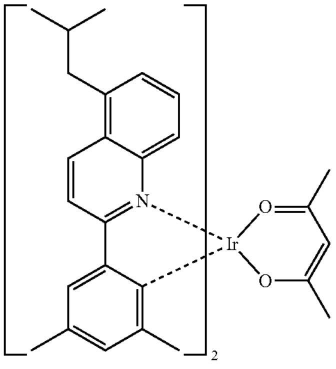 D-39 |
| Electron Transport Layer/ Electron Injection Layer | 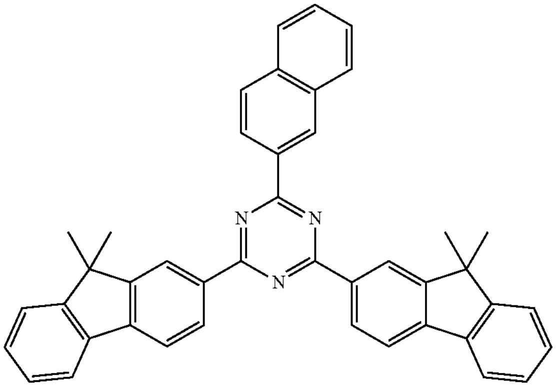 [SMILES: CC1(C)c2ccccc2-c2ccc(-c3nc(-c4ccc5c(c4)C(C)(C)c4ccccc4-5)nc(-c4ccc5ccccc5c4)n3)cc21] ET-1 |
| | 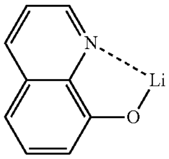 EI-1 |

The invention claimed is:

1. A plurality of host materials comprising a first host material and a second host material, wherein the first host material comprises a compound represented by the following formula 1-1 or 1-2 and the second host material comprises a compound represented by the following formula 2:

(1-1)

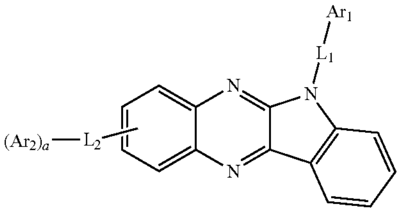

-continued (1-2)

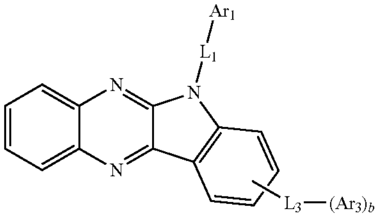

wherein, $L_1$ represents a single bond, $L_2$ and $L_3$ each independently represent a single bond or a substituted or unsubstituted phenylene;

$Ar_1$ represents pyridyl substituted with deuterium or (C6-C30)aryl;

$Ar_2$ and $Ar_3$ each independently represent (C6-C30)aryl unsubstituted or substituted with deuterium or (C6-C30)aryl;

a and b each independently represent an integer of 1 or 2; and when a and b are an integer of 2, each of $Ar_2$ and each of $Ar_3$ may be the same or different;

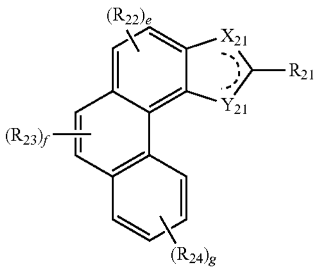

(2)

wherein, $X_{21}$ and $Y_{21}$ each independently represent —N═, —$NR_{25}$—, —O—, or —S—, provided that one of $X_{21}$ and $Y_{21}$ is —N═, and the other of $X_{21}$ and $Y_{21}$ is —$NR_{25}$—, —O—, or —S—;

$R_{21}$ represents a substituted or unsubstituted (C6-C30)aryl or a substituted or unsubstituted (3- to 30-membered) heteroaryl;

$R_{22}$ to $R_{25}$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30) alkenylamino, a substituted or unsubstituted mono- or di- (C6-C30)arylamino, a substituted or unsubstituted (C1-C30)alkyl (C6-C30)arylamino, a substituted or unsubstituted mono- or di- (3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl (3- to 30-membered)heteroarylamino; or may be linked to the adjacent substituents to form a ring(s);

provided that at least one of $R_{22}$ to $R_{24}$ is —$L_{21}$-$Ar_{21}$;

$L_{21}$ represents a single bond or a substituted or unsubstituted (C6-C30)arylene;

$Ar_{21}$ represents a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, or —$NR_{31}R_{32}$;

$R_{31}$ and $R_{32}$ each independently represent a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl;

e and f each independently represent an integer of 1 or 2, and g represents an integer of 1 to 4; and when e to g are an integer of 2 or more, each of $R_{22}$, each of $R_{23}$, and each of $R_{24}$ may be the same or different.

2. A plurality of host materials comprising a first host material and a second host material, wherein the first host material comprises a compound selected from the following compounds:

C-1

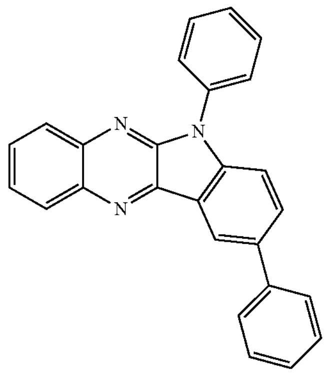

C-2

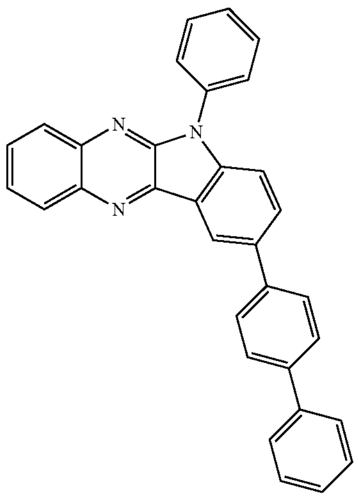

C-3

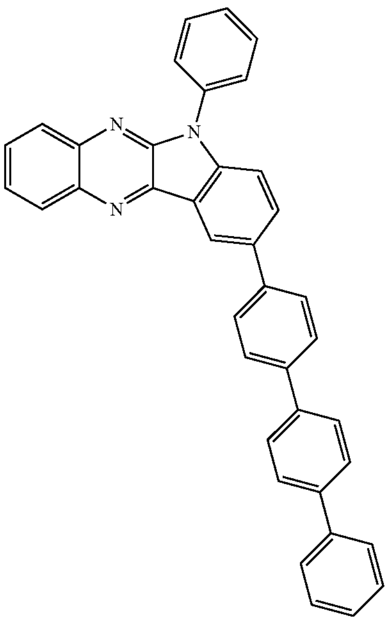

-continued
C-4
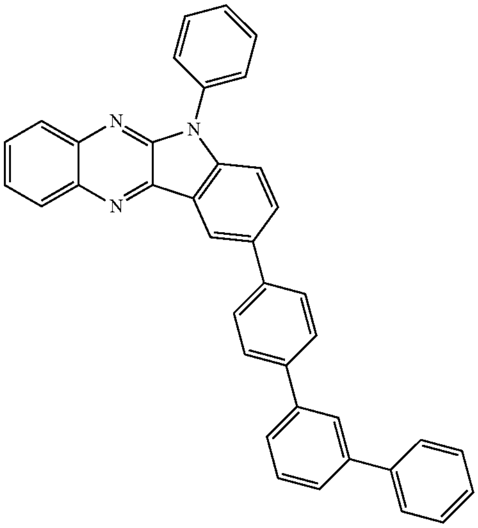
C-5
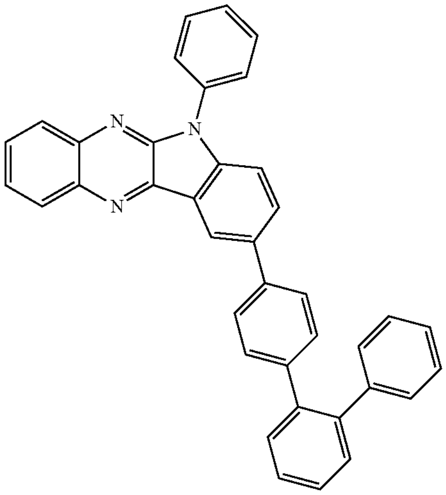
C-6
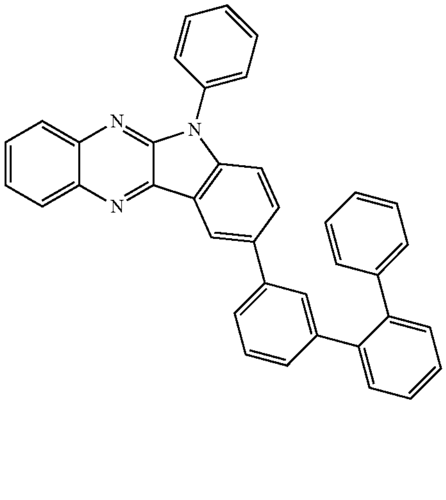
-continued
C-7
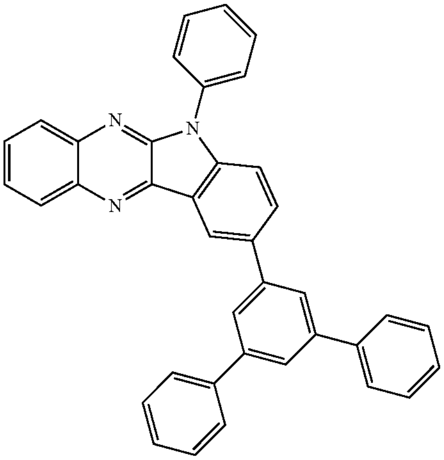
C-8
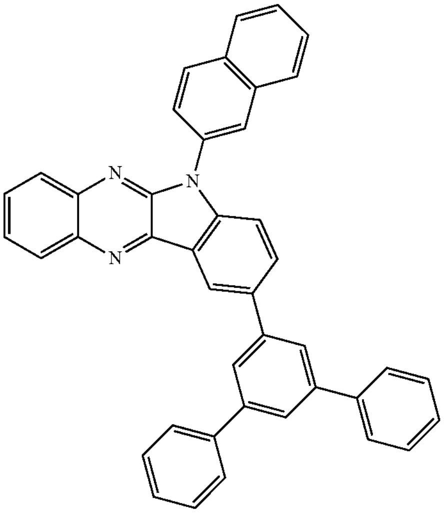
C-9
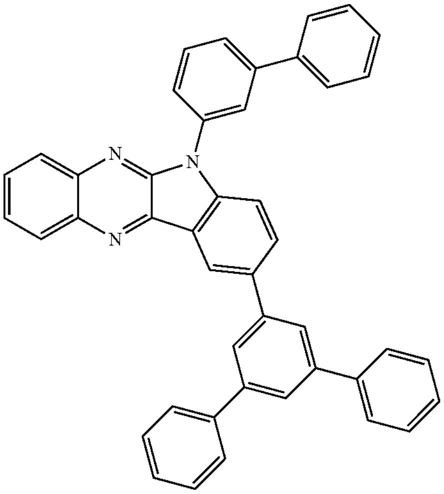

-continued
C-10
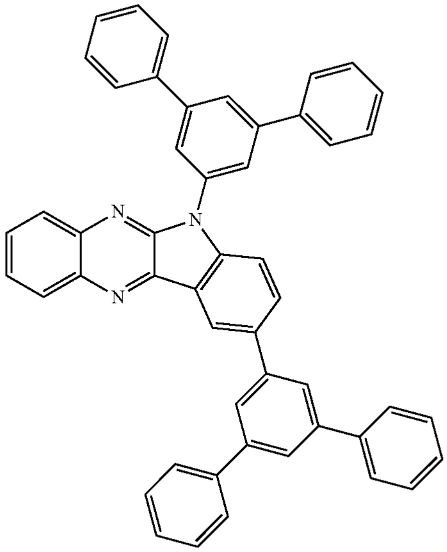
C-11
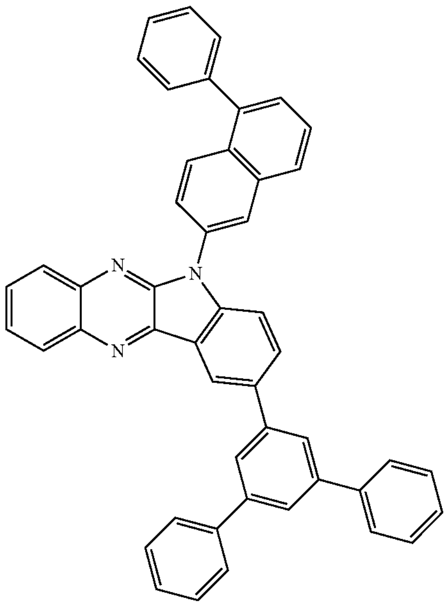
C-12
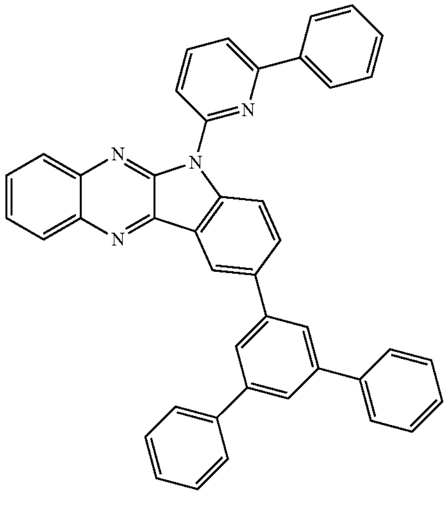
-continued
C-13
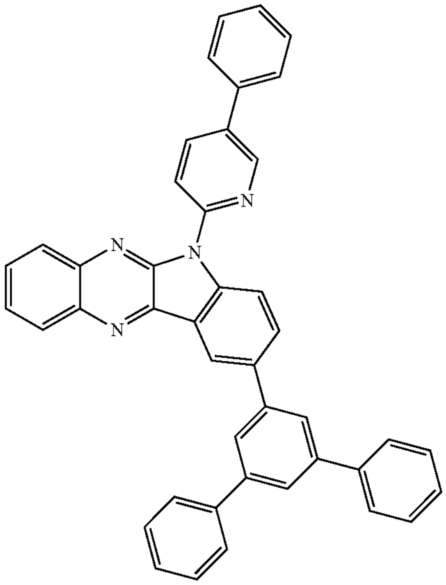
C-14
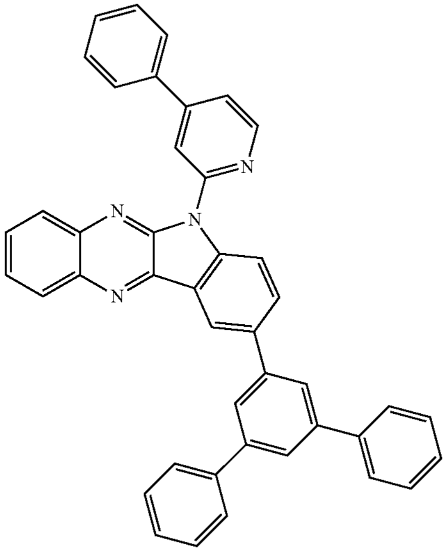
C-15
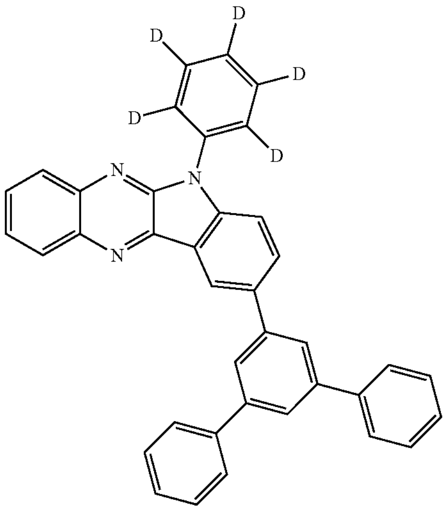

-continued
C-16
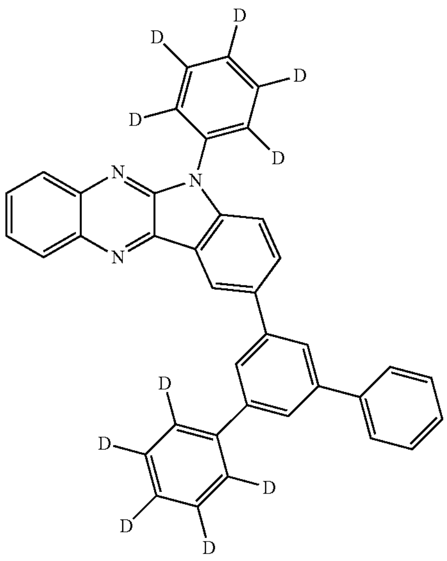
C-17
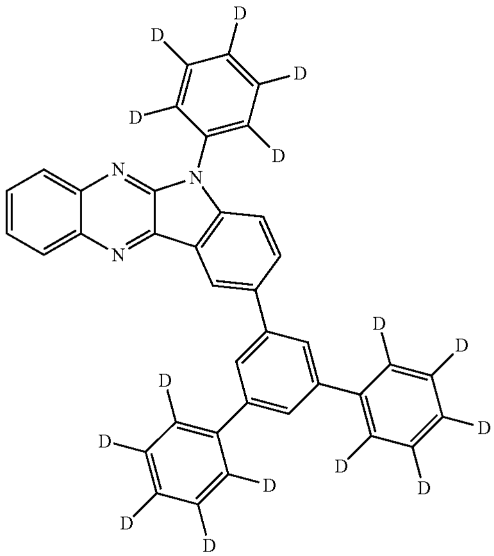
-continued
C-18
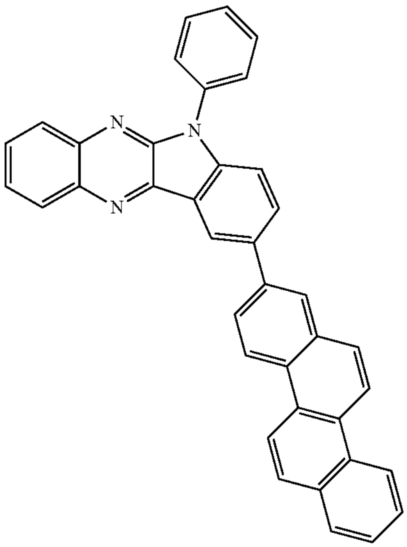
C-19
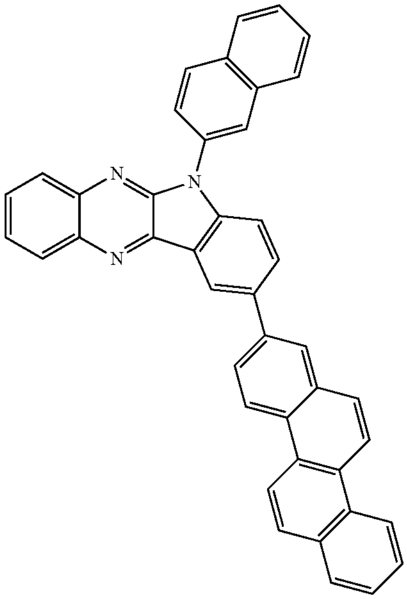

-continued
C-20
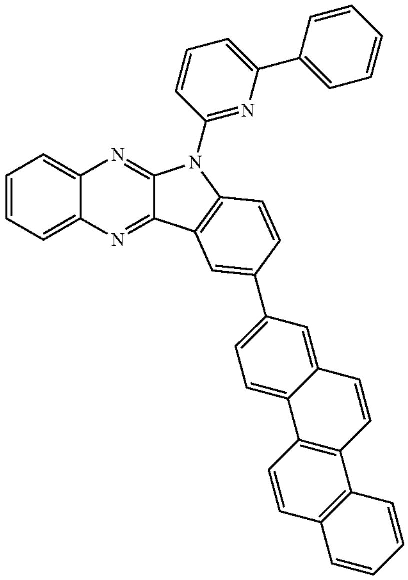
C-21
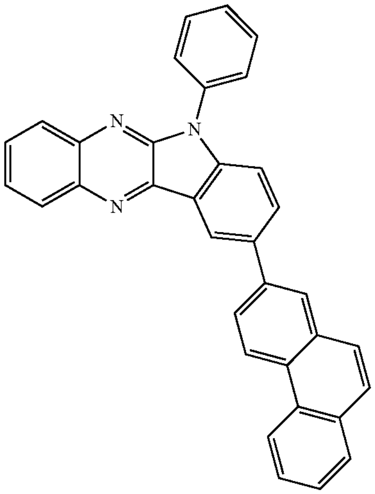
C-22
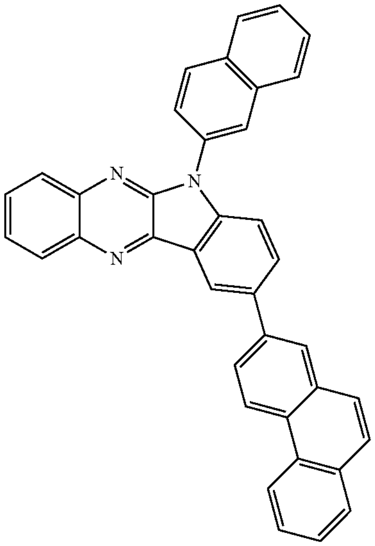
-continued
C-23
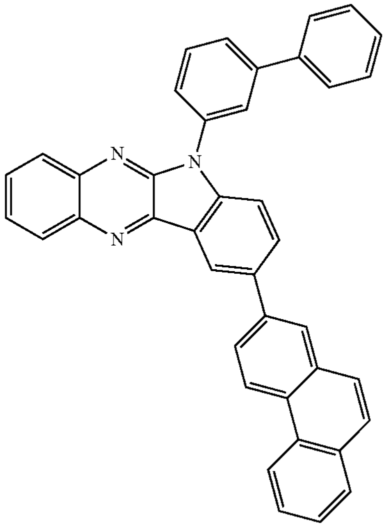
C-24
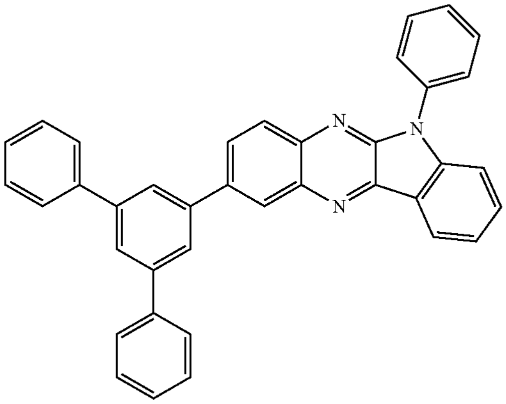
C-25
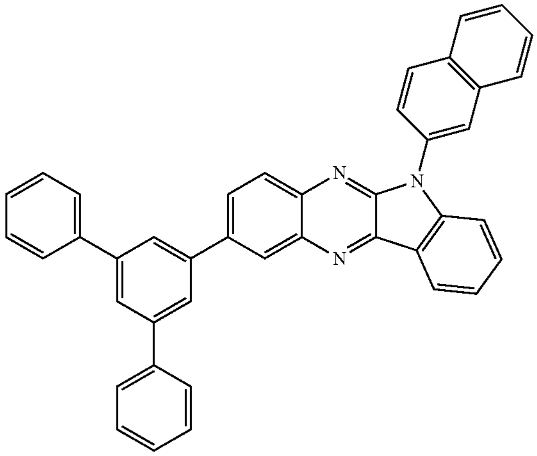

-continued
C-26
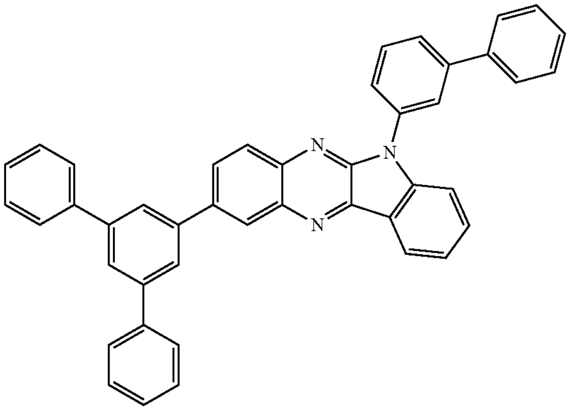
C-27
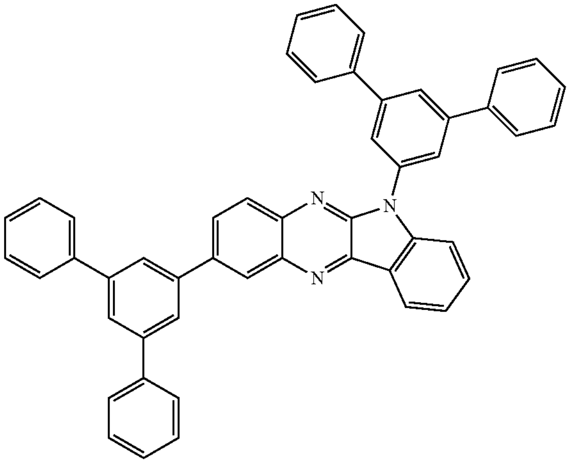
C-28
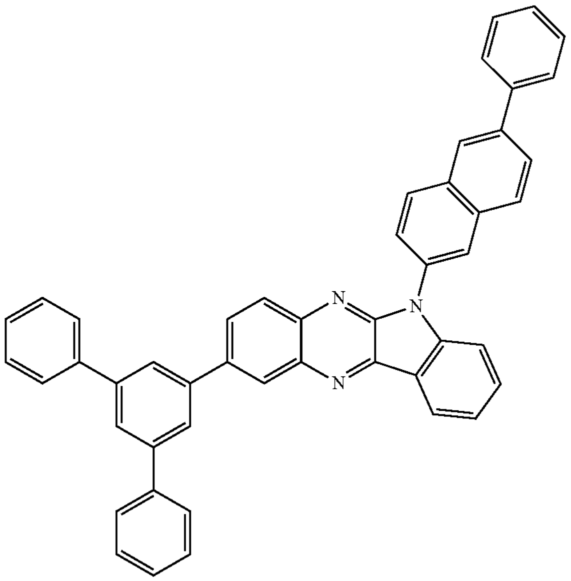
-continued
C-29
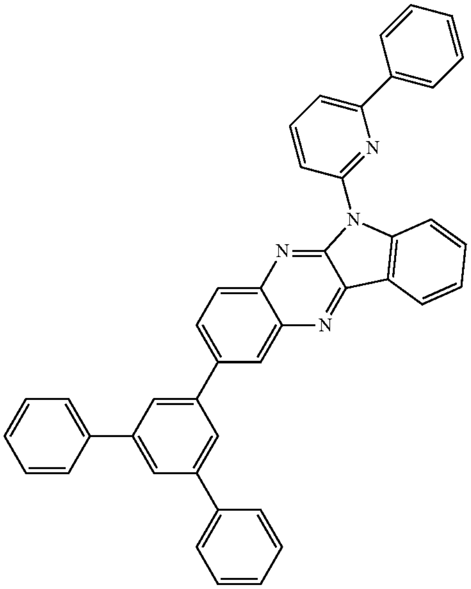
C-30
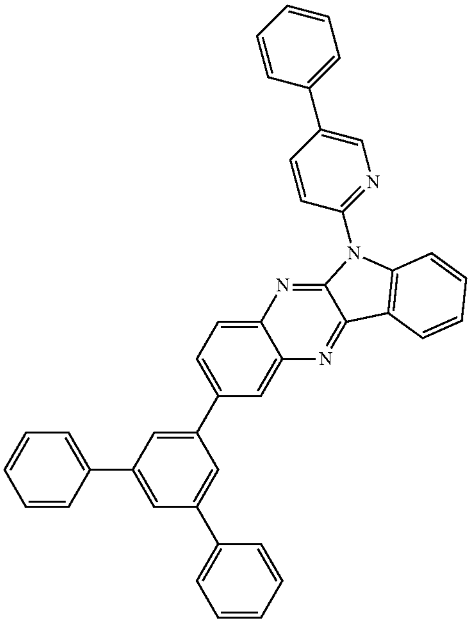

-continued
C-31
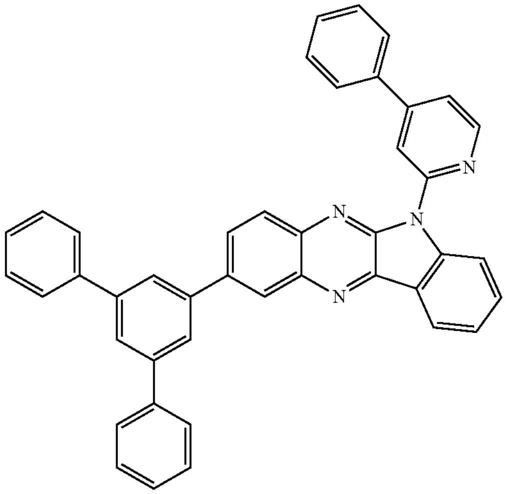
C-32
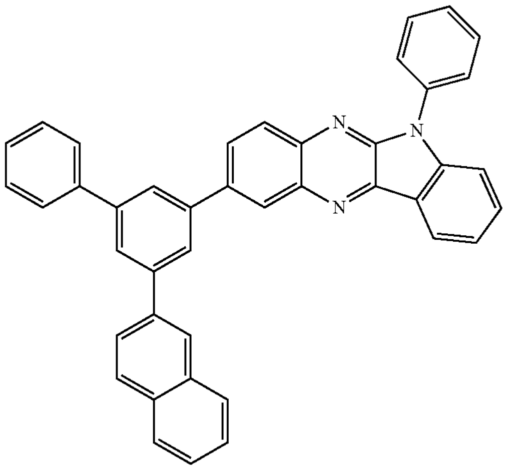
C-33
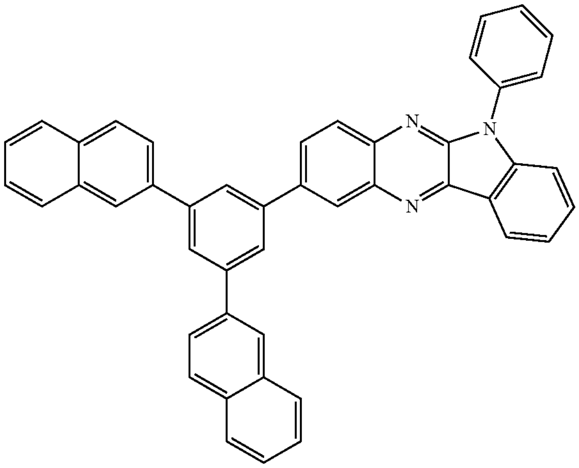
-continued
C-34
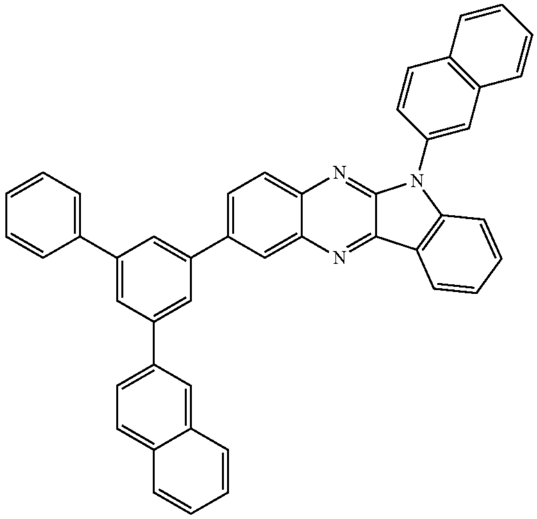
C-35
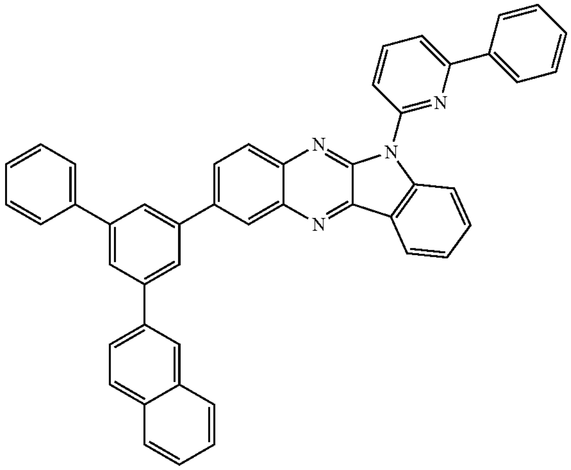
C-36
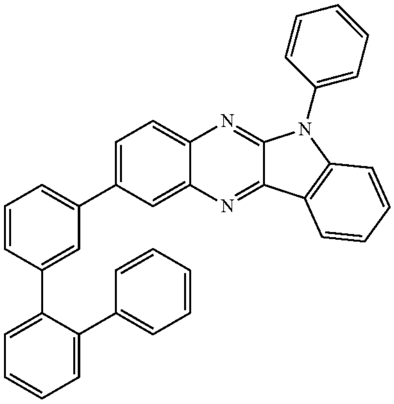

-continued
C-37
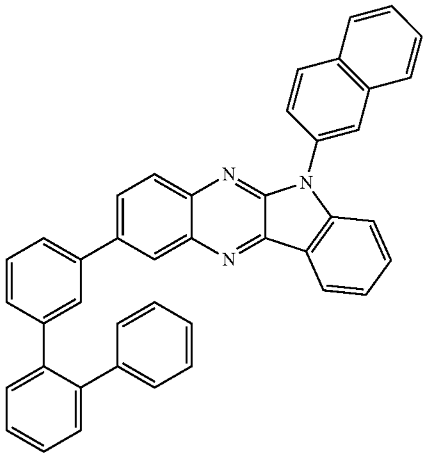
C-38
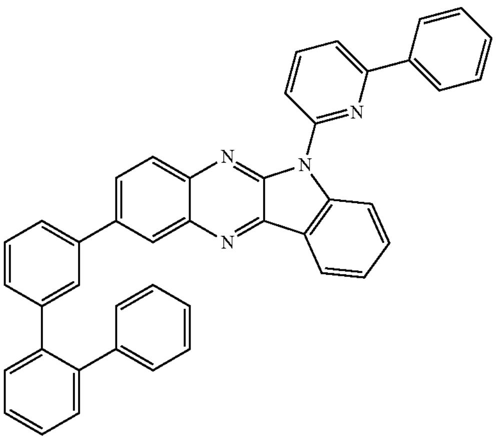
C-39
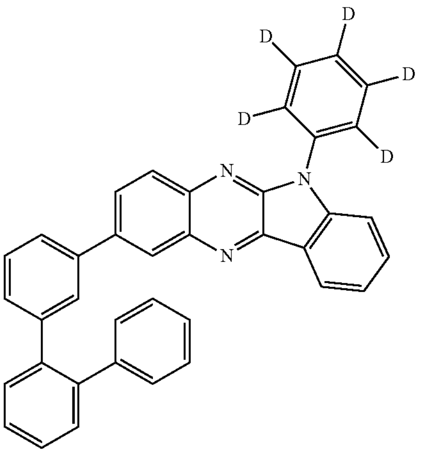
-continued
C-40
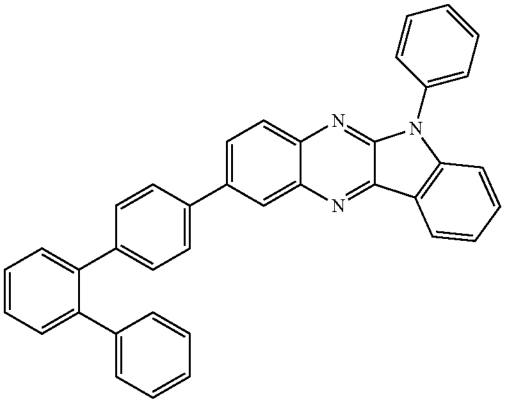
C-41
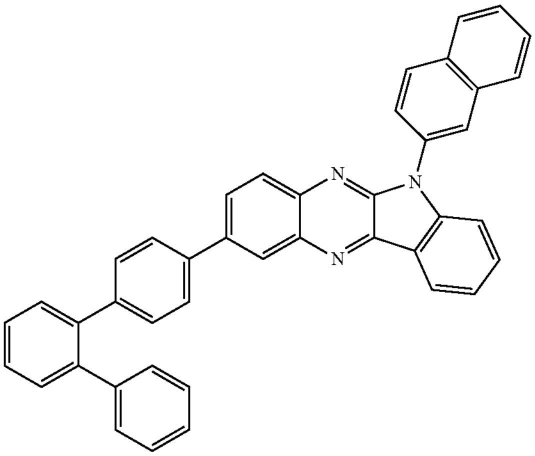
C-42
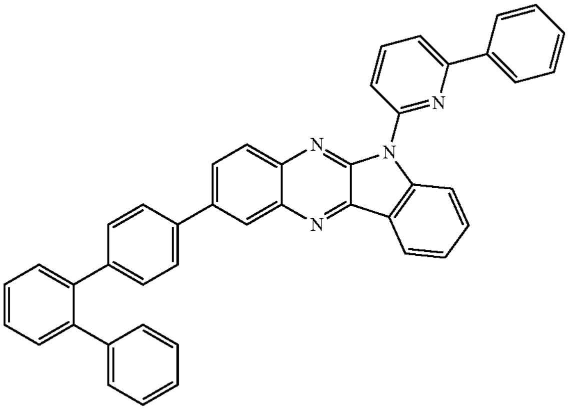

-continued
C-43
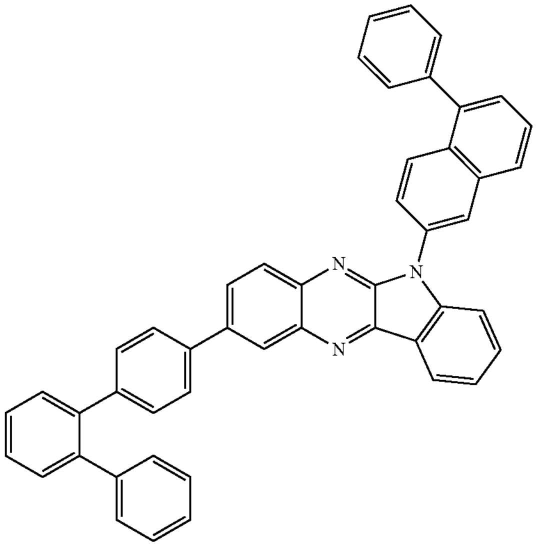
C-44
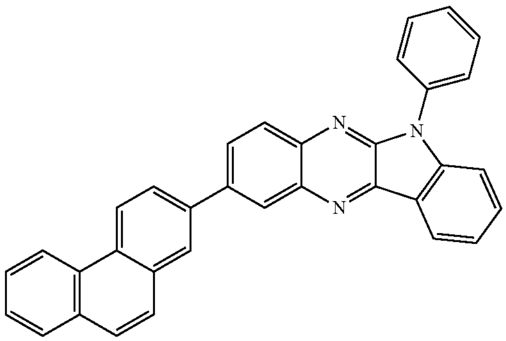
C-45
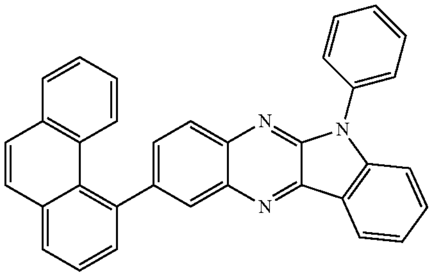
C-46
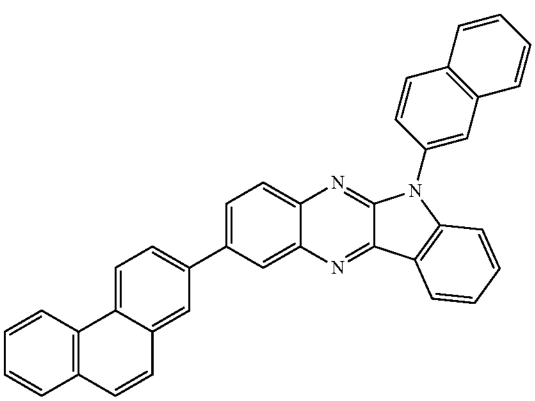
-continued
C-47
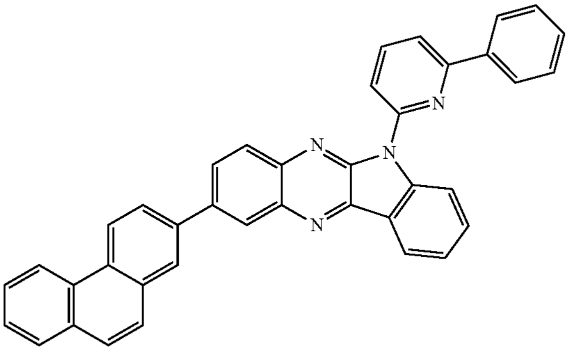
C-48
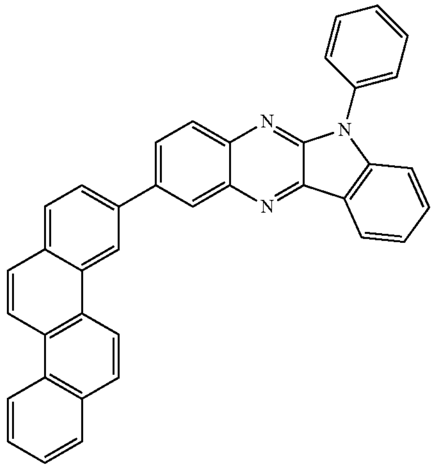
C-49
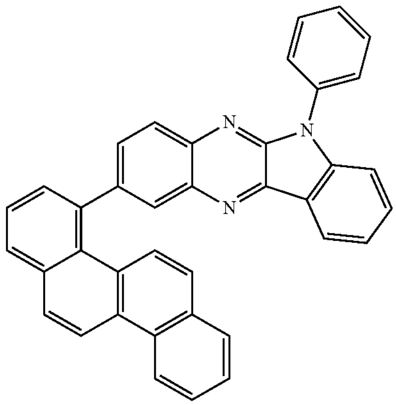
C-50
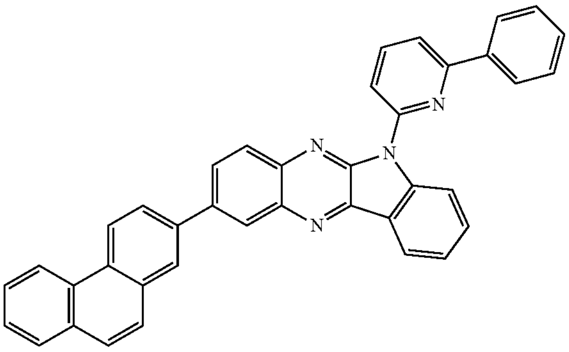

-continued
C-51
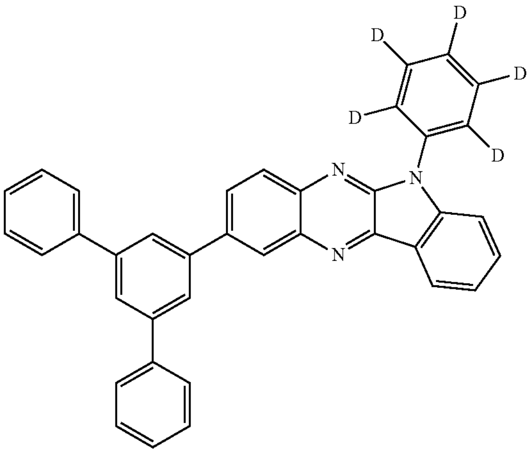
C-52
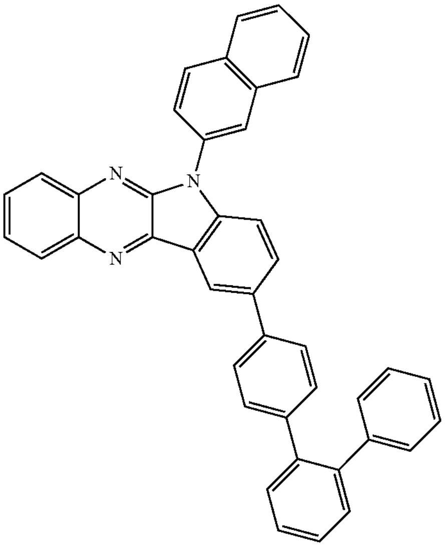
C-53
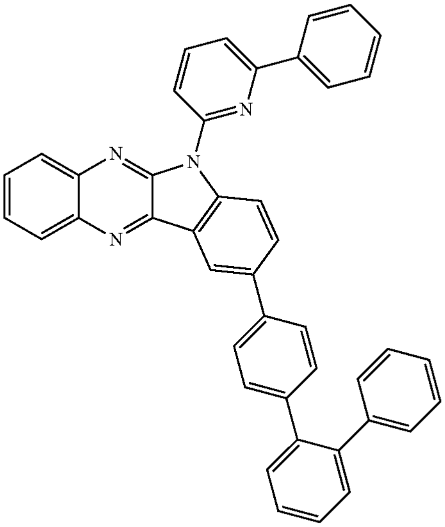
-continued
C-54
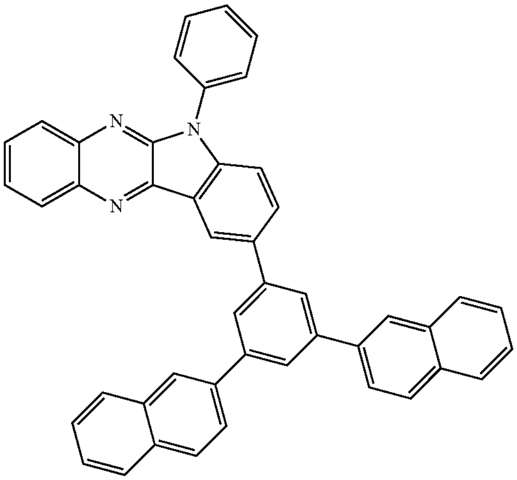
C-55
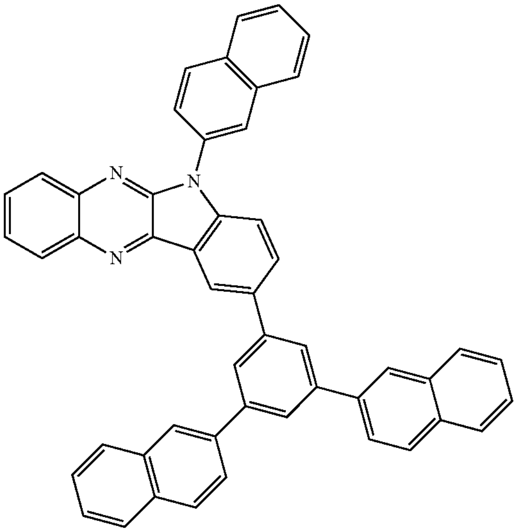
C-56
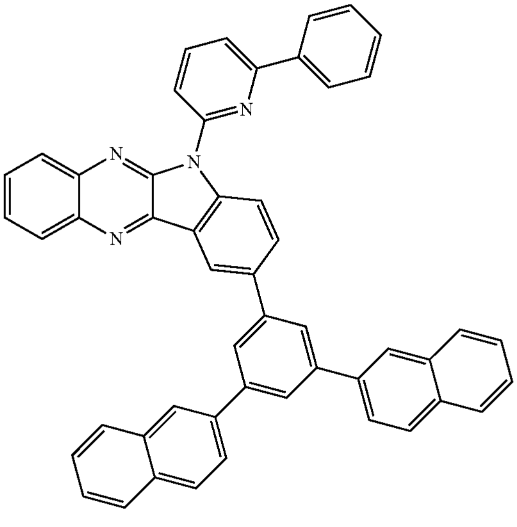

-continued
C-57
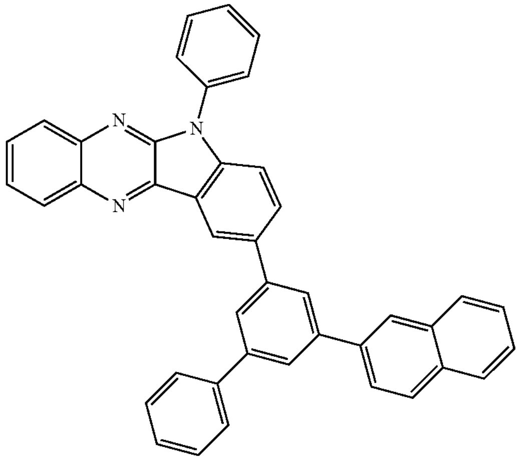
C-58
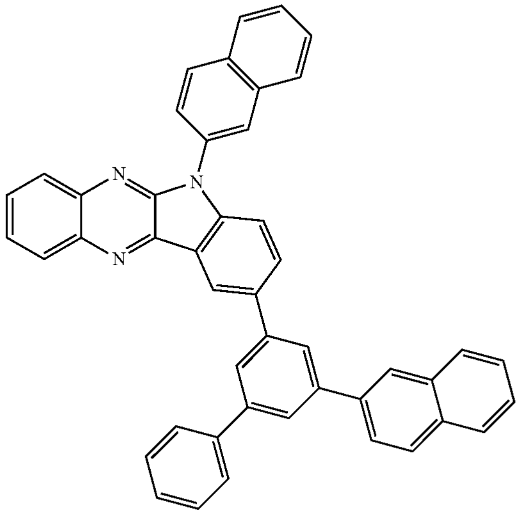
C-59
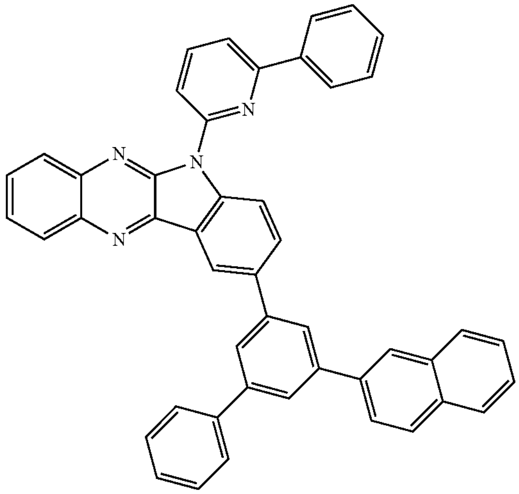
-continued
C-60
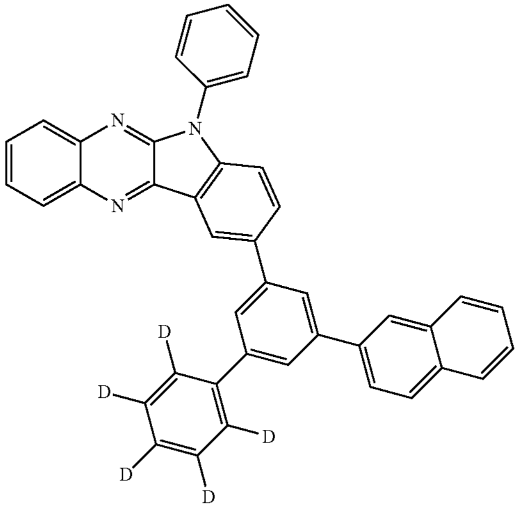
C-61
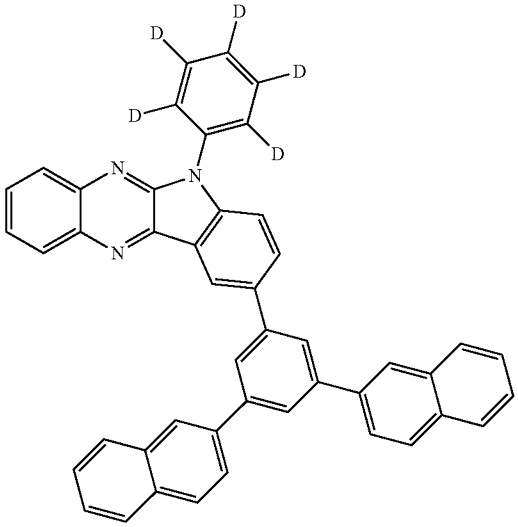
C-62
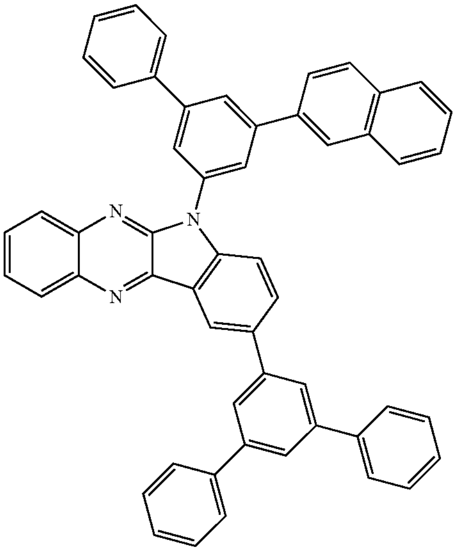

-continued
C-63
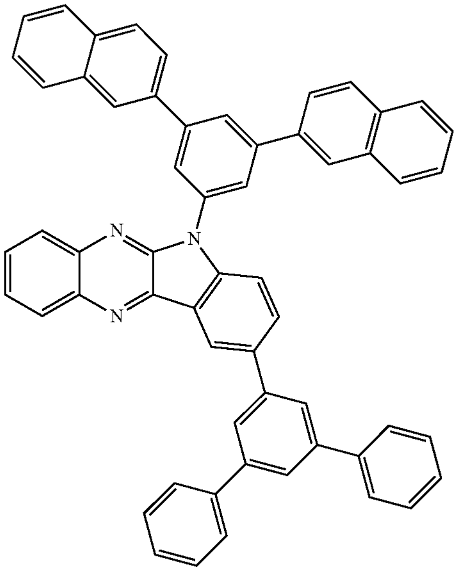
C-64
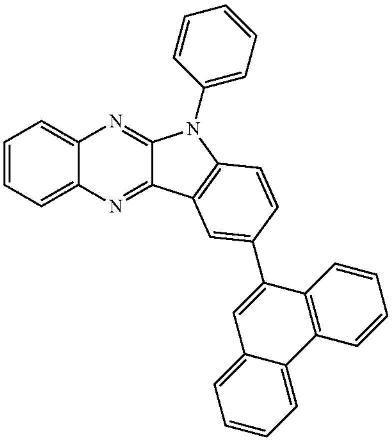
C-65
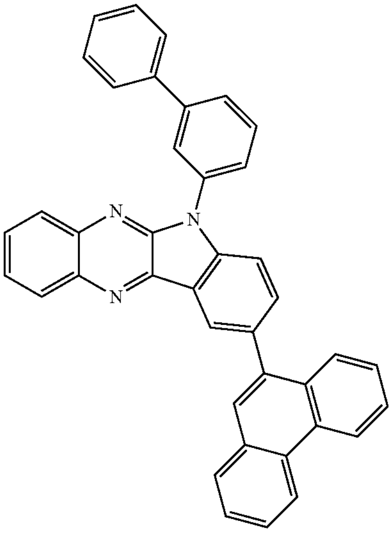
-continued
C-66
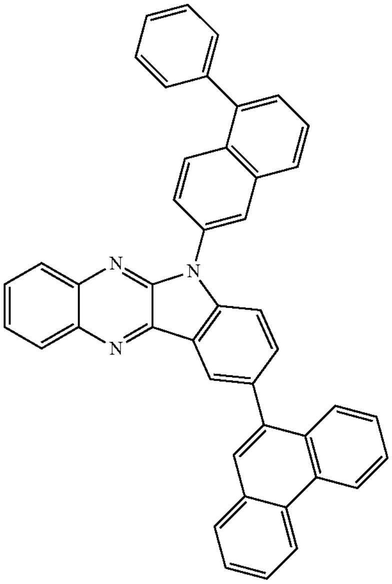
C-67
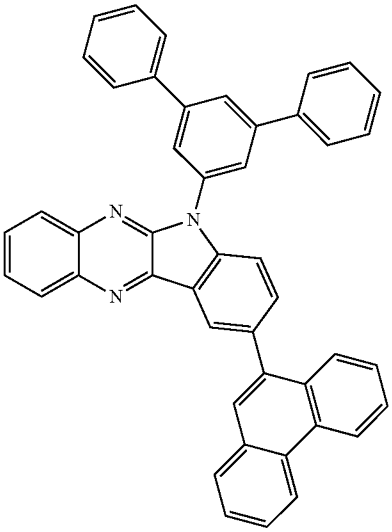
C-68
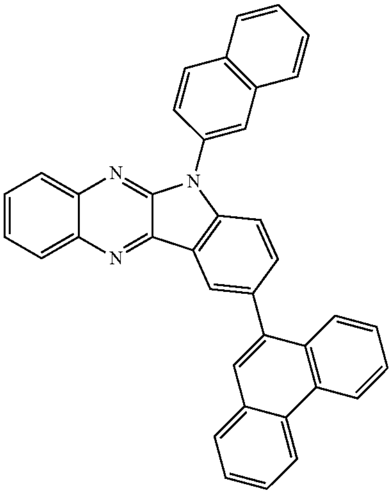

-continued
C-69
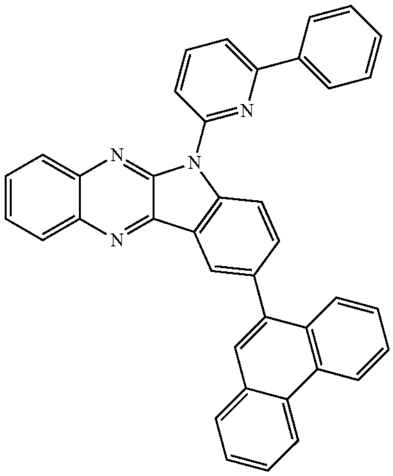
C-70
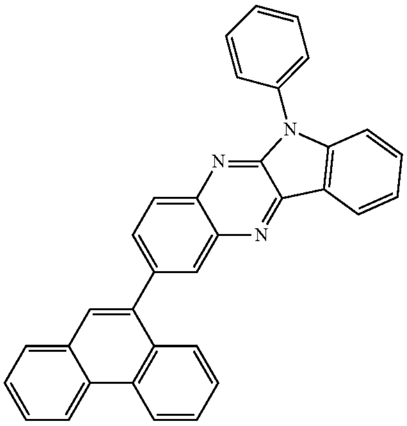
C-71
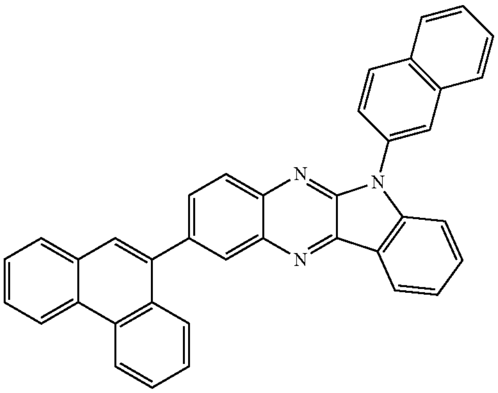
-continued
C-72
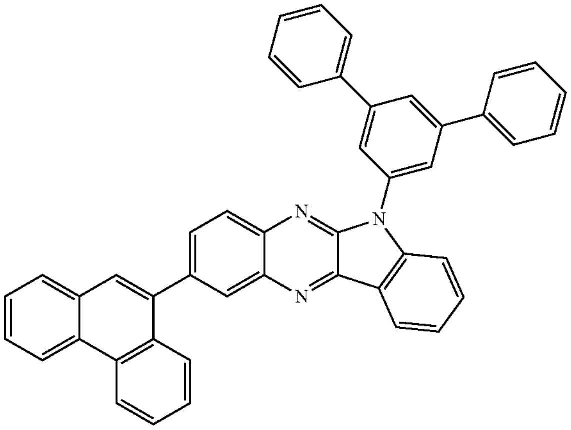
C-73
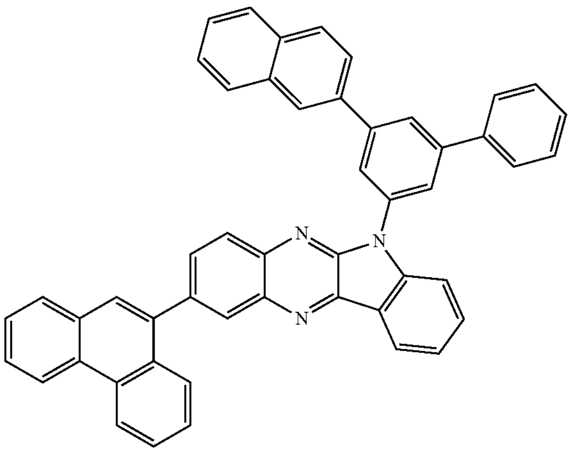
C-74
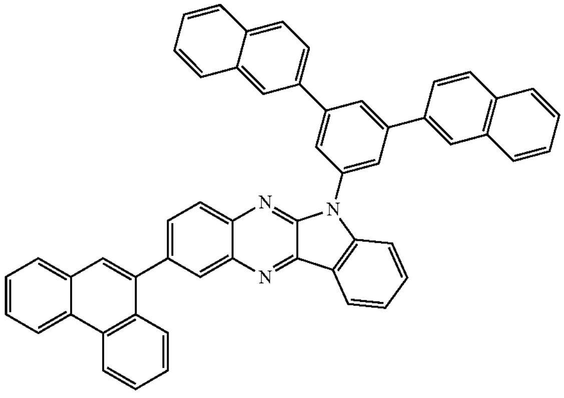

-continued
C-75
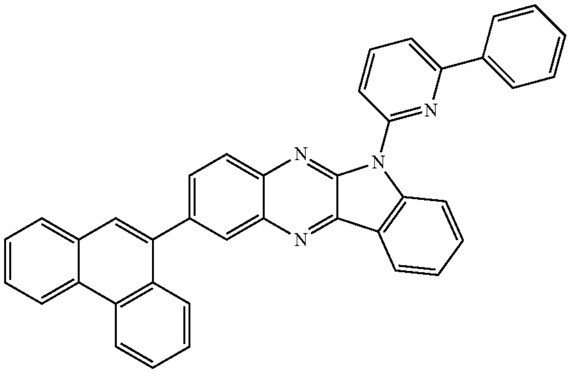
C-76
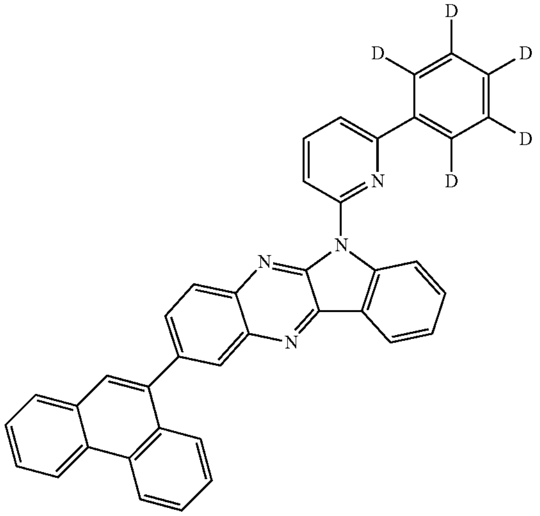
C-77
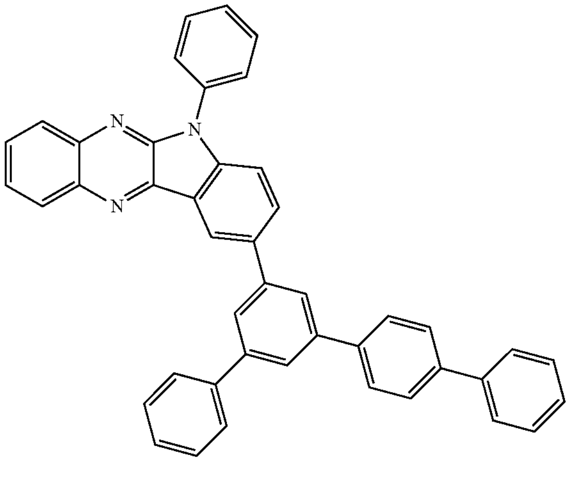
-continued
C-78
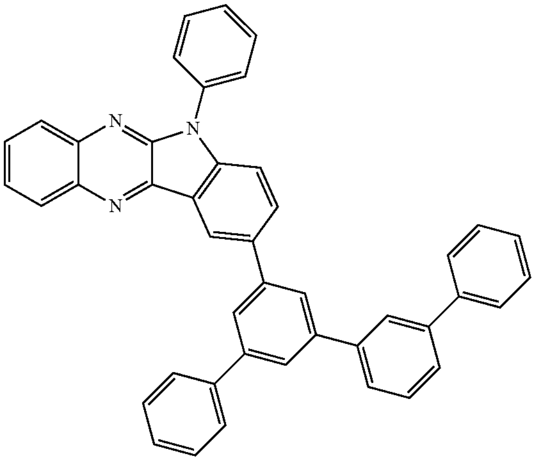
C-79
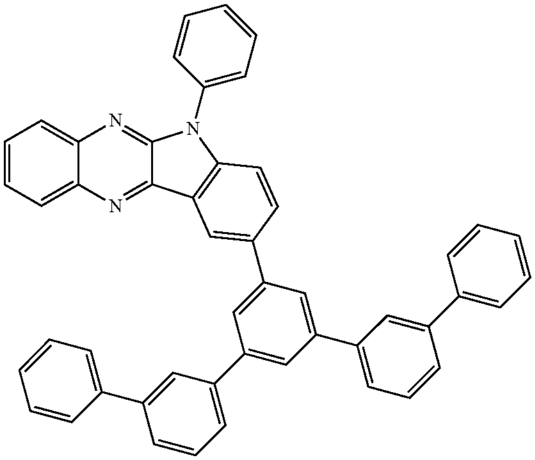
C-80
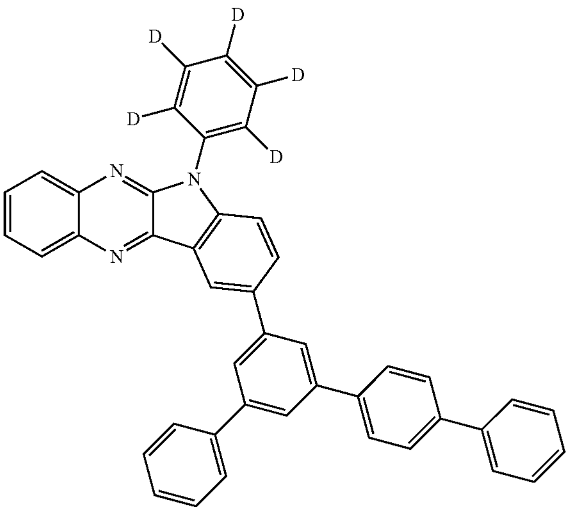

-continued
C-81
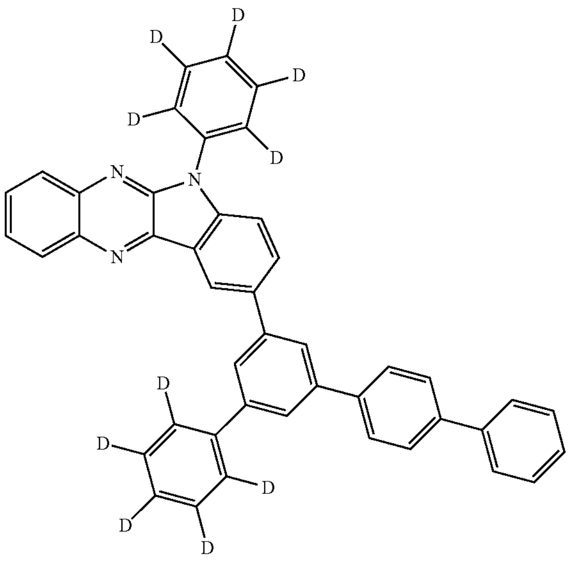
C-82
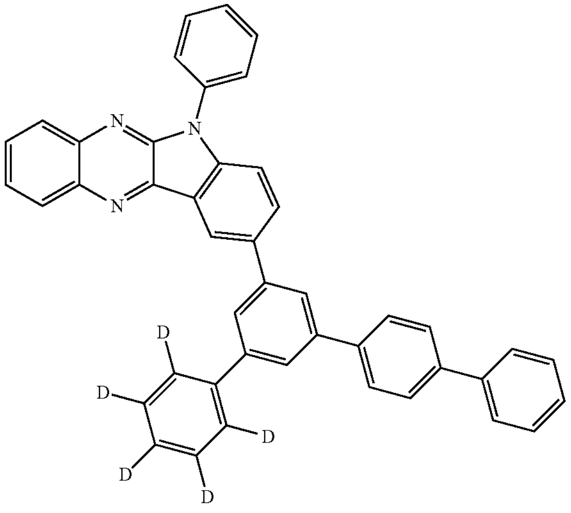
-continued
C-83
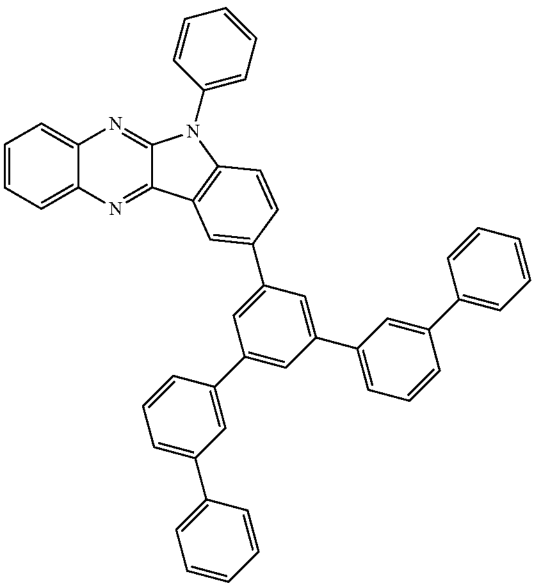
C-84
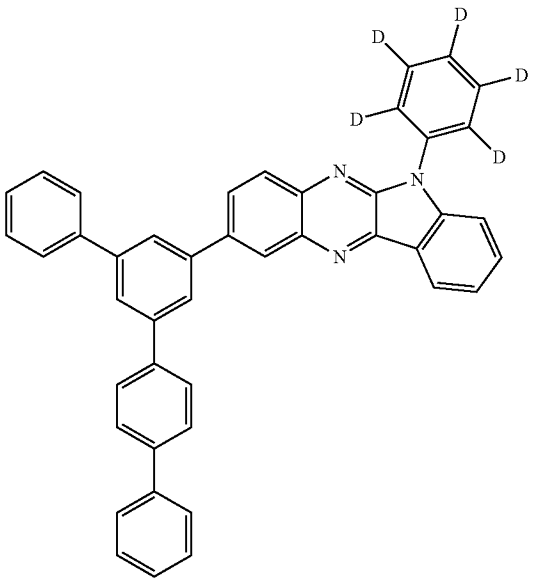

-continued
C-85
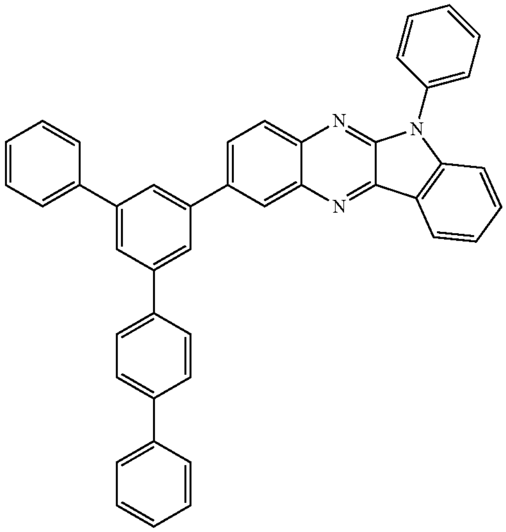
C-86
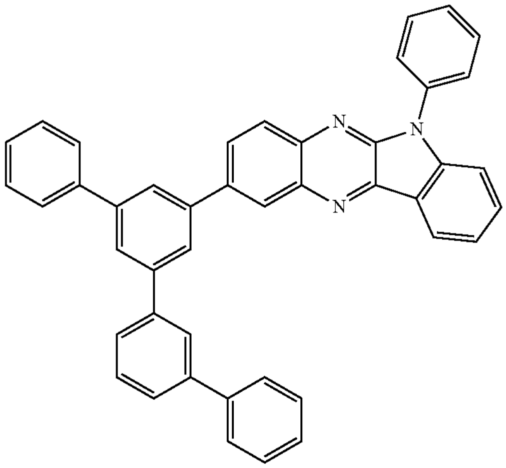
C-87
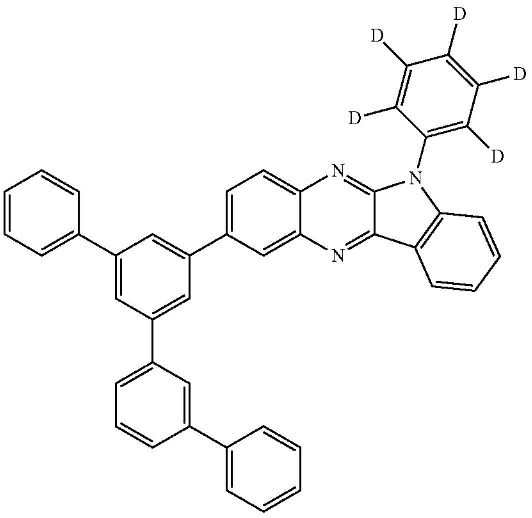
-continued
C-88
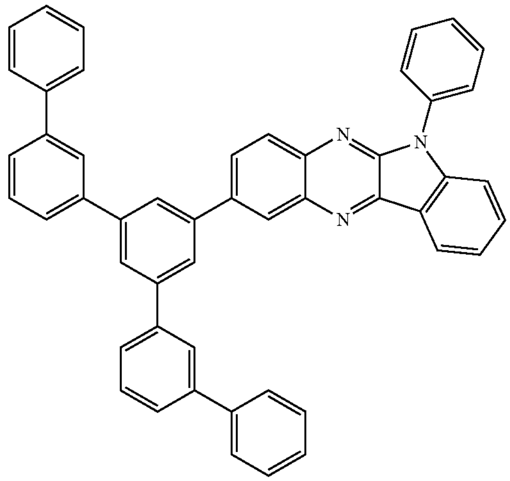
C-89
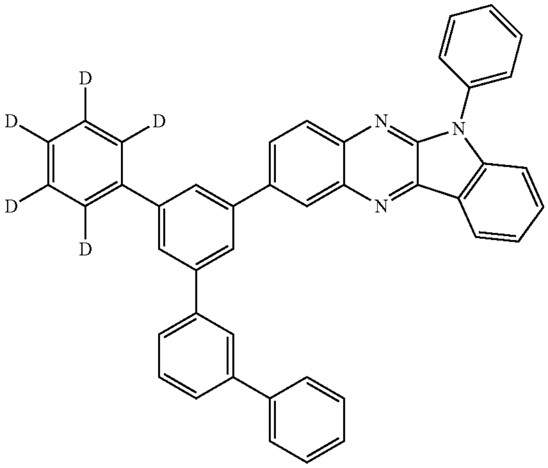
C-90
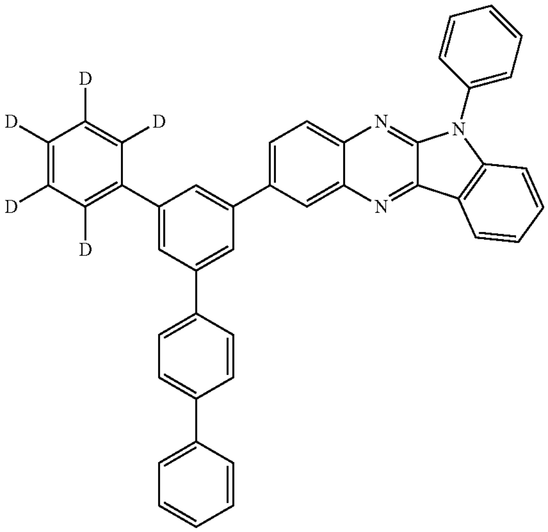

-continued
C-91
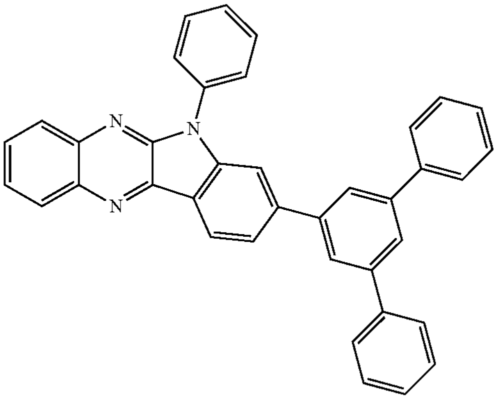
C-92
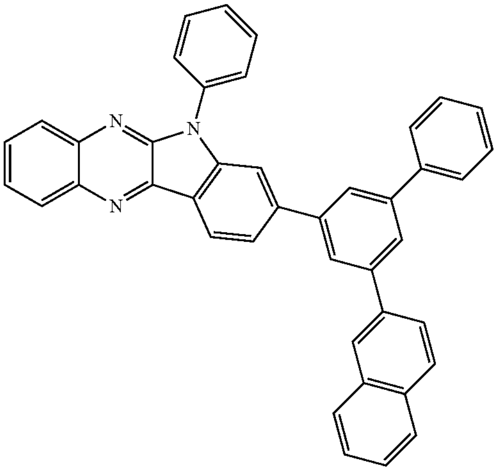
C-93
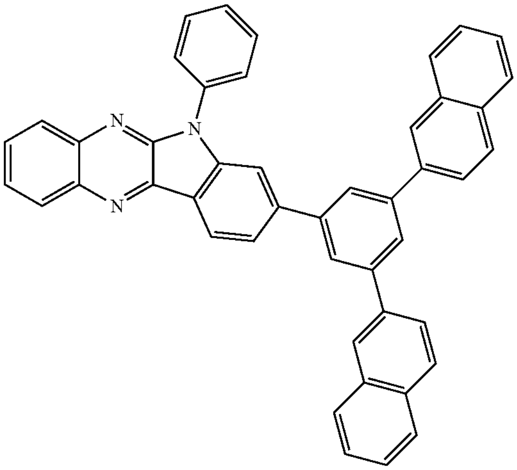
-continued
C-94
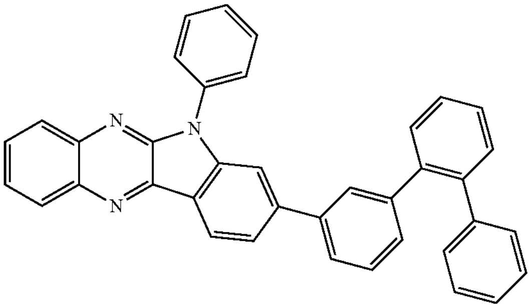
C-95
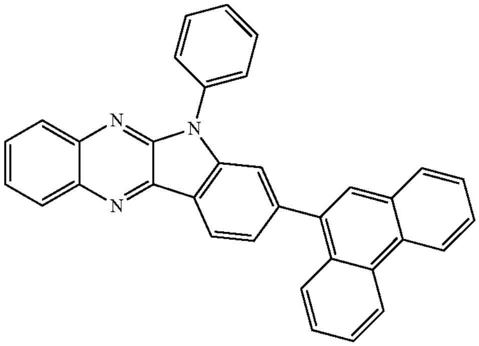
C-96
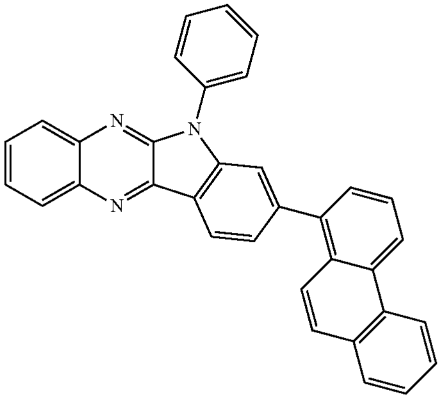
C-97
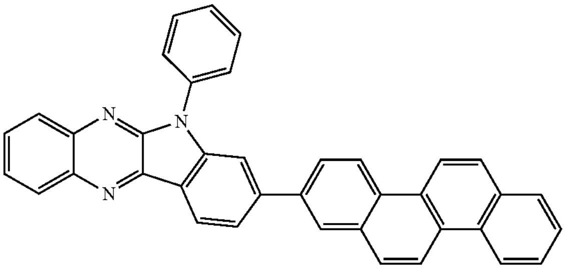

-continued
C-98
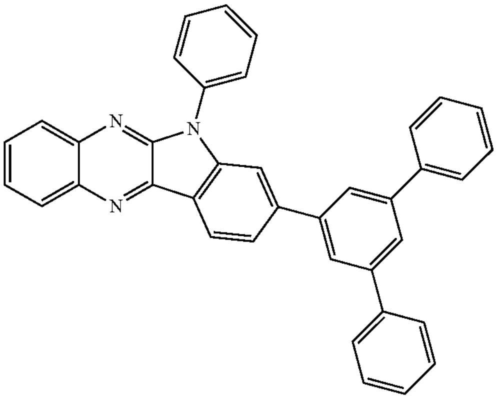
C-99
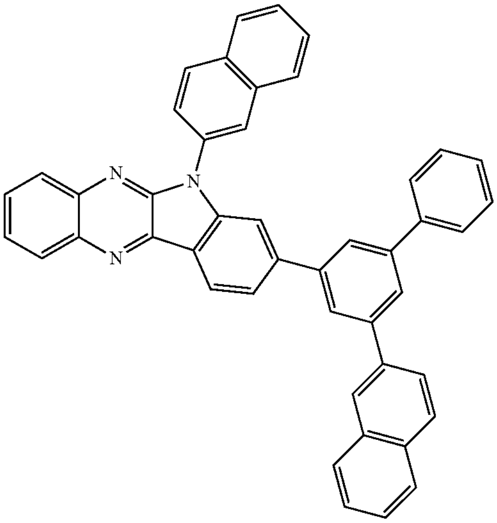
C-100
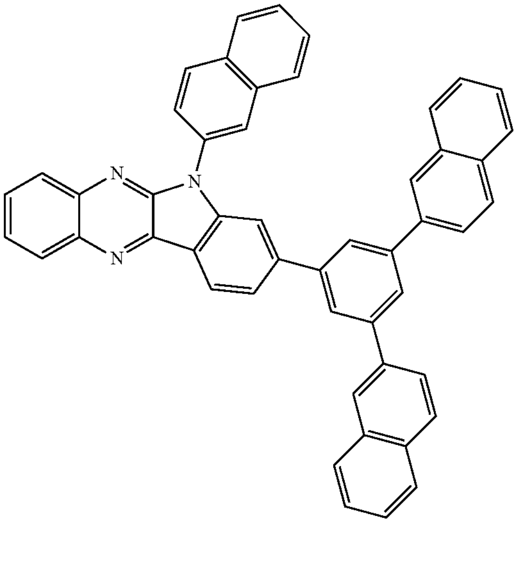
-continued
C-101
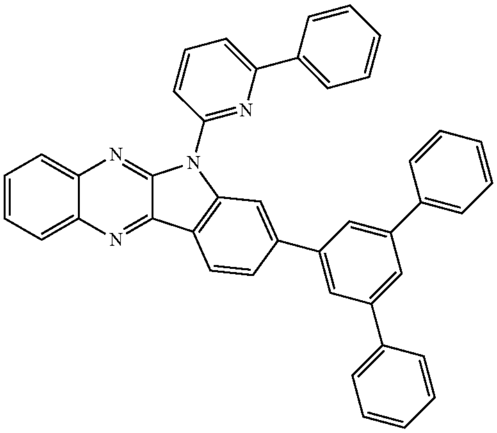
C-102
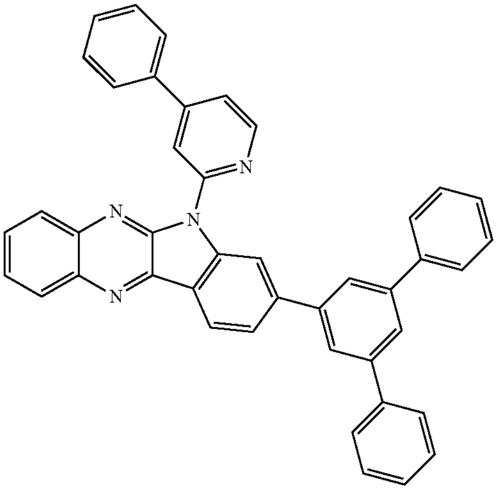
C-103
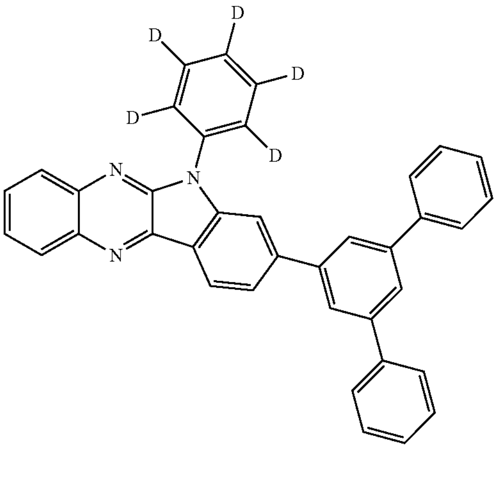

-continued
C-104
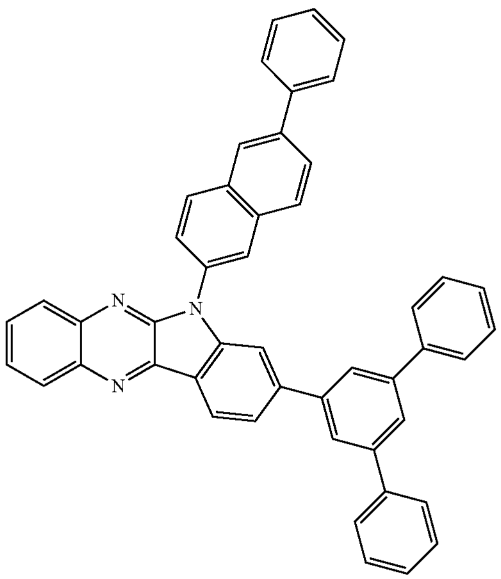
C-105
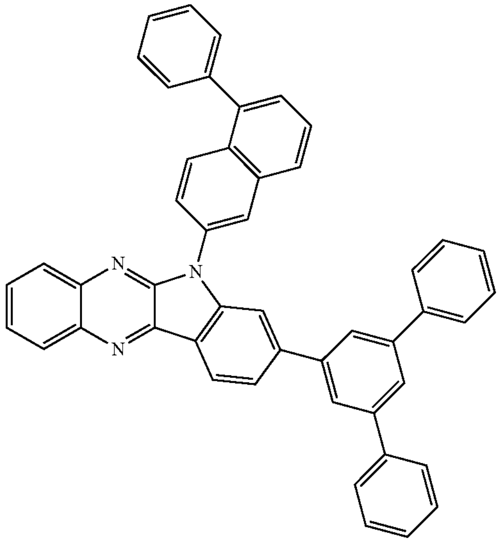
C-106
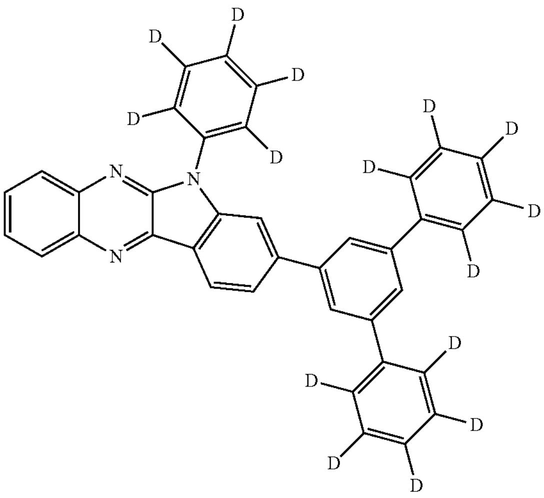
-continued
C-107
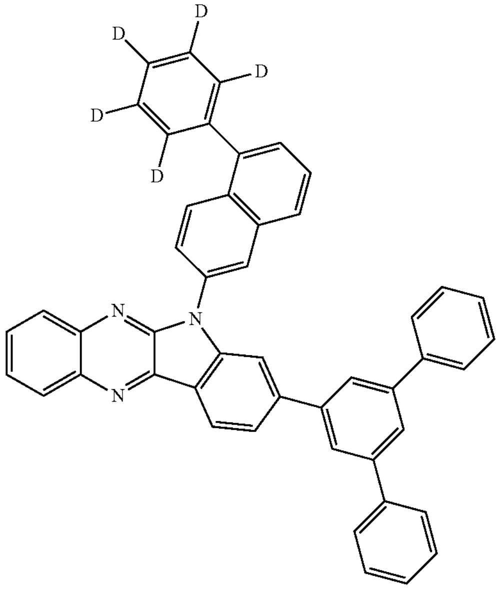
C-108
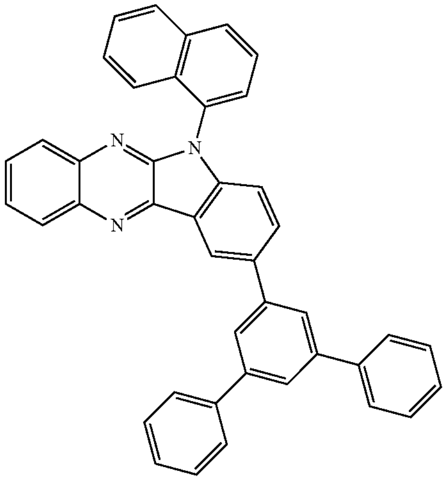
C-109
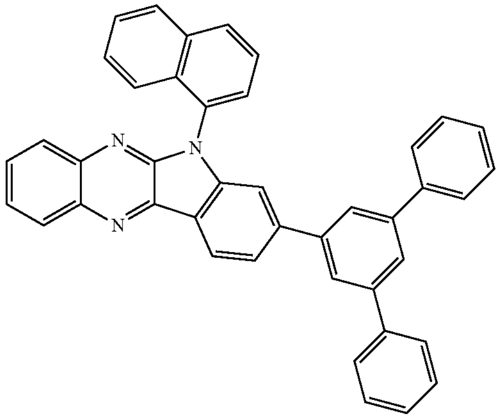

-continued
C-110
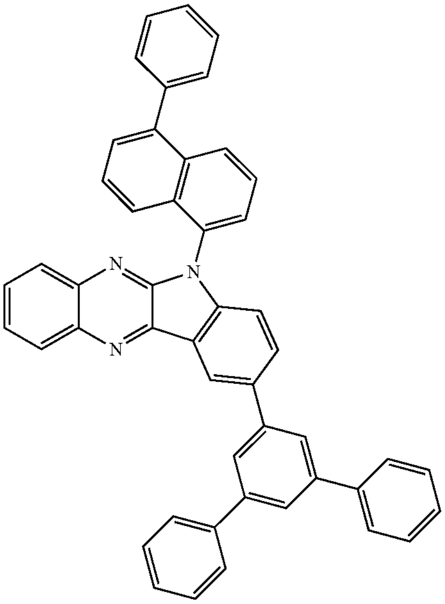
C-111
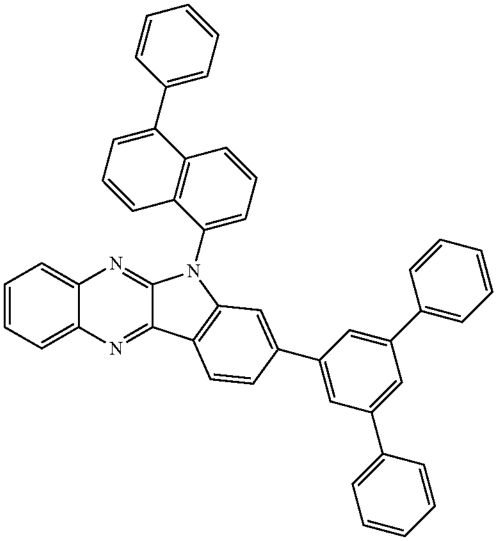
-continued
C-112
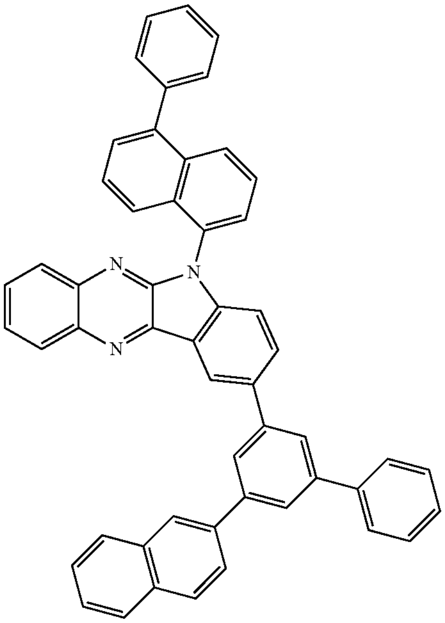
C-113
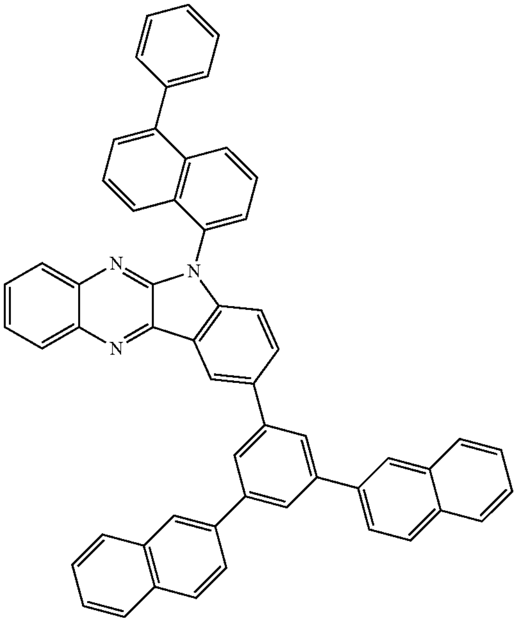

-continued
C-114
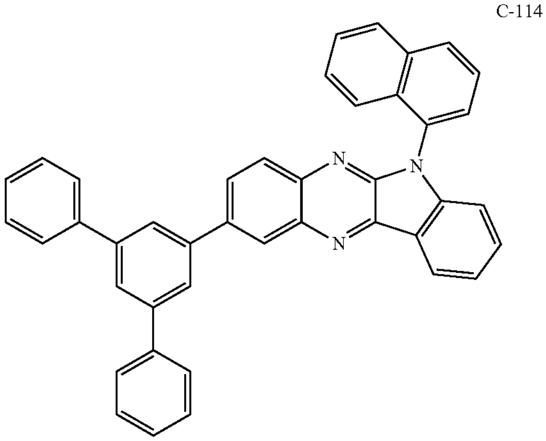
C-115
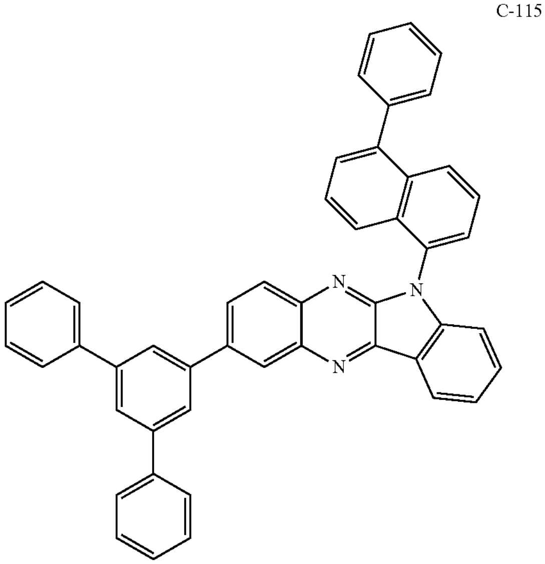
C-116
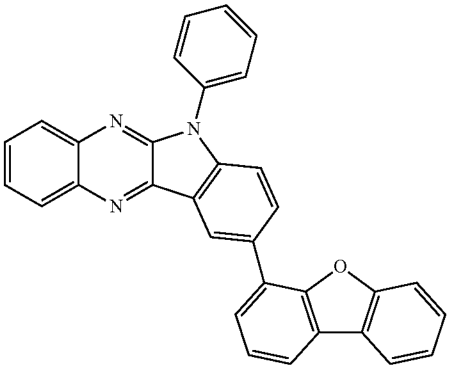
-continued
C-117
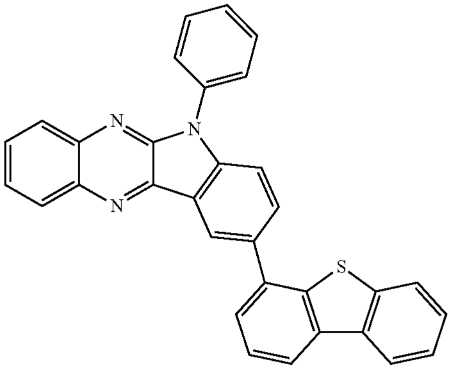
C-118
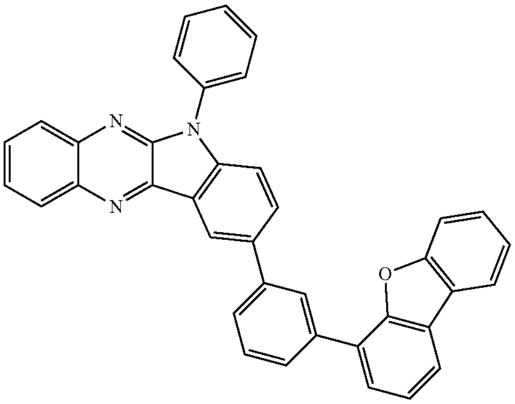
C-119
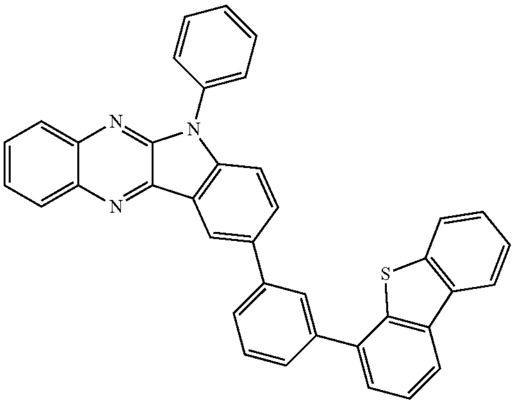

-continued
C-120
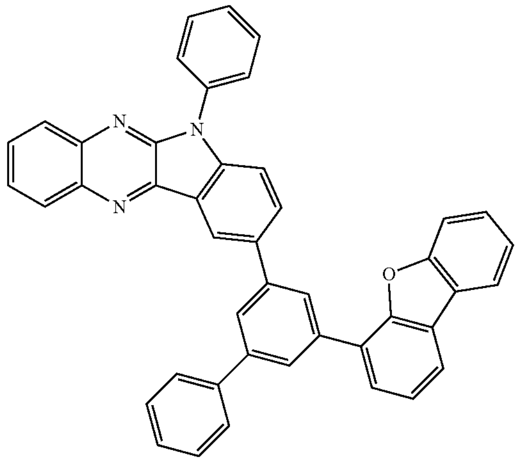
C-121
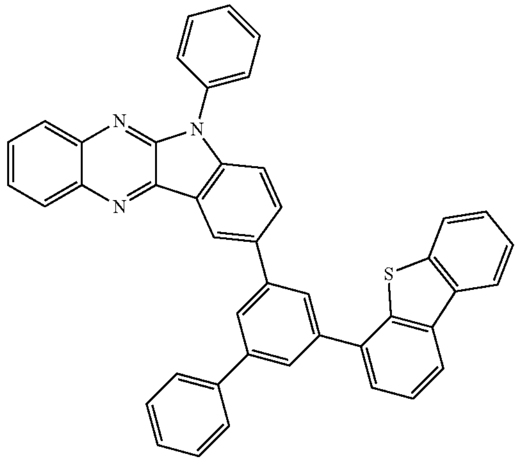
C-122
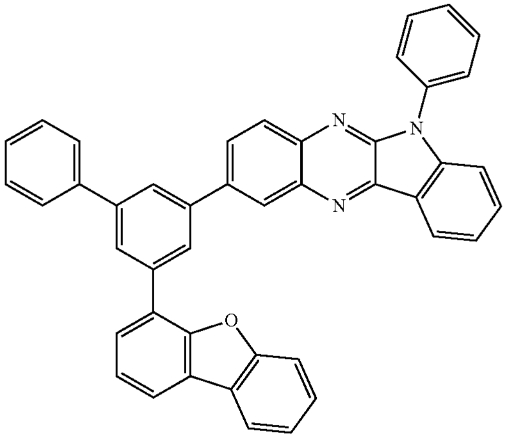
-continued
C-123
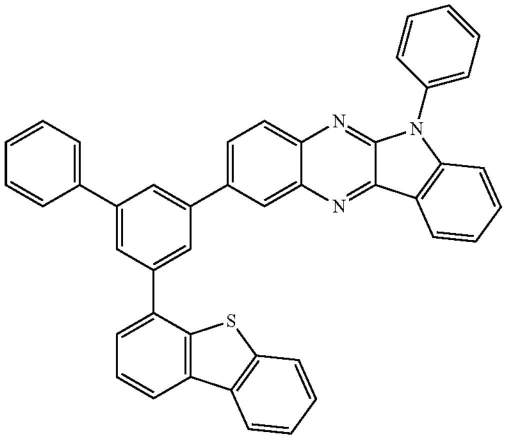
C-124
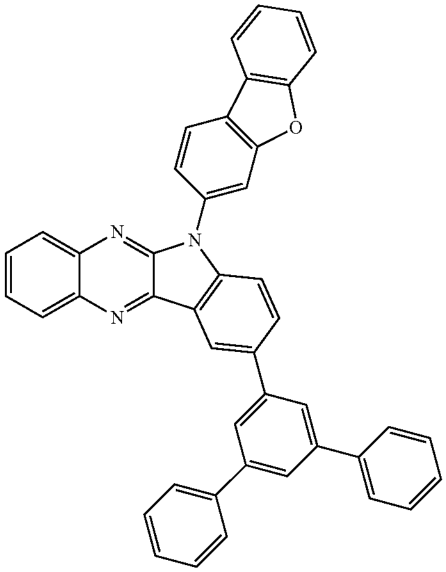
C-125
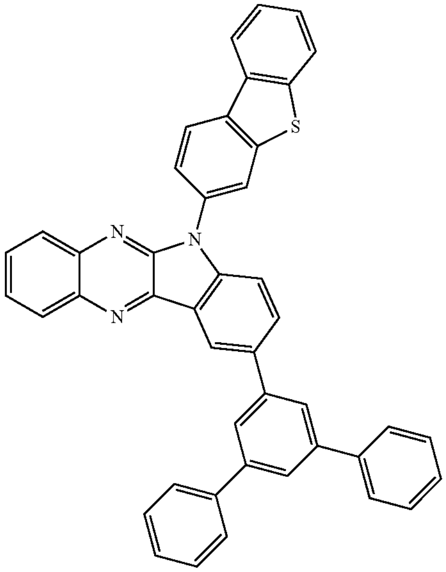

-continued
C-126
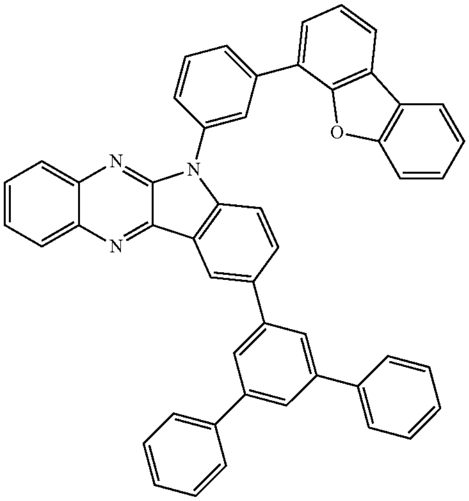
C-127
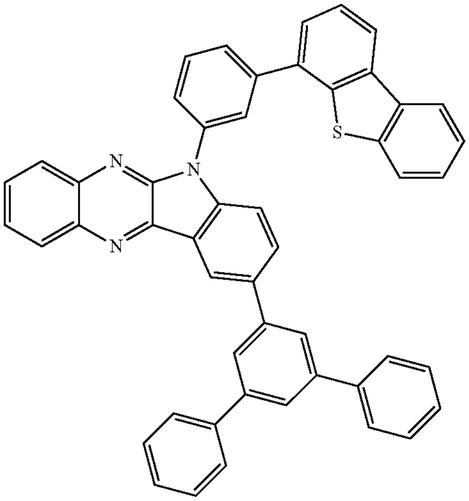
C-128
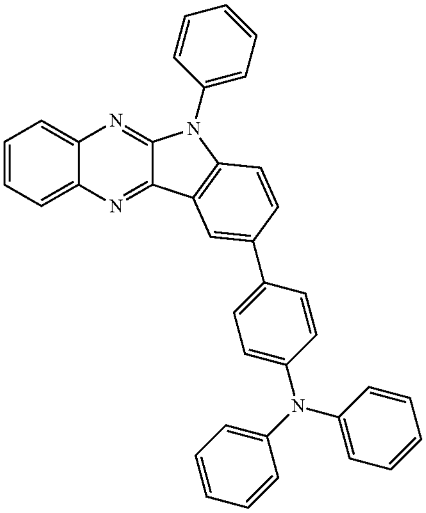
C-129
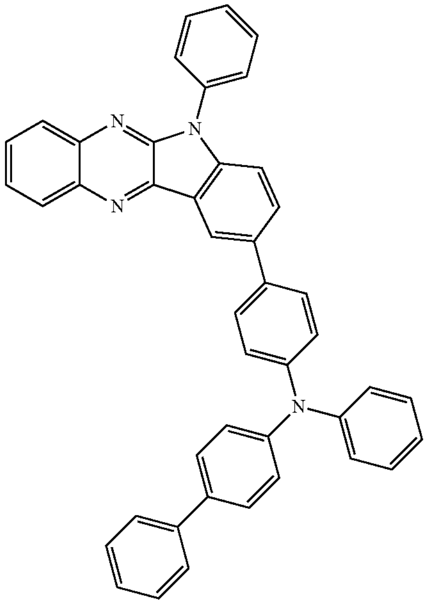
C-130
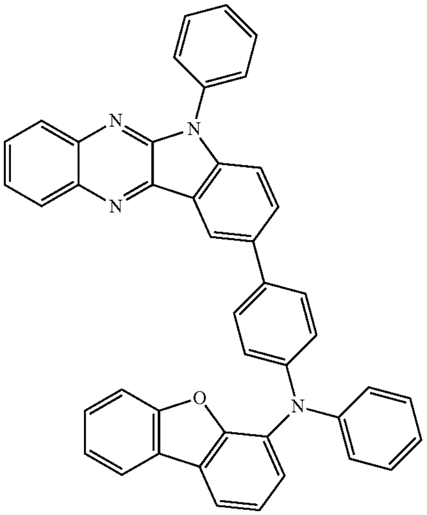
and
C-131
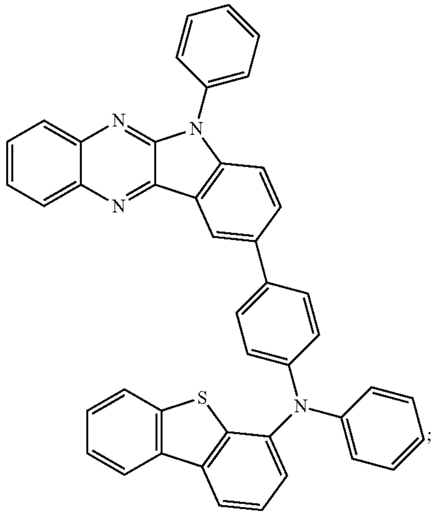
;

and the second host material comprises a compound represented by the following formula 2:

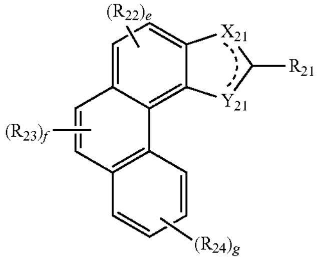

(2)

wherein, $X_{21}$ and $Y_{21}$ each independently represent —N═, —$NR_{25}$—, —O—, or —S—, provided that one of $X_{21}$ and $Y_{21}$ is —N═, and the other of $X_{21}$ and $Y_{21}$ is —$NR_{25}$—, —O—, or —S—;

$R_{21}$ represents a substituted or unsubstituted (C6-C30) aryl or a substituted or unsubstituted (3- to 30-membered) heteroaryl;

$R_{22}$ to $R_{25}$ each independently represent hydrogen, deuterium, halogen, cyano, a substituted or unsubstituted (C1-C30) alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri (C1-C30) alkylsilyl, a substituted or unsubstituted di (C1-C30) alkyl (C6-C30) arylsilyl, a substituted or unsubstituted (C1-C30) alkyldi (C6-C30) arylsilyl, a substituted or unsubstituted tri (C6-C30) arylsilyl, a substituted or unsubstituted fused ring of (C3-C30) aliphatic ring and (C6-C30) aromatic ring, a substituted or unsubstituted mono-or di-(C1-C30) alkylamino, a substituted or unsubstituted mono-or di-(C2-C30) alkenylamino, a substituted or unsubstituted (C1-C30) alkyl (C2-C30) alkenylamino, a substituted or unsubstituted mono-or di-(C6-C30) arylamino, a substituted or unsubstituted (C1-C30) alkyl (C6-C30) arylamino, a substituted or unsubstituted mono-or di-(3- to 30-membered) heteroarylamino, a substituted or unsubstituted (C1-C30) alkyl (3- to 30-membered) heteroarylamino, a substituted or unsubstituted (C2-C30) alkenyl (C6-C30) arylamino, a substituted or unsubstituted (C2-C30) alkenyl (3- to 30-membered) heteroarylamino, or a substituted or unsubstituted (C6-C30) aryl (3- to 30-membered) heteroarylamino; or may be linked to the adjacent substituents to form a ring(s);

provided that at least one of $R_{22}$ to $R_{24}$ is-$L_{21}$-$Ar_{21}$;

$L_{21}$ represents a single bond or a substituted or unsubstituted (C6-C30) arylene;

$Ar_{21}$ represents a substituted or unsubstituted fused ring of (C3-C30) aliphatic ring and (C6-C30) aromatic ring, a substituted or unsubstituted (C6-C30) aryl, a substituted or unsubstituted (3- to 30-membered) heteroaryl, or —$NR_{31}R_{32}$;

$R_{31}$ and $R_{32}$ each independently represent a substituted or unsubstituted (C1-C30) alkyl, a substituted or unsubstituted (C2-C30) alkenyl, a substituted or unsubstituted (C6-C30) aryl, or a substituted or unsubstituted (3- to 30-membered) heteroaryl;

e and f each independently represent an integer of 1 or 2, and g represents an integer of 1 to 4; and when e to g are an integer of 2 or more, each of $R_{22}$, each of $R_{23}$, and each of $R_{24}$ may be the same or different.

3. The host materials according to claim 2, wherein the formula 2 is represented by any one of the following formulas 2-1 to 2-3:

(2-1)

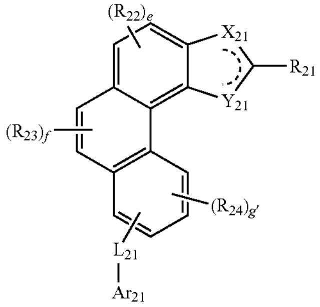

(2-2)

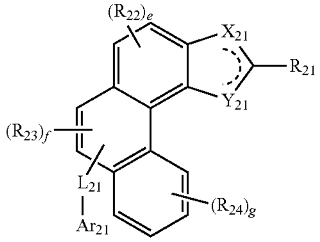

(2-3)

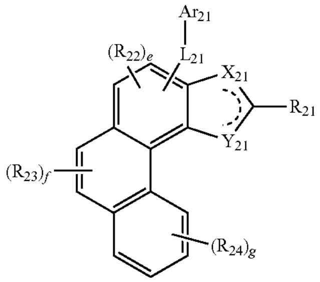

wherein, $X_{21}$, $Y_{21}$, $L_{21}$, $Ar_{21}$, $R_{21}$ to $R_{24}$, e, f, and g are as defined in claim 1;

g' represents an integer of 1 to 3; and when g' represents an integer of 2 or more, each of $R_{24}$ may be the same or different.

4. The host materials according to claim 3, wherein $Ar_{21}$ represents a substituted or unsubstituted phenyl, a substituted or unsubstituted naphthyl, a substituted or unsubstituted o-biphenyl, a substituted or unsubstituted m-biphenyl, a substituted or unsubstituted p-biphenyl, a substituted or unsubstituted o-terphenyl, a substituted or unsubstituted m-terphenyl, a substituted or unsubstituted p-terphenyl, a substituted or unsubstituted triphenylenyl, a substituted or unsubstituted phenanthrenyl, a substituted or unsubstituted chrysenyl, a substituted or unsubstituted fluoranthenyl, a substituted or unsubstituted fluorenyl, a substituted or unsubstituted benzofluorenyl, a substituted or unsubstituted spirobifluorenyl, a substituted or unsubstituted spiro [cyclopentane-fluoren]yl, a substituted or unsubstituted spiro [dihydroindene-fluoren]yl, a substituted or unsubstituted spiro [benzofluoren-fluoren]yl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthothiophenyl, a substituted or unsubstituted dibenzofuranyl, a substituted or unsubstituted benzofuranyl, or a substituted or unsubstituted benzonaphthofuranyl; or amino substituted with at least one selected from the group consisting of phenyl; naphthyl; naphthylphenyl;

phenylnaphthyl; o-biphenyl, m-biphenyl; p-biphenyl; o-terphenyl; m-terphenyl; p -terphenyl; fluorenyl; benzofluorenyl; phenanthrenyl; dibenzothiophenyl;

benzonaphthofuranyl; and dibenzofuranyl.

5. A plurality of host materials comprising a first host material and a second host material, wherein the first host material comprises a compound represented by the following formula 1:

(1)

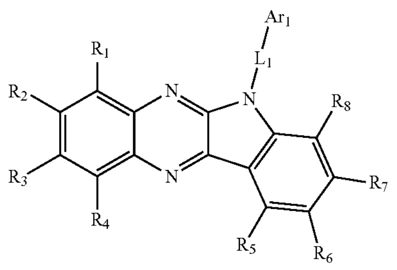

wherein, $L_1$ represents a single bond, a substituted or unsubstituted (C6-C30) arylene, or a substituted or unsubstituted (3- to 30-membered) heteroarylene;

Ar1 represents a substituted or unsubstituted (C6-C30) aryl or a substituted or unsubstituted (3- to 30-membered) heteroaryl; and $R_1$ to $R_8$ each independently represent hydrogen, deuterium, halogen, cyano, a substituted or unsubstituted (C1-C30) alkyl, a (C6-C30) aryl that is either unsubstituted or substituted with one selected from the group consisting of deuterium, a (C6-C30) aryl, a dibenzofuranyl or a dibenzothiophenyl, a dibenzofuranyl that is either unsubstituted or substituted with deuterium, a dibenzothiophenyl that is either unsubstituted or substituted with deuterium, a substituted or unsubstituted tri (C1-C30) alkylsilyl, a substituted or unsubstituted di (C1-C30) alkyl (C6-C30) arylsilyl, a substituted or unsubstituted (C1-C30) alkyldi (C6-C30) arylsilyl, a substituted or unsubstituted tri (C6-C30) arylsilyl, a substituted or unsubstituted fused ring of (C3-C30) aliphatic ring and (C6-C30) aromatic ring, a substituted or unsubstituted mono-or di-(C1-C30) alkylamino, a substituted or unsubstituted mono-or di-(C2-C30) alkenylamino, a substituted or unsubstituted (C1-C30) alkyl (C2-C30) alkenylamino, a substituted or unsubstituted (C1-C30) alkyl (C6-C30) arylamino, a substituted or unsubstituted mono-or di-(C6-C30) arylamino, a substituted or unsubstituted mono-or di-(3- to 30-membered) heteroarylamino, a substituted or unsubstituted (C1-C30) alkyl (3- to 30-membered) heteroarylamino, a substituted or unsubstituted (C2-C30) alkenyl (C6-C30) arylamino, a substituted or unsubstituted (C2-C30) alkenyl (3- to 30-membered) heteroarylamino, or a substituted or unsubstituted (C6-C30) aryl (3- to 30-membered) heteroarylamino; or may be linked to the adjacent substituents to form a ring(s);

and the second host material comprises a compound is selected from the following compounds:

H-1

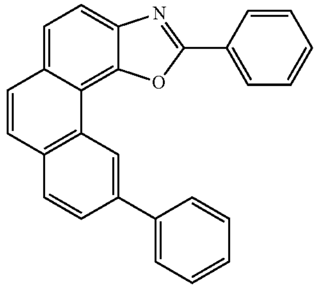

H-2

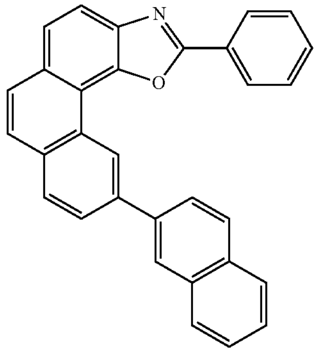

H-3

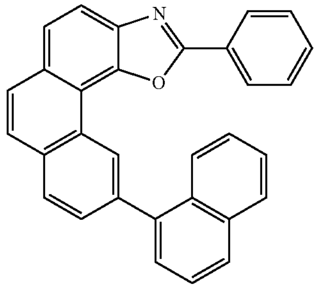

H-4

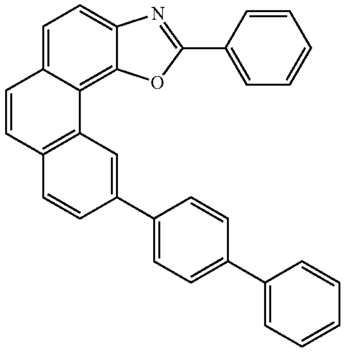

-continued
H-5
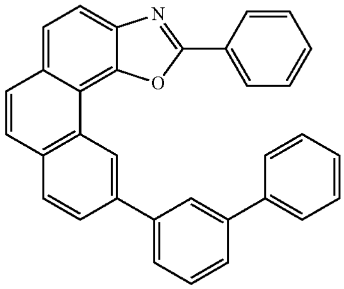
H-6
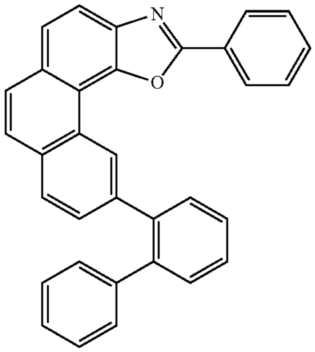
H-7
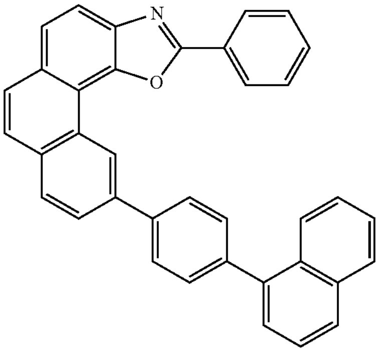
H-8
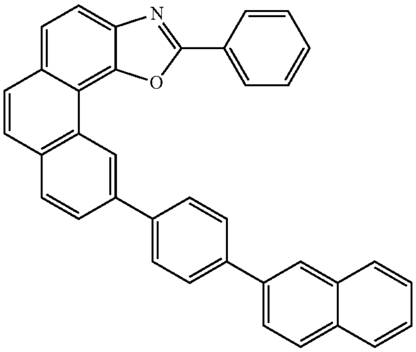
-continued
H-9
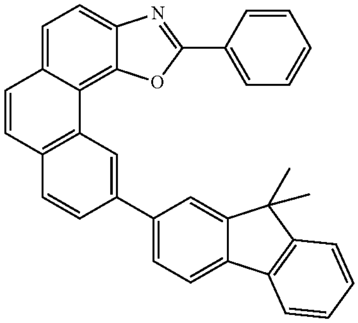
H-10
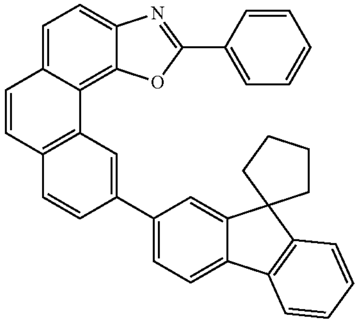
H-11
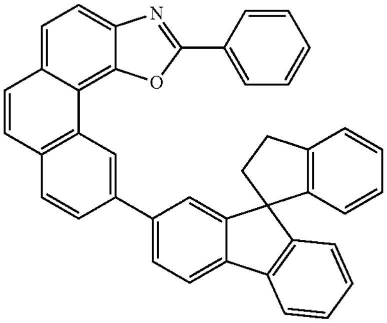
H-12
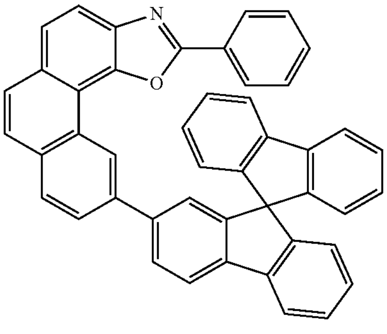
H-13
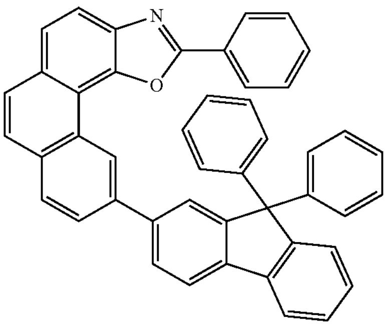

-continued
H-14
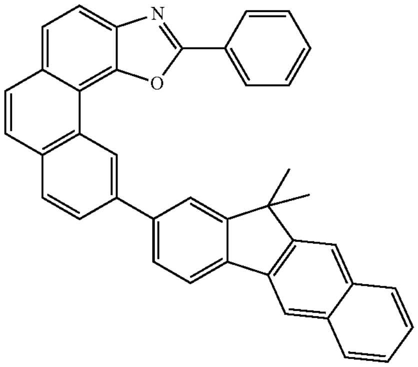
H-15
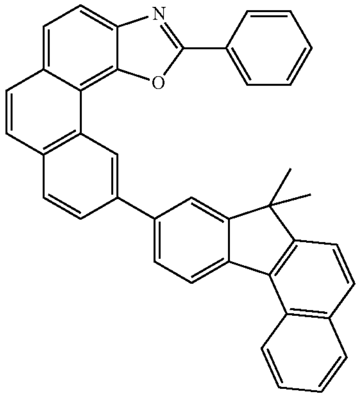
H-16
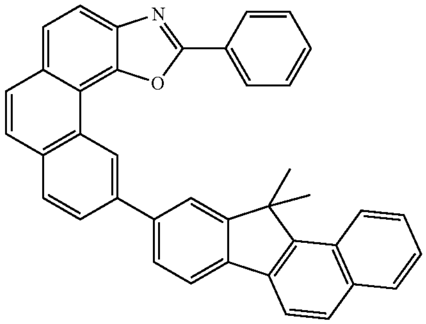
H-17
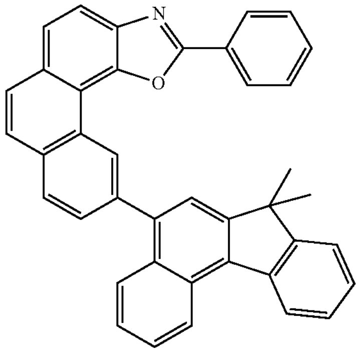
-continued
H-18
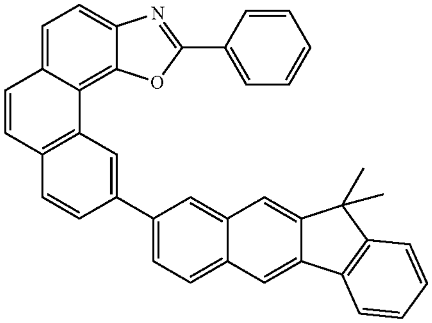
H-19
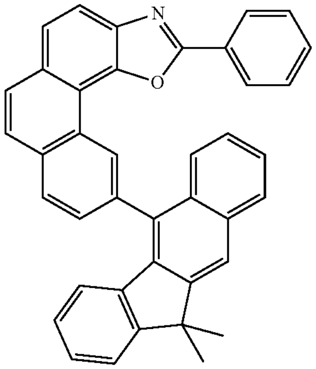
H-20
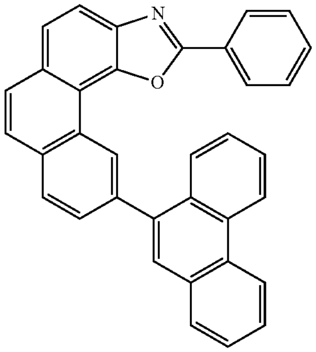
H-21
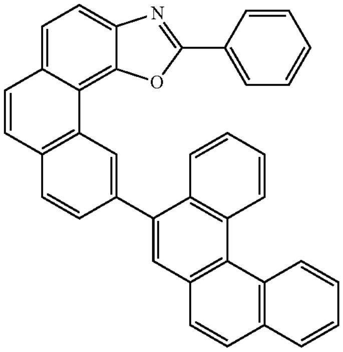

H-22
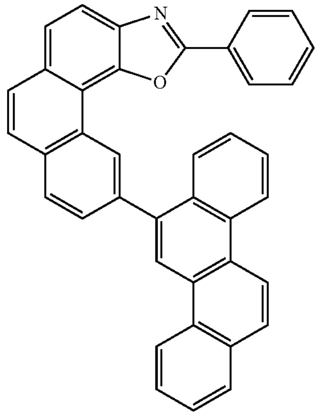
H-23
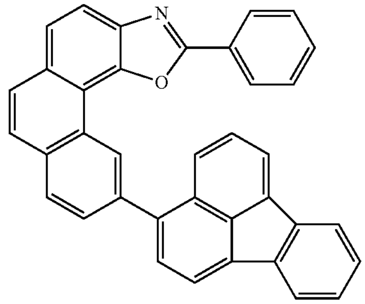
H-24
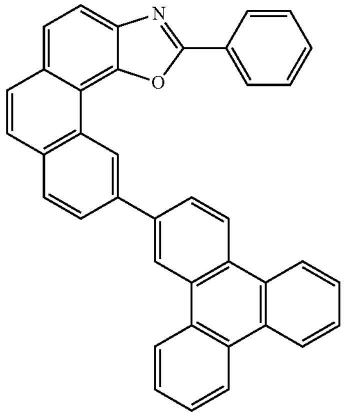
H-25
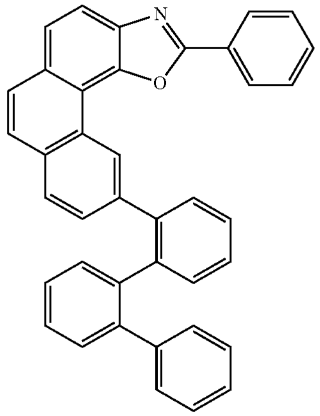
H-26
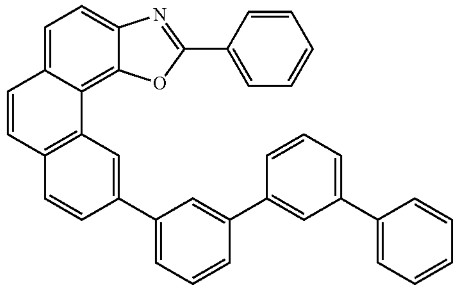
H-27
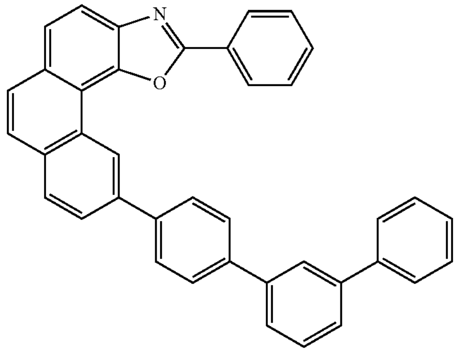
H-28
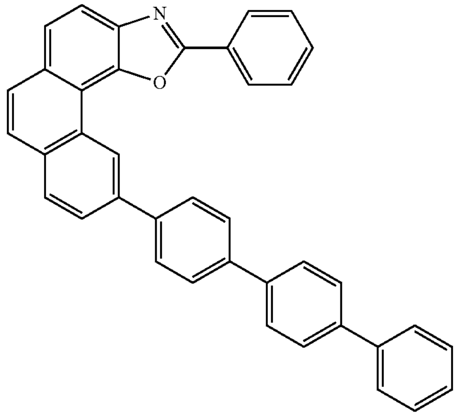
H-29
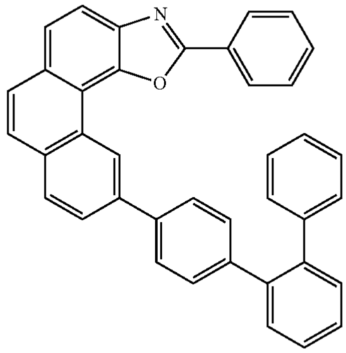

-continued
H-30
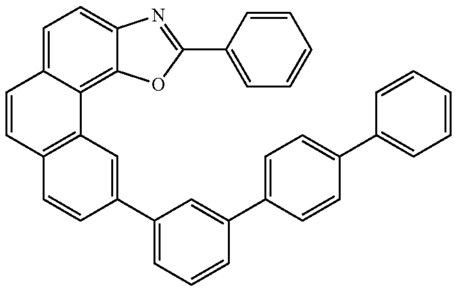
H-31
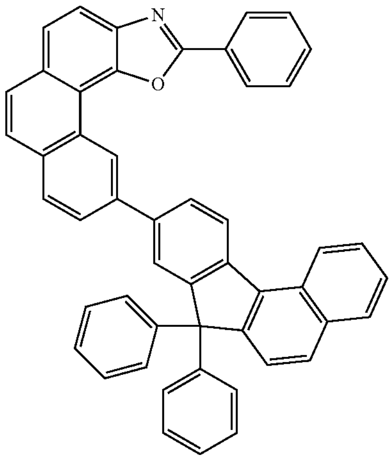
H-32
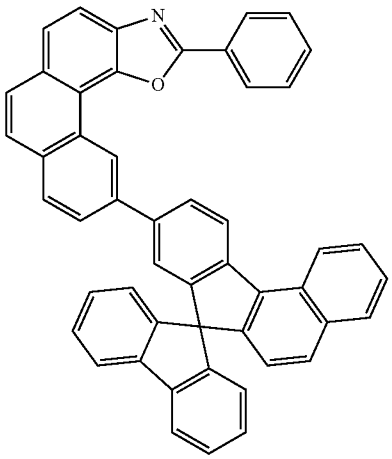
-continued
H-33
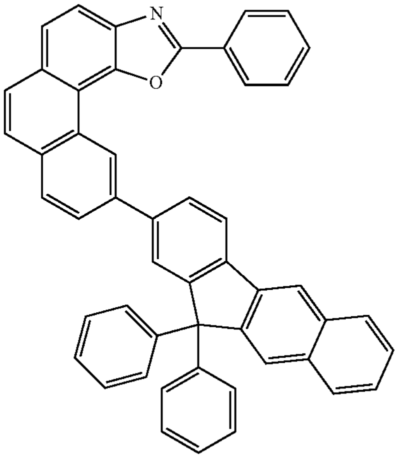
H-34
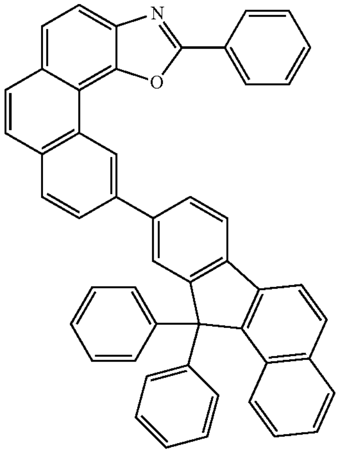
H-35
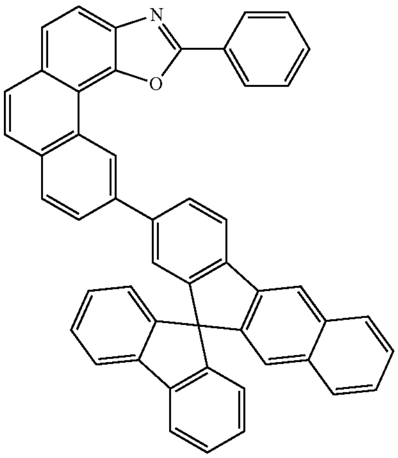

-continued
H-36
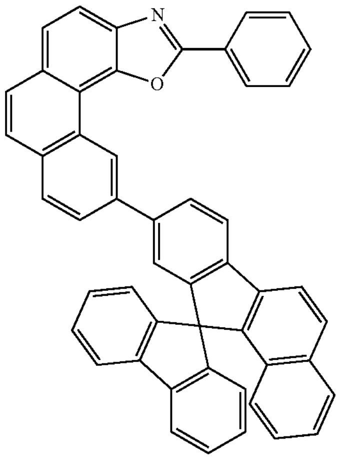
H-37
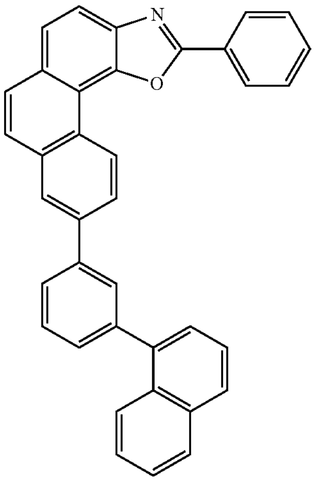
H-38
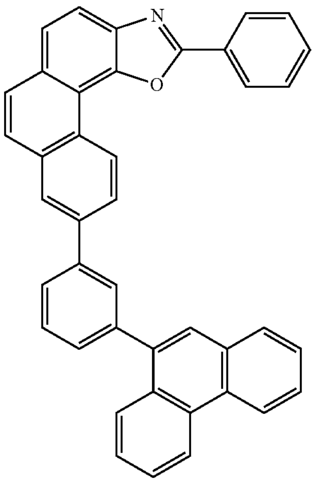
-continued
H-39
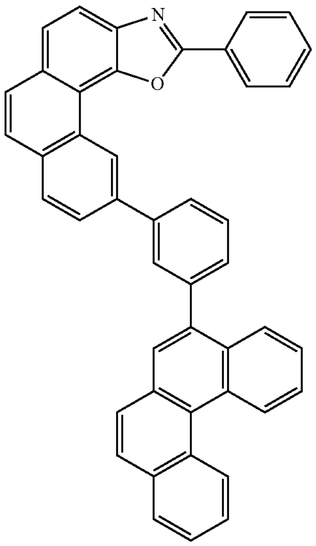
H-40
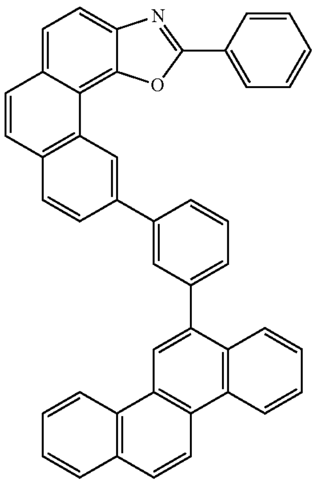
H-41
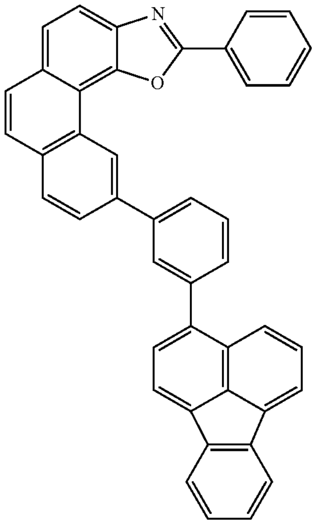

-continued
H-42
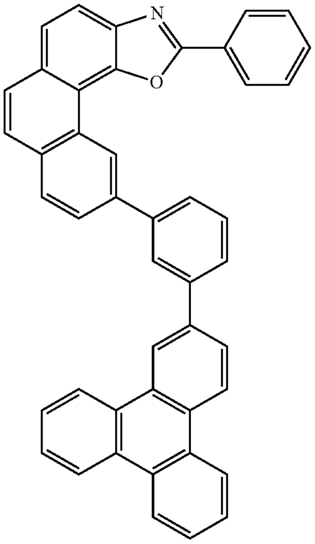
H-4
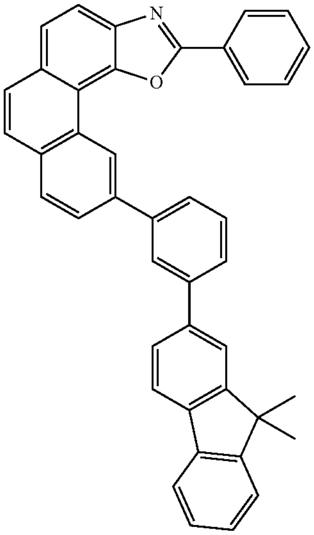
H-44
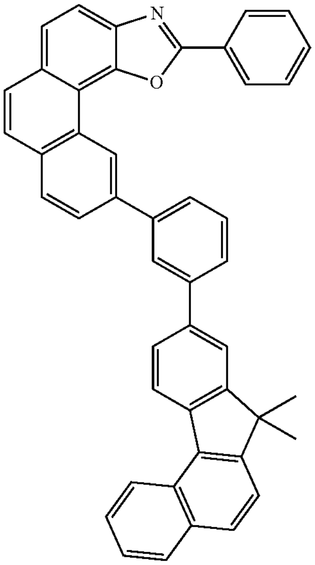
-continued
H-45
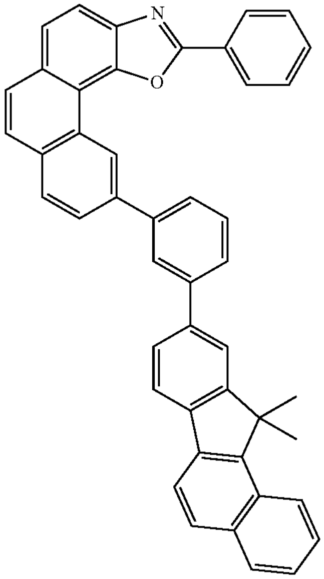
H-46
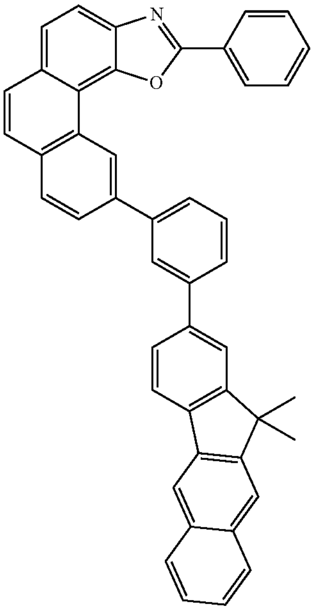

-continued
H-47
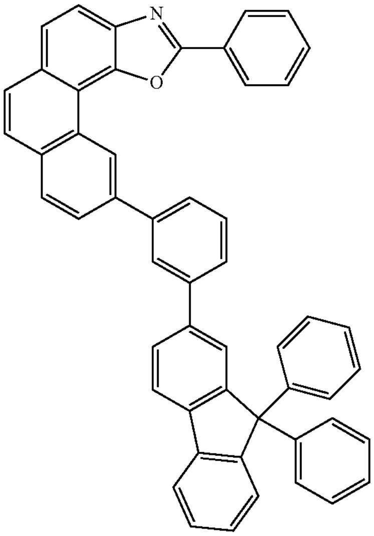
H-48
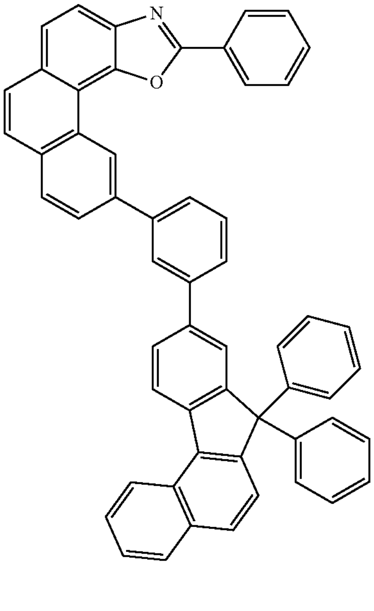
-continued
H-49
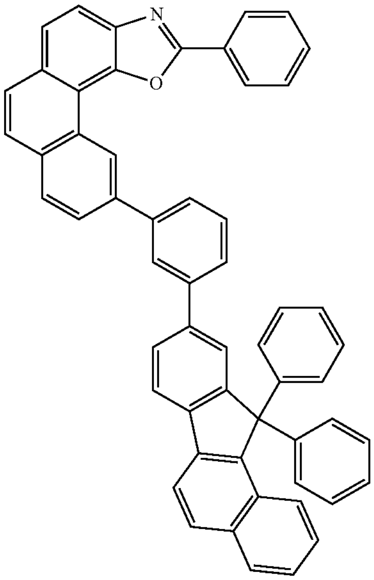
H-50
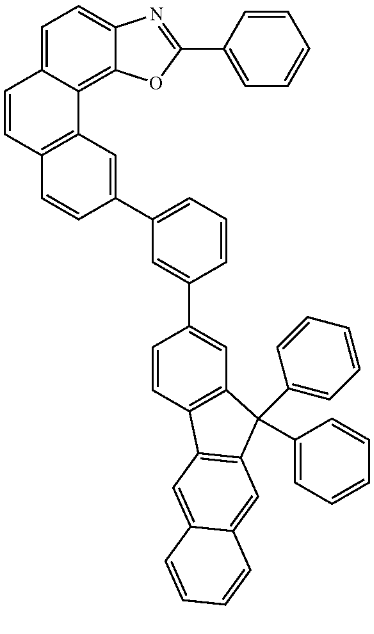

-continued
H-51
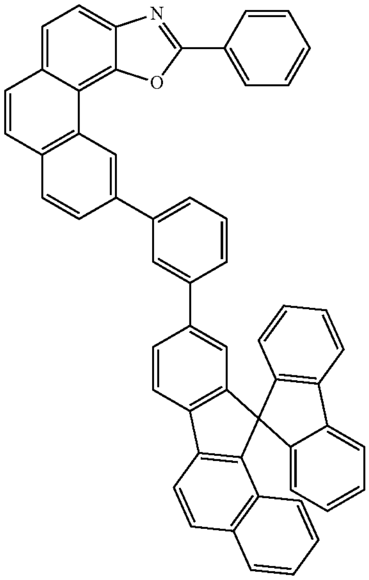
H-52
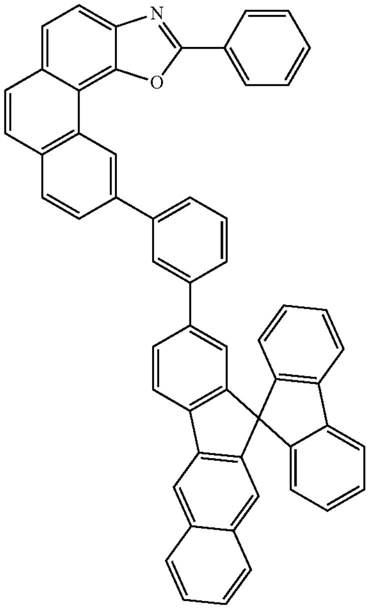
-continued
H-53
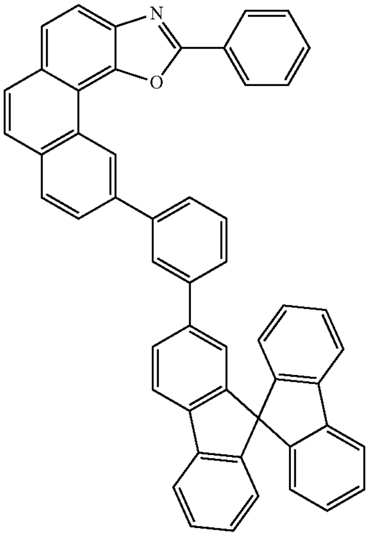
H-54
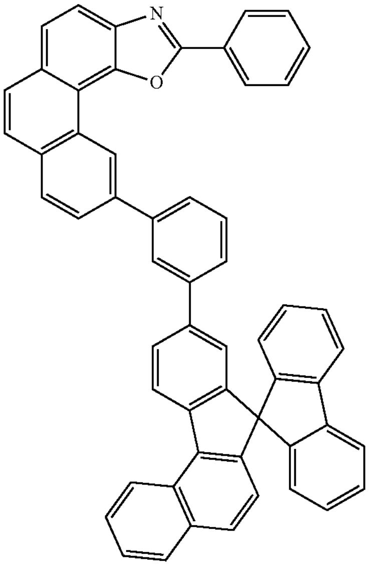
H-55
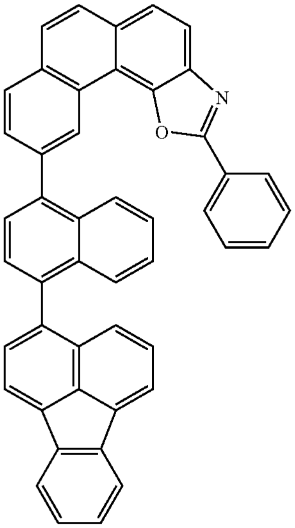

-continued
H-56
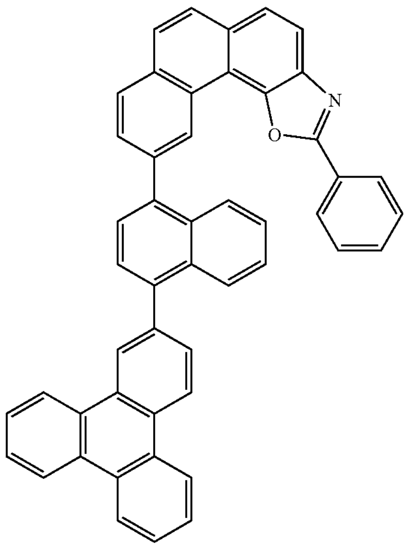
H-57
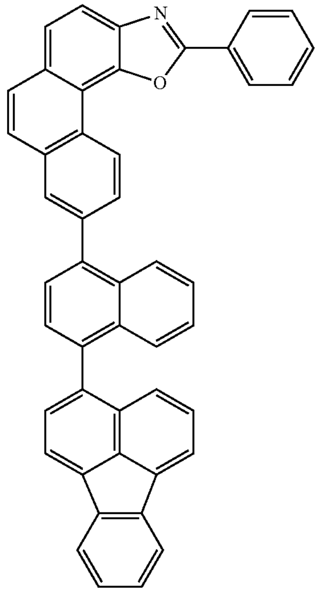
-continued
H-58
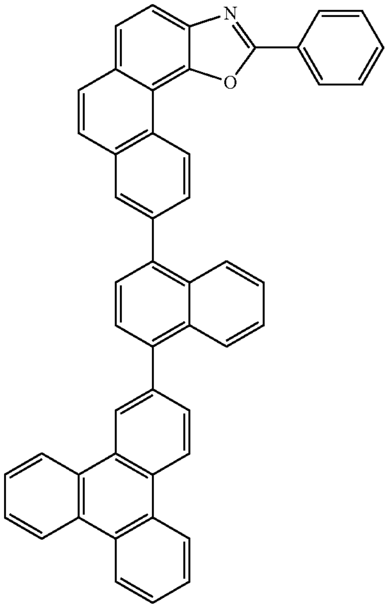
H-59
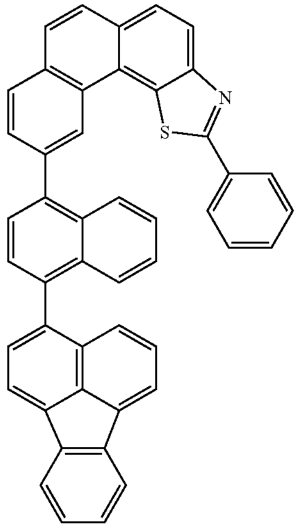

-continued
H-60
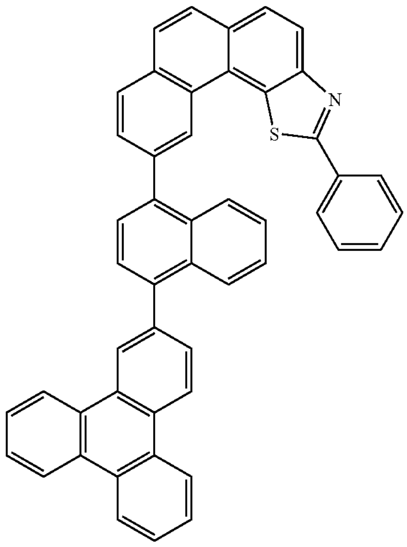
H-61
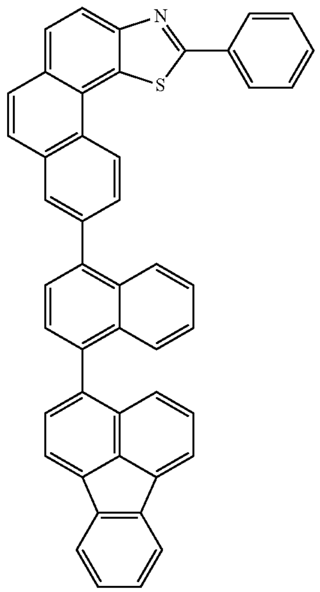
-continued
H-62
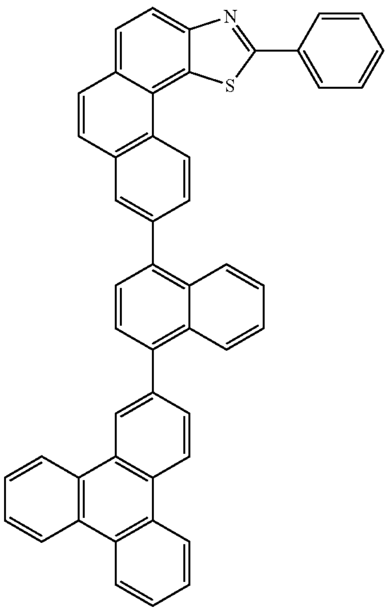
H-63
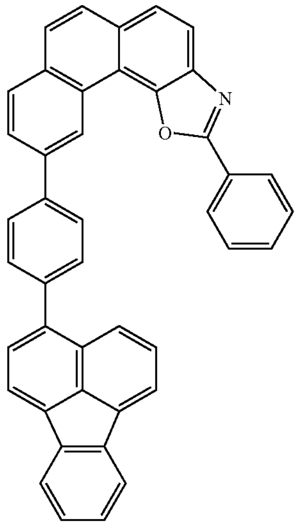

-continued
H-64
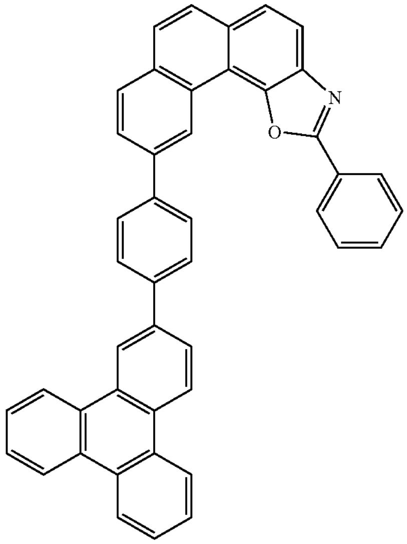
H-65
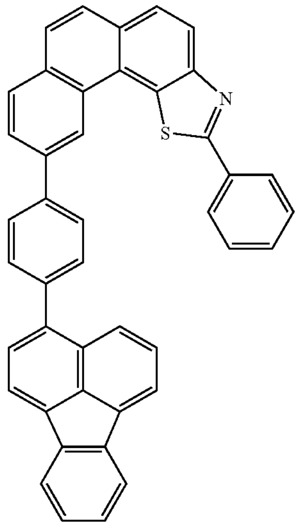
H-66
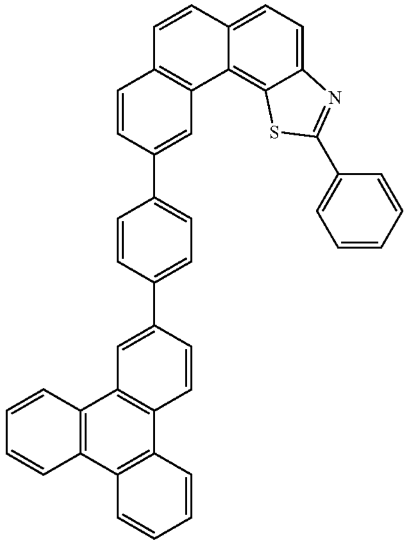
-continued
H-67
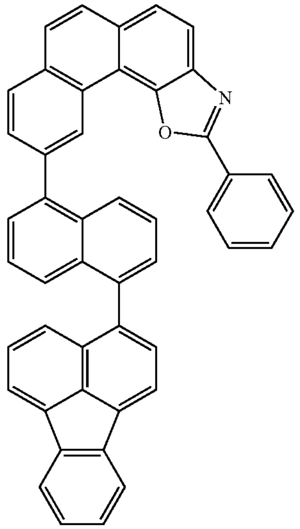
H-68
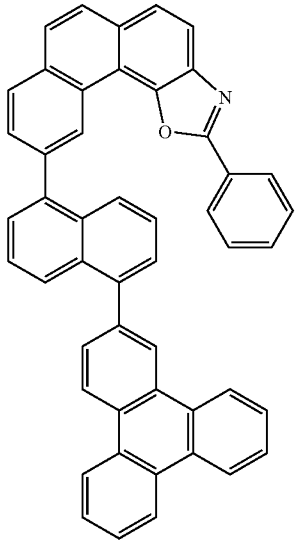
H-69
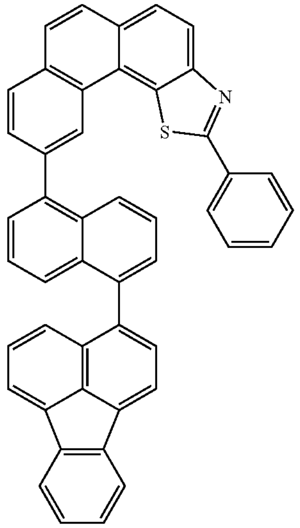

-continued
H-70
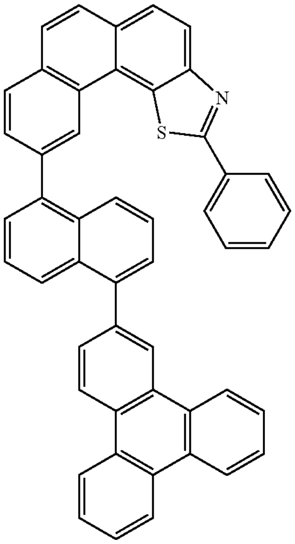
H-71
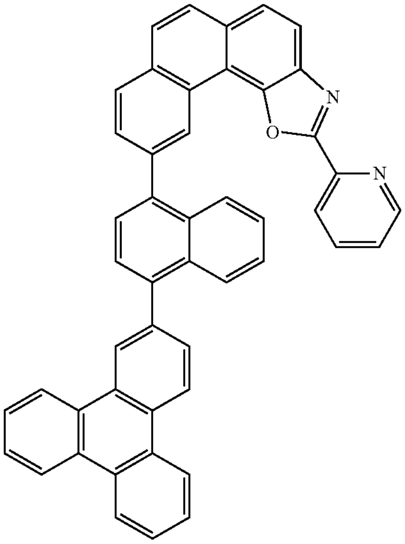
H-72
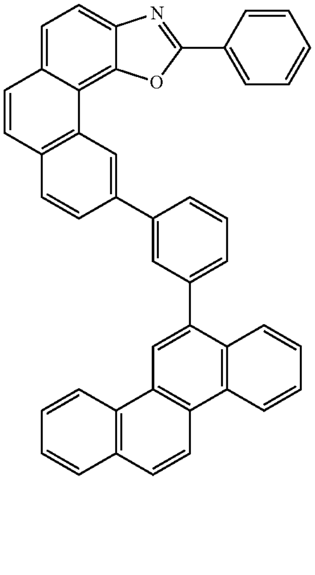
-continued
H-73
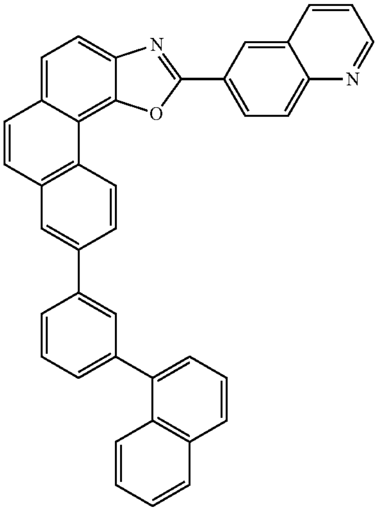
H-74
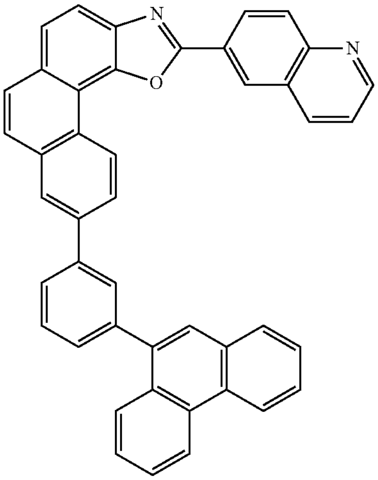
H-75
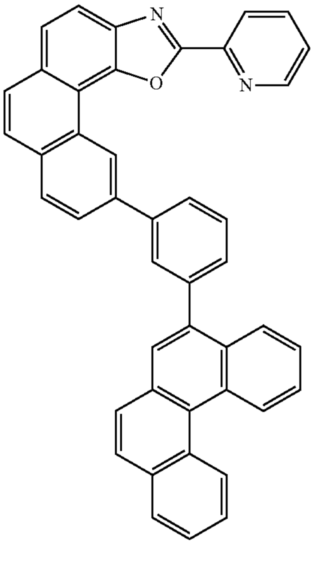

-continued
H-76
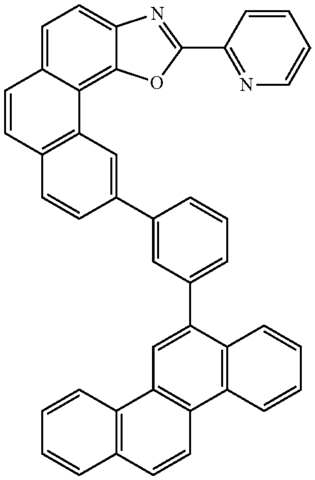
H-77
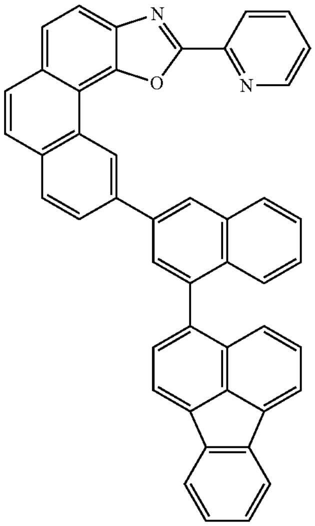
H-78
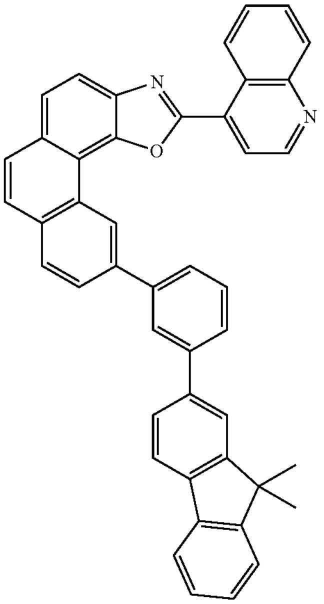
-continued
H-79
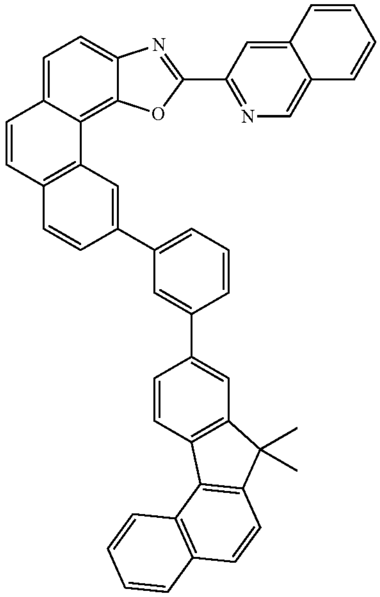
H-80
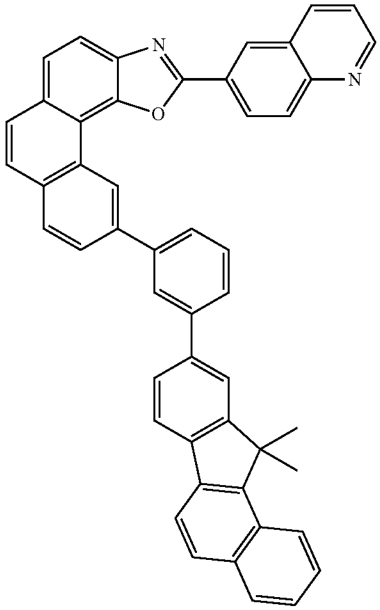

-continued
H-81
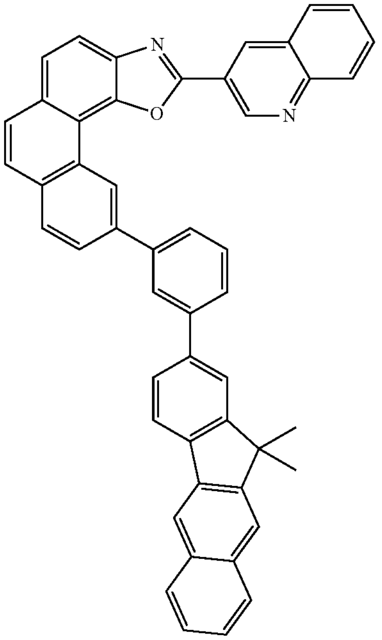
H-82
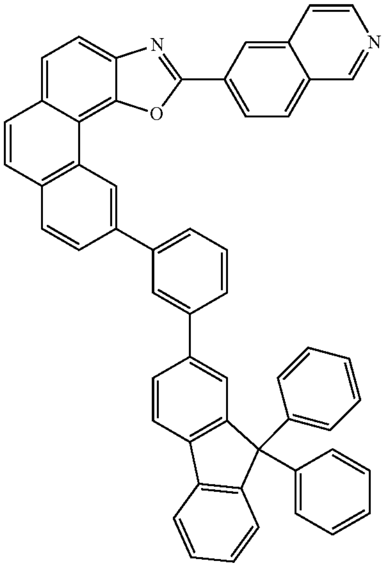
-continued
H-83
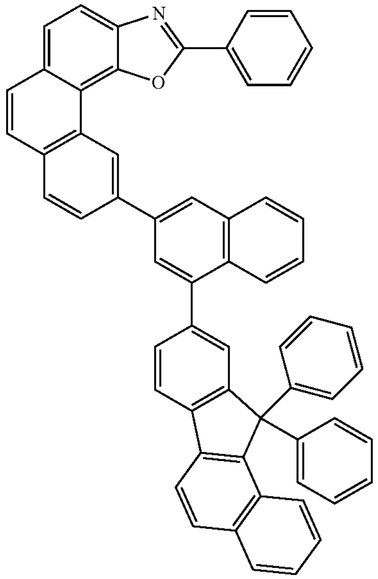
H-84
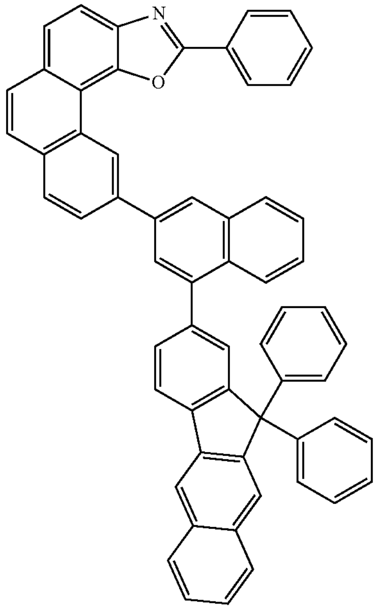

-continued
H-85
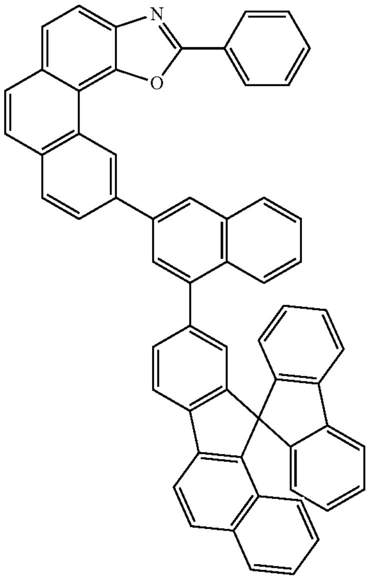
H-86
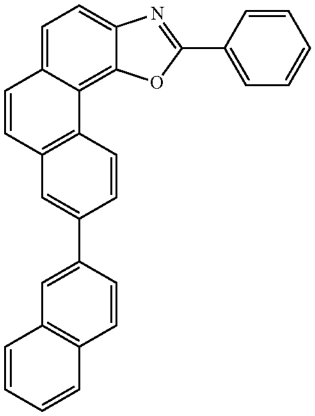
H-87
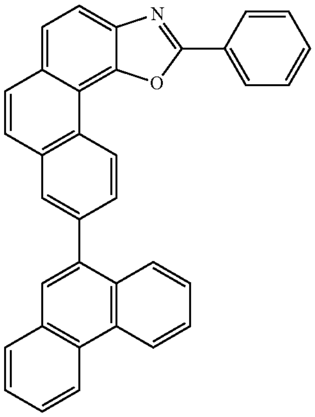
-continued
H-88
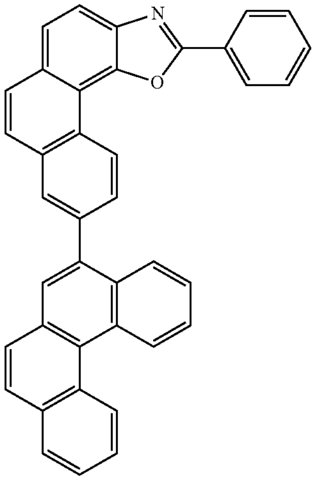
H-89
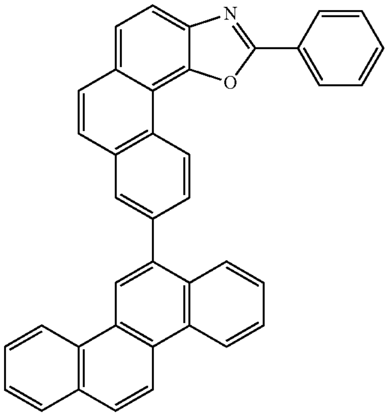
H-90
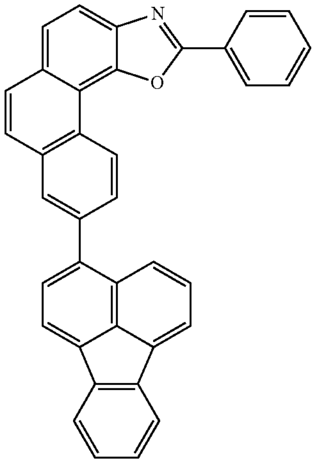

-continued
H-91
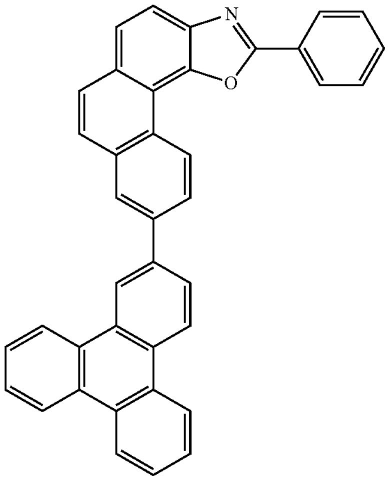
H-92
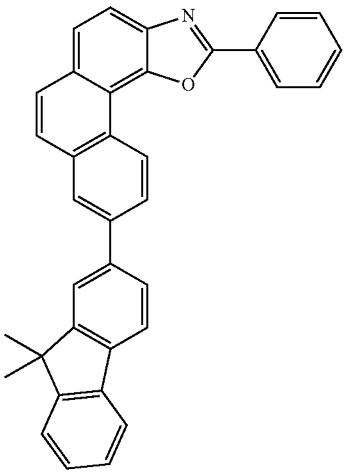
H-93
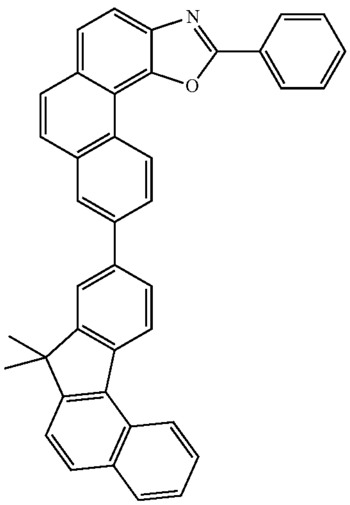
-continued
H-94
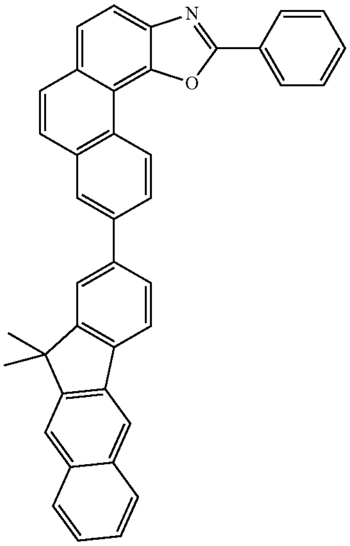
H-95
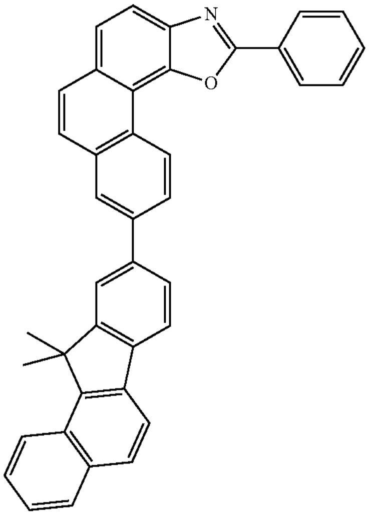
H-96
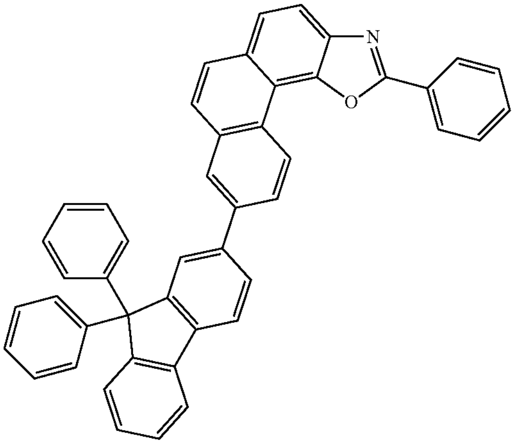

-continued
H-97
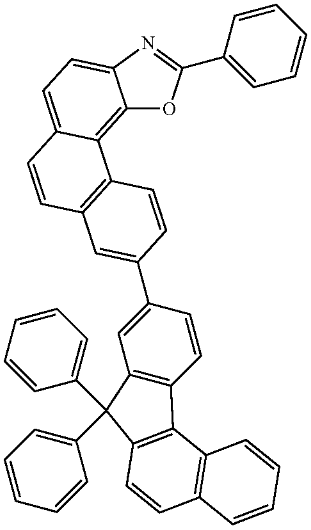
H-98
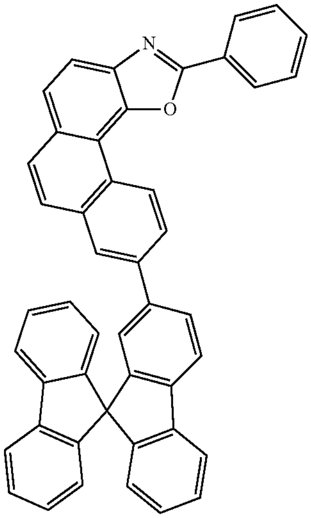
H-99
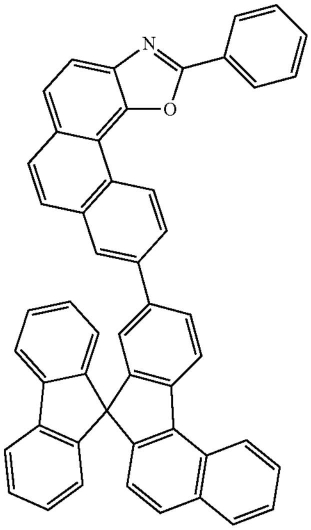
-continued
H-100
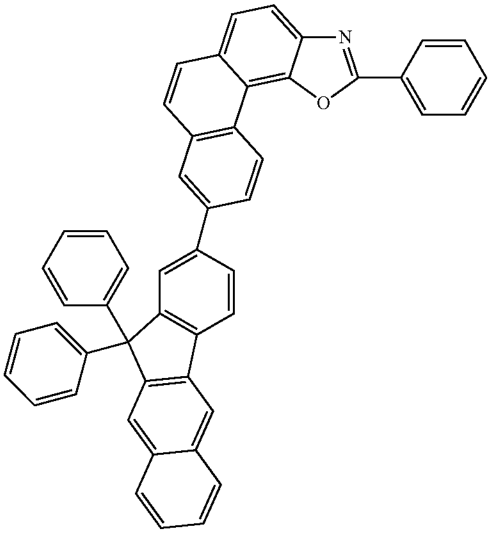
H-101
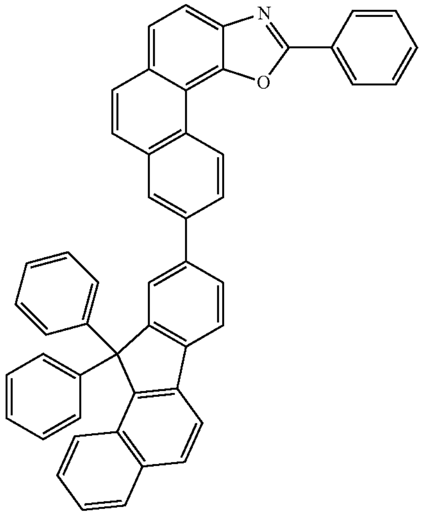
H-102
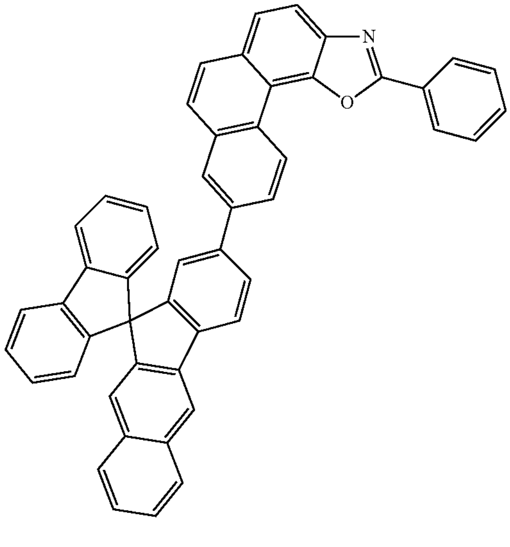

-continued
H-103
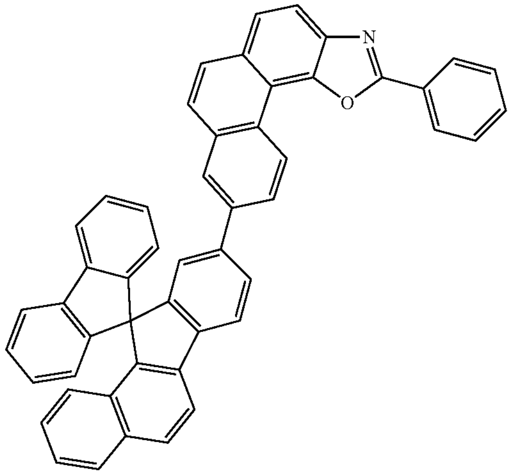
H-104
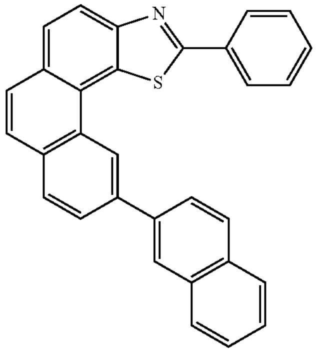
H-105
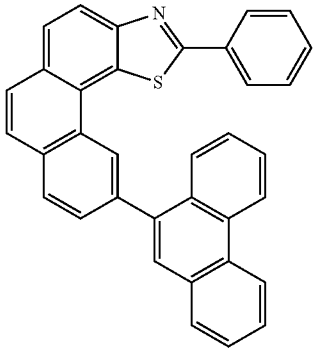
H-106
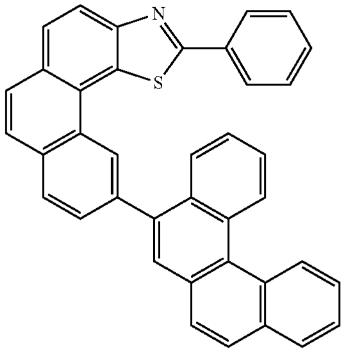
-continued
H-107
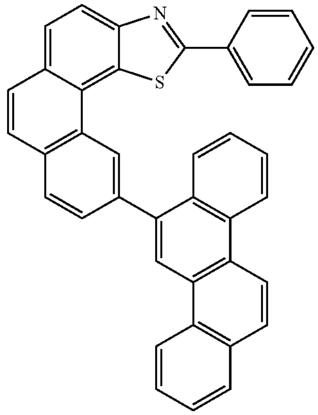
H-108
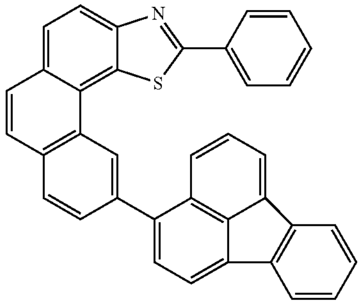
H-109
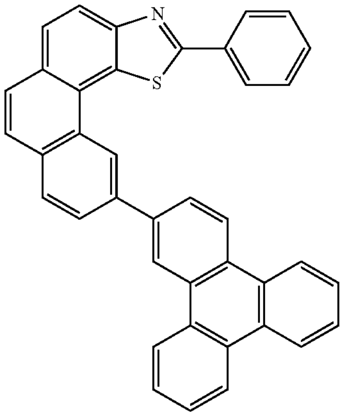
H-110
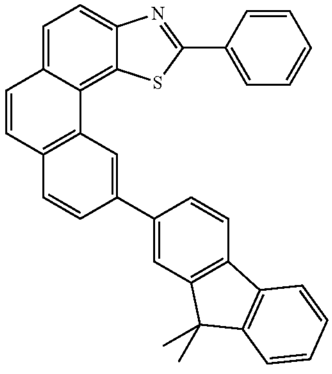

-continued
H-111
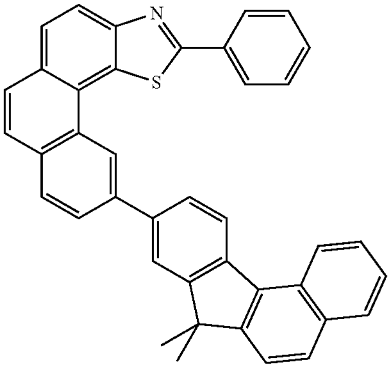
H-112
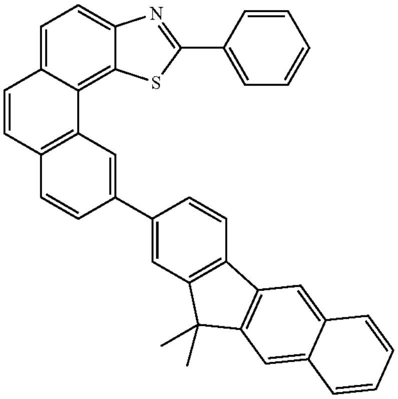
H-113
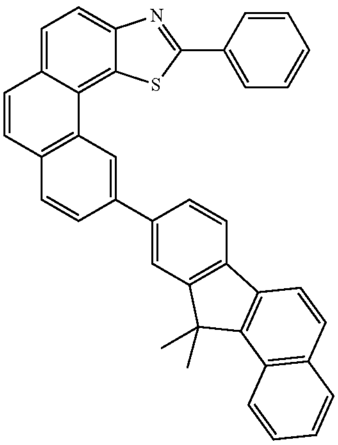
-continued
H-114
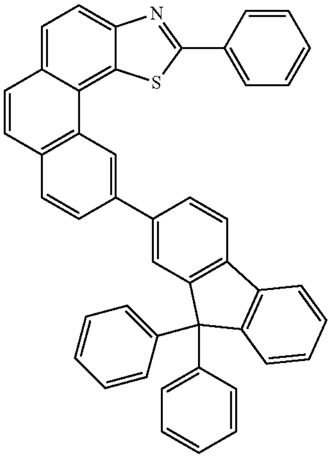
H-115
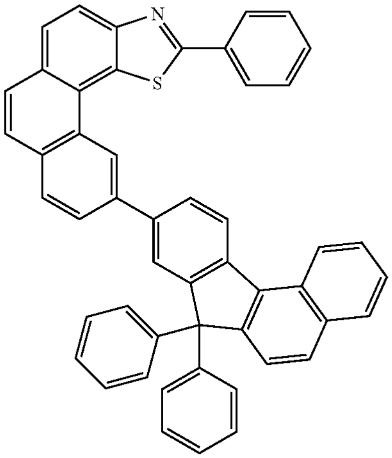
H-116
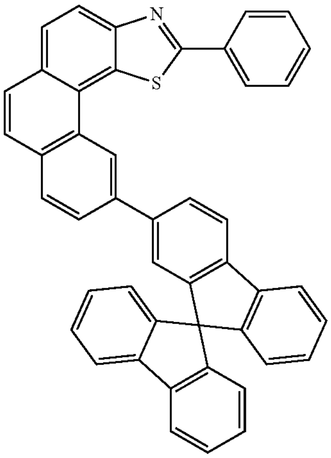

-continued
H-117
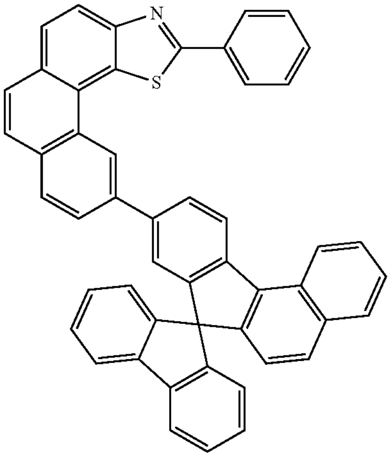
H-118
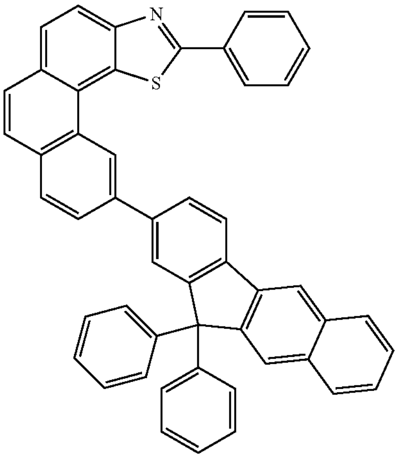
H-119
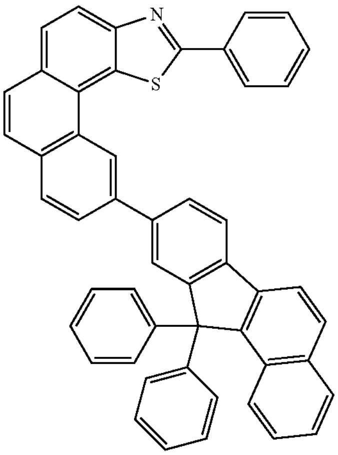
-continued
H-120
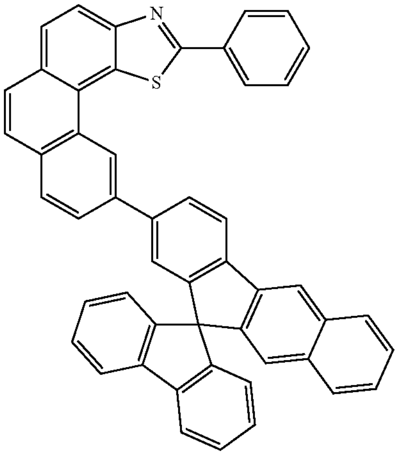
H-121
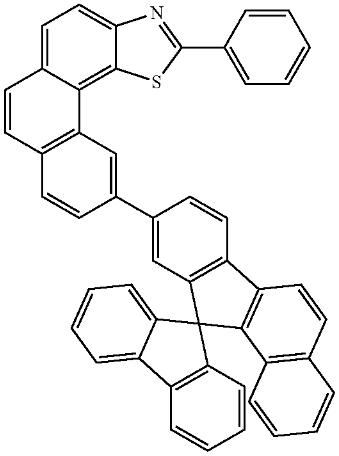
H-122
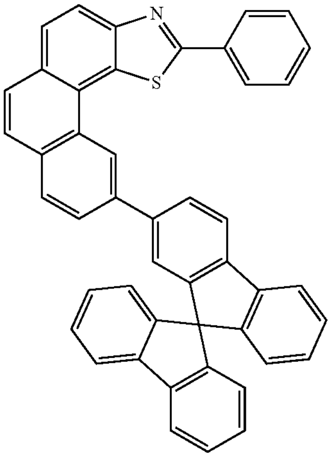

-continued
H-123
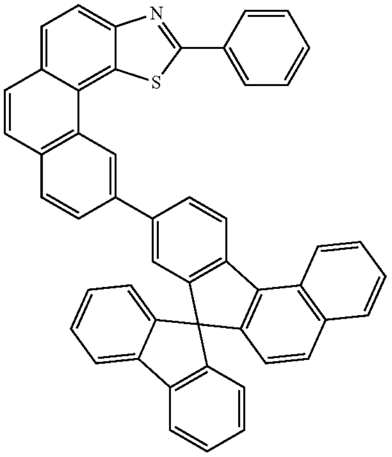
H-124
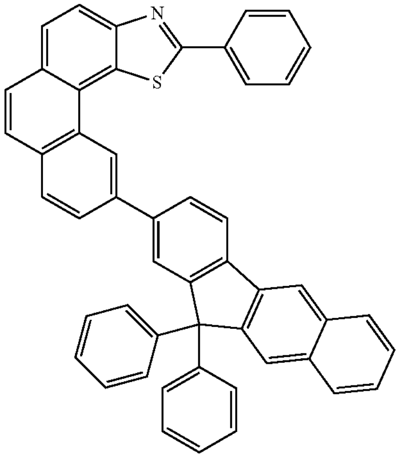
H-125
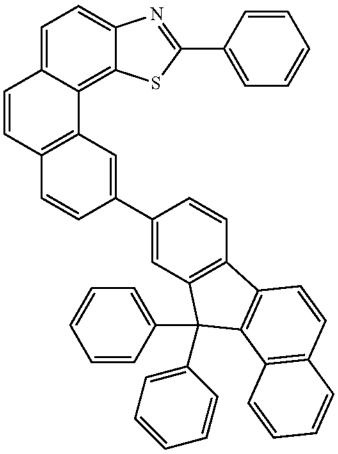
-continued
H-126
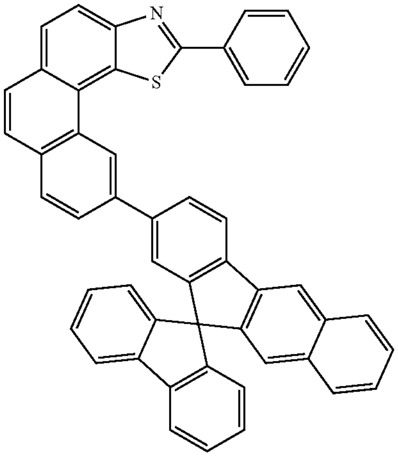
H-127
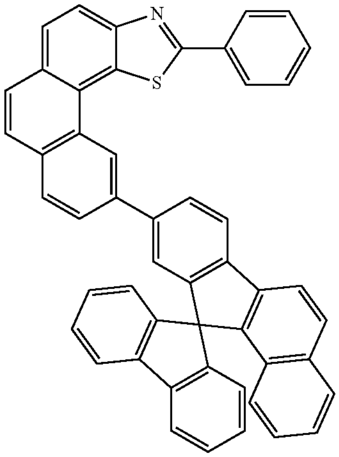
H-128
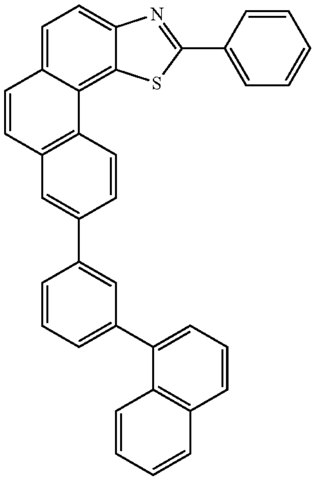

-continued
H-129
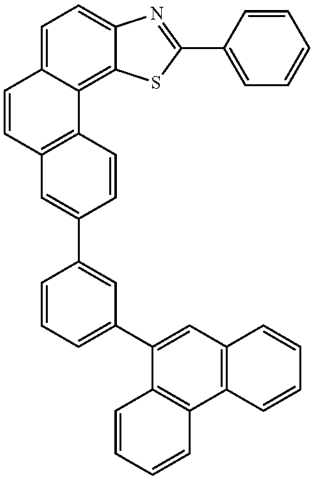
H-130
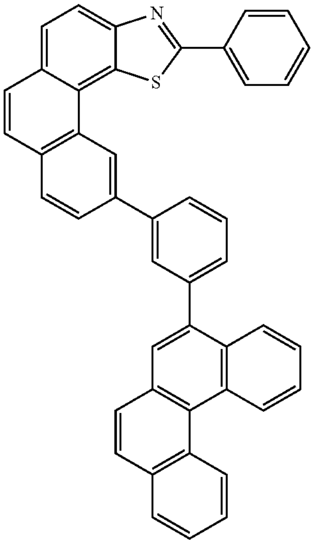
H-131
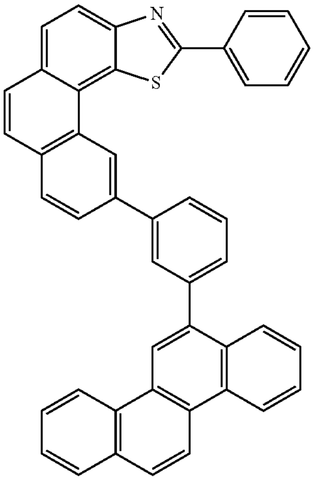
-continued
H-132
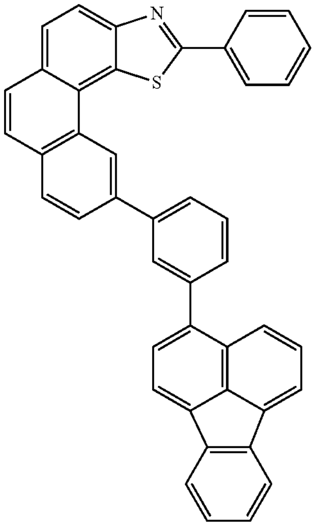
H-133
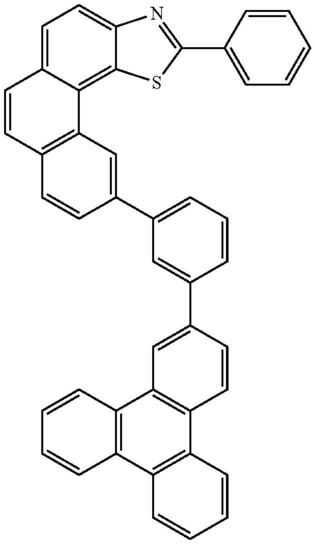
H-134
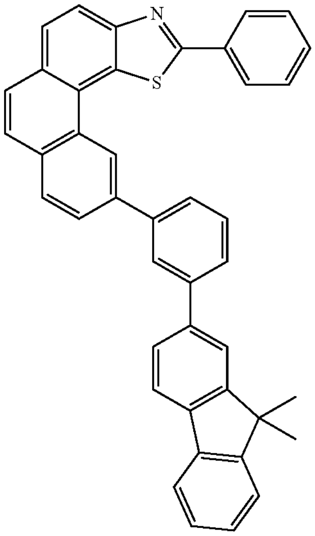

-continued
H-135
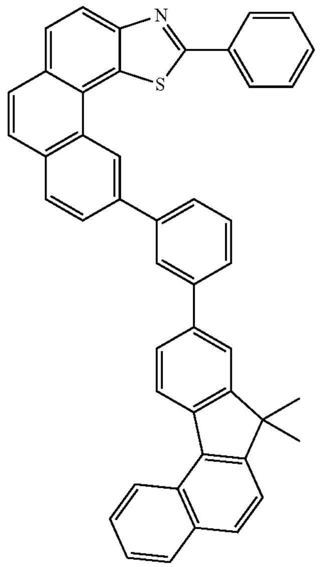
H-136
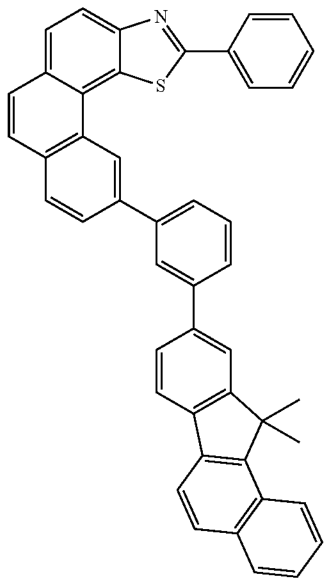
-continued
H-137
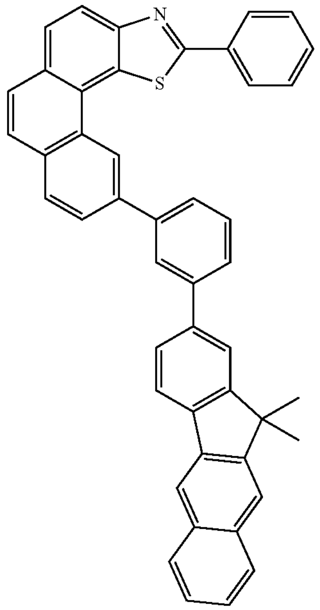
H-138
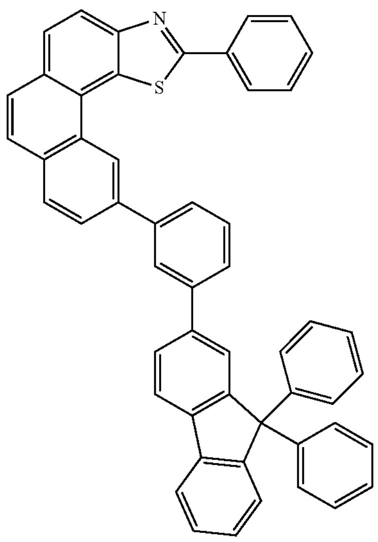

-continued
H-139
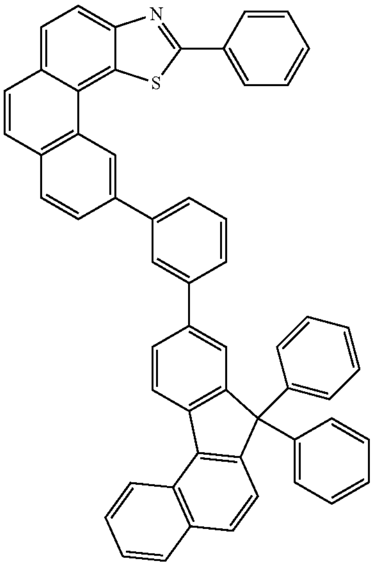
H-140
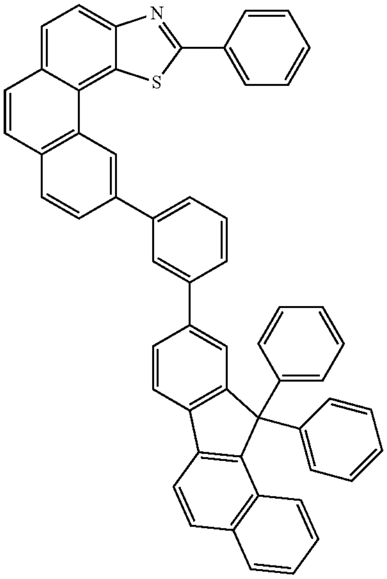
-continued
H-141
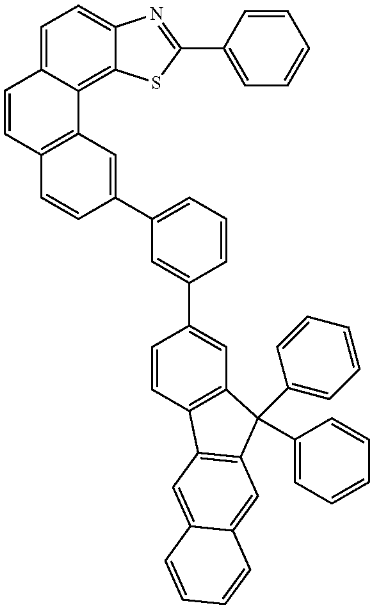
H-142
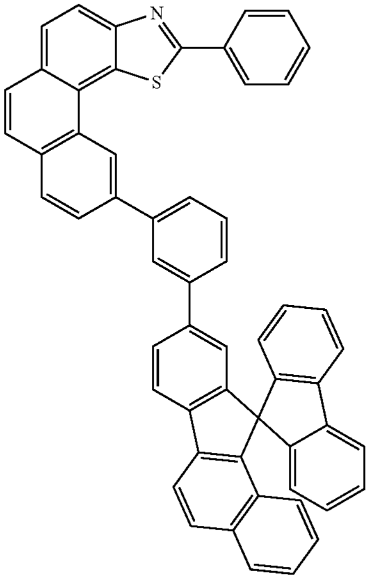

-continued
H-143
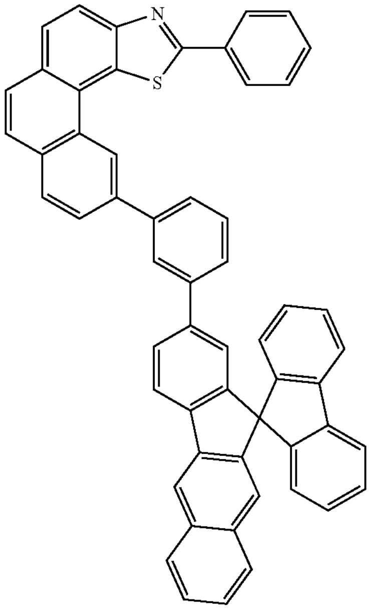
H-144
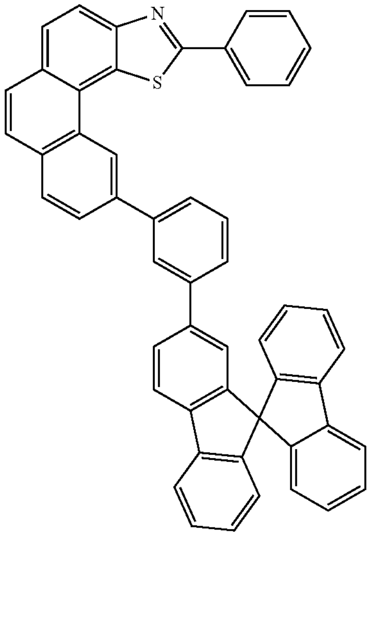
-continued
H-145
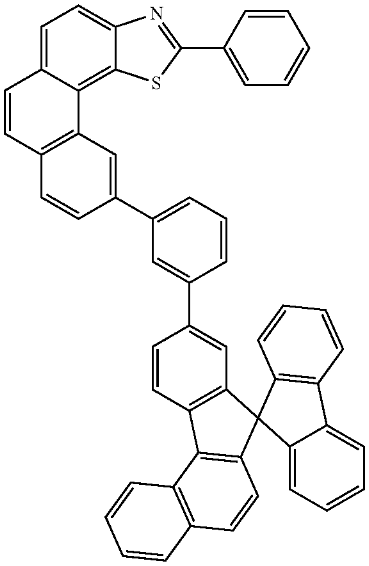
H-146
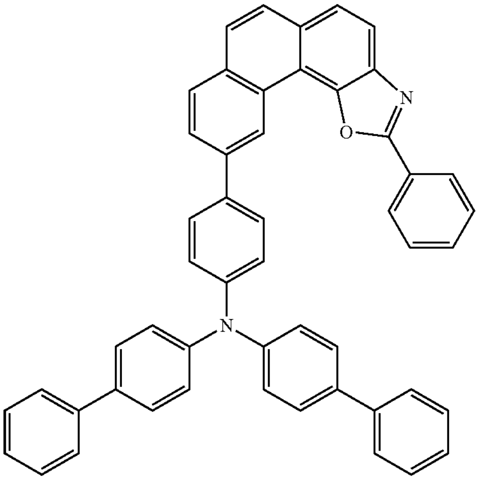
H-147
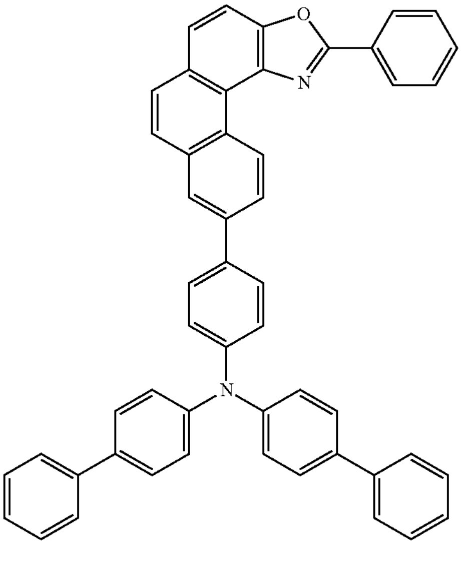

-continued
H-148
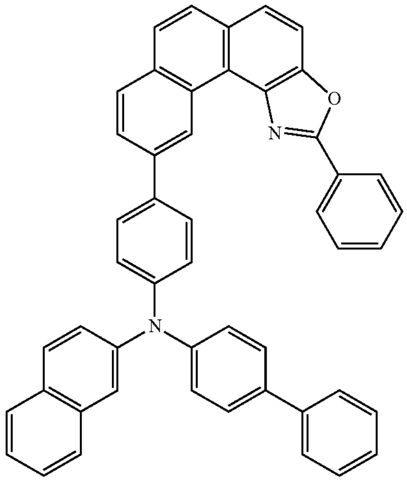
H-149
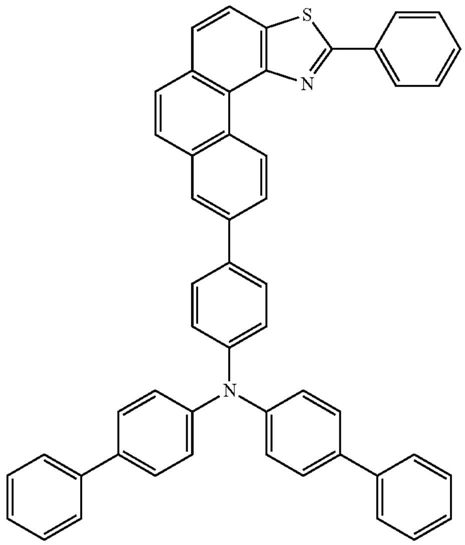
H-150
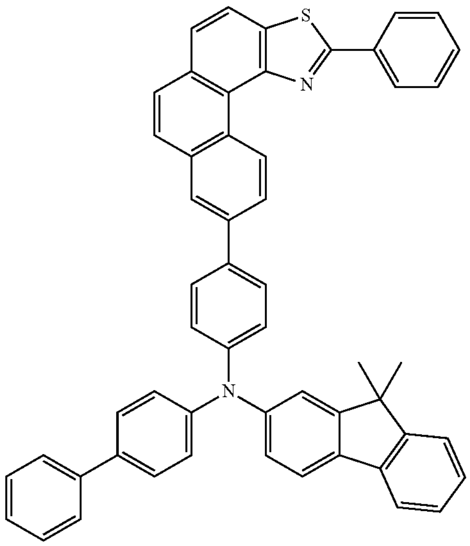
-continued
H-151
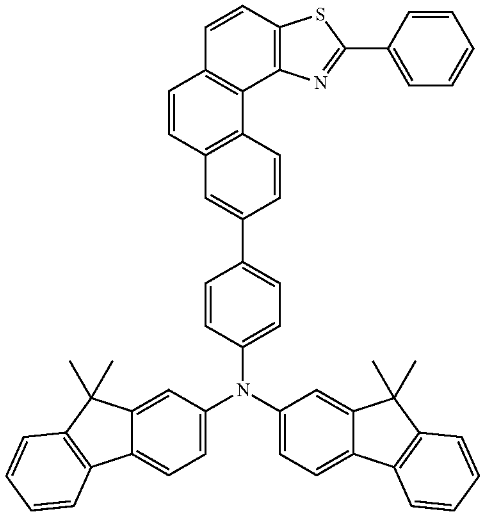
H-152
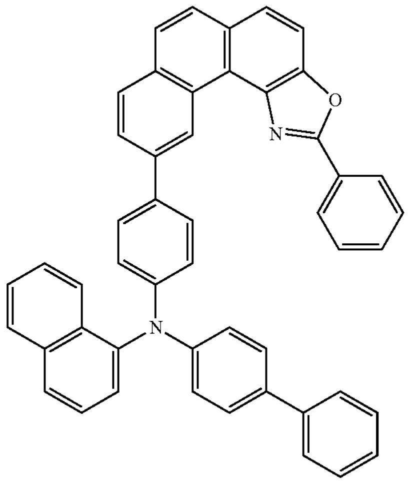
H-153
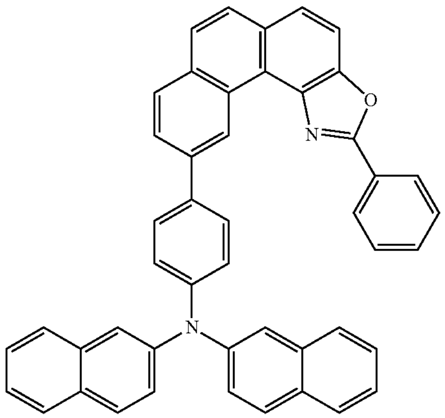

-continued
H-154
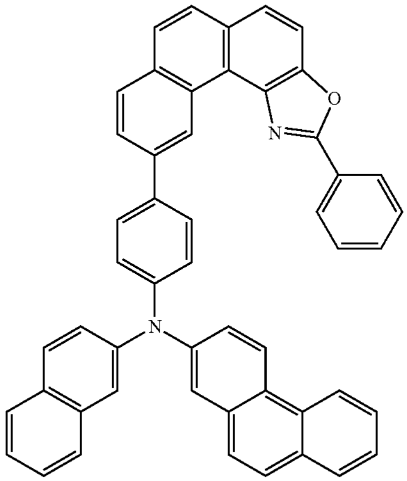
H-155
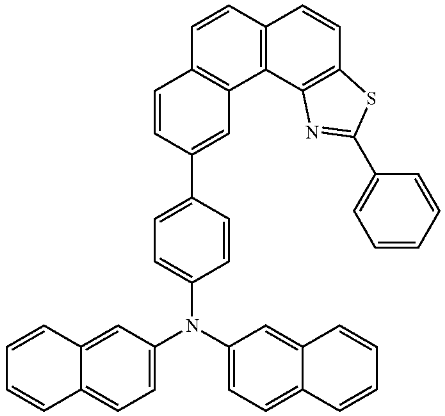
H-156
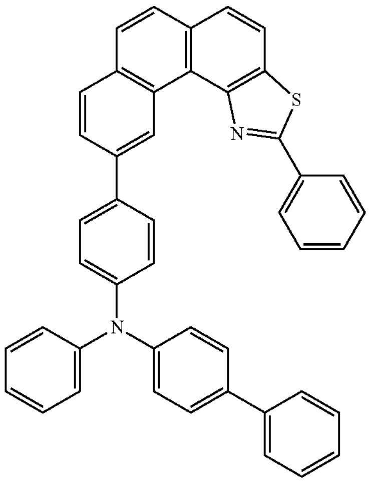
-continued
H-157
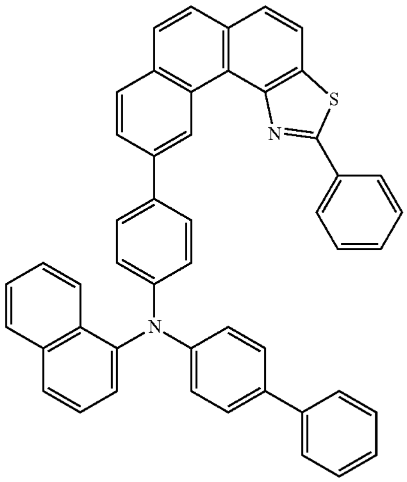
H-158
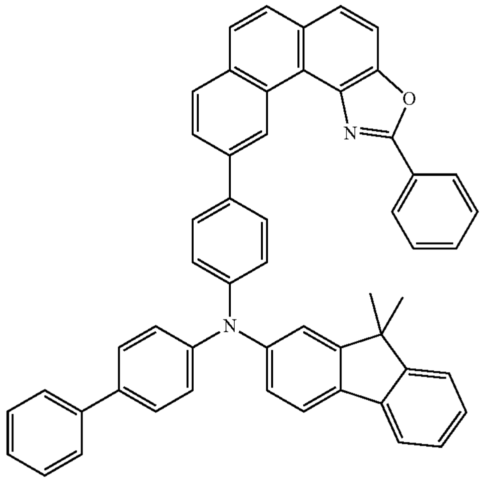
H-159
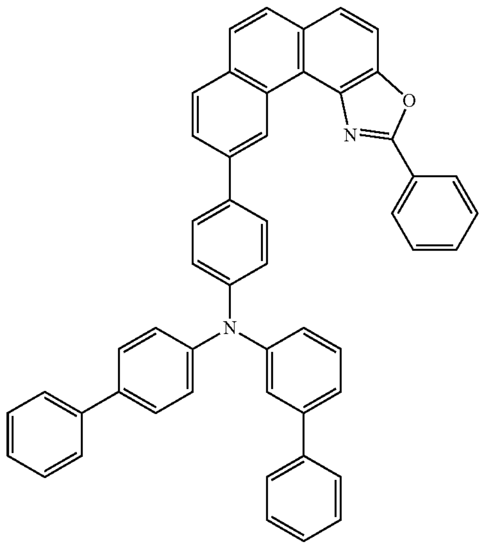

-continued
H-160
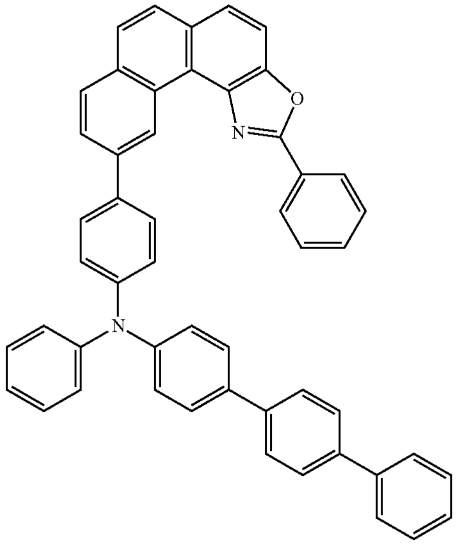
H-161
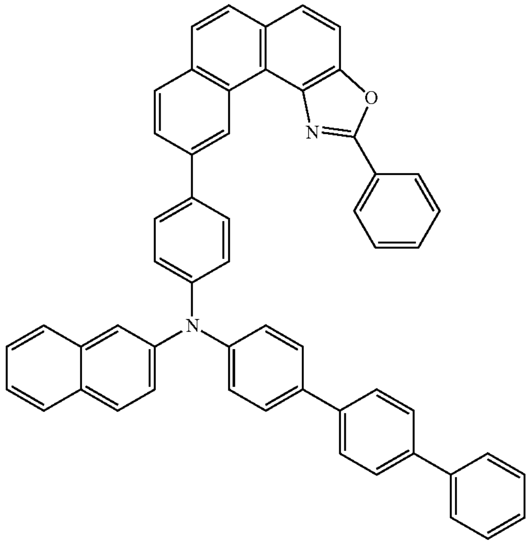
H-162
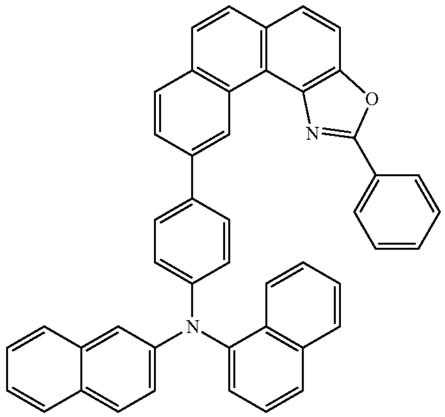
-continued
H-163
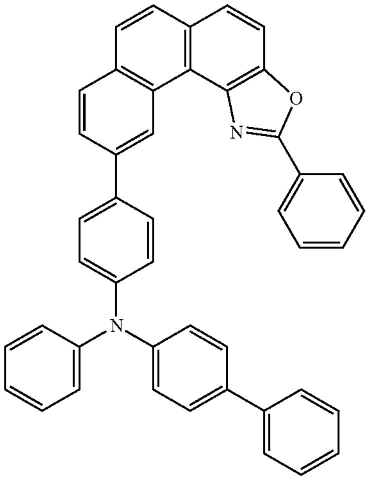
H-164
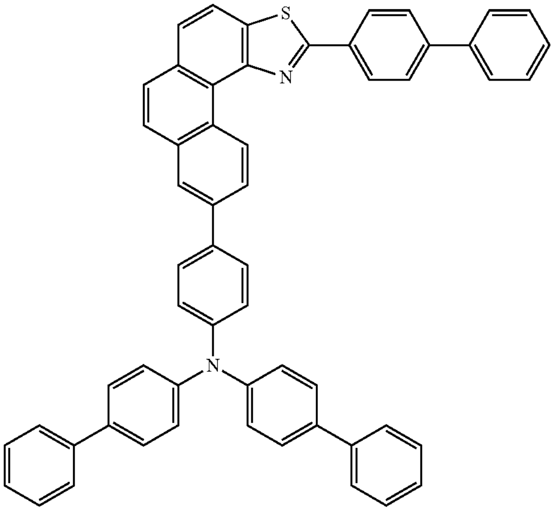
H-165
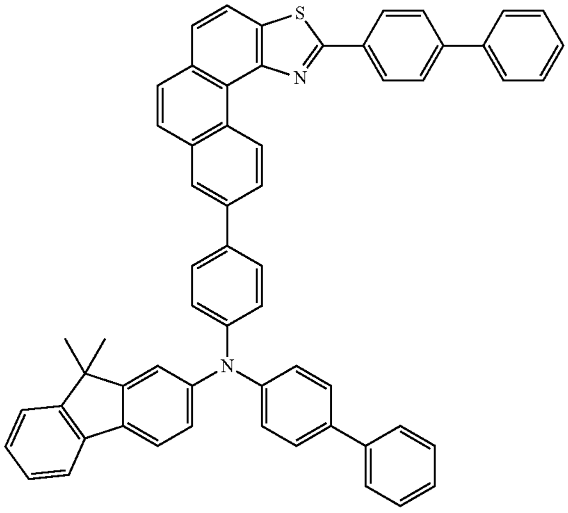

-continued
H-166
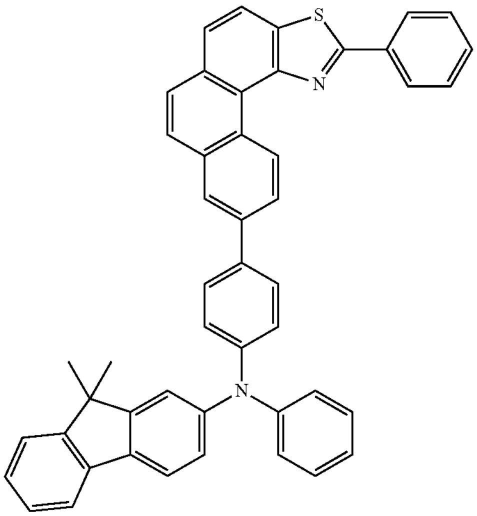
H-167
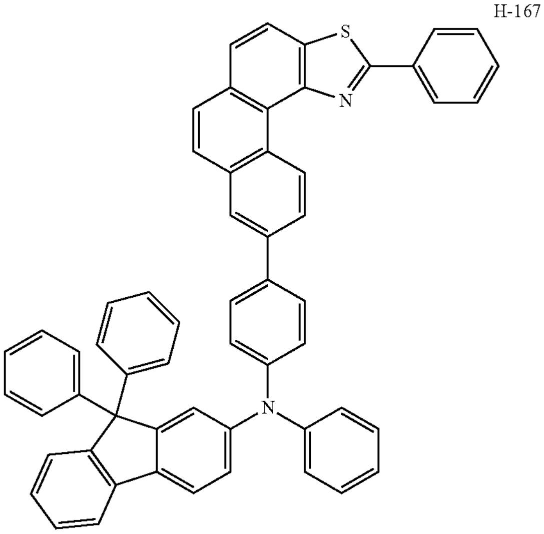
H-168
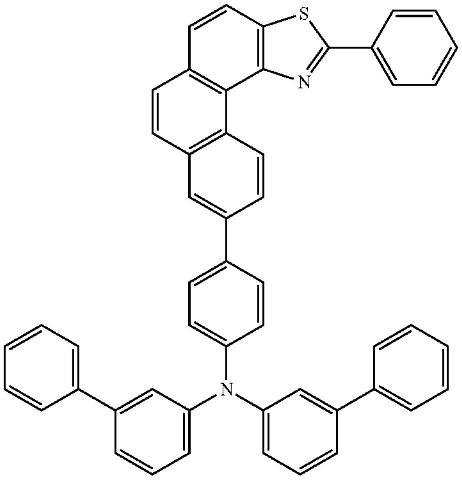
-continued
H-169
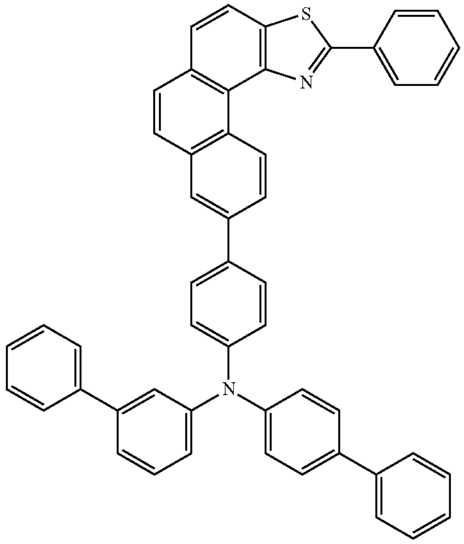
H-170
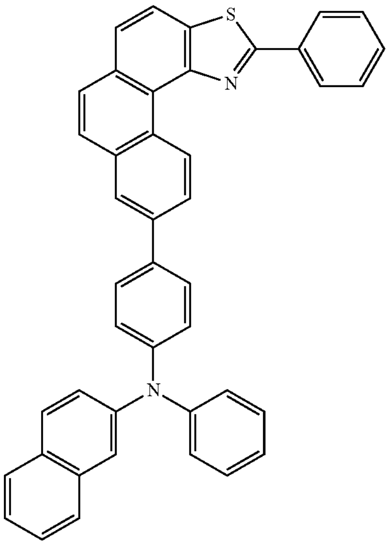
H-171
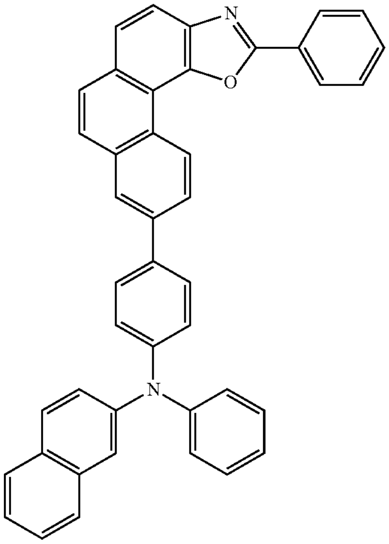

-continued
H-172
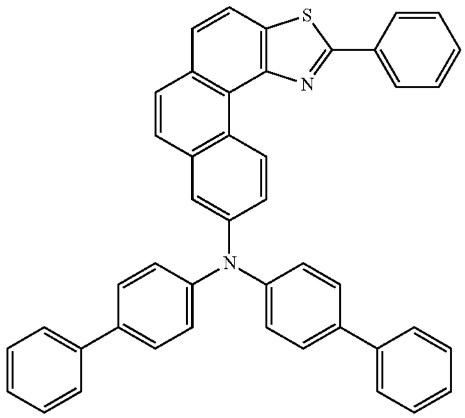
H-173
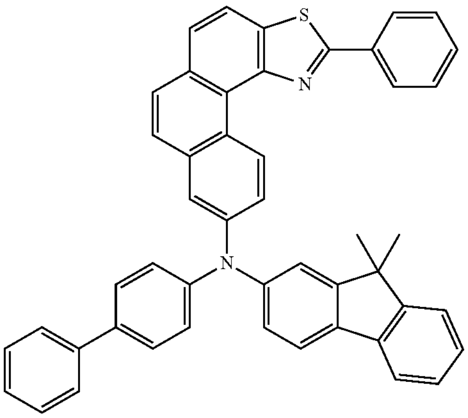
H-174
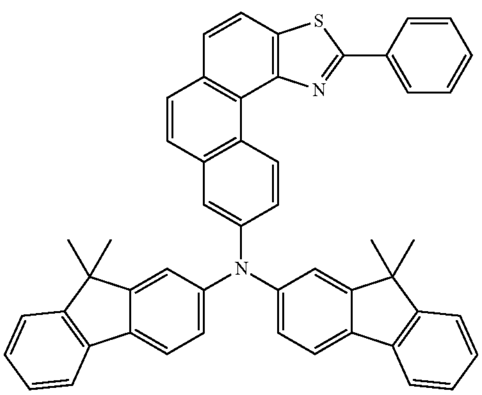
-continued
H-175
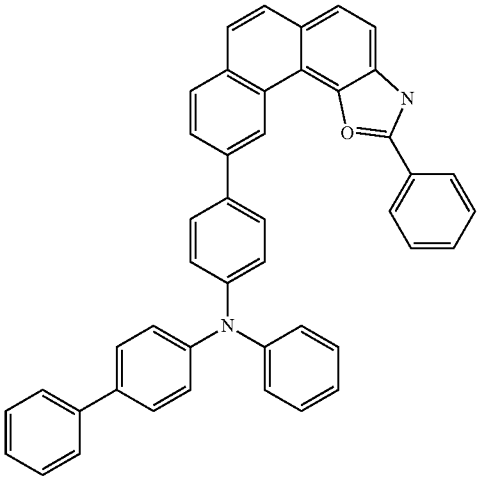
H-176
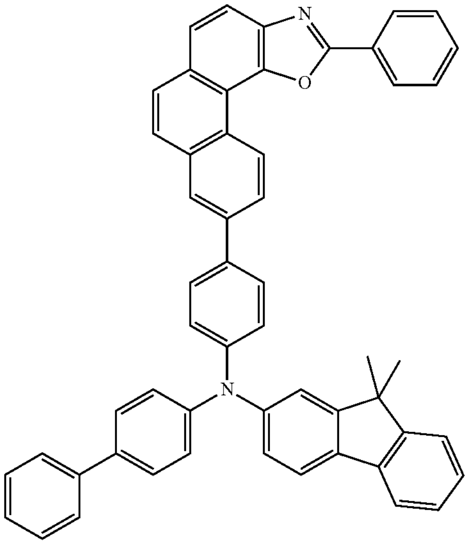
H-177
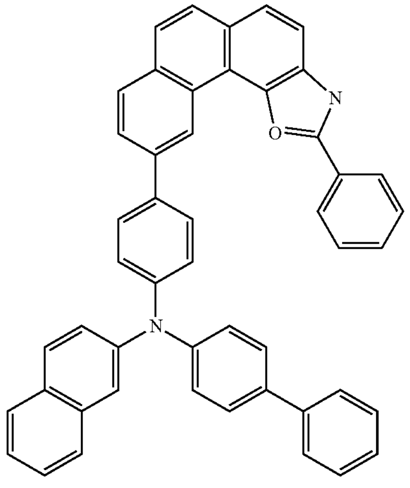

-continued
H-178
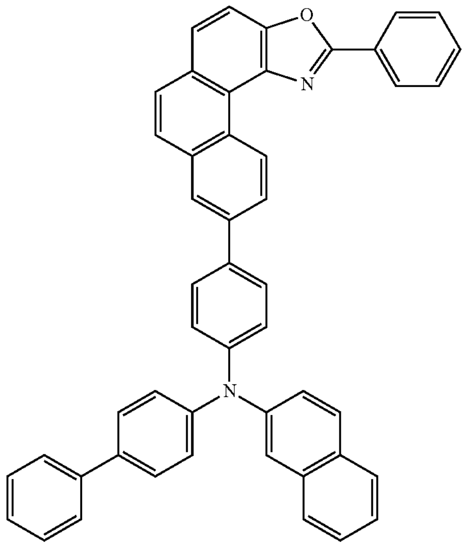
H-179
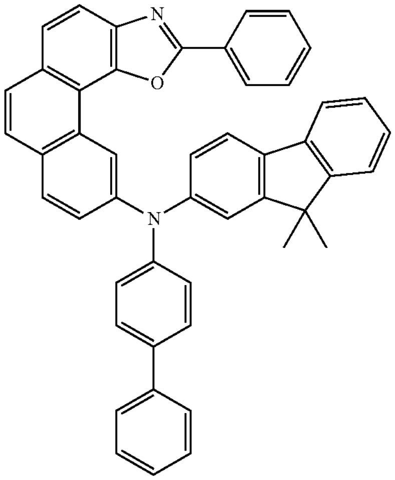
H-180
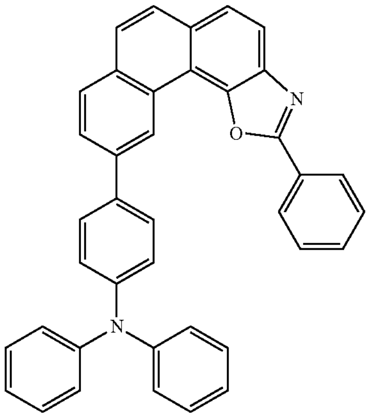
-continued
H-181
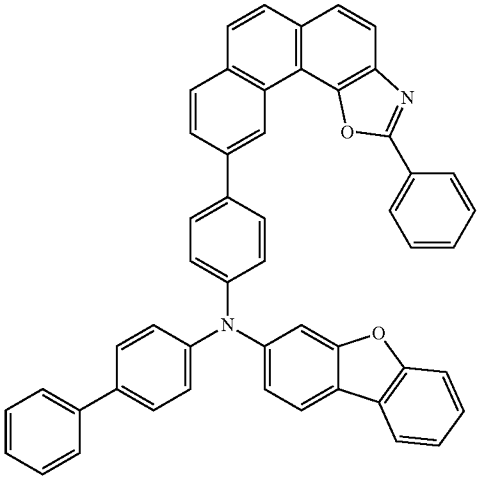
H-182
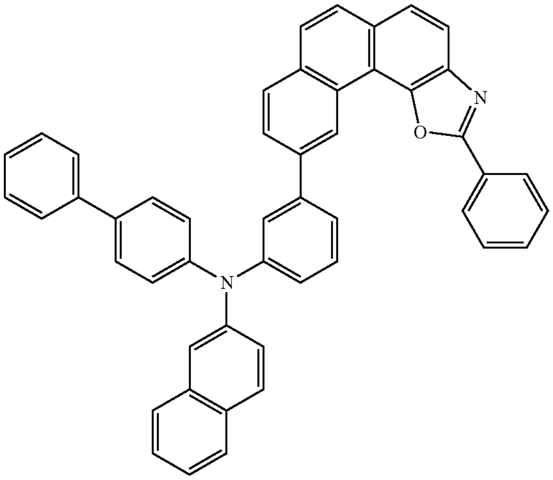
H-183
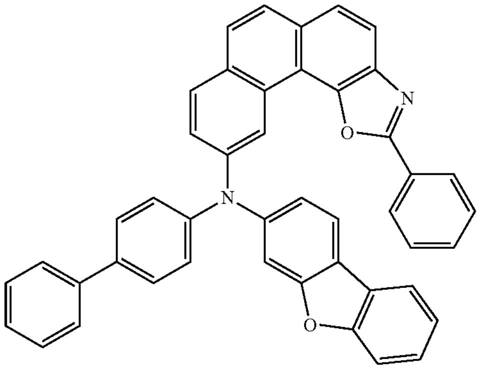

-continued
H-184
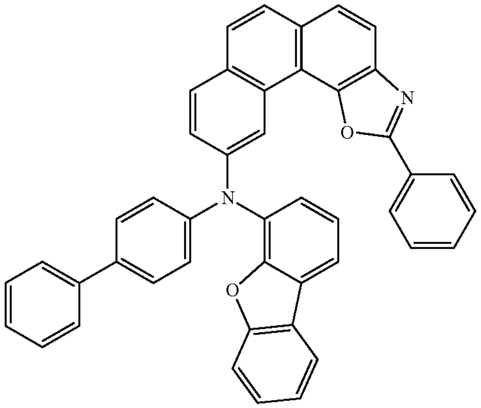
H-185
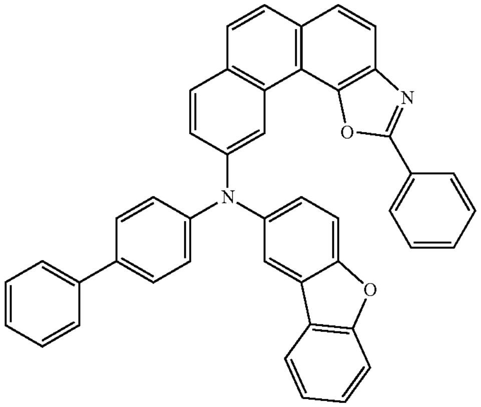
H-186
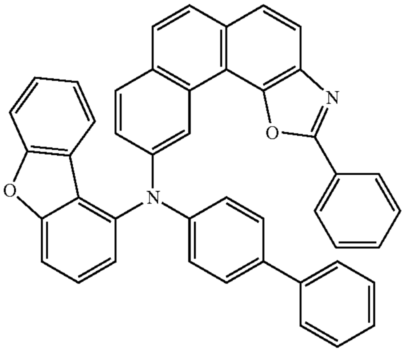
H-187
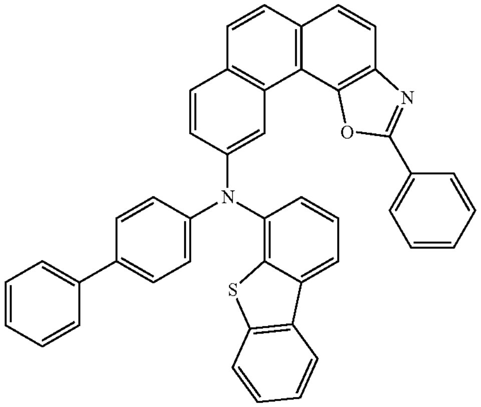
-continued
H-188
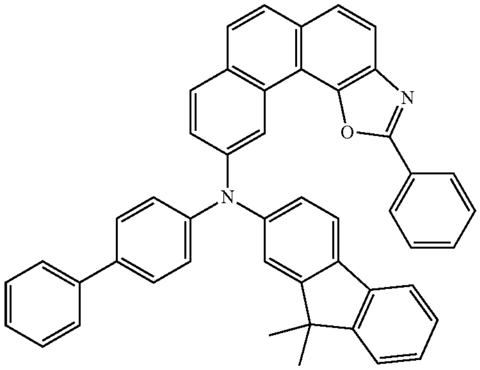
H-189
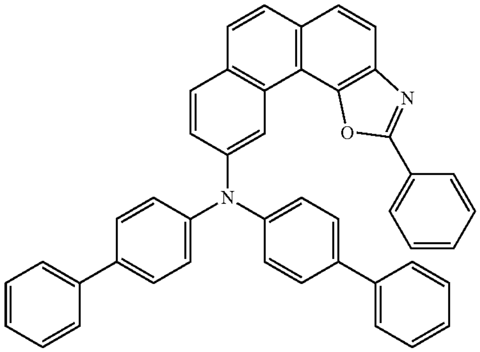
H-190
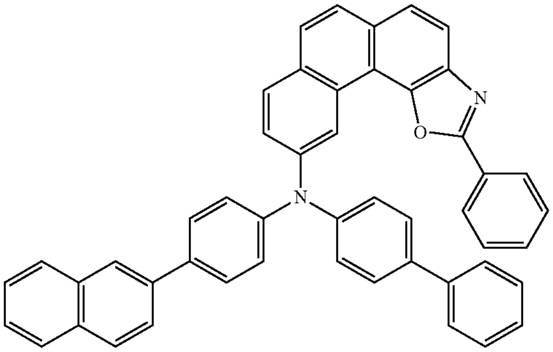
H-191
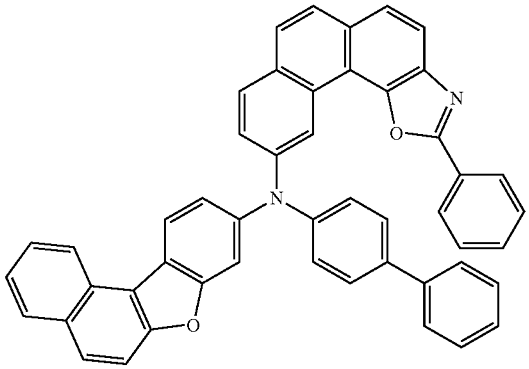

-continued
H-192
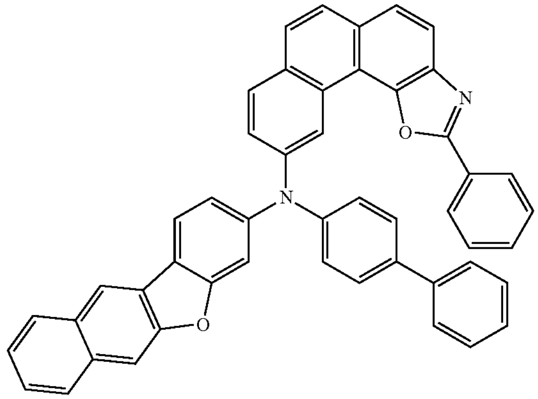
H-193
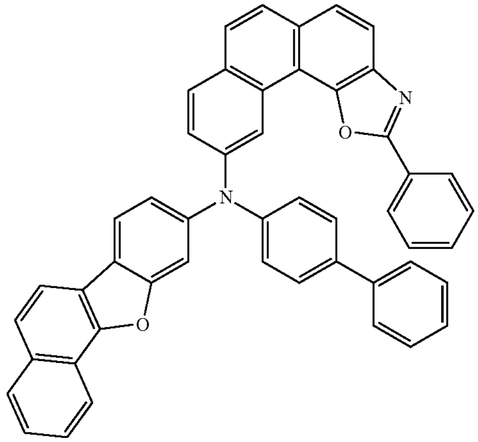
H-194
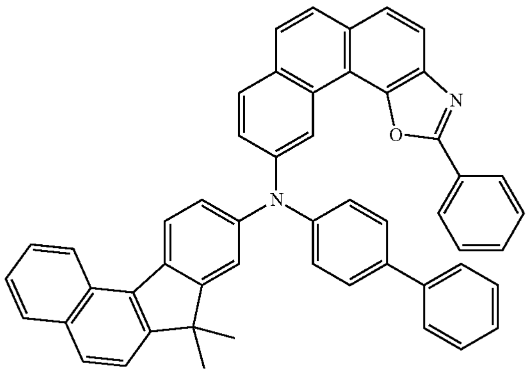
-continued
H-195
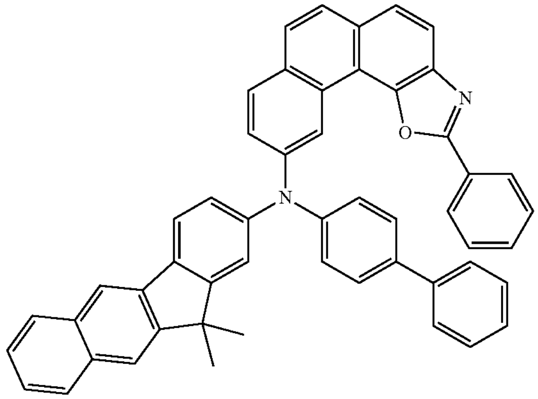
H-196
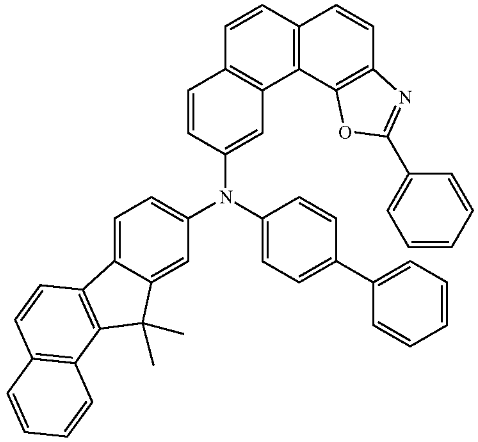
H-197
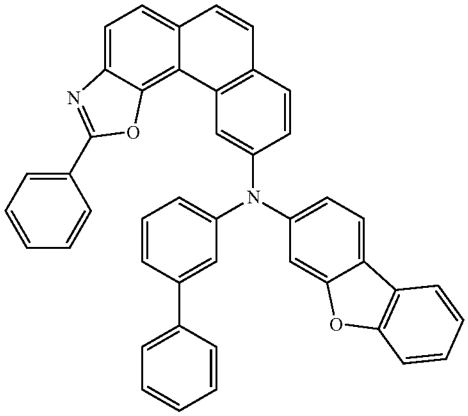

-continued
H-198
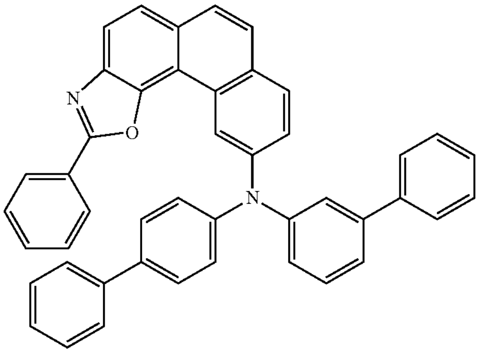
H-199
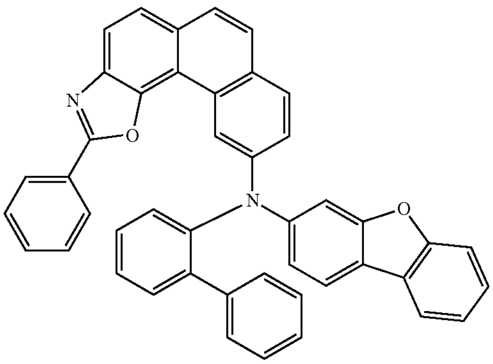
H-200
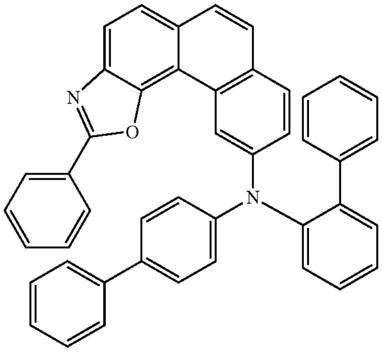
H-201
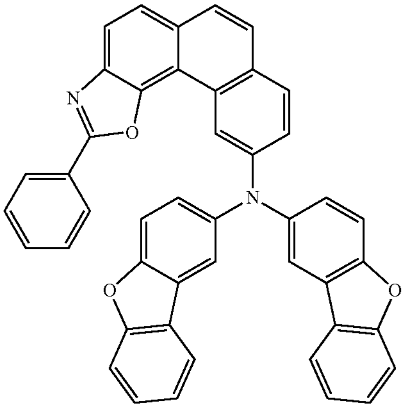
-continued
H-202
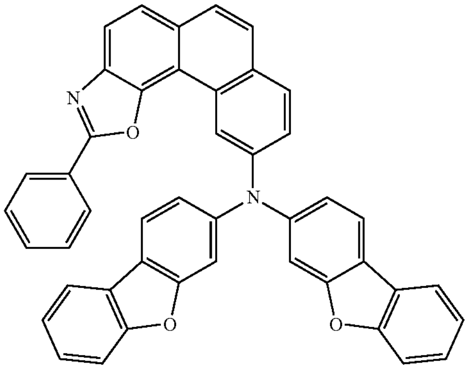
H-203
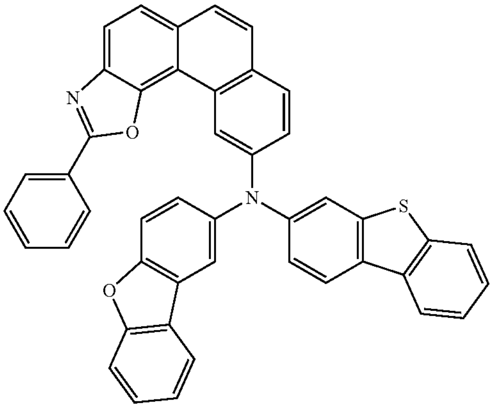
H-204
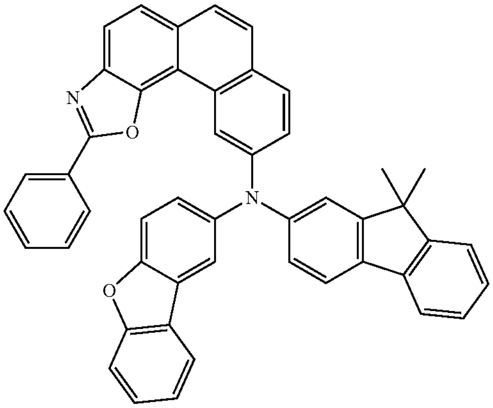
H-205
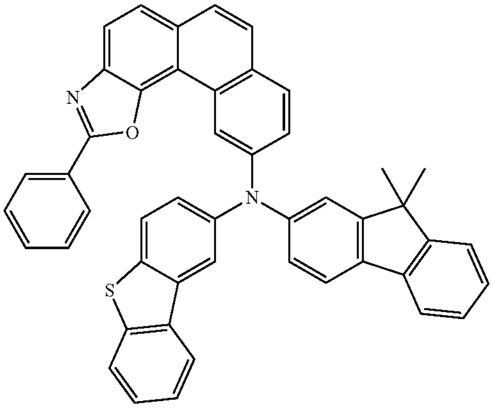

-continued
H-206
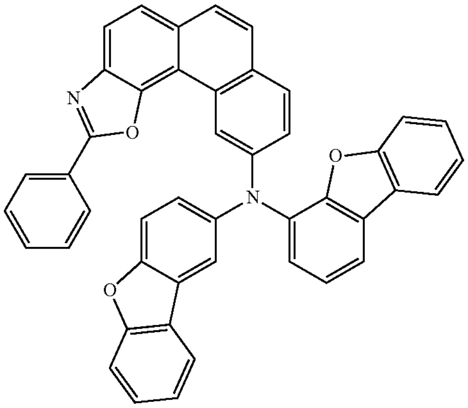
H-207
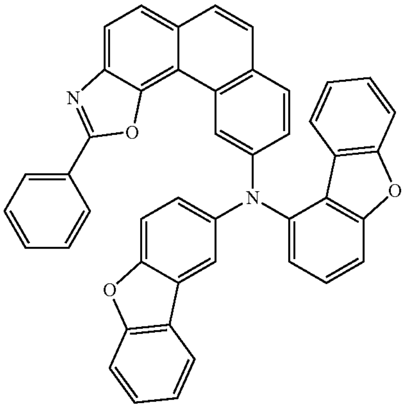
H-208
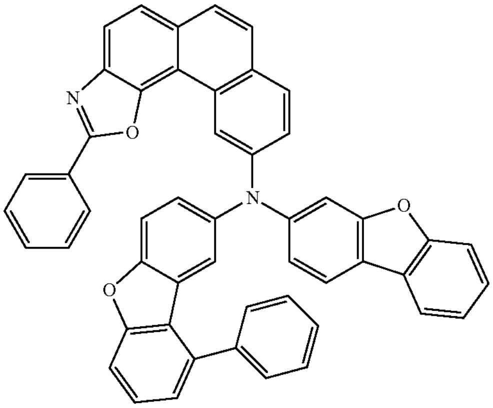
-continued
H-209
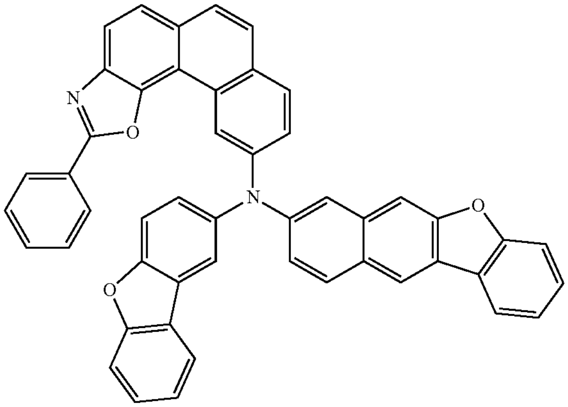
H-210
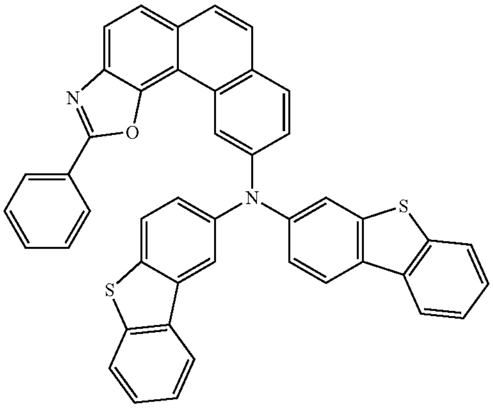
H-211
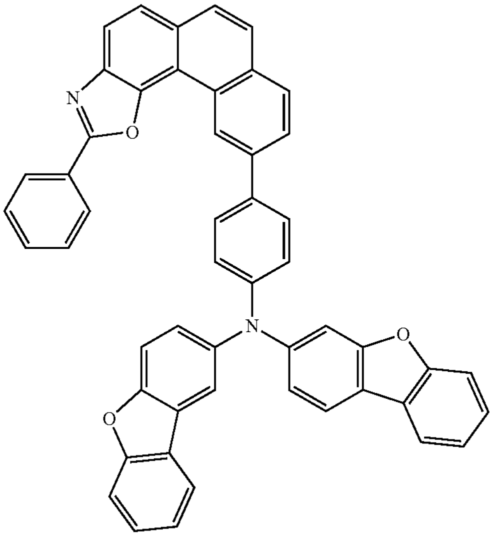

-continued
H-212
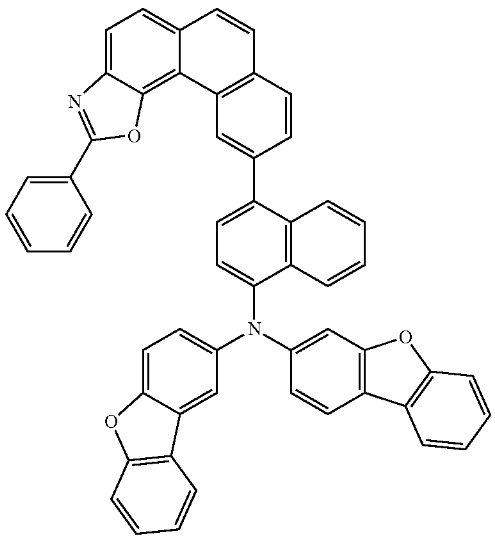
H-213
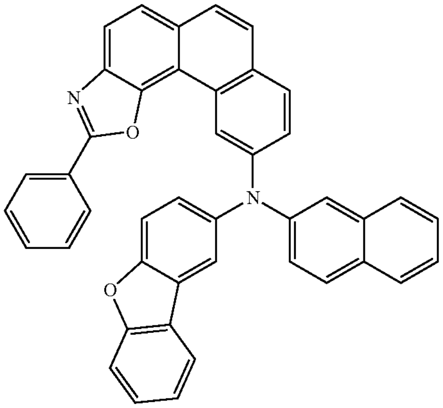
H-214
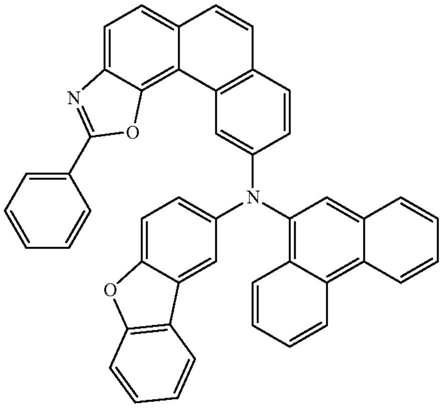
-continued
H-215
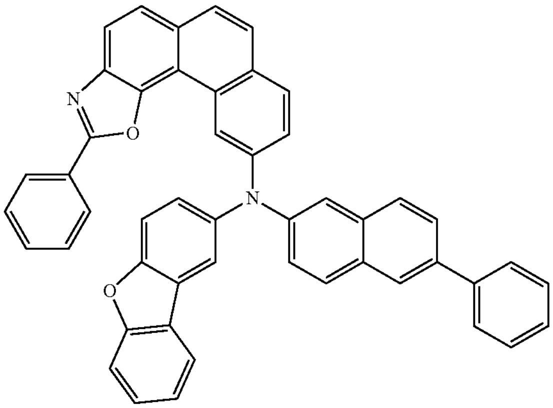
H-216
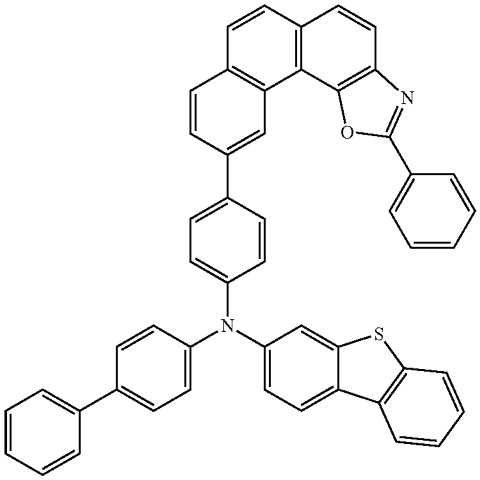
H-217
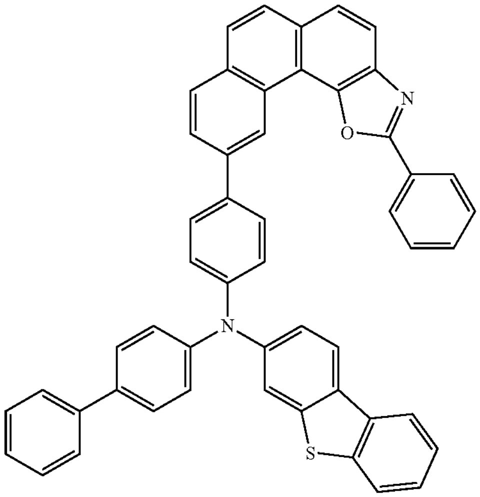

-continued

H-218

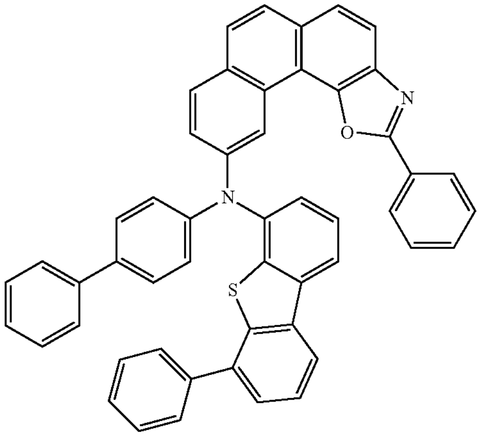

H-219

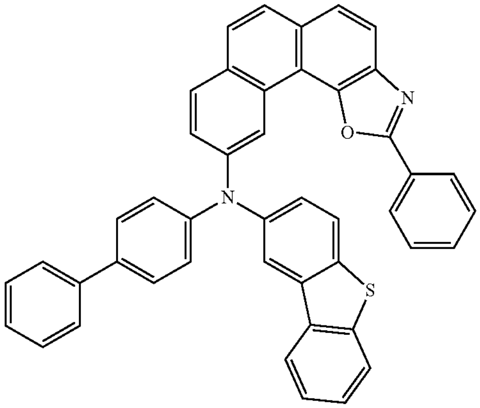

and

-continued

H-220

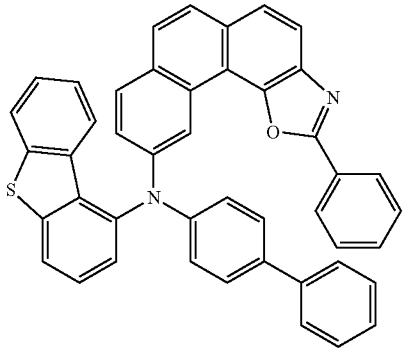

.

6. An organic electroluminescent device comprising an anode; a cathode; and at least one light-emitting layer between the anode and the cathode, wherein the at least one light-emitting layer comprise a plurality of host materials according to claim 1.

7. An organic electroluminescent device comprising an anode; a cathode; and at least one light-emitting layer between the anode and the cathode, wherein the at least one light-emitting layer comprise a plurality of host materials according to claim 2.

8. An organic electroluminescent device comprising an anode; a cathode; and at least one light-emitting layer between the anode and the cathode, wherein the at least one light-emitting layer comprise a plurality of host materials according to claim 5.

* * * * *